(12) United States Patent
Safadi

(10) Patent No.: US 9,243,294 B2
(45) Date of Patent: Jan. 26, 2016

(54) MODULATION OF NLGN4 EXPRESSION, NK CELL ACTIVITY IN NON-ALCOHOLIC FATTY LIVER DISEASE (NAFLD)

(71) Applicant: Rifaat Safadi, Nazareth Elit (IL)

(72) Inventor: Rifaat Safadi, Nazareth Elit (IL)

(73) Assignee: Hadasit Medical Research Services and Development Ltd., Jerusalem (IL)

( * ) Notice: Subject to any disclaimer, the term of this patent is extended or adjusted under 35 U.S.C. 154(b) by 0 days.

(21) Appl. No.: 14/501,160

(22) Filed: Sep. 30, 2014

(65) Prior Publication Data

US 2015/0094355 A1    Apr. 2, 2015

Related U.S. Application Data

(60) Provisional application No. 61/884,153, filed on Sep. 30, 2013.

(51) Int. Cl.

| | |
|---|---|
| A61K 48/00 | (2006.01) |
| C07H 21/02 | (2006.01) |
| C07H 21/04 | (2006.01) |
| C12Q 1/68 | (2006.01) |
| A61K 31/7088 | (2006.01) |
| A61K 45/06 | (2006.01) |
| C12N 15/113 | (2010.01) |
| A61K 31/713 | (2006.01) |
| A61K 31/7105 | (2006.01) |

(52) U.S. Cl.
CPC .......... *C12Q 1/6883* (2013.01); *A61K 31/7088* (2013.01); *A61K 31/713* (2013.01); *A61K 31/7105* (2013.01); *A61K 45/06* (2013.01); *C12N 15/1138* (2013.01); *C12N 2310/11* (2013.01); *C12N 2310/14* (2013.01); *C12Q 2600/158* (2013.01)

(58) Field of Classification Search
CPC .............................. A61K 48/00; C12N 15/113
See application file for complete search history.

(56) References Cited

U.S. PATENT DOCUMENTS

| | | | |
|---|---|---|---|
| 4,816,567 | A | 3/1989 | Cabilly |
| 5,641,870 | A | 6/1997 | Rinderknecht |
| 5,910,573 | A | 6/1999 | Pluckthun |
| 7,579,392 | B2 | 8/2009 | Gan |

FOREIGN PATENT DOCUMENTS

| | | |
|---|---|---|
| EP | 0404097 | 12/1990 |
| WO | 93/11161 | 6/1993 |
| WO | 93/15210 | 8/1993 |
| WO | 96/13583 | 5/1996 |
| WO | 96/37621 | 11/1996 |

OTHER PUBLICATIONS

Bian and Ma (2012) Liver fibrogenesis in non-alcoholic steatohepatitis. Front Physiol 3: 248.
Björkström et al., (2010) Expression patterns of NKG2A, KIR, and CD57 define a process of CD56dim NK-cell differentiation uncoupled from NK-cell education. Blood 116(19): 3853-64.
Bolliger et al., (2001) Identification of a novel neuroligin in humans which binds to PSD-95 and has a widespread expression. Biochem J 356(Pt 2): 581-8.
Bolliger et al., (2008) Unusually rapid evolution of Neuroligin-4 in mice. Proc Natl Acad Sci U S A 105(17): 6421-6.
Cooper et al., (2001) Human natural killer cells: a unique innate immunoregulatory role for the CD56 (bright) subset. Blood 97(10): 3146-51.
Lopez-Vergès et al., (2010) CD57 defines a functionally distinct population of mature NK cells in the human CD56dimCD16+ NK-cell subset. Blood 116(19): 3865-74.
Melhem et al., (2006) Anti-fibrotic activity of NK cells in experimental liver injury through killing of activated HSC. J Hepatol 45(1): 60-71.
Moreira (2007) Hepatic stellate cells and liver fibrosis. Arch Pathol Lab Med 131(11): 1728-34.
Moretta (2010) Dissecting CD56dim human NK cells. Blood 116: 3689-3691.
Sans et al., (2000) A developmental change in NMDA receptor-associated proteins at hippocampal synapses. J Neurosci 20(3): 1260-71.
Seki et al., (2011) Antitumor immunity produced by the liver Kupffer cells, NK cells, NKT cells, and CD8 CD122 T cells. Clin Dev Immunol 2011: 868345.
Zelber-Sagi et al., (2011) Nutrition and physical activity in NAFLD: an overview of the epidemiological evidence. World J Gastroenterol 17(29): 3377-89.
Clinical Trial No. NCT01133184: Improved Prevention of Perinatal Hepatitis B Transmission. Updated May 27, 2010, http://www.clinicaltrials.gov/ct2/show/NCT01133184?term=nct01133184&rank=1.
Bird et al., (1988) Single-chain antigen-binding proteins. Science 242(4877): 423-6.
Clackson et al., (1991) Making antibody fragments using phage display libraries. Nature 352(6336): 624-8.
Holliger et al., (1993) "Diabodies": small bivalent and bispecific antibody fragments. Proc Natl Acad Sci U S A 90(14): 6444-8.
Huston et al., (1988) Protein engineering of antibody binding sites: recovery of specific activity in an anti-digoxin single-chain Fv analogue produced in *Escherichia coli*. Proc Natl Acad Sci U S A 85(16): 5879-83.
Kohler and Milstein (1975) Continuous cultures of fused cells secreting antibody of predefined specificity. Nature 256(5517): 495-7.
Marks et al., (1991) By-passing immunization. Human antibodies from V-gene libraries displayed on phage. J Mol Biol 222(3): 581-97.

(Continued)

*Primary Examiner* — Amy Bowman
(74) *Attorney, Agent, or Firm* — Roach Brown McCarthy & Gruber, P.C.; Kevin D. McCarthy

(57) ABSTRACT

The present invention provides a method of treating, attenuating or preventing a liver disorder by inhibiting NLGn4 expression and thereby modulating the activity of NK cells. The present invention further relates to diagnosing a liver disorder by evaluating NLGn4 expression in NK cells.

6 Claims, 7 Drawing Sheets

(56) References Cited

OTHER PUBLICATIONS

Muhanna et al., (2007) Lymphocyte-hepatic stellate cell proximity suggests a direct interaction. Clin Exp Immunol 148(2): 338-47.

Muller et al., (1998) A dimeric bispecific miniantibody combines two specificities with avidity. FEBS Letters 432(1-2): 45-49.

Wang et al., (2010) Delivery of siRNA therapeutics: barriers and carriers. AAPS J 12(4): 492-503.

Zapata et al., (1995) Engineering linear F(ab')2 fragments for efficient production in *Escherichia coli* and enhanced antiproliferative activity. Protein Eng 8(10): 1057-62.

https://en.wikipedia.org/wiki/Small_interfering_RNA—obtained Jul. 27, 2015.

Page 661 left column of Microbiol Mol Biol Rev. Dec. 2003; 67(4): 657-685 http://www.ncbi.nlm.nih.gov/pmc/articles/PMC309050/).

MODULATION OF NLGN4 EXPRESSION, NK CELL ACTIVITY IN NON-ALCOHOLIC FATTY LIVER DISEASE (NAFLD)

CROSS REFERENCE TO RELATED APPLICATIONS

This application claims priority from U.S. Provisional application Ser. No. 61/884,153 filed on Sep. 30, 2013.

FIELD OF THE INVENTION

The present invention relates to the involvement of NK cells in Nonalcoholic-Fatty-Liver-Disease (NAFLD), mediated by a novel Neuroligin-4 (NLGn4) synaptic pathway. The present invention provides compositions and methods for modulating the action of NLGn4 to attenuate Nonalcoholic-Fatty-Liver-Disease (NAFLD).

BACKGROUND OF THE INVENTION

Nonalcoholic fatty-liver disease (NAFLD) is one of the most prevalent liver diseases in western countries. The full pathophysiology of NAFLD is still unknown. Both obesity and insulin resistance are considered to play a strong role in the disease process. Indeed, the rising rates of obesity and diabetes mellitus correlate with the increasing incidence of NAFLD, which is the hepatic and early manifestation of metabolic syndrome. Estimates suggest that about 20% to 30% of adults in developed countries have excess fat accumulation in the liver, 50% among people with diabetes, and about 80% in the obese and morbidly obese individuals.

Non-alcoholic steatohepatitis (NASH) is the most severe form of NAFLD, and can progress to more severe forms of liver disease, including fibrosis progression, cirrhosis, and even hepatocellular carcinoma.

The disease begins with the aberrant accumulation of triglycerides in the liver, resulting in simple steatosis; most patients who develop steatosis are stable and further disease does not develop. However, some individuals progress to NASH, the severe form of NAFLD. In NASH, up to 20% of patients' progress into cirrhosis.

The normal liver is composed of hepatocytes and non-parenchymal cells, which include kupffer cells, sinusoidal endothelial cells, and myofibroblasts known as Hepatic Stellate Cells (HSCs). HSCs are considered to be involved in the pathogenesis of liver fibrosis from any etiology, including NASH-related hepatic fibrosis. In normal liver, HSCs are described as being in a quiescent state and serve to store retinoids (vitamin A). Quiescent stellate cells represent 5-8% of the total number of liver cells. When the liver is damaged, HSCs can change into an activated state characterized by contractions, loss of lipid droplets and enhanced of proliferation, cell migration as well as cellular adhesion. HSCs are also unequivocally the main cells involved in the production of excessive ECM seen in liver fibrosis. Since activated HSCs themselves secrete inflammatory chemokines, a vicious cycle is formed, whereby fibrogenic and inflammatory cells stimulate each other and perpetuate a process of liver damage and repair.

Natural killer (NK) cells are a key component of the innate immune system, and play a critical role in the early stages of the immune response against tumor cells, as well as those infected by viral and microbial pathogens.

In humans, two NK-cell subsets have been characterized according to the cell-surface density of CD56 and expression of CD16. $CD56^{dim}CD16^{bright}$ NK cells (hereinafter $CD56^{dim}$) compose approximately 90% of circulating NK cells; $CD56^{bright}CD16^{dim}$ NK cells (hereinafter $CD56^{bright}$) constitute approximately 10%. $CD56^{bright}$ NK cells proliferate and produce interferon in response to stimulation with interleukin-12 (IL-12), whereas $CD56^{dim}$ NK cells are more cytolytic and produce significant amounts of cytokine when their activating receptors are engaged.

In a paper published by some of the inventors it was found that, as opposed to CD8 immune cells, NK cells have anti-fibrotic activity through stimulation of HSC killing. (Melhhem et al., J. Hepatology; 2006; 45: 60-71). It has also been reported that the function of NK cells decreases when the liver disease progresses into cirrhosis, suggesting that attenuating NK function is a prerequisite for the progression of the disease (Seki et al.; Clin Dev Immunol.; 2011; Article ID 868345).

Human neuroligin-4 (NLG4, NLGn4, NLGn4X) encodes a member of a family of neuronal cell surface proteins called the Neuroligins. FIG. 1 illustrates the neuroligins and their interactions. Members of this family may act as splice site-specific ligands for beta-neurexins and may be involved in the formation and remodeling of central nervous system synapses. The encoded protein interacts with discs, large (*Drosophila*) homolog 4 (DLG4). Mutations in this gene have been associated with autism and Asperger syndrome. NLGn4 is also detected with high levels of expression in heart and lower in liver, skeletal muscle and pancreas.

The clinical implications of NAFLD are derived mostly from its potential to progress to cirrhosis and liver failure. There is an unmet medical for compositions and methods for treating NAFLD and preventing the progression to cirrhosis. Nowhere in the art has it been suggested that disease progression of NAFLD can be modulated by attenuating NLGn4 expression and thereby NK cell activity.

SUMMARY OF THE INVENTION

The present invention relates to preventing, treating and attenuating liver disease by inhibiting NLGn4 expression and thereby modulating the activity of NK cells. The invention, according to some embodiments relates to attenuation of the progression of NAFLD into cirrhosis and liver failure by modulating the expression of human neuroligin-4 (NLGn4, NLGn4, NLGn4X) and thereby activating cytotoxic NK cells.

There is provided herein according to some embodiments, a method of treating, attenuating and/or preventing progression of a liver disorder in a subject, the method comprising administering to the subject a composition comprising a therapeutically effective amount of an agent capable of inhibiting expression of a NLGn4 gene product, thereby treating, attenuating and/or preventing progression of the liver disorder.

According to some embodiments, the human NLGn4 gene product is encoded by a nucleic acid sequence comprising SEQ ID NO: 1. According to some embodiments, the NLGn4 gene product is encoded by a nucleic acid sequence with the accession number NM_020742. According to some embodiments, the NLGn4 gene product is encoded by a nucleic acid sequence with the accession number NM_181332. According to some embodiments, the NLGn4 gene product is encoded by a nucleic acid sequence with the accession number NM_001282145. According to some embodiments, the NLGn4 gene product is encoded by a nucleic acid sequence with the accession number NM_001282146.

According to some embodiments, the NLGn4 gene product comprises an mRNA sequence set forth in SEQ ID NO: 2.

According to some embodiments, the accession number of the NLGn4 mRNA is AY358562. According to some embodiments, the accession number of the NLGn4 mRNA is BC032567. According to some embodiments, the accession number of the NLGn4 mRNA is BC034018.

According to some embodiments, the NLGn4 gene product comprises a peptide sequence set forth in SEQ ID NO: 4. According to some embodiments, the accession number of the NLGn4 polypeptide is NP_001269075.1. According to some embodiments, the accession number of the NLGn4 polypeptide is NP_001269074.1. According to some embodiments, the accession number of the NLGn4 polypeptide is NP_851849.1. According to some embodiments, the accession number of the NLGn4 polypeptide is NP_065793.1.

According to some embodiments, the agent comprises one or more inhibitory nucleic acids complementary to at least a portion of SEQ ID NO: 2.

According to some embodiments, the one or more inhibitory nucleic acids is selected from the group consisting of: an antisense molecule, an siRNA, and an shRNA. Each possibility is a separate embodiment of the invention.

According to some embodiments, the siRNA comprises a sequence set forth in SEQ ID NO: 3. According to some embodiments, the accession number of the siRNA sequence is SI03083395.

According to some embodiments, the liver disorder is selected from the group consisting of: non-alcoholic fatty liver disease (NAFLD), non-alcoholic steatohepatitis (NASH), cirrhosis, hepatitis, liver adenoma, insulin hypersensitivity, liver cancer and any combination thereof. Each possibility is a separate embodiment of the invention.

According to some embodiments, the liver disorder is characterized by NLGn4 overexpression. According to some embodiments, NLGn4 overexpression comprises a 2, 3, 4, 5-10 fold or more increase in NLGn4 expression relative to the expression level obtained in normal subjects. According to some embodiments, the overexpression attenuates NK cell activity, inhibits the expression of NLGn4 and modulates and/or activates the function of the NK cell.

According to some embodiments, administering to the subject the composition comprising a therapeutically effective amount of an agent capable of inhibiting expression of a NLGn4 gene product comprises administering the composition to an immune cell population of the subject. According to some embodiments, administering the composition to an immune cell population comprises infecting the immune cell population with a vector comprising the agent capable of inhibiting NLGn4 expression.

According to some embodiments, inhibiting the expression of the NLGn4 gene product reduces the activity of hepatic stellate cells. According to some embodiments, inhibiting the expression of the NLGn4 gene product increases apoptosis of the hepatic stellate cells.

According to some embodiments, the composition further comprises a GLUT4 antagonist. According to some embodiments, NLGn4 expression is regulated by a specific type of ionotropic glutamate receptor N-methyl-D-aspartate (NMDA or GLUT4 receptor; NMDAR). According to some embodiments, NLGn4 is linked to NMDR and both localize and bind PSD-95; a post synaptic density protein (PSD) According to some embodiments, the composition comprises an NMDAR antagonist selected from the group consisting of: Ketamin, Amantadine, Phencyclidine, Nitrous oxide, Dextromethorphan (and dextrorphan), Memantine, Ethanol, Riluzole, Xenon, HU-211, Lead (Pb2+), Conantokins, and Huperzine A.

According to an alternative embodiment, administering an N-methyl D aspartate receptor (NMDAR) agonist can increase NMDAR-mediated NLGn4 expression and as a result attenuate NK cell activity. Non-limiting examples of NMDAR agonists are Aminocyclopropanecarboxylic acid, D-Cycloserine, cis-2,3-Piperidinedicarboxylic acid, L-aspartate, L-alanine, Quinolinate, Homocysterate, D-serine, and ACPL.

There is provided herein according to some embodiments, a pharmaceutical composition for the use in treating, attenuating and/or preventing progression of a liver disorder in a subject, the composition comprising a therapeutically effective amount of an agent capable of inhibiting expression of a NLGn4 gene product, wherein the composition is capable of treating, attenuating and/or preventing progression of the liver disorder.

According to some embodiments, the pharmaceutical composition further comprises a pharmaceutically acceptable carrier.

There is provided herein according to some embodiments, a method of diagnosing and/or monitoring a liver disorder in a subject, the method comprising: isolating an immune cell population from a biological sample of the subject; detecting expression level of an NLGn4 gene product in the immune cell population and diagnosing and/or monitoring the liver disorder according to the NLGn4 gene product expression level.

According to some embodiments, the NLGn4 gene product is encoded by a nucleic acid sequence comprising SEQ ID NO: 1. According to some embodiments, the NLGn4 gene product comprises SEQ ID NO: 2.

According to some embodiments, the agent comprises one or more inhibitory nucleic acids complementary to at least a portion of SEQ ID NO: 2. According to some embodiments, the one or more inhibitory nucleic acids are selected from the group consisting of: an antisense molecule, an siRNA, and an shRNA. Each possibility is a separate embodiment of the invention.

According to some embodiments, the siRNA comprises a sequence set forth in SEQ ID NO: 3.

According to some embodiments, the liver disorder is selected from the group consisting of: non-alcoholic fatty liver disease (NAFLD), non-alcoholic steatohepatitis (NASH), cirrhosis, hepatitis, liver adenoma, insulin hypersensitivity, liver cancer and any combination thereof. Each possibility is a separate embodiment of the invention.

According to some embodiments, the immune cell population is a natural killer (NK) cell population. Additionally or alternatively, the immune cell population is a subpopulation of NK cells According to some embodiments; the NK subpopulation is the $CD56^{dim}$ subpopulation. According to some embodiments; the NK subpopulation is the $CD56^{bright}$ subpopulation. According to some embodiments, the method comprises modulating the activity of the NK cells and/or a subpopulation of NK cells. According to some embodiments, modulating the activity of NK cells comprises enhancing the cytotoxicity of the NK cells. According to some embodiments, enhancing the cytotoxicity of NK cells comprises, but is not limited to, elevating CD107a expression in the NK cell and/or NK subpopulation.

According to some embodiments, the NK cell is a liver NK cell, and the activity of the NK cell is attenuated in patients with a liver disorder. According to yet another embodiment, NK cells from patients with a liver disorder, overexpresses NLGn4.

According to some embodiments, the biological sample comprises a blood sample, a tissue sample, a biological fluid, or any combination thereof.

According to some embodiments, the NLGn4 gene product expression level is detected by Polymerase Chain Reaction (PCR), Reverse-Transcriptase-PCR (RT-PCR), Northern Blot, Real-time PCR, hybridization to an oligonucleotide or any combination thereof. Each possibility is a separate embodiment of the invention.

According to some embodiments, the oligonucleotide comprises deoxyribonucleic acid (DNA), RNA, complementary deoxyribonucleic acid (cDNA), genomic DNA, synthetic oligonucleotide, or any combination thereof. Each possibility is a separate embodiment of the invention.

There is provided herein according to some embodiments, a kit for diagnosing a liver disorder, the kit comprising: means for isolating an immune cell population from a biological sample of a patient; and at least one reagent capable of detecting NLGn4 gene product expression level.

According to some embodiments, the reagent comprises NLGn4 specific primers.

According to some embodiments, the NLGN4 primers were designed to specifically amplify the NLGN4 copy on the X chromosome (Xp22.32-p22.31).

DETAILED DESCRIPTION

Figure 1:
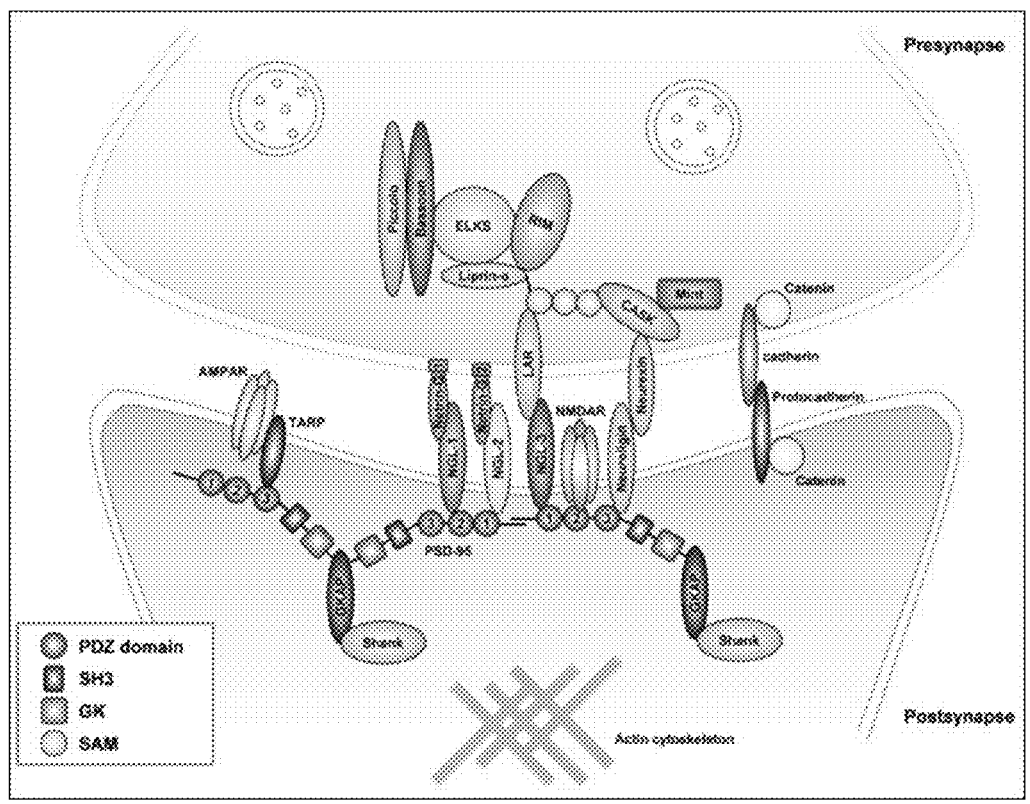
FIG. 1 shows a schematic representation of the Neuroligins and NLG interactions.

The present invention provides methods and compositions for treating and diagnosing liver disorders by activating attenuated natural killer (NK) cells and thereby reducing Hepatic stellate cell (HCSs) induced fibrosis.

In the following description, various aspects of the invention will be described. For the purpose of explanation, specific details are set forth in order to provide a thorough understanding of the invention. However, it will also be apparent to one skilled in the art that the invention may be practiced without specific details being presented herein. Furthermore, well-known features may be omitted or simplified in order not to obscure the invention.

The following are terms which are used throughout the description and which should be understood in accordance with the various embodiments to mean as follows:

As referred to herein, the terms "liver disorder", "liver disease" and "hepatic disease" are used interchangeably and refer to diseases and disorders that cause the liver to function improperly or stop functioning.

As referred to herein, the term "gene product" refers to a DNA sequence that is transcribed into mRNA that is then translated into a sequence of amino acids characteristic of a specific polypeptide. Hence it is understood by the skilled in the art that the term gene product encompasses non-processed RNA, mRNA, splice variants thereof, corresponding cDNA sequences, polypeptides and proteins.

As used herein the terms "polynucleotide" "polynucleotide molecules", "oligonucleotide", "nucleic acid" and "nucleotide" may interchangeably be used. The terms are directed to polymers of deoxyribonucleotides (DNA), ribonucleotides (RNA), and modified forms thereof in the form of a separate fragment or as a component of a larger construct, linear or branched, single stranded, double stranded, triple stranded, or hybrids thereof. The term also encompasses RNA/DNA hybrids. The polynucleotides may include sense and antisense oligonucleotide or polynucleotide sequences of DNA or RNA. The DNA or RNA molecules may be, for example, but not limited to: complementary DNA (cDNA), genomic DNA, synthesized DNA, recombinant DNA, or a hybrid thereof or an RNA molecule such as, for example, mRNA, shRNA, siRNA, miRNA, and the like. Accordingly, as used herein, the terms "polynucleotide molecules", "oligonucleotide", "polynucleotide", "nucleic acid" and "nucleotide" sequences are meant to refer to both DNA and RNA molecules and refers to nucleic acid or ribonucleic acid sequence.

As used herein the term "complementary" is directed to base pairing between strands of nucleic acids. As known in the art, each strand of a nucleic acid may be complementary to another strand in that the base pairs between the strands are non-covalently connected via two or three hydrogen bonds. Two nucleotides on opposite complementary nucleic acid strands that are connected by hydrogen bonds are called a base pair. According to the Watson-Crick DNA base pairing, adenine (A) forms a base pair with thymine (T) and guanine (G) with cytosine (C). In RNA, thymine is replaced by uracil (U). The degree of complementarity between two strands of nucleic acid may vary, according to the number (or percentage) of nucleotides that form base pairs between the strands. For example, "100% complementarity" indicates that all the nucleotides in each strand form base pairs with the complement strand. For example, "95% complementarity" indicates that 95% of the nucleotides in each strand from base pair with the complement strand. The term sufficient complementarity may include any percentage of complementarity from about 30% to about 100%.

As used herein the term "short hairpin RNA" and "shRNA are used interchangeably and refer to, refer to an RNA agent having a stem-loop structure, comprising a first and second region of complementary sequence, the degree of complementarity and orientation of the regions being sufficient such that base pairing occurs between the regions, the first and second regions being joined by a loop region, the loop resulting from a lack of base pairing between nucleotides (or nucleotide analogs) within the loop region.

As used herein the term "small interfering RNA" and "siRNA" are used interchangeably and refer to a nucleic acid molecule mediating RNA interference or gene silencing. The siRNA inhibits expression of a target gene and provides effective gene knock-down.

As used herein the term "antisense oligonucleotide" refer to nucleic acids, preferably, DNA, RNA or its derivatives, that are complementary to the nucleotide sequences of a target mRNA, characterized in that they binds to the target mRNA and interfere its translation to protein.

As used herein the term "vector" refers to expression constructs engineered to express shRNAs such as, but not limited to, retroviral and lentiviral vectors. Such expression constructs may include one or more inducible promoters, RNA Pol III promoter systems such as U6 snRNA promoters or H1 RNA polymerase III promoters, or other promoters known in the art.

According to an aspect of the invention, provided is a method of treating, attenuating or preventing a liver disorders such as Non-alcoholic fatty liver disease (NAFLD), and Non-alcoholic steatohepatitis (NASH) in a patient in need thereof. Alternatively other disorders such as cirrhosis, hepatitis, liver adenoma, insulin resistance, and liver cancer, or any NK related inflammatory or neoplastic disorder, can be the subject of treatment as well. The clinical implications of NAFLD are derived mostly from its potential to progress to Non-alcoholic steatohepatitis, cirrhosis and liver failure. In accordance, the invention, addresses the long felt need to attenuate the progression of NAFLD into cirrhosis and liver failure by inhibiting NLGn4 expression and thereby modulating the cytotoxic activity of NK cells. According to some embodiments, the invention provides a method for modulating the activity of a natural killer (NK) cell.

According to some embodiments, the method comprises administering to the patient in need thereof, a composition comprising a therapeutically effective amount of an agent capable of inhibiting the expression of the ribonucleic acid (RNA) encoded by NLGn4 nucleic acid molecule. The agent can for example be one or more polynucleotides, capable of hybridizing with the NLGn4 nucleic acid, such an inhibitory nucleic acid that is complementary and specific to at least a portion of NLGn4. The inhibitory nucleic acid can for example be an antisense molecule, an siRNA, or an shRNA. According to some embodiments, the siRNA comprises the sequence set forth in SEQ ID NO: 3. CGGCTGCAACTTCTCGCGCAA.

The NLGn4 mRNA sequence is set forth in the following sequence SEQ ID NO:2:

```
agaaggggaaggctcctgggctttcaatacatcctcctgaatcatacctcgtttcgggttccctagaaaaatctggacgtgtaaa aagaactcttaacggccgatgcagctcttccaaagctaaggctgccttggagttttcataagaaattgtccctggaggtgttgga tgatcacagcttccttggagcattgcagttgctggaatccagtttcaggattaagggagggctgcctccttgcaatgggctgcca agaaaacggctgtgcttgttataacctcaggctctgtctgtgatcagtctgagagtctctcccaggtctactgctccctggaaag ccctatctctctgcaggctcgcctctgggctttgtctccttggagccacatcactgggacagctgtggatgtggatgcagatttg aaccatgtcacggccccagggactgctatggcttcctttgttgttcaccccggtctgcgtcatgttaaactccaatgtcctcctg tggttaactgctcttgccatcaagttcaccctcattgacagccaagcacagtatccagttgtcaacacaaattatggcaaaatcc ggggcctaagaacaccgttacccaatgagatcttgggtccagtggagcagtacttaggggtcccctatgcctcacccccactgg agagaggcggtttcagcccccagaaccccgtcctcctggactggcatccgaaatactactcagtttgctgctgtgtgccccag cacctggatgagagatccttactgcatgacatgctgcccatctggtttaccgccaatttggatactttgatgacctatgttcaag atcaaaatgaagactgcctttacttaaacatctacgtgcccacggaagatgatattcatgatcagaacagtaagaagcccgtcat ggtctatatccatgggggatcttacatggagggcaccggcaacatgattgacggcagcattttggcaagctacggaaacgtcatc gtgatcaccattaactaccgtctgggaatactagggttttttaagtaccggtgaccaggcagcaaaaggcaactatgggctcctgg atcagattcaagcactgcggtggattgaggagaatgtgggagcctttggcggggaccccaagagagtgaccatctttggctcggg ggctggggcctcctgtgtcagcctgttgaccctgtcccactactcagaaggtctcttccagaaggccatcattcagagcggcacc gccctgtccagctgggcagtgaactaccagccggccaagtacactcggatattggcagacaaggtcggctgcaacatgctggaca ccacggacatggtagaatgcctgcggaacaagaactacaaggagctcatccagcagaccatcacccggccacctaccacatagc cttcgggccggtgatcgacggcgacgtcatcccagacgacccccagatcctgatggagcaaggcgagttcctcaactacgacatc atgctgggcgtcaaccaaggggaaggcctgaagttcgtggacggcatcgtggataacgaggacggtgtgacgcccaacgactttg acttctccgtgtccaacttcgtggacaaccttttacggctaccctgaagggaaagacactttgcgggagactatcaagttcatgta cacagactgggccgataaggaaaacccggagacgcggcggaaaaccctggtggctctctttactgaccaccagtgggtggccccc gccgtggccaccgccgacctgcacgcgcagtacggctccccccacctacttctatgccttctatcatcactgccaaagcgaaatga agcccagctgggcagattcggcccatggtgatgaggtcccctatgtcttcggcatccccatgatcggtcccaccgagctcttcag ttgtaacttttccaagaacgacgtcatgctcagcgccgtggtcatgacctactggacgaacttcgccaaaactggtgatccaaat caaccagttcctcaggataccaagttcattcacacaaaacccaaccgctttgaagaagtggcctggtccaagtataatcccaaag accagctctatctgcatattggcttgaaacccagagtgagagatcactaccgggcaacgaaagtggctttctggttggaactcgt
```

-continued

```
tcctcatttgcacaacttgaacgagatattccagtatgtttcaacaaccacaaaggttcctccaccagacatgacatcatttccc tatggcacccggcgatctcccgccaagatatggccaaccaccaaacgcccagcaatcactcctgccaacaatcccaaacactcta aggaccctcacaaaacagggcctgaggacacaactgtcctcattgaaaccaaacgagattattccaccgaattaagtgtcaccat tgccgtcggggcgtcgctcctcttcctcaacatcttagcttttgcggcgctgtactacaaaaaggacaagaggcgccatgagact cacaggcgcccagtccccagagaaacaccacaaatgatatcgctcacatccagaacgaagagatcatgtctctgcagatgaagc agctggaacacgatcacgagtgtgagtcgctgcaggcacacgacacactgaggctcacctgcccgccagactacaccctcacgct gcgccggtcgccagatgacatcccacttatgacgccaaacaccatcaccatgattccaaacacactgacggggatgcagcctttg cacacttttaacaccttcagtggaggacaaaacagtacaaatttaccccacggacattccaccactagagtatagctttgcccta tttcccttcctatccctctgccctacccgctcagcaacatagaagagggaaggaaagagagaaggaaagagagagagaaagaaag tctccagaccaggaatgttttgtcccactgacttaagacaaaaatgcaaaaaggcagtcatcccatcccggcagacccttatcg ttggtgttttccagtattacaagatcaacttctgaccctgtgaaatgtgagaagtacacatttctgttaaaataactgctttaag atctctaccactccaatcgatgtttagtgtgataggacatccaccatttcaaggcccgggtgtttccaacgtcatggaagcagct gacacttctgaaactcagccaaggacacttgatatttttaattacaatggaagtttaaacatttctttctgtgccacacaatgg atggctctccttaagtgaagaaagagtcaatgagattttgcccagcacatggagctgtaatccagagagaaggaaacgtagaaat ttattattaaaagaatggactgtgcagcgaaatctgtacggttctgtgcaaagaggtgttttgccagcctgaactatatttaaga gactttgtaaaaagaaaaatgtatatagctgtgagtttaaacaaaaaccacaaacagacaaacaagaaaaaaagcttttattgg tgttttcactttgaaagagcttttagcaaggttgtgcttttcattgtgctctgtacgtatataaatatatatatatacacaca cacacacacattagtcatatcacctctgtttcctccccaacaaaagaggcttttcttcttaattacttgtggtaaacaaagacat gggattttcttacatgagattctcatttgtaggaggatgtgatgtcccacagaagacccagacggtctgtgtggcctatttcccc cgtcaggttgcacaggtgcatgcaagagcattcttaggagaccactgttttgaaaaacttttgacttgtacgtgttagccttcat gaaattgcagtacagagatgggtccccaaagtggagtgtatttacagcttgttaaattagagacatgcacacacaaagaatcagt agggagaaacaaaaatacaagtcccgttctgtagctctggccctttgaatatgtttaggaagagttgcttcccatttcagggccc tgccaaaaaagaagaaagcttgcctttggtggggctatgccccttggagtaaatacggctctgtgttccctagcagctgcggga gggtttggccgatgaagtacctgctcagcttagctaatcagattgaaggaagacatgtgtctttccttttttgtttaagcactcgg tcccttatttatcagtaagcaggttttaaaaatctttatatcatttatgggatcaaacatatgattgtctgaaaacatcactt tttgtggatttgtgtatccggtcaccaaacggtgaatattatagaagaatggggaagaaaggatagaatattaaactgctttgc atgggttttctgggaaattaggataacttcactgagaagacattgaatgaaattattcacccatttaaattggtgacctaggg atcagagatttgtctttccaacagcttgtcattttttcattctcttctcattttcaggaaagttttgagtgttataaggtgga aggaaacatagtagcaatggatactttttgaaaaattattgcattaccaagaaacagtagccaaagatatttgaagatcatgtt cctcggctccattgtgggttattctagaaatccagtcttaaatctctccgctaaagtggacattcccataaaaattgtccagct gcctggctcttttgcaataacaacctttgattactgaatccctacactcaaactatagtgatatatcagtgtttgagagtgacct ctagaaaaagaaaagtgtttttagaaatgcgtacaagtcaccccaaatcctattgatatcttgggttaaatttgagagtgatt ctctgtatataaatatgtgaaatattattatctcaacttagcacacgtgaagcaacatttctttcctacagagaggtgtcatggt aagatttcattccgaattcattgtttcatagagctatgatcaggccatttctgcaagcaatgtatgaccccacctgagcaaccac aaataggctctctgtgaaactacaaaggaagttatgtgtggcatccatgttggtttcgtctgtctgtaatgtgaattccagtatt tgtttagtatttccagttgtctcctgctagcaatatgtacagtaacgcgtcaggcttgtgacatttgaataaggaaaaacagagt tcctgttaagtgaataactttagcttttacaggggattatgatcaaaagtgattttagtacatcttaaatgatatcttatttcta catggaaagaagttatagaatcttcatagagttctatgagaaaaaatatacttgctatctataaaaaagagaaaaagaaaaaaa atgagaaaaaagtaagaaaaaaaaaaatcctgtcctaggcttttactcttgatcttcaaaggcacgcagggtttaatggttcctt
```

-continued

```
gggttattattttgcagttttgttttttattttgccttaagtaatgatagaagatatatatggccggacacatatgtataaactt ttcagcagcatttttaataataaaatatcacagtattttctaaaaaaaaaaaaaaaaaa
```

Additionally or alternatively, the method comprises administering to the patient in need thereof, a composition comprising a therapeutically effective amount of an agent (such as for example an antibody) capable of inhibiting the expression and/or function of NLGn4 protein.

The NLGn4 polypeptide sequence is set forth in the following sequence SEQ ID NO: 4:

MSRPQGLLWLPLLFTPVCVMLNSNVLLWLTALAIKFTLIDSQAQYPVVN

TNYGKIRGLRTPLPNEILGPVEQYLGVPYASPPTGERRFQPPEPPSSWT

GIRNTTQFAAVCPQHLDERSLLHDMLPIWFTANLDTLMTYVQDQNEDCL

YLNIYVPTEDDIHDQNSKKPVMVYIHGGSYMEGTGNMIDGSILASYGNV

IVITINYRLGILGFLSTGDQAAKGNYGLLDQIQALRWIEENVGAFGGDP

KRVTIFGSGAGASCVSLLTLSHYSEGLFQKAIIQSGTALSSWAVNYQPA

KYTRILADKVGCNMLDTTDMVECLRNKNYKELIQQTITPATYHIAFGPV

IDGDVIPDDPQILMEQGEFLNYDIMLGVNQGEGLKFVDGIVDNEDGVTP

NDFDFSVSNEVDNLYGYPEGKDTLRETIKFMYTDWADKENPETRRKTLV

ALFTDHQWVAPAVATADLHAQYGSPTYFYAFYHHCQSEMKPSWADSAHG

DEVPYVFGIPMIGPTELFSCNESKNDVMLSAVVMTYWTNFAKTGDPNQP

VPQDTKEIHTKPNRFEEVAWSKYNPKDQLYLHIGLKPRVRDHYRATKVA

FWLELVPHLHNLNEIFQYVSTTTKVPPPDMTSFPYGTRRSPAKIWPTTK

RPAITPANNPKHSKDPHKTGPEDTTVLIETKRDYSTELSVTIAVGASLL

FLNILAFAALYYKKDKRRHETHRRPSPQRNTTNDIAHIQNEEIMSLQMK

QLEHDHECESLQAHDTLRLTCPPDYTLTLRRSPDDIPLMTPNTITMIPN

TLTGMQPLHTENTFSGGQNSTNLPHGHSTTRV

According to some embodiments, the NK cells are liver NK cells which are attenuated in patients having a liver disorder. According to yet another embodiment, the liver disorder is characterized by overexpression of NLGn4 RNA. Such overexpression can attenuate NK cell activity.

According to some embodiments inhibiting the expression of NLGn4 modulates the function of the NK cell for example by activating the NK cell and/or the CD56$^{dim}$ NK cell subset. As a result of NK activation, the activity of hepatic stellate cells (HSCs) and hence fibrosis is reduced. In addition, and according to yet another embodiment, modulating and/or activating the NK cells increases the apoptosis of the HSCs.

According to yet another embodiment there is provided a method for modulating the activity of a natural killer (NK) cell and/or treating, preventing and/or attenuating a liver disorder by administering to a patient a composition comprising a GLUT4 antagonist. Such antagonist can according to the present invention inhibit GLUT4 mediated NLGn4 expression. The antagonist can be selected from the group comprising Ketamine, Amantadine, Phencyclidine, Nitrous oxide, Dextromethorphan (and dextrorphan), Memantine, Ethanol, Riluzole (used in ALS), Xenon, HU-211 (also a cannabinoid), Lead (Pb2+), Conantokins, and Huperzine A. According to an alternative embodiment administering a NMDAR (also known as GLUT4) agonist can increase GLUT4 mediated NLGn4 expression and as a result attenuate NK cell activity. Examples of a GLUT4 agonists are Aminocyclopropanecarboxylic acid, D-Cycloserine, cis-2,3-Piperidinedicarboxylic acid, L-aspartate, L-alanine, Quinolinate, Homocysterate, D-serine, and ACPL.

According to another aspect of the invention, there is provided a method of modulating the expression of the ribonucleic acid (RNA) encoded by NLGn4 nucleic acid. According to one embodiment, modulating the expression NLGn4 can serve to treat, attenuate or prevent a liver disorder, such as Non-alcoholic fatty liver disease (NAFLD), Non-alcoholic steatohepatitis (NASH), cirrhosis, hepatitis, liver adenoma, insulin resistance, a liver cancer, any NK related inflammatory or neoplastic disorder, or any combination thereof.

According to another embodiment, modulating the expression of NLGn4 comprises contacting the immune cell, such as an NK cell and/or a CD56$^{dim}$ NK cell subset, with a composition comprising an effective amount of an agent that inhibits NLGn4 expression. Such agent can for example be an inhibitory nucleic acid that is complementary and specific to at least a portion of the NLGn4 nucleic acid molecule.

According to yet another embodiment, the inhibitory nucleic acid can for example be an antisense molecule, an siRNA, or an shRNA.

Inhibiting NLGn4 can according to the present invention enhance the cytotoxicity of the NK cells and or specific NK cell subpopulations. According to certain embodiments enhancing the cytotoxicity comprises enhancing the expression of CD107a on said NK cell.

In certain liver disorders NK cell function can be attenuated. According to the present invention such attenuation can be a result of NLGn4 overexpression. In accordance, inhibiting the expression of NLGn4 modulates and/or activates the function of attenuated NK cell. In turn, activating the NK cell may reduce HSC activity and/or increase their apoptosis.

According to yet another aspect of the invention there is provided a method of diagnosing or monitoring a liver disorder and/or the severity of a liver disorder in a patient such as Non-alcoholic fatty liver disease (NAFLD), Non-alcoholic steatohepatitis (NASH), cirrhosis, hepatitis, a liver adenoma, insulin resistance, a liver cancer, any NK related inflammatory or neoplastic disorder, or any combination thereof. The method comprises, according to one embodiment, detecting the expression level of a ribonucleic acid (RNA) encoded by NLGn4 nucleic acid molecule in a biological sample, such as a blood sample, a tissue sample and/or a biological fluid, of a patient.

According to some embodiments, the method further comprises isolating the RNA from the biological sample prior to detecting the NLGn4 RNA expression level. The detection of NLGn4 expression comprises Polymerase Chain Reaction (PCR), Reverse-Transcriptase-PCR (RT-PCR), Northern Blot, Real-time PCR, Flow Cytometry (FACS) or any combination thereof.

Alternatively, the expression level of NLGn4 is detected by hybridization to an oligonucleotide such as a deoxyribonucleic acid (DNA), an RNA, complementary deoxyribonucleic acid (cDNA), a genomic DNA, a synthetic oligonucleotide, or any combination thereof.

According to yet another aspect of the invention, there is provided a pharmaceutical composition comprising a therapeutically effective amount of an agent that inhibits the expression or function of NLGn4.

The agent can be one or more polynucleotides, capable of hybridizing with said nucleic acid. For example the agent can be an inhibitory nucleic acid, such as an antisense molecule, an siRNA, or an shRNA that is complementary and specific to at least a portion of said NLGn4 nucleic acid molecule According to some embodiments, the pharmaceutical composition further comprises a vector capable of expressing the inhibitory nucleic acid molecule. Non-limiting examples of vectors comprise lentiviral vectors, retroviral vectors, plasmids as well as other suitable vectors.

According to another embodiment, the composition comprises or additionally comprises a GLUT4 antagonist. Such antagonist can according to the present invention inhibit GLUT4 mediated NLGn4 expression. The antagonist can be selected from the group consisting of Ketamin, Amantadine, Phencyclidine, Nitrous oxide, Dextromethorphan (and dextrorphan), Memantine, Ethanol, Riluzole (used in ALS), Xenon, HU-211 (also a cannabinoid), Lead (Pb2+), Conantokins, and Huperzine A According to an alternative embodiment administering a GLUT4 agonist can increase GLUT4 mediated NLGn4 expression and as a result attenuate NK cell activity. Examples of a GLUT4 agonists are alanine, Aminocyclopropanecarboxylic acid, D-Cycloserine, cis-2,3-Piperidinedicarboxylic acid, L-aspartate, L-alanine, Quinolinate, Homocysterate, D-serine, and ACPL According to yet another aspect of the invention, there is provided a kit for prevention, treatment or attenuation of a liver disorder such as, but not limited to, Non-alcoholic fatty liver disease (NAFLD), Non-alcoholic steatohepatitis (NASH), cirrhosis, hepatitis, a liver adenoma, insulin resistance, a liver cancer, any NK related inflammatory or neoplastic disorder, or any combination thereof. The kit comprises the pharmaceutical composition as essentially described above and a pharmaceutically acceptable carrier.

According to yet another aspect of the invention, there is provided a kit for diagnosing a liver disorder such as but not limited to Non-alcoholic fatty liver disease (NAFLD), Non-alcoholic steatohepatitis (NASH), cirrhosis, hepatitis, a liver adenoma, insulin hypersensitivity, a liver cancer or any combination thereof. The kit comprises at least one reagent capable of detecting the expression of a nucleic acid in a biological sample such as a blood sample, a tissue sample, and/or a biological fluid.

According to some embodiments, the reagent comprises NLGn4 specific primers. According to some embodiments, the NLGn4 specific primers are selected from the group set forth in table 1 below.

TABLE 1

NLGn4 specific primers

| Exon | Forward | Reverse |
|---|---|---|
| 2.1 | AAAGCCCTATCTCTCTGCAGG (SEQ ID NO: 5) | TGAGTAGTATTTCGGATGCCAG (SEQ ID NO: 6) |
| 2.2 | AAGAACACCGTTACCCAATGAG (SEQ ID NO: 7) | GAGACATTATAAAACCCTCCTAG (SEQ ID NO: 8) |
| 3 | TTAGCATTGGTGAGTCAGTGTG (SEQ ID NO: 9) | CCGTCAAAACGAGAAGTGGACT (SEQ ID NO: 10) |
| 4 | CTTTTTCTATTTGGCCACCA (SEQ ID NO: 11) | TTCTTGGTTCAGGGTATTTGC (SEQ ID NO: 12) |
| 5.1 | AGCTGCATTTCTGTCCTGTG (SEQ ID NO: 13) | TCTCCCGCAAAGTGTCTTTC (SEQ ID NO: 14) |
| 5.2 | CCAACTTCGTGGACAACCTT (SEQ ID NO: 15) | ACCCCAACACGAAGATGAAC (SEQ ID NO: 16) |
| 6.1 | CACGTCACATGTGGAAGAGT (SEQ ID NO: 17) | GACGGCAATGGTGACACTTA (SEQ ID NO: 18) |
| 6.2 | TCCTCATTGAAACCAAACGA (SEQ ID NO: 19) | AACATTCCTGGTCTGGAGAC (SEQ ID NO: 20) |

The following examples are presented to provide a more complete understanding of the invention. The specific techniques, conditions, materials, proportions and reported data set forth to illustrate the principles of the invention are exemplary and should not be construed as limiting the scope of the invention.

EXAMPLES

Example 1

Methods Used for Evaluating the Role of NLGn4 in NK Activity a) Knockdown of NLGn4: Lentivirus expressing NLGn4 siRNA were used to infect NK cells of either mouse or human origin and thereby inhibiting NLGn4 expression.
b) NLGn4 expression: NLGn4 expression level was evaluated by real-time PCR. In short, RNA was extracted from the cells using Tri Reagent. The extracted RNA was converted to cDNA using random hexamers and reverse transcriptase. NLGn4 expression level was assessed by real time PCR using NLGn4 specific primers. The results were normalized to the expression levels of a-actin using a-actin specific primers.
c) Isolation of NK cells from human blood samples: Blood samples obtained from patients were centrifuged at 4000 rpm for 5 min. After centrifugation, the buffy coat fraction of the blood containing most of the leukocytes was collected and NK cells were isolated using the RosetteSep NK isolation kit according to manufactures instruction.
d) Flow cytometry using FACS analysis of CD107a, NLGn4, a-SMA, annexin.

Example 2

NLGn4 is Overexpressed in Patients with Cirrhosis and in a Non-Alcoholic Fatty Liver Disease (NAFLD) Mouse Model Human peripheral blood cells (PBLs) were isolated in accordance with Example 1c from cirrhotic patients and healthy controls, as well as from NAFLD/control mice. RNA was extracted and converted into cDNA and a gene array analysis was performed using an Affymetrix expression array. The results were collated in order to identify the genes having an at least two-fold change in the expression profile. It was found that NLGn4 showed the most significant change in that an approximately 4-fold up-regulation was observed among the cirrhotic patients.

Example 3

NLGn4 Expression can be Reduced Using siRNA

Figure 2:
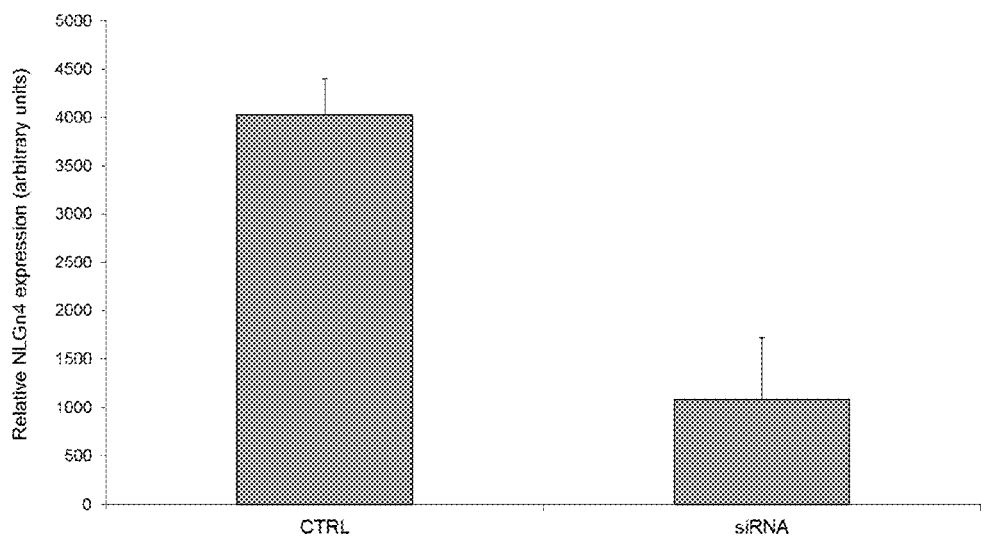
FIG. 2 shows NLGn4 expression upon NLGn4 siRNA expression in mouse NK cells.

Mouse liver NK cells were infected with a lentiviral vector expressing an siRNA against NLGn4 or a scrambled control. 48 hours post infection, the cells were harvested, RNA extracted and converted into cDNA in accordance with example 1b. NLGn4 Expression levels in cells infected with the NLGn4 siRNA or the scrambled control were evaluated using real-time PCR using primes specific for NLGn4. The expression levels obtained were normalized to those obtained for α-actin. As seen in FIG. 2, a significant reduction in NLGn4 expression is observed in cells infected with the siRNA expressing vector, as compared to the control.

Example 4

Figure 3A:
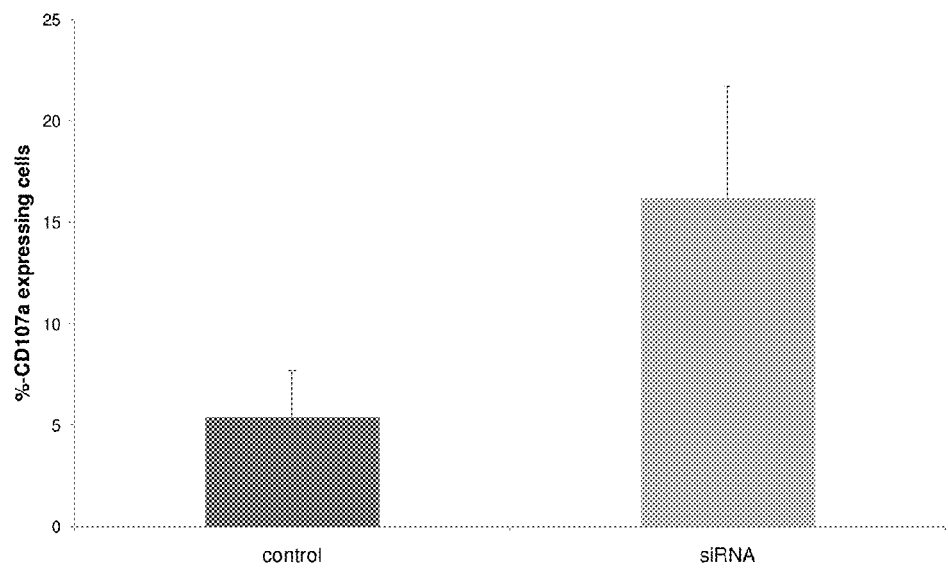
FIG. 3A presents the percentage of viable NK cells expressing CD107a (control or infected with NLGn4 siRNA) co-cultured with HSCs isolated from a WT mouse.

NLGn4 Knockdown (KD) Increases NK Activation and Hepatic Stellate Cell (HSC) Apoptosis and Reduces HSC Activity NK cells obtained from mice livers were pre-incubated with IL2 in order to obtain a mature NK cell population. Following infection with the NLGn4 siRNA or with the scrambled control, the cells were co-cultured with freshly isolated HSC from a NAFLD mouse model. The activity of the NK cells was evaluated by the expression of CD107a, a marker of active NK cells. The percentage of viable NK cells expressing CD107a was evaluated by FACS using an anti-CD107a antibody and gating annexin negative cells. As seen in FIG. 3A, as a result of the KD of NLGn4 a significant increase in CD107a positive cells amongst the viable NK cell population was observed.

Figure 3B:
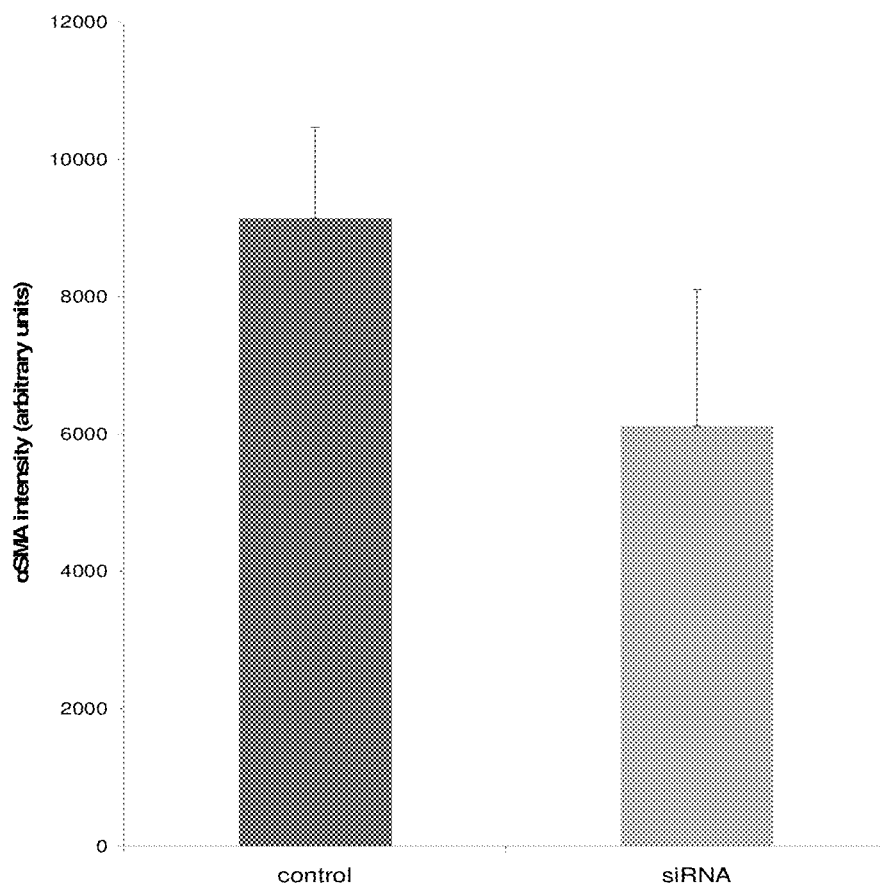
FIG. 3B presents aSMA intensity of HSCs co-cultured with control or NLGn4 siRNA infected NK cells.
Figure 3C:
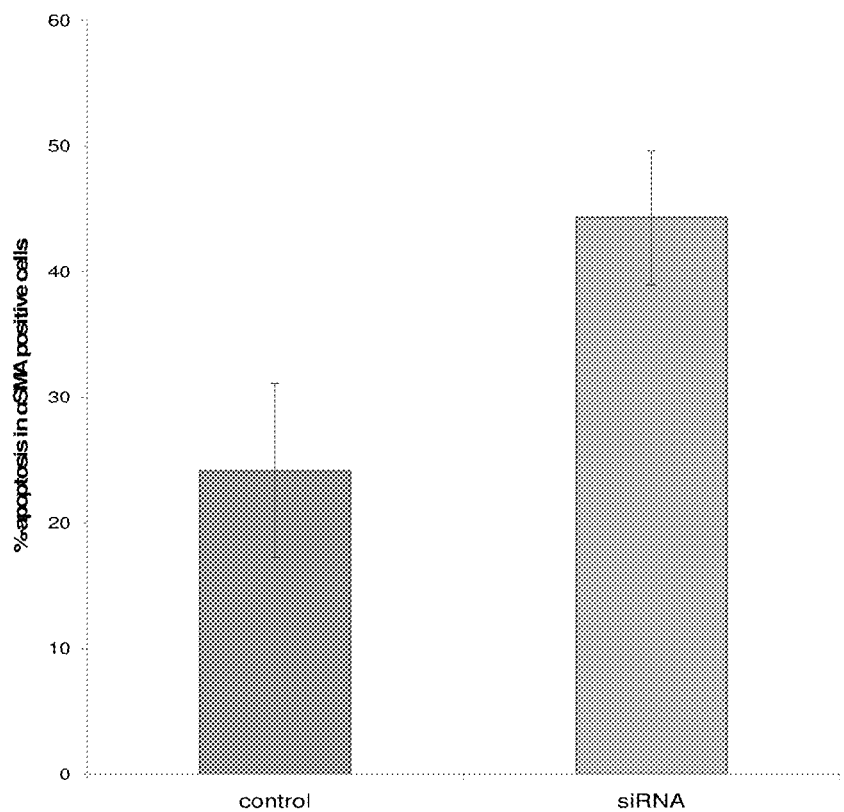
FIG. 3C shows apoptosis of HCS upon co-culturing with control or NLGn4 siRNA infected NK cells.

The impact of NK cell activation by NLGn4 KD on HCSs was evaluated by co-culturing the HSCs with the control or the NLGn4 KD NK cells and assessing aSMA intensity (marker of HSC activation). a-SMA intensity was significantly decreased upon co-culture with NLGn4 KD NK cells (FIG. 3B) and amongst the a-SMA expressing cells an increase in apoptosis was observed (FIG. 3C).

Example 5

Figure 4:
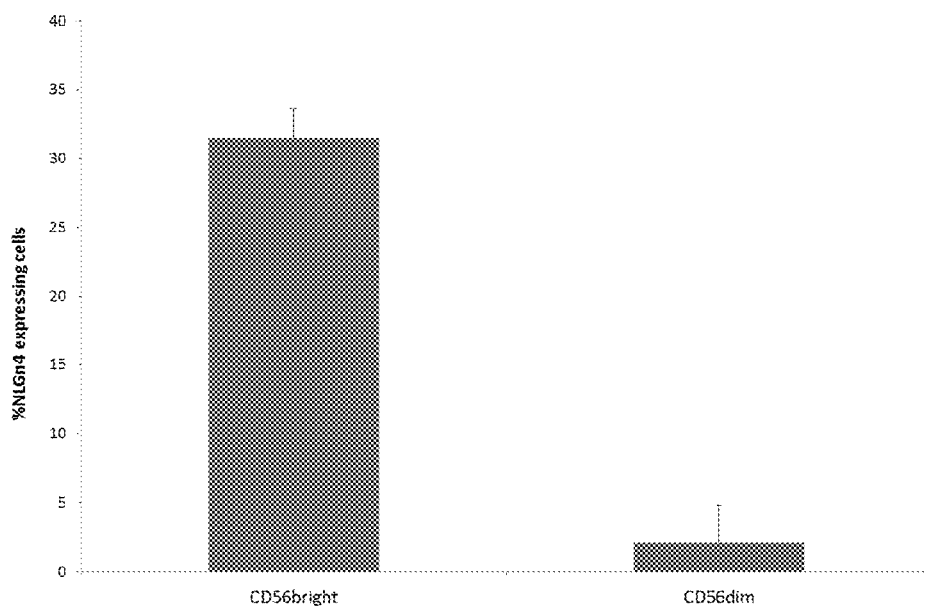
FIG. 4 presents NLGn4 expression in the $CD56^{bright}$ and $CD56^{dim}$ NK subpopulation.

NLGn4 is Expression is High in the $CD56^{bright}$ NK Subpopulation and Low in the $CD56^{dim}$ NK Subpopulation Human peripheral blood cells (PBLs) were isolated in accordance with Example 1c. The isolated NK cells were then co-stained with an anti-CD56 antibody and with an anti-NLGn4 antibody. FACS analysis of the cells showed that NLGn4 is significantly more abundant in the $CD56^{bright}$ cell population as compared to the $CD56^{dim}$ cell population (FIG. 4).

Example 6

NK Activity as Assessed by CD107a Expression is Attenuated in NAFLD Patients

Figure 5:
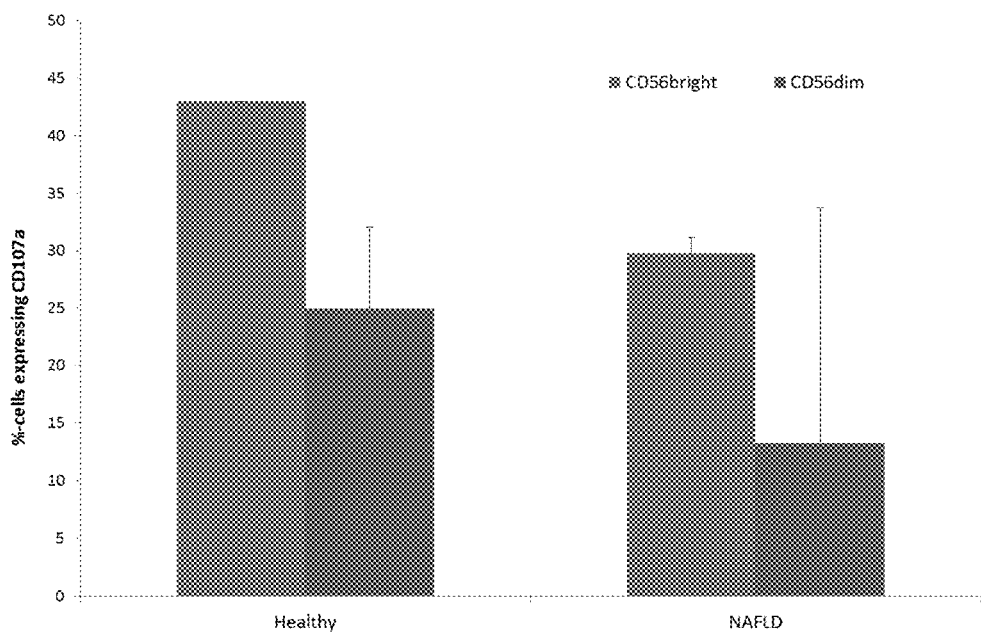
FIG. 5 presents CD107a expression in NAFLD patients and healthy controls.

Human peripheral blood cells (PBLs) from NAFLD patients (n=9) and healthy controls (n=3) were isolated in accordance with Example 1c. The isolated NK cells were then co-stained with an anti-CD56 antibody and with an anti-CD107a antibody. FACS analysis showed that CD107a expression was reduced, corresponding to an attenuated NK activity in NAFLD patients (FIG. 5).

Example 7

Figure 6:
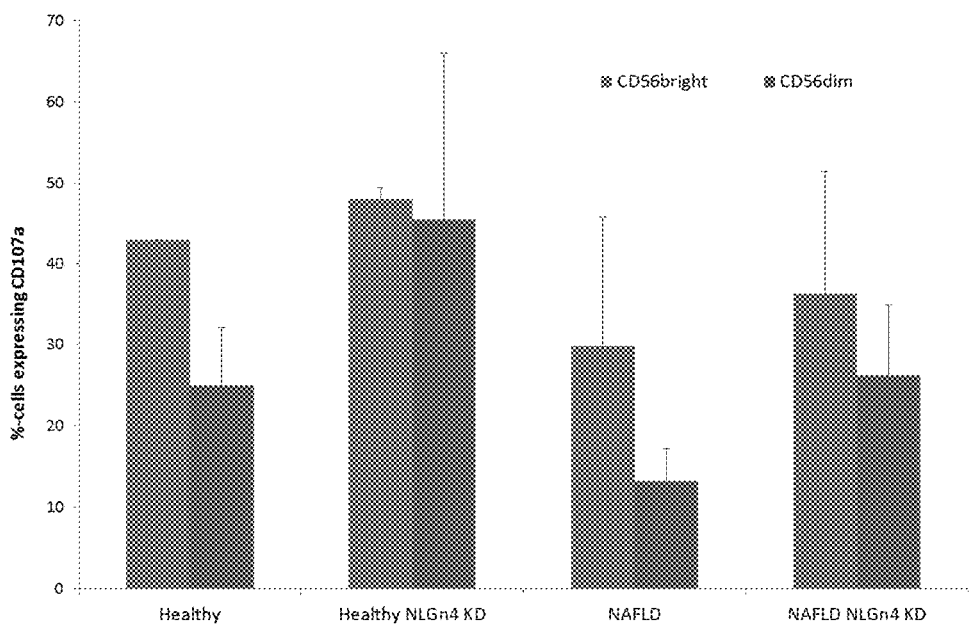
FIG. 6 presents on NK cell activity as assessed by CD107a expression.

NLGn4 KD Increases $CD56^{dim}$ NK Cell Activity as Assessed by CD107a Expression Human peripheral blood cells (PBLs) from NAFLD patients (n=9) and healthy controls (n=3) were isolated in accordance with Example 1c. The isolated NK cells were then infected with a lentiviral vector expressing an siRNA against human NLGn4 or a scrambled control. NK activity in response to NLGn4 KD was assessed by CD107a expression. That is, the isolated NK cells were co-stained with an anti-CD56 antibody and with an anti-CD107a antibody. As seen from FIG. 6, CD107a expression was significantly elevated in the $CD56^{dim}$ subpopulation. This might suggest that reducing the expression of NLGn4 can effectively enhance NK cytotoxicity. Since NLGn4 is primarily expressed in $CD56^{bright}$ cells it may be suggested that overexpression of NLGn4 by $CD56^{bright}$ cells inhibits the cytotoxicity of $CD56^{dim}$ cells.

Example 8

NLGn4 KD does not Alter NK Viability

Figure 7A:
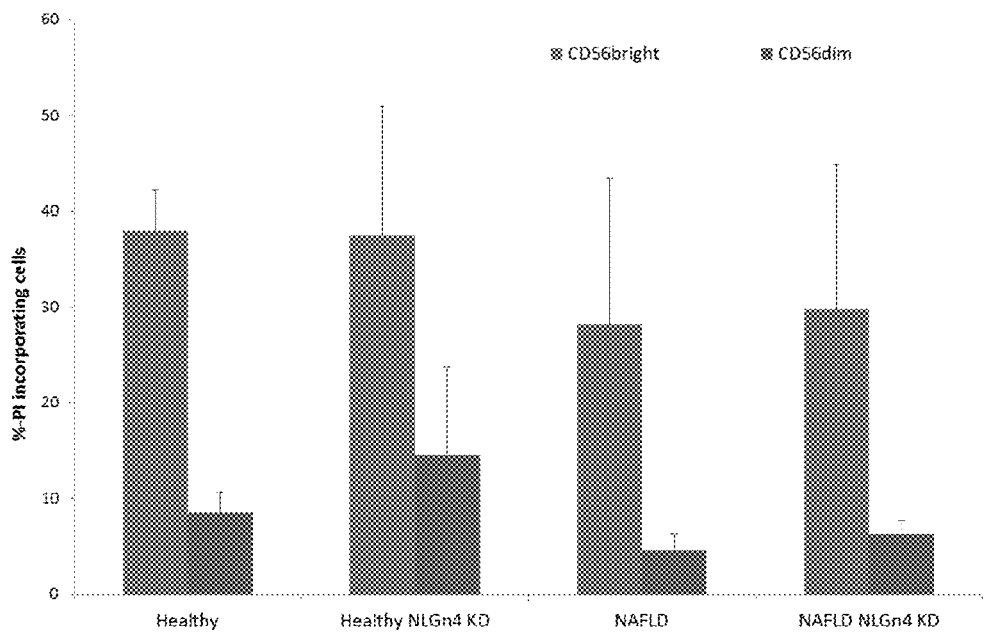
FIG. 7A presents the effects of NLGn4 KD on NK cell viability, as estimated by PI incorporation.
Figure 7B:
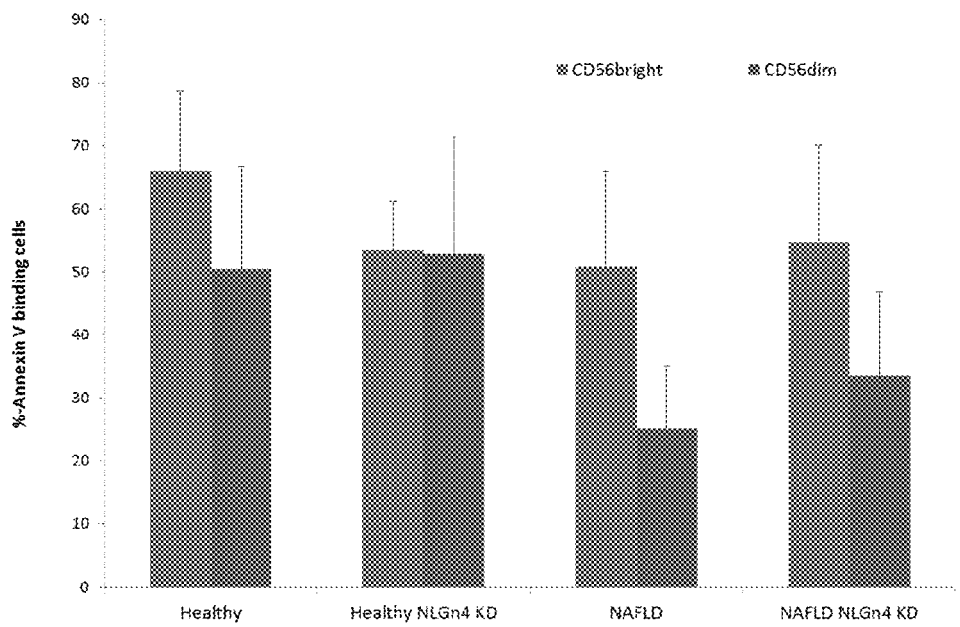
FIG. 7B presents the effects of NLGn4 KD on NK cell viability, as estimated by annexin binding.

Human peripheral blood cells (PBLs) from NAFLD patients (n=9) and healthy controls (n=3) were isolated in accordance with Example 1c. The isolated NK cells were then infected with a lentiviral vector expressing an siRNA against human NLGn4 or a scrambled control. The viability of the NK cells was assessed by FACS analysis estimating annexin binding and PI incorporation. As seen in FIGS. 7A and B, NLGn4 knockdown did not alter cellular viability neither of $CD56^{bright}$ nor of $CD56^{dim}$ NK cells in either NAFLD patients or healthy controls. This indicates that $CD56^{dim}$ cytotoxicity toward foreign cells is elevated without compromising self-recognition.

Example 9

NLGn4 Overexpression Correlates with High Insulin Levels

Figure 8:
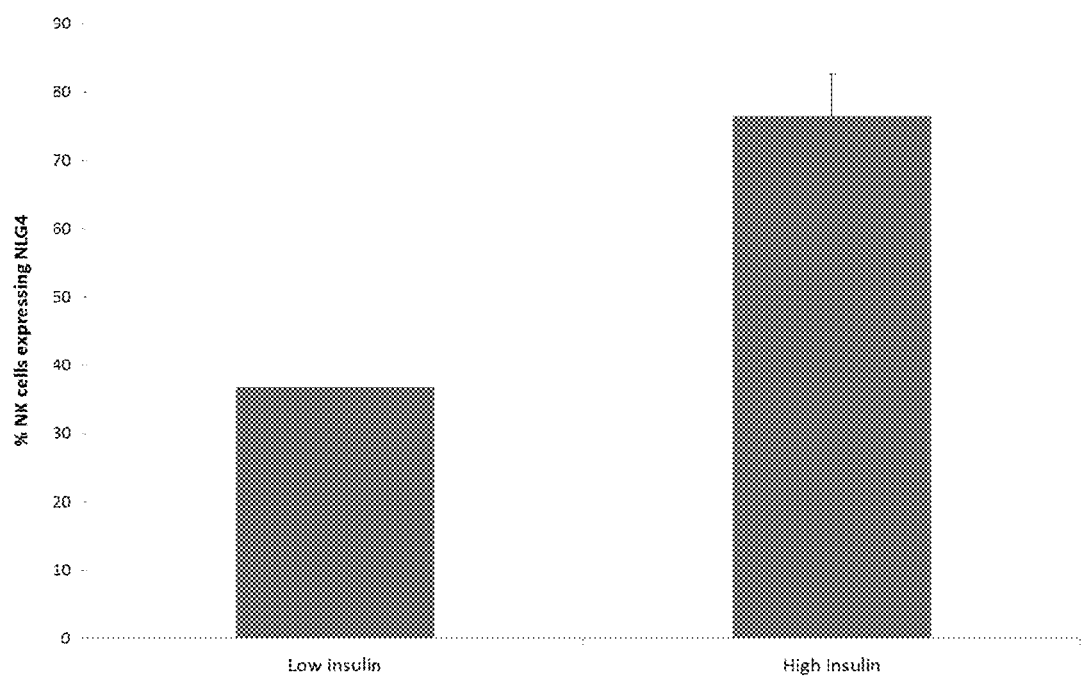
FIG. 8 shows the correlation between insulin and NLGn4 expression.

Human peripheral blood cells (PBLs) from patients with low insulin levels (n=3) and patients with high insulin levels controls (n=3) were isolated in accordance with Example 1c. The isolated NK cells were stained with an anti-NLGn4 antibody. FACS analysis of the cells showed that NLGn4 was significantly higher in NK cells from patients with high insulin levels as compared to those with low insulin levels (FIG. 8). This may suggest that the increased prevalence of NAFLD among insulin resistant subjects may be due to insulin mediated NLGn4 overexpression.

Example 10

Treatment of Mice with a GLUT4 Agonist Elevates NLGn4 Expression

NK cells from livers of mice treated with the GLUT4 agonist alanine or control mice are isolated. The isolated NK cells are then co-stained with an anti-CD56 antibody and with an anti-NLGn4 antibody.

Example 11

Treatment of Mice with a GLUT4 Antagonist Reduces NLGn4 Expression

NK cells from livers of mice treated with the GLUT4 agonist or control mice are isolated. The isolated NK cells are then co-stained with an anti-CD56 antibody and with an anti-NLGn4 antibody.

---

The invention claimed is:

1. A method of treating and/or attenuating non-alcoholic fatty liver disease (NAFLD) in a subject, the method comprising administering to the subject a composition comprising a therapeutically effective amount of an agent capable of specifically inhibiting expression of a human NLGn4 gene product, said human NLGn4 gene product comprising SEQ ID NO: 2, and said agent comprising one or more siRNAs having a length of 20-25 base pairs and a sequence with at least 95% complementarity to at least a portion of SEQ ID NO: 2, thereby treating and/or attenuating the NAFLD.

2. The method of claim 1, wherein the NLGn4 gene product is encoded by a nucleic acid sequence comprising SEQ ID NO: 1.

3. The method of claim 1, wherein the siRNA comprises a sequence set forth in SEQ ID NO: 3.

4. The method of claim 1, wherein inhibiting the expression of the NLGn4 gene product reduces activity of hepatic stellate cells.

5. The method of claim 1, wherein inhibiting the expression of the NLGn4 gene product increases apoptosis of the hepatic stellate cells.

6. The method of claim 1, wherein said composition further comprises a GLUT4 antagonist.

* * * * *

SEQUENCE LISTING

```
<160> NUMBER OF SEQ ID NOS: 20

<210> SEQ ID NO 1
<211> LENGTH: 338857
<212> TYPE: DNA
<213> ORGANISM: Homo sapiens

<400> SEQUENCE: 1
atctctcttt ttcttgcaga accgtctctc tcccttctct gtctcttagc acagagctct      60
tattcagcca ctagcttggc ccttcctgct tcaattgtaa tgcttgttct gcccgtccac     120
agactattgg cggcagaaac aacgaatttc ctccaaacta ggcggtgttg gtggctcttg     180
cattcctctg gatgaggaaa tctagttggg gggttccaga aggggaaggc tcctgggctt     240
tcaatacatc ctcctgaatc atacctcgtt tcgggttccc tagaaaaatc tggacgtgta     300
aaaagaactc ttaacggccg atgcagctct tccaaagcta aggtaggtgc agttttaaga     360
cctgtctctg ggacattatt ctcattttaa aaagccgttt aaacattttg acttgcagca     420
aaggatggaa agcctcactg cagatacttg agcttcactt catctgatct ttattttttc     480
cttttatgat tattaatatt attttggaa aatttggaca ggactttctc ccatctgtct     540
cgctgcattt cttaggtgtg ggtgggagtg tagaccttca tacggttttt acatgcaacc     600
tctccacaga aatatttggt tttatttca cttaaagaga aaaatccaga ccaccgttgt     660
ttggaagcgt tttgctgcaa tcagctattt gaacggctct ggggccgtgt gtgatgtgtt     720
tacaaagtag cgctgccttc cacacaaata aacagaagac tgtggcgggg agaggaggaa     780
aaaaatatat atgtatctgc agtacaggga gaagaaggag agaagcggcc agggctggag     840
atggtgaagg caggaagact tctgcaaact gtgaggcatg ggaggctttt cttttctttt     900
tctctccccc cccaccccccc ccccttattc tttaagaaaa ctgtcagcta ccaccgcctg     960
gggtgctttt ttgaggggtt ggggggggtgc tgttaaccag aaagaaaaag ggaaaaccgg    1020
cttggttggg gtcgcattta agcgattttt tttccctcct tcatctccgg gcctcggata    1080
agatgacggc ttgggtgatg cacgaaataa cgcacgtgat tgattagacc tggcttggct    1140
tggctaggga acgatccagg cgcgctggag accccgcgtg aagatgaaat gacggtagct    1200
ccgggctgct tctgtaaacc ggggagcggg ctccatgcac cccttttccg tgtgtgtggg    1260
tttcgaggcg ggtgggaagg gtgaggcaag ccgcagaagg agggtagagc tggtggtttt    1320
gcttctttcg gagcctttga gtgtagtctg aacctttgag gggggcgcgg ggggggcttgc    1380 agctgccgcc ctgggaacca tctctgaact gcccgctttt ccgaaggagc ggaaaagttg    1440
gaagctgcga ggacagacta ccggagccct ggtctgggtc tcgggggatc tggagcccta    1500
gtcggtgccc actgagaaca ccccttctcg gagcgagggt gtcgggggga gtgttaagcc    1560
tgcggggcgc acggtccgcc agtccccgag gtggggacgg gggaggaggc tgaggagtcg    1620
gttccaatag gcgcaccacc tctacagccc tggaaaacgc aaccgccacc ccctcttccc    1680
ttccatccca tcccaagcct ctctgctgtc ccgggccgat ttcatctcgt ctcttccccc    1740
```

-continued

```
gcctccccgc ttccccgcct cccaattccc gcgcggctcg gctcagcccc ttcccactcc    1800
agtgggcaga actgatggag aagatccgcc aagcgcgcag ccggcggcgg aggagacagt    1860
gcggggtggg cgaggggctt cgagaccacg cagagagaga gtgaacttca gtcctgaccc    1920
ctccccaagg ccgcggctgg ggcgcccaca gcccgcgctg caccccgcgt ggcctgacct    1980
gcggaagcgc gagcggggat gaggtaggga gagggaggta ggtgccgctc ggctgcagat    2040
gatgcgtggg tgggggggctt gctgtgggag gagaggccca ggtcccggcc tgcgccctcc    2100
actccgcggc tgctccctcc gcctctggtt ttccaagagg ccggtcgcta ccccggagga    2160
cactctcatc cttcagtcag tctcctggac accccttcct cctcctgtcc ctcaacctga    2220
cctggctctt tcgcccctcc gagaaccggt aggctggggt ccctcggcgg ggttctcctg    2280
ggccgcaccc gaagctttgc gccccggta tccgggccca gtgctccgtg caaccctggg    2340
cccgagcgca cgattccggc gcctgctcgc cgccagacac agcgcccttt cttcccggag    2400 cggcggggc gggagcaggg gggtcaggcc aaccccttgca cccccgaggc ctggcccggg    2460
ccaccctggg aacggatgtt ctgcatggag agcgaggggc agccggagga cgtcctccgc    2520 atcataccccc tcccccttccc cagaaggctt ttttttttttc cggactgcgg gtttcttttt    2580
ctctgccttc ttcctctgaa cctacggcag gtgtcagcct cttttttgtgt atgtgctgct    2640 gctatctcgg ggatggcggg ggaggggggtg caggaggcag cgtgaagggg tcctaggagg    2700
ttccggcggg gttttggccc ctgcggtgcg ccggggcttg caactcgccc gggtgctggg    2760
cgcgcgcgtc acgaattcag cctagggctt gggcgagtct gcggggagtg aggacagagg    2820
atcccgatct gtcatttgga cccaacttaa gaaatttggg gtgggggttg ggtgggggtt    2880
ttggaactaa gcaggtgatg ttcttgcgag ctggatccac aaggtggtag tatggcttct    2940
ttttattttt attttatttt atttctattt ggtcattttt tttggggggg gcggtggttt    3000
gttgttgttg ttgttgctct tatcttatgc ttttttgaagg catccgttgc ccgtagggtt    3060
tacatcggag cgcgttgcat tatatttttct tgaaaggggg tggtgtgcgt gagctcccat    3120
ctcagaatca gcccttccgg tgatgtgagg aaggcaaaag caaaaaaaaa aaaaaaaaa    3180 aaaaaaaaaa aaagaaaaaa agaaagaaaa aaaaggaaaa gaaaaagttt agggagacct    3240
cgttatcctg acgaagcaga attgccagtt tgtgtgggcg ttctgcgggc aacatagaag    3300
tgcatgctta agaaatccgg ggtagcttcc ttctccagct agaaattaaa tggccagggt    3360
gcaaacacct gactttgatg agaacaaagc ggcagaaact gcaagagacc tgcatggttt    3420
gaatggacgc actgagcctt tcctaggggg atggcagagc ggggtgaaat cagatagcaa    3480
agaaatctgc cgttttgtgg gggcagattt ggagagtgga gaattatttc atacctttag    3540
ttggctgtgg ggaagatgtt agcagtaatc cattaaatcc tcagcataga ttttcctgtg    3600
gaaatgagca aaatgttaag tgggggaggg atggctaatg gcacatggtt gcattaatcc    3660
ctgtatttcc agaaaaaaat atggaatttc tgtgtatcct aaaattaaga atacaggaat    3720
ttcatggaga actctgcaag catgtatttt ctcagattag aaattcagta ttttattact    3780
caatgaaatg tagaatgcgt gtgtgtgtat gtgtgtatac agacatacac acacgcattc    3840
tacatttcta catatatgtg tgtgtgtgtg tatatatata tatatatata tatatatata    3900
tatatggcca ttttaaagag tattttcttt gacatgtaag aacataatca gggccagttg    3960
tagcaagtgg aaaattactt catcagttt aagtcagtag attaaaatgg aaggcttcat    4020
ttttttttga aatcagaata ataattgcat tttcataata atgcctgtgc gtggatgcag    4080
```

```
ttttaaagat gctttgatgt tttcttctcc agtggaagaa ttgctacttt tctttgcgtt      4140
ttatttaaat aaactaatgc cgagtataca gttggccctc aaaccagtaa cctagctgat      4200
ttttacccaa acctgagaat gtaacagata cttgataagg gactggtggc tgcataaggt      4260
agataatgaa gttatcttga tgctgtgaaa tttacaagca gacttgaaag aatttgaaag      4320
ttcatagttg ttggcctgga atgtagccta atggtaaata tatagatttt ttaaaatttg      4380
tgaacttggc tatttcattg ttttgtgtgt agtaatttgt ggaaagctta tagtctctcc      4440
acaaagatga gagtgttgac tgactccgca acagagactt gcttttggaa gtgcaggggt      4500
ctctttaaaa gccatttgga atactgtgct tttatttcta gaccacaacc aaaaggttct      4560
caaaaaacta acattcaag tgcacgaggg aatgacctcc gtttaacatt cttctttttt       4620
aattggtacg ccacatttca aacctttgt aatactgttg aatattgcca ataatgcaac       4680 tgttgagcg aatgcattgc attcaaatga agtagcaata tacaaatatt ttaagtcctt       4740
tagtatcctc cttctaaaga taggcttatc tggttaaaat atacttatat tccaaataag      4800
gtgagagttg gtcttaagat gtgaatgtca agtgtaagag acacgatttt agtttgtaaa      4860
ccagaatgta ttcttctgt actgctttct gccttttaac aatatgtatt ctattcccaa       4920
atggggaaat atgttcagtt tagttttaat ctgttgctct ttttgtgtgt gttttgtct       4980 gagtactgta cttttcaga ggagagactt cgtctcctat ttaattatgt gaatggatat       5040
tcagacagat ttgaatagcc accactgatt tcttaaactc ctgagctacc agttttaaat      5100
caaagataca tcttttgcac agtcaattag aggaagtgag aatcaaaatt gaagcccagg      5160
ctgctgaggc aattaggtca tctgctgtgc tctctactac cattcactca acgaatattt      5220
tccagttctg tcattttct ctaaacaacc tacatttgga ctttgaaagg ctccactgtt       5280
ctttgttaag tgaacggcag tgtaggaagc ccttcctcat ttttcttgga gcacagtagc      5340
acacatgaac aagaaaaaaa agaaggtgat agctcctagc agtttgtcat tgtgccattt      5400
ataggctttg aataaatgta tagatgaaaa ggctttccct ctgcaggtgg ttacattaaa      5460 caaaaataa gtaaataaaa gcctcataaa atcattacgg gagtggaagg ttggtggtgg       5520
aaaacagccc atctacctcg ggctgagatt tcaaactta gacatctcgt gttcagttca      5580
cgtgtcccag gtgtgtgcgg aacacctcca tacaccacat cttcccaagg cactctcatc      5640
ttcccagaaa tggtacctga aggagaacag acctaaccc aacaatacta aaatacgtat       5700
ataaaaaact atatatagta agatatgtat cctactatat aatatatata tggtaataca      5760
tattatagta aggtctgcat catgtatata aaaatacact atatatctta ttattatata      5820
tatagtgaga tgaggtgtat taatccattc tcaggctgct aaaaaagaca tacccaagac      5880
tgggtaattt gtaaaggaaa gaggtttaaa tgactcacag ttcagcatgg ctggagaggc      5940
ctcaggaaac ttacaatcat ggtggaaggg gaagcaaata cttccttctt cacatgatgg      6000
caggaaggag aggaatgaga accgagtgaa gggggaaacc ccttataaaa tcaacagatc      6060
ttgtgagaac ttactcacta tcataagaat agcatggggc aaactgcccc catgattcaa      6120
ttacttccca ccacatccct ccacgacacg tggggattat gggagctaca atccaagatg      6180
aggtttggtg gggacaaagc caaaccatat catgaggttt tattgaattt atttgagaca      6240
ggaaaagagt aatcctccat aatttagaaa ggagatgaag tacaatgaac atttaggtcc      6300
tcattagttg aggaatacat ttcaaagaga gaaatgttaa tttcagtata gtgctaatga      6360
aacgatctag gctttcactg ctctctggaa atgtggataa atggcccaga attttgtttg      6420
ggttgtttta tttaaaatgt atattatata aagaaatcat ggtttgtcaa agtaacagag      6480
```

```
tgctatttttt ggcttacaac aggactttct tagctccacc tgttaatatc ggtgatcatt   6540
ttggttttaa gaggctggta cctgattgga tgatgaaaac ttggatctca aagccatcac   6600
cccagacatg tgattttatt aacatctgtg ggcatctgtc cggctcccac atcaaccctt   6660
catccaggct cattttctgt ttgttttgt ttggttgttt gtatgctttg gttggggaga    6720
ggggacacgg attttgctaa ggcacccttt tcaggagtg aaacttagcc tgtcatataa    6780
gctgaaaagg aacttgggtt gtttcaagtt gcattacttg gtaagttttt ggatccttta   6840
aaaaagaaag gactgaggtt actaaaagtg ttattggcac tgataaaaga gctatggtga   6900
attgtggttt gttttttgtaa agtgcagaaa aggcctcttt ggttctgtga tgatggctgt   6960
ggtgaagttg catgcggtgc cattttccat gtttagtatt tcaacaccac caatatgtgg   7020
ctctggagta tgggacgggc aagtccaaga actcagtgag gcatgccgtg tgactccaat   7080
ggtcagagct gttcagcatg gaactgtggt ctcaaaagca tggggatgg gggcagaaga    7140 agctcgctgc aactgagtgc ctttaactta ttccactctt cagtactctc tgtgactata   7200
actctgtgaa tgggttaggt ggggaaactc acaaagtaa atgcatgttt tcacaaacaa    7260
aatatgtcat tgttaactgt tttcctaagt gagacaatat gccctcatgc cctgaagcta   7320
catggtaaga atggcagtgt gtatgagcgg gtgtatacac atacatgtat gcatatgcta   7380
acacattaac taggaactag tctttgctga aaatgttttt ctcagccatt gcaacacatt   7440
agataaaagc aaatatatat atatatatat atatatatat atatatatat aatataagaa   7500
ggaaaaatgt ggttttccat tattttcttt tcttatcct catcattcac caaatctata    7560
ttaaacaact cataacatct ggcctgggta atagagtgag accccaactc cacaaagaaa   7620
caaaaattaa aaacaaatta gccgggcctg atggcaagta cctgtggttc cagctgaggt   7680
gggaggatca cttgagccca ggagttcagg gctgcagtga gctatgatta cgccagtgta   7740
ctccagcctg ggagacagag caagacccta tctctaaaaa tataaataaa taaataaata   7800
aataataaat aaaaatagaa aatgtacaat gaaagttata aagttggcca ggcgtggtgg   7860
ctcacgcctg taatcccagc actttgggag gctgaggtgg gcgaatcacc tgaggtcagt   7920
agttcaagac tagcctggcc aacatggcga atcctgtct ctactaaaaa tacaaaaact    7980
agctgggtgt ggtggtgtgt gcctgtaatc ccagctatac aggaggctga ggccggagaa   8040
ttgcttgaac ctgggagggg gaggttcag tgagccaaga tcgtgccatt gcactgtagc    8100
ttgggtgaca gagcgagact ctgtctcaaa aaaaaaaaa aaaaaaaga aagttataaa     8160 gttacctatg atgggtctgg atgtactcct tatttaggag tgaagacatt cgttaacatg   8220
agacctaagt aagtagaaag tatgtgttta agggacaggt gtccattttc tctaggtctc   8280
ctggaagctt ttttttttcta atttgagtac tagttccaaa aaaggtgtta ccgcctatgt   8340
ttatagtgaa actatctatg tgtgacaaaa ttctacccct tcttgtccat caatattgtg   8400
caatgttgtg tacttgtatg gagaaatada caacttttac aaagatcaaa ctaggcaccc   8460
tttaccaacg ctaaactcat aacccttta tctgcctttg tagaagattc tcaccttat    8520 ttctcttggt ccctctgaga aatattttcc tctgagacaa tgcaatctat gcctcatctt   8580
taagcaatcc tagctcacca gtatgagtaa tgttgtctat ttttaaggtt atctcattat   8640
tctaaaagac tttaaattgt tgaaaaataa attgtgtgag gggtggtaga gtttgaaaca   8700
attatctgtg atgttaccag atattttaga ctaaaatata ttagaatcca aggtattgtt   8760
catgccttaa aaatgctgaa atatctgact gttgcttatt aattttaaaa agaatatagg   8820
```

```
aaatagccat taattaatga ggctgtttcc actaccacat aaaaaaaaaa aaagctcaca   8880
ggtgcctgta tgtttttgtc gaatcaaagt aatctgcttt atgtatgcat ttattcatag   8940
aatttactaa aatcaaaatc aaggttttat aaatataggg tttgacaaag ttttaaaata   9000
taaccagcta tacaaatatg gcatgtggga aattctatta aattgtcatg aacatgcttc   9060
tttgtcattc caggagtctt tcttttcatt actctttcct atttgatctg ttattctata   9120
gaattatctt cattttctct ttaatacttt aaggatccct gagaccttgt cactcatcca   9180
aatagaataa aggaatgagg gaagaaagaa ggaagggaag aaggaaggaa gaaaggacgg   9240
aaggaagaag gaagggatgg aggaacgaag ggaggaaggg aggaaggaa agaaggaagg   9300 aaggaaggaa gaaagaaaga aagaaagaaa gaaagaaaag agaaaggaa ggaagaaagg   9360 aagcagggag ggagggagaa ggatgataga tcgaagggaa ggagagaagg agggaaggag   9420
ggaaagaaga aaggaaggaa agaaagaaga gaaaaaggaa ggagagaggg agggaatgaa   9480
ggaaagaagg aaaggaaggaa ggaaagaaag aagagaaaaa gaaggaagga aggagggaag   9540
gaaggaagga aagaagaaag gaagggaaga gggaaggaag ctgtggtttc tgtgcaccat   9600
taactaacaa tagctcctgt gaaccagcct ggaagttcat tcaccacata caatatagtt   9660
tcttttggaa aatgcatgtc aaactatata tatggtttgt gtgtgtgtat atatatat    9720 acacacacac acatacatat atatacgtat atatgtatat acatataaaa tttgcatgta   9780
cttttcatac aaaagaacaa gaactatata tatacaatat atatacattg gaatatattt   9840
attatagatg tatatggatt ttactatata ttatttcttg aaaaagtata agaactcccg   9900
aatcagggat tctttcttga agaggctgcc tggtccaata ttttggaaa accatatatc   9960 atttgcctct cttcaattat atcctgaaaa tggacacatt atggccttaa agtctcctgt  10020
actaatgggt ttagcagctg tgacggataa cttagggttc tttgtaatga gttttaacca  10080
aattaaccac aagagtgttg agaatacttc tgttgacaca gagcagaaag aagtactaac  10140
agggtatgaa gatacttgaa agtgtttaaa ttaccaagac tacttggaga tatgaacttg  10200
ttggtttttt tctttatttc acgaatttat tcaaaacttg ttgagtacca ataagtgggg  10260
tacaaagaag atgaaattgc ttatctttcc tatattaacc atacactaat gttatttgc   10320 acctctggtt ttatgtttaa gaacaaataa gttttaccag aatttttctt ctggtgtgtg  10380
tgtgtgtgtg tgtgtgtgtg tgtgtgtggg tttaatctct catgtcctat ttcaaaagtt  10440
aaggaaaaca acagcttgat tcagtcttca tacatctttc ttaaatagtt aagggcaaaa  10500
tcatcagagc tacatagccc aaatattagg aattaggttc atgttcgaat tctcagaggg  10560
taattatata gttcgatttt aacttcttca acagaccgac tactacagtt gatgagcaag  10620
gagatgaaag tatttgataa acatcatgga gttaatatga ttcttgaggg aggggagaag  10680
gctgcttgtc ttaggtaatg cttttgaggg taggtttgtc ctagccttga ggtagcaggc  10740
ttgctctgtt ggctgaagaa gccttaacat gcatgcccgt attgcaaatt tacccacatg  10800
ccaactgtat gctgtgggaa gaaatgaata atgtagatgc cattacaggg aattaggcgg  10860
aacggataga cttagtgcat cagaaccaat gagaagtaga caagacattt agaaaatagc  10920
aacagcaatg aaaacaaata taagtaaacc acaatcaaaa cccttacatt tgggtttcta  10980
gttgcctgtt accacagagg gttctggtta ctagctaaaa tgtaacccag taggaaggtc  11040
aagacaaggc ccctcatgct gtctcaaaca gtaacaaaca gtaaggatga cccagggaga  11100
aagggtaaca agttacatgg aagttaaata ccagttacct gtgcagagac tgaaaacata  11160
aagcagacac aggaatggca gtagtagaaa gtggggaaaa tctgaatttg ttgcagcata  11220
```

```
aaaccaacca accaacccta gtgagggaat caatacctca aaaaaaaaat cttctgacaa   11280
tctaggttca tggtagagat taaacggtac catattatga ggacagaaca ataaatcaca   11340
catggcttcc catagaattt gtgtgacagt ggttgtgtac tatgattcag tctgtcatga   11400
caatttcacc agtaaaataa ccttccagga tttatttgat atctcaattg ataagcctcc   11460
cgtaagtgaa taaccagaat atgacataat ttataaaaat taacttaaaa ttacacaaga   11520
agttatgtgt ctagtcattt cacaatcaaa tgtatttagg catttaatct agtaagatcc   11580
caaataataa aaaattgttt cttttctagac caacatgtat cctgatgtta taaatacata   11640
tgtaaattat atacatatat ttgtatatgt aaaatacaca tacatttaca tatgcataca   11700
tagctcactt tttattgggg agcacatctt cctgaaggtt tttcaaagaa taattattct   11760
acctgtaatg ctgtagcagt atttgtaaaa agttcaaatg tggctgggta cagtggctca   11820
tgcctgtaat tccagcattt tgagaggcca aggaaggagg gttacttgag cccaggactt   11880
tgagaccagt ctaggaaaca ccatccatac gaaaaaaatt taaaaataag tcaggtgtgg   11940
tggtgcatgt ctgtagtccc tgttactcag gaggctgagg tgtaaggctc acttgaggag   12000
tatatcagga gtttgaggct gcagtgagct atgacctcac tactgcattg cagcctgggc   12060
aacagagtga cactccatct cttaaaaaga attcaaatgc ctcatttatc tggacagaat   12120
ttgattggtg ttattctatt gctgaataat tccagggtat gcatttacct tttctctatt   12180
gactttaaac atagcttatg aaaacaaac aaacaaaaac caaacagagg agtttgcaaa   12240
actatattta aaagtaaacc atactccctc acccctgact ccacaaaaat actgtttaat   12300
gtagagaaac cacagacggt gcagccccca aatctggagc atcctcaggt acctgggggc   12360
attctggagt gaggggctga gcctcagagg catttggtca cacttgggtg gggatgcctc   12420
attggctagt gaagaagcag ctgtctcttc catgtagtgg tcagttgtgg cctctcctgg   12480
aagggaattt atccagcagt gtgtgttcct gaagatgcta atagcaaatt atgttcagtg   12540
aagccagctg catcctgttg gtcttgctag tcccgggatt cttgccacag caggtcagaa   12600
tggaagggag ctgcttatct ttcctcctta cttcctctcc ccatcccagc tctcatctga   12660
catccttcca acacctatat gacaggaaaa aaattctctc ttcaaattaa gaaaagggtc   12720
tggtctgggt acgatggctc atgcctgtaa tcccagcact ttgggaggac gaggtgggtg   12780
gatcatatga ggtcaggagt tcaagtagtg aaacccatc tctactaaaa atacaaaaat   12840
tagccaggtg tggtggcacg tgcctgtagt cccagctact caggaggctg aggcaggaga   12900
atggcttgaa ctcaggagtc ggaggttgca gtaagctgat atcacgccac tgcactccag   12960
cctgggcgac agagcaagac tctctctcaa aaaaaaaaaa aaagtgtttt gagtatttac   13020
tctccacatc tttcagctat ttcacttcac tgggagtaga caggacagga tggctccagg   13080
gacagtgcta ttgttaccct gttatccact tccaatttgg aaaggtaaaa atatgcttca   13140
gtgtctacta aattgcctgc attgaatttg aagtacagtt tgttgggata ctcatgatga   13200
aattggaaaa cagaatcaca gattgttagg acttgaatgt acttgagcaa tcatttgtat   13260
tccctcatgt acacaaggaa attgagtcac agagagtttc agtgattat cctcatcctt   13320 tttttttttt tttgagacgg agtttcgctt tcgttaccca cgctgagtg caatggcgca   13380 gtctcggctc accgcaacct ctgcctccca ggttcaagtg tttctcctgc ctcagtctcc   13440
caagtagctg ggattacagg cacacaccac cactgctggc taattttgta ttttagtag   13500 agacagggtt tctccatgtt ggtcagctgg tctcgaactc ccgacctcag gtgatccacc   13560
```

```
tgccttggcc tctcaaagtg ctgggattac aggcgtgagc caccatgccc ggccgtgatt   13620
tatctccata attttaaaca ctatccctgc aatgaaaaag gatacccccc aattttttaac  13680 atatctgctt acgccagttc atgacaagct tacaaaatta gaagtaattt taaatgggca   13740
aaataaagca aagtgcatta tttaattttc aaaacagact tttctttatt atgcagcagc   13800
gatttaaaca gataaatcat ttctatgaaa gggactagca gagaaagcag gaaaagacat   13860
gtcccacatt aaaagctgaa cttgttggtg ggaactcatt ttgttttatg agttatgatg   13920
aatgcacctt agctgtttct aaccccgctc ccattccctg ttttttatttg taagtcagaa   13980 cccagcattt ttacattttt tgaagtgtta attaattgcc tttgtttaat gcaccttgct   14040
gtgtctcaag cattgttaag aaaggataag atcttttttca gggatgattc tttcctttcc   14100
ttacagggct ttgtctgtga tgagaacttt ctatacacat attttttcttt ttaagagacg   14160 gggtctcact atgttgcgca ggctggtctc gaacgcctgg gctcaaggga tccttcggac   14220
tgacctcctg aaatactggg attactggtg cgagccaccg cacttggctc tatctttctg   14280
caaaaactgg tggattctac ttctctctcc atctatgttt agtcctggga gatataatca   14340
agagaaaaga aacatctacc ttcattagat taagagtcaa acaaaagggc ctagaggcaa   14400
agaggctcca cgaccctctt ttgcgggtga gcctgtgcat tgaaatcctc agcttcaaag   14460
agacacagaa ggcaaaatag gaagttggat ttgcaggagt tagtctcttg gagggtcttg   14520
taaaattgaa gggttcacat atgccctgtc aactctccaa gagagagatg acttggtgaa   14580
atctgtattt tgtgatgatt agtctttctc agagggctgg ttcaagggca aacgaagggc   14640
agaataagga cttgcagatg tgttaagaac agaacccgct gtgttgtgcg tcaacgacaa   14700
aagcccactc cactcctgac attcatattt tggggtaact gttttttgca gtgcagacct   14760
gtgaaacctg gagtattttc agtcacagct tttatcgaga tgctttctgt tgacctgaga   14820
attaattatg gtttgtcaaa cagcttgacg accttgtcag tggtgttttt tggttttttac   14880 aactccccat ctaaggattt gagaatgccg cagtggataa aactgtgtga ctgacgttca   14940 ttatttttttt ccacaatgct ttaaagtaag tgcgctggga atgctccatt tattatgtag   15000
aggagagaca tttccaaact ttaacttttgt tgctgttgct tttgtacact gaggcattga   15060
ttctgcagga ttaaaagaag gtgctgatta ttccatttgg tggaaagttt caggagtgga   15120
agccagcaga attgttccac tgagatgata attctgactc tttgattctt acacattgac   15180 tactttttaca aaatacaaac ctgttttaat cttttttaaag gacatttgtg cgctactgtt   15240
ttcatttttt aaaataaccct tttaaaaatt ttaggatagt ttcaggtttg ctgaaaggtt   15300
gcaaagatag tacagagagt tactctttaa ctccacacgc atatcgcatc ttacgtgacc   15360
atctgttaca cttaaggaac caacattagt acgttactaa gaactgacat cacaatttgt   15420
ttggatttca ctggtgtcca cctaatgtcc ttttttctctt ctgaggtacc atctgaaata   15480
ccacactgca tggatttgcc ctattttctt agcctcatct agtctgtgac agtttctcag   15540 ttttttccttg tttttcatga ccttaatagt tttgaggtat taatgtcatg agaatgtcc   15600 accaactaga gccagtctga tgttttagac aggggtatgt gtttgggggga ggaaatccac   15660 agagatgaag gttccttcca tctcacccta gcaacggtga ctactgtcca gaagacttttt  15720 gctgctggtg ttggctttga tcacctggct gacagagagt ttgtcacttt tctctgctgt   15780
aaagttgtac tctcccctcc ctgcccaagt ctagtctttg aaaccaagtc cctaaagtgg   15840
ggtgggggtg ggagaagagg cagaattaag ctccactttc cggatggtgg aatatcgata   15900
aattatttgg aattcttctc taagaaagat gggtctctcc cctttattta cttaatcaat   15960
```

```
catttatatc agtatggaca catggatatt ttagatatgc tttgggctac attgctgtga    16020
cttattccac tttatattcc ttgtggccat gatgtagaca ccagagagtc tattcacttg    16080
aatagcaagt aaatgagggg actcaatggt aaatgactct tagagaaact ctcagccctg    16140
ctggttcatg gatgctcagc ttgcaaaaac accttcttcc atcaggaaac ctcagtggat    16200
gggcaaacat tacagcgtcc ttgaatatgc ttcattgctt taatctacga acttcctatg    16260
cagtaagcaa aaccacccat accacagctt aagagtgggg ctttcctccc aacactcatc    16320
ctagtgtctt ttgataaaga ggtataaagt tgaaggaaca tgttactaac cagaagactt    16380
ccagaggacc ccattgatca gggtagatga atggctgtgt gcgtcttgtc acaaccatca    16440
gtatttcaaa aggtgatatc atcctcttaa ccttatgatg tgttttaaca taaaatttta    16500
atatgcatac aggcggttat tacttaagca ttgcttaaga agcagtcttt ttttttttaat    16560 tcatgtaact ggatctattc tctgaataag gaatataagc aaatcgtagc catttcaagg    16620
actctttttt ttttttttta aatggagtct tgctctgtcg cccaggctgg agtgcagtgg    16680
cgcgaccttg gctcactgca acctccacct cctggttcaa gccattctcc tgtctcagcc    16740
tcccaagtag ctgggattac aggtgcccac gagcacacca ggctgatttt tgtgttttta    16800
gtagagatgg tgtttcacca tgttagccag gctggtctcg aactcctgac ctcagatgag    16860
ccgcccacct caacctcctg acgtgctggg attacagaca tgagccactg tgcccagcct    16920
caaggaggct tttaagggca ggatgttttt ttttcttatg gtgaaggaat gaagagtagt    16980
atgggaaaga aatacagaaa ctttgaaaaa agaaatgtaa aactggatca tcattccata    17040
ggctagtagt taatagtaaa taactgtata gtttgttcaa gggattttgt gaatatttta    17100
aacacagatg ataattctct atctacatct acgtgtttac ctgcatttat atcatatgta    17160
cgtatggaca tatatatttg cctgtagatc acatctttgt atggtatctg taccaatatt    17220
agagtctata gctacagcat atcaataaca gtatctattc ttatctatat cttaatcata    17280 tctattttg tatctgtaca catatcttta ccgatattca cattatattt ctatgtctag    17340
atctatatat atctctatct ataccatttt gaactttaca tttcctacag tatgatagca    17400
taagctattt taggattatt aaaaatcttc ataagcattg ttttttcatgg ttaattttct    17460 caaaagacta tgctttaaca tacccagttc tttatatatt ttttgacatt tggcttattt    17520
taatgttttt gctcctctaa tgtattttc tttttttact ccacacccct cccgcctcta    17580
attttcaaat tgggcattct tcattatagg ggcattgctt attttctttt gtatgtttca    17640
aaaaacattc tgcattggtc tgtacacatt tttccctctt gtatcccttc tgtaaacatt    17700
tgtattcact tgaaacctta tggaatattt tactacagaa aatttctggt tatgataaaa    17760
aaaggcagag aagatagaat aaaggatccc atgtgcccat cagttggctt cagcaattat    17820
gaatggatag cctaatcttt agtatctaac ttcattcata tttccattct tattatggca    17880
tgatgtaatt catttaaaga tatgtctgta cgttgctcta aaatatagga accatttat    17940 tttacacagc tgcagaatct tttccatgcc taaaattatc aacagtagtt cctctgtatc    18000
atccactata aagttgtaac tgtcaaaatg atcttctcgt agttttgtaa ctcacgcaag    18060
gtcaaggtct agcactgcaa taggttgatt tgtcttttac atttcttta attgatatag    18120 cttccctatc tttttatgca cattcttgtt gaaaaaactg ctcttttac tctacatgaa    18180 agtgggtttt agaattggaa aatgtagttg tcaagttatt ttagaaggaa cgtgtgtatt    18240
ttccgtaatg cacagtctta agttactaac tccttaggag caaacgctgt gtgacttggt    18300
```

```
agtgttctac ccagaaggaa tgctgctggg taaatttggc cagctacgtg acagctcttt    18360
ggactcagta tatctcagtt ttatctattt ttaacaaggt tttattttga agacagggtc    18420
tcgctctgtc gcccatgctg gagtgcagtg atgcaatcat agctcgatgc ggtcttgaac    18480
ttctgggctc aagcaatctt cccacctcag cctcatatta tctagtacct ggcagagata    18540
cagatctgat gagaagcaaa gatagagggg tgtcagaagg tagcttttgt tgcaccatta    18600
catacataca cacacacaca cacacacaca cacacacaca aacgggcgca cacgcacgca    18660
caaagaatca actgcaattt tttcctcttt gccaacccac agttaagtaa aattattagt    18720
tctattgaac tccacattgc atgtgatatt ttgaatgata gaggctaaag agaggccaaa    18780
gagggaggat tgcttgaggc caggagttca agacgagctt cgacaacata atgagaccgc    18840
gtttctacag aaaaaaagaa aaaaaatagc cagatgtgat ggctcgctcc tgtaatccca    18900
gctactggag aggctgagac aggaggatgg cttgagccga ggagttggag gctgcagtga    18960
actctgatag tgccactgca ctccagcctg ggtgacagag agattctgtc tctaaaaaac    19020
aggaaaaata tgactaaaga aaaccaaact aatctaatct atacagttat agatagttgg    19080
ctatcattct tatgctaatg taagtatgcc tcattttaag aagagttgtg tgtgtgtatg    19140
tgtgtgtatc tgtgagtgtg tgtgtatgca tgatataaat ccagacttct aagcgagtat    19200
cagggatggt gaactattat tagtagatca ttggaacctg ttacacaagg atgcactaga    19260
gaattttaca aactattaaa ttctgtataa tttaaaatgt gacttgattt actcagatat    19320
tttaaaagga tgcatgtctc ttacaaaaca agatttacta actttggtgc tcttgacgtt    19380
gaggctggat aattctttgt tgtggtggct gtcctgtgcc ttgcgtgatg ctgaatggta    19440
ttgctggact caagcttcta ggtgcccgtt gtatacacgt tcctgttttα aaaaaaactt    19500 atataaattt aacgggcaca agtgctgttt tgttacatgg atatattgca tagtgatgaa    19560
atctgggttt ttagtgtaac caccacccaa ataacataca ttgtatccat taagtaattt    19620
ctcattcctc atcatcctac caccctccca ccttttttgat tctccagggt ctattattcc    19680
actctctgtg tccatgtgta cacattattt agctcccact taggagtgag gacatgtggt    19740
ttttgacttt ctgtttccga gttgtttcac ttaaggtaat ggcctccagt tccatccatg    19800
ctcctgcaaa agagatagtt tcgttctttt tatggctgaa taatatttcg ttattcatat    19860
ataccacatt ttctttattc atttatccat tgatggatgc ctagctggat tccatatctt    19920
tgctattgtg aatagtgcgg tattaaacgt atgcgtgcag gtatccttt gacatagcga    19980 tttctttta tttgcgtaga tacccagtag tgggattgct agataagatg gtagttctat    20040
ttttagttct ttgaggactc tccatactgt tttccataga acttatacta atttacattc    20100
ccatcaacag tgtatgtgga ttcccttctc tctgcatcct catcaacctc tgttatgttt    20160
tgagtttgac atccacaatg tctgcagaca gtctcagata tccccttggg agtaaaatcc    20220
atcccagtta aaaagctctg ttatgaaatg aggtgtactt attccaagtt ttacatgggg    20280
aatttcactg gttttgggt tctagtagcc ccgacgtgta tactgggcat gaccagataa    20340
gataaactgg gcaaagagtg caatgagaga tagtaaccac attattttgg aagatgtttt    20400
tcataaccag aatagacttt atgaattcta tcaattgtaa tgagaatcgg attgacattt    20460
ggggacagtt aatataacgc acgttatccg aaaggaggtg gcattgattt atataagtga    20520
gagcttacga gaaaacaaag actggaaata aagaaaaaga aaatccttga taagtatctg    20580
atagaacaaa gtgcagaacg aaatgcagct agccttatcta aaattgggca aaatcatgtt    20640
ccaaatgaaa gctcagtaga tgggaagaga gtatttgaac atttgatgtg aaaaatgaga    20700
```

| | | | | |
|---|---|---|---|---|
| tttactgttc | cacagatatg | aacacattga | tgagagctgt | cagttattag aacttattaa | 20760 |
| catcaatggg | aacaccagaa | atgtgctgca | cagaaaatta | aatttaagac tgtttgaaaa | 20820 |
| tggtgttata | ttttctgaac | tgttacattg | attgattaaa | attagattat ccaacaaaat | 20880 |
| aagaactttt | gatattctgt | gagtgaatat | gagatgaatt | tatgtggcag atgtgttttt | 20940 |
| aaaagatgta | ttattaaccg | cagagattca | gaattaatgt | cgccaacccc aaagaatgca | 21000 |
| gtataacatt | tgtcataagt | gacctcataa | taggttattt | tataatatcg ttttaattt | 21060 |
| tgataataaa | tggacacctt | ttacatcttt | aataataaaa | ggatatatgc aaaaccagtt | 21120 |
| atttttattc | caatgttaat | aaaatagcaa | taagcctcat | ttcatttgaa gcaccaactt | 21180 |
| tcactccata | tcaaatttct | aaaagtctgg | gagatactca | ccaactagtc aagaagattt | 21240 |
| tcattctata | aaattgtata | atgcagtgaa | tcctgttctt | ttcccatatg catttattta | 21300 |
| atatttatat | ttgatacaag | gaatctatat | tattttcatt | aagccactca taaacgtaag | 21360 |
| tgttttactt | cttcttgggt | acattttaa | aaatttggtt | acattttga gatgttgatg | 21420 |
| ccatggttaa | aatattccaa | ctaagtaatg | ggatgggttt | acaataagtt tttgctctac | 21480 |
| aaggaaatag | gtcaataaat | caggctccag | ccaattatag | gagaaaagga aaagttaact | 21540 |
| tattatacat | tattgcacac | agtgtttgat | gtatgtatgc | aaattgctcc caaatacagt | 21600 |
| ttggttgcag | ttgtgctcca | catttatggt | ggatgcagtt | ttgaatatgt gcagagagaa | 21660 |
| tatattctga | cctcattcat | caatgtgatg | caaatgtgta | gaaatggcaa ggtcattttt | 21720 |
| gtatgatgat | aaaatgcctg | tttgaaagta | aactcatcca | cccatccatc caaaggttgc | 21780 |
| attttctcaa | ttcccaattc | taaatatgtc | tgtgtgtgtg | tgtgtgtatg tgtgtgtgag | 21840 |
| agagagagag | agagaatcta | gtgcaatttt | attgttctac | tttgttccag gcttgacatt | 21900 |
| ttagtgattg | aaactaaaat | accttgattc | ttaccctcta | attttacaaa taaaatctgg | 21960 |
| tttactgtta | tggattgaac | tgtgttacag | attgaattgt | gttccccaaa aagatatatt | 22020 |
| gaaatcctaa | tgcccagcac | ctcagaatgt | gatcttattt | tgaaataagg tctttgcaga | 22080 |
| tgtaattaca | atgaggtgat | taaggtggcc | cttattccgt | acaactggtg tcgtaaccac | 22140 |
| catgtgaaga | cacagacact | cacagggtga | agacggccat | ctgatgatgg aaggttggca | 22200 |
| tgatgcagct | acaaaaaggg | aatgccaagg | attactggca | actccctgaa tttagaagag | 22260 |
| acaggaaagt | atcctcacca | agaaccctca | gagggagcat | ggccaacatc atgatttttgg | 22320 |
| acttctagac | ttcagaactt | tgagagagta | tattcctgtt | tcctgagaca taagccttgt | 22380 |
| gattctttt | gatagtaact | ctaggaaact | catacaccaa | gacacagagt tatttattta | 22440 |
| aattcatttt | ttttcatta | aaaatactta | tttgacaaag | actgtaatat ggaaagtgtc | 22500 |
| cagtgtgatg | actggatgta | cgtatacatt | gtgtaacaat | gatcacaatc aaattaatga | 22560 |
| acatatcact | catagcccat | gtggtacata | atggatggac | ctgaagttat gcagccagct | 22620 |
| tggggcagag | ctgggtttga | agggcagact | cctcacccag | ccacacttgt cttccagaat | 22680 |
| cactttcaca | tcgtcatgag | gattttagag | actccactgc | tccatgtcac tgcatcaaca | 22740 |
| cattgtggag | tggggggtct | cataattcat | tgcaggtgtc | tgaagatcaa cagttgggtt | 22800 |
| tcccttccct | caactgtaaa | atgagtgagt | tggacctgtc | tccagggcct ttctaagcta | 22860 |
| tatgatttga | gaacaatgat | cattgtaatt | aagacgcttg | acttgaatac tgctcatttt | 22920 |
| aaaccatgat | tagggatatg | agatgctccg | tgtgttttct | aaataaactt cattgtgacc | 22980 |
| tggttaagtg | ttggatatga | attggcaaga | ggaggcttgc | tagtagaaat ggtgtaattt | 23040 |

```
aaaacccatt cacaagtatt tacacactgc aagacatcta gatcctcaga agtcaggtag    23100
tatcctaaaa gcacagtgtg taatttatgg tagataattg aaattgcact gaaattgaac    23160
ttggtggtgg ggagtacact tcatagtatt caattttgc cttcactta ttctatgtct     23220 gactctcagg aaataggaac tgcaacgttg ggtttctcca gtgtattttc aacttcaaac    23280
ttgtgaattg taaaccatta aacaaatgat caaacactac atctttccct gctcttgtat    23340
ggacatagag ttttgttatt catgccttct cttttcttat ctgggaagag atctttctta    23400
acctttagaa attggattaa tgcgaccctc tttaacctca catttgatgt gaatgtcaga    23460 acttttgaa acttagctgt gcttttagta cactgatcac tgagtgcccg ttgactggca     23520
ggcactgggc tgctcagtga ggtaggtgaa gaagagacac cagctccctc ctggagtgtg    23580
tgctctgctg gaggataaag acacttatca agcaatagca taaatgcttc tgacaccatg    23640
actctaatca gagtggcaca gccaatgggc atggggctag gagaatatga gaattcgtag    23700
gtatggggat gctgtcaggg ttcatgaaag gtcttcccaa tgatgagaaa actgcaagtt    23760
gggaggaggt agaaataact gaaagaaatg gttgtagaga tgaatacatt gggggatgat    23820
cgtgttgcag ggtgacatct tttagtgata aaagggatag agtttgagct cctgctgcag    23880
accctcagcg atgtgttgta atggtaagaa ttggctcatg gtttcctggt ttgcctgatt    23940
gctgcatcca caaaccatg ggttctgggg ttaattccca tccattttgt tgctgaattt     24000
ctcagaatga tagtcttcgg tacattgtta ctgaaaggag gtgctaaacc caatgtcttc    24060
attgcttttg aagcagatgg tccagtgtag tgtttctcaa acataagcat cagagtgtcc    24120
tagaggtctt gttaaaggca aattgctggg atccatccca ggagtttctg agtcagcaga    24180
tctgagatgg gacccataat tccccagttg aagttgccgt tactggtctt gggatcactc    24240
ttttagaact actgccttag ggtatttctg ggttacatgt gcacacatga cctgcttaag    24300
ttttgagctc aacattctgt tttattcctt cctgttcaga ggccggcatc cacagctctg    24360
ggtctcatca tttgcttttt gtcatccagt tgtgctctac tgatttataa gttatcttta    24420
tgttttcagt ttcccagtca attcaagcca atgcatattt attgggcatc taccatgtgc    24480
tatggactgt gagggactta aagattaata acaacaacca taaaaactca ttgacgtgct    24540
gggcattatt tatttcccca tggcccccaa atgctaggct tatcattcaa aacactacag    24600
caacttgaag gcagcagatt gtttctcatt tcagggatcc acaggtatat ggcttctcaa    24660
acgaaggtct ggtaattcca ggctgcatgc agctattctt cctttaaaga ctgagaaacc    24720
atgcatacaa catctttttct tccttcttcg tttatacatt tgataactat gtactgacat    24780
cttactttga gaaggtcacc atgccagata ccgtcagtga tagaaacaca gataagattc    24840
aacctctgat cccagggaga ctctcagtaa ggaagagaaa atgagaaatg aaagtaccta    24900
tactacaagg catgcacgtc acacattcca taagtgggta aaaacacaga ccttggcagc    24960
acagaatctt gttttccatt tgtgtcattt aggacactgc attggttatc tattgctgca    25020
taaaaaattc ttctaaacct taggttaaaa ctgcaaacat ttatcatctc atgcatttct    25080
atacatcagg gatttaggag cagtgtagct ggccagttct agctcagggt ccgtcatgat    25140
gttgtggtca agttgtagac agggcttgca gtttttatgac ggtgttggag aatctcactt    25200
atgtgtcact tggcaggagg cttcagttct tggccacatg ggcttctccc tagggctaga    25260
cgtgtgacat taacagctgg cttttctgaa agtgaggaga gaaagaggga ggctgaaaga    25320
gagtctaagg tgaaagccac acactcttag aacttgatct tggaggtgac accttgtcac    25380
ttttgcactt gatttggagg tgacaccttg tcacttttgc tacatgctat ggttgttca    25440
```

```
aatcaaatct ggcaccatgt ggatgaggat tccaggaagg tgttaattgc aggtgtcagt   25500
tggccatctc agaagctaga ctatcaccag aagctcttcc aaaggaggtg gcttatgagc   25560
tgcatagaat tttgtcataa ggacaaagga gaaagtgtga acaaacacat aggtacagca   25620
agtgttgagg aatgggctgt gttgtgttga gtgttgtctc aagggcatgt tgagtttggg   25680
tgatgaaatt gaaatcagat catttcaggt ggtgcaactt gatggtaagc catatagatg   25740
ttattctgta ggcaatgggg caatcatatt aggacttttg cagaattatt taaggaatag   25800
cagtttcatg atagtagagg tagggataga agacagaagg tcagtaatgc aagttgagat   25860
ctagttatag attcaactgt ggtagagatt gaggaaatgg ggatggcatg aggctctgca   25920
gaggcattgg aaggatgata ctgatagaat cttgcaaact attggataga ggccaagaca   25980
atgaataacc atccaaggtt gcagttatgg gtggagttgt ccagttaaga aaagggagag   26040
agttcagagg taggtgaagg tcagcattat tagatgcttt ggagacacat gagactgaca   26100
gagatgttta ctattttttt tggtgattat aaggtaatca atagactttg agagattact   26160
gtttttcagt cttccatatt atgttgcttg gatgcatttt tcttttttcc tgaaacttgg   26220
cagacatatc cattatcaag acgttttcag aggggcatgg tggctcatgc ctgtaaatcc   26280
agcactttgg gaggctgaag caggattgct tgagctcagg agttggagac cagccggggc   26340
aacatggtga aactccatct ctacacaaag tacaaaaatt agtcaggcat ggcagcatat   26400
gcctgtagtc ctacctactc gggaggctga ggttggagga ttgcttgagc ctgggaggcg   26460
gaggctgcag tgagcccaga tcacactact gcactccatc ttgggtgaca cagtgagacc   26520
ctgtctcaaa aaaaaaaaa aaagaaaat gaaaagacct tttcaaccat tctaatcata   26580
attccaagac ctatttgtgt cctgacttca agagcaggta ctcttattga gaaacatttc   26640
tgtaattgtt cccacttccc ttatacccttt ttttctgaca gcaggtggca tcccctcagt   26700
tgtctagctg accactggaa gggctgaccc ctcaacaaac ccatatcctg cttggagttt   26760
ctctataggc cctgtcttat ttattgctcc tgctttgagt aactttctcc ttcctcaaat   26820
ctattcttct aattttcctt cactgcctat taattgaact gactttttctg attgtctgtt   26880 cctcctgcct ttgcagttac tgtcgctccc taaattccat cctcgaatca ctcctcttcc   26940
ttccgtactg tcctatgtag cttttgcatct actcatggtt tgatgattat ttccatcgga   27000
gagaccacag gggtctctat cttctgctct cacttctctt ccaagttcct tcctgccctt   27060
acagctcccc tttcaacaac attgcctata tgctctggcc aaaactcaat tcagtgttcc   27120
caaaattgtc ccatcatctt tcttgccaag cttaccctgc tccctgctca tggcatcttc   27180
tcctctcaat tcctcatctt ggatttgaat ccctctctt tcccatcccc agtgtaaatc   27240
actttcagaa ataacaggtc ctgtcatttc ttcttctgag atacatctgt actttccttg   27300
gtcatcttct cactttatgt gttactattt taatcatatc ctgtctatga cttgtacact   27360
ctccaatcta ttttttaaagc tattctttct tcatcttcac aaataattga ttatgtaaga   27420
ctactatctc gttcaaaatt cataaacaag catccactgt gcttcaccac ctgccccatc   27480
tccgccgtta caactgcagt catcatttta ctcctctggg tgttatactt catcctccac   27540
ccaacctgag tatggatagg aatcactgca tttcaccttg gtttcttgct ttttctcatt   27600
cttctcaggc tctctttcaa cctggaatac tgttattttc ccatctccac accttattca   27660
tgactgaggg ctaaaatgct gtttctttca ctgctctctc taacatgcat tgtttgtatt   27720
cctctgtggt agtcatcaat ttccattaca gaggccagga gacctgatac tttcttgagt   27780
```

```
gtgaatttca gtagttgacg tcttgtgtct cagtttcctc agctgttgag ggctgtgaga    27840
agagtaccta cctcgaggga tgtttgcaaa ataaataagt taaggtcagg cactgtggct    27900
catgcctgta atccaagcac tttgggaggc tgaggcagga ggactgcttg atcccaggag    27960
ttcgagacca gcctgggcaa catagggaga ccctgtctgt acaaagaata ataataataa    28020
taataaaaat taggcaggta tgatggcaca tgcctgtgat cccagctact tgggaagctg    28080
agacaggagg attgcttgag cctgggtatt caaggttata atgagctagg attgcaccat    28140
tgcactccag cgtgtgtgac agagcaagat cttgtaaaaa aaaaaaaaaa aaaagaaaa     28200 ggaaaggaat aaattaagca tataaagcac tttaaaacag gtatttagaa agtgttgaag    28260
gcggccttga cattacttat ctttggccca tccttgtctt tctccttcgt agtctaaaat    28320
gttttacaaa ggactgtttc tcatgacact gagaatgaac cccaaattcc tttcactgac    28380
ctattccact tttatacagt aagcctcttg ctcacttctc caccttcatc ccaggccatc    28440
ctcttctcac tgaactgctg tcccagtcct cttttggttt tgtgatctga gtggataccg    28500
tgttaggaca tttttgtgtg ccactccctc tgcccagagc accctgtcct gttcccattt    28560
aaagtgggtt ccaccctcga ttgtgttctt atttaaccca ttatttactt tcttctctga    28620
gctcacctga tctcaaggc ttttttattc tttgtctact tatggatatg tgtggaggat     28680 ctgggggtt agtgaatttt tctctgcatt ctctaaacat gtgtattgca tgaatctgga     28740
atagatcagc ccttactggg tatttattaa agaaatgagt agttgtaaga cactctatag    28800
atattcattt aatgaatgag aaaatcaaat gttgcctggt aaaaacaagt gttaagtcag    28860
ctatcacagt tttctgagat atgcagccaa gccaggagga ctgagggaag gatgtctttc    28920
attgtaaaat caacgcactg tagggggaaag ttcctctctc acctaaggga atatcgatct   28980
tccttgattg tttgctttgg tatttctaaa ttagcatgat ttaccaaaaa tgtttggatc    29040
actcagtaca tgcatgtgat ttttctaaa tggctatctt taaaaaaact tcctcatctg     29100
tattaatgtc cctagagttt ttacattttt tgcctgtatt tcattaaaga tgatgtcata    29160 gaaattttt gtcaaatttc tcattctggt ccgtgcctgg aagattgaca gtgatgcagt     29220
ctaagaaagt tcaggatttt gaggtttaat catttacatt ctaacactaa agctacaaat    29280
ctgccgtgca gtgttgctta cttctactgc tcactggatg gatgagtcta tgtgctttttt  29340 aaattcctta taaagatgtg ggtcaaaact agcagtgtgg tcaataaatt aatttcttga    29400
gagtttatca gaattgtggg atgatttggg aggagcaaaa ttgtgtaaaa tcaatcctct    29460 attttttaaac ttattcttct aaaattctaa atagaatttt tttattcatt aatatttct    29520 tgatttcata atgctaaaaa ttaagtaaga tgaatgttgt gttgagaaat gggagcaaat    29580
ccaagaccaa aaatcagatg atttattaaa tttgcaagtt aaaaaaataa atacagtttg    29640
aaagattgct ctgtttgagg aaaggacata caattttgtt gagataactt agggtacaaa    29700
tcaaggtcat ttatgttcat ttgaacattc atattcacat ccggaaatat ccagaatgac    29760
tacactaaaa cctgcaggta aattctttc tcagctgagc ataccatatt gttgtagtta    29820
atcaagaaat ctaccaaaat taaatttgtc ctcctacttt ttagtttaga aatttagggg    29880
gtcactggga ctcaaaagaa aattcaataa ataatggacc atcctagaga tacttcttt    29940 taacttaaaa atccctctga gatatcctca ggttttaaaa ataccttgt attttcctgt     30000 ttttgtgtgt gtttgtgtag gcctacatct tcatattagt catcagtgtt gtcagaacct    30060
tggctagaat catagtctag acctcttgag gtcactgggt ggttggctac attttccacc    30120
tcttgctttt catgggtccc actctgagaa acatgctcct tctctctctc tcctcttca    30180
```

```
aggtcatctt tgaggacatc ttctgaagct ttttctgaga tgctgcctct tctgagcacg    30240
acactgtcta ttcttgtatc accagtatag gagctcatgc aatttgtaag cacttgcctt    30300
aatgatgcgc tccctgaaag accctgagga gagggatcag gtggcgttca tctttaggat    30360
cccttccctg tcctcacagc acattcatgg tccacgttca gcaaacactt gtacaatgac    30420
atgacttagg gtttctagac aatctgtatt gtaatttctg ttgatataaa gggataacat    30480
tagcatcata tgaaaagtca gagttctatc aatgtcatct tgatgaaaat atttatatcg    30540
ttatatctta tgtcctaggt gtcttcttga ctgactaccc agggcgagtt ggaatggcta    30600
tgtgcatctc tctgaacccc caaatcttta gttgtaatga tgaacttaca tggagaggct    30660
tattcgaaac gtcattatag tgtggatgat aaccttctta gtttccacag ctgatattcc    30720
tccaaagttt tgtatgcttt gactaatgta ttctctttat gctaagcttt ctttaaaatg    30780
atatgaatgt tccataaatg ctgatttttt ttgttttttg agacagggct tcactctgtc    30840
acccagggtg gagtgcagtg gcgtaactac agctcactgc agcctctgct cctgggctca    30900
agcaatcctc ccacctcagc ctgtggagta gctgggacta caggcgtgca ccaccaaacc    30960
tcgctaattt ttgtattttt ttgtagagac agagtttcgc catgttgccc aggctggtct    31020
caaattcctg agctgaagca atcctccctc ctcagcctcc cgaagtgctg ggattacagg    31080
catgagccac cacgcccggc cccataactg ttagtttaat tagcaccttt ctgctttagt    31140
tcatgttgac tattgaaaat ctatcatcct gtataattaa tgttttttaaa agatactttt    31200 agatagtgat caaaaactta tttattaagt agaatgtaaa ttattacaaa tgatatgaat    31260
accataggat aaagttttta tatgacaact tagattataa aatgcaattc tagccaggca    31320
cattggctca tgcctgtaat cccagcactt tgggaggccc agcaggcacc aaccgcttgc    31380
ttccaggagt tcgagagcaa ccagggcaac atagtgagac tccgtctcta taaaaaatac    31440
aaaaaaaaaa aaaaatagct gagcatggtg gtgcatgcct gtagtcccag ctattcagga    31500
gactgaggtg agaggattgc ttgagcctgg gaggttgagg ctgcagtgat ccaaggttgc    31560
accgttgcac tccagtctag gcaacagata aatatgagta caaatggctg atcatcttca    31620
tattaatatg aaattgcatt ttttgataca ggatctcgtt ctgtcttgtg gccttctgta    31680
ataggttatc ttgtccaaat tctggaataa agtccagaag aattttaatc tagataattt    31740
attctttaac ctttgaaata ttgtatcagc tacatgacaa tggcttataa ctagctctaa    31800
ataaatgaaa taacgtttgc gagagtgaat cacatcactg agaaccaagg ggaaacatga    31860
aatagtgatt atttgaacag agagtgttag tggtctgcat tctgccttgc acccaaatgg    31920
catcacctat gggtgtgata aaaagcccct gcctttctct ccctcctcag tgcttgggat    31980
ttccaacaac agcaaaagag aagccaggaa gaatgctgtg ttgtgagtac ccccaggaag    32040
ggttttcctt tatgaagagg cagacctagt taggaaatac ataaccatgg actgcaggaa    32100
agacagttga gtctgcatgg aggatagaga ccagggaccc cataaaagga gaggtggtga    32160
ccgaggcctg caggatgcat ggaaacattc ctgacctcaa gggcagcaac tgtgaacaca    32220
ctcctactag gcagaactag aatggatgaa cagagttctt ttcagggaga ctcaccaggt    32280
agatgactac acatgagaca cttttttttt ttttttttt tttttttttt tgagacagag    32340
tctcgctctg tcgcccaggc tggagtgcag tggcgccatc tcggctcact gcaagctccg    32400
cctcccgggt tcacgccatt ctcctgcctc agcctcctga gtagctgaga ctacaggcgc    32460
ccgccaccac gcccggctaa ttgttttgta tttttagtag agacagggtt aaaccgtgtt    32520
```

```
agccaggacg gtcttgatct cctgacctcg tgatccgccc acctcggcct cccgagtagc   32580
tgggattaca ggcgtgagcc accgaaacac tttcagtggg aatattttgt tccatcagat   32640
tttagcaata tcggatttga aaatagggga agcacacaca gatacaatta gtttcaccat   32700
ctcacttgtg tatttaaaca aacctgtaaa caaagctaag cgaaccaaga aacaaacaaa   32760
acctcaaacc taatacagta ataataggct gggggtggtg gctcatgact attattaatc   32820
tcagcacttt ggtaggctaa tacagaagaa ttgcttgagc ccagagttcg agaccagcct   32880
gggcaaaata gtgagatcct atctctataa agattattta aaaaattagc caggtttcga   32940
ggcatccacc tgtagtccca ggtacttggg aggctgagag gcaggggat cacctgagcc    33000 taggaatttg agattacagc cagctgtgat cgtgccattg aattccagcc tgggtaaaag   33060
agtgaggtct gtctccaaag ttaataaata agtaaaataa taataataat ttttaccgta   33120
tcacaaaaaa tatagccagt cagatacaat gcacactaat tattgtaaaa ttttctgaaa   33180
cacacataca tcactaactt gataattgta aatttaacac tgattggagg gtgtgaacaa   33240
aggtatgatc aagtaaaata aatgtatagg caatttcaaa gtcttaataa tacaatttca   33300
agagctaata ttaattgagc atttactata tgcacactca tgcatcatgg gactgtgttt   33360
ggtgctaata tcacaaaact ttattttttc ttccactggt aattttttgtc actgttgaaa   33420 actgtttcag ccatggatcc ccacagtgcg gagattgcgg gatgtgggag agaaatgatg   33480
gtctcaatcc ccacctgagc cagtgtccta tggcaggcag gtgaaagcca agccacccag   33540
cttgagttct ggctccactt ttatagttct gtggtgttgg gcaggttagc taatctgtcc   33600
ctgcattagt gttctcaact aatggggata aagctcacat ataccttata tgttttttgga  33660 gacaattaag agttagtata tgtaaagaat tcagcaagtt agatgctgac ccactatgta   33720
catattagct attataactt attattcgga caaacagcta atgcatgtgg agcttaatac   33780
ctaggtgacg ggttgatagg tgcagcaaac cactatggca cacgtttacc tatgtaagaa   33840
acctgcacat tctgaacatg tatcccggaa cttaaagtaa aataaaaata aaaaataaaa   33900
aaataactat tattactact attattagaa ttgtttggat gaggaggtag cttgatatct   33960
tgaaaaaatg catggtcttt ggagtcaaga taggtcttac tccctgcttc agtgagctgc   34020
gttacttaac acctggatat catttttttc ccaatgtaaa ataagatgtc ataataactc   34080
ctgcccttgg ctgtagaagg gtcagtgaag atgaatgtta ttatgattgt tgttaaatat   34140
aaattcattt ttacaaatac agtttcatca acaatattta tgataatgcc tattaataac   34200
aaaatgtgct aggtgttatg agaaatcaaa aacatagtta aaatatgatc ttgtcttcct   34260
gtaatttaat aatgtgctgg ctcattagct atgaaaccca aaggccttat ctactttgta   34320
ttaatatttt ttcaagcatg gaagtaagcc cagaagggga ttgagtgatg tatcctcttc   34380
ttcccttacc atctttccta tagatgcaaa atcctgagtg tgaaaggcca cgtggtactc   34440
tgttagatat ctcgcaggtg ttacttatcg atggttcttg cttaaaagta gaaggaggag   34500
tgtcgcatga gacgcatcct ataaagagag cattccgggt gagatggcaa gaaaaactcc   34560
gaatggtcct gagatgataa ctgatccaat ggagatgata tatctgttca gttgacgcaa   34620
acataattgc ggtttatacc cgtgaatgta aggcaaaaac tgcaattacg cttgcaccaa   34680
cctaatatat atatctttg gagacagggt cttgctctgt cgcccaggct gtagtgtagt    34740
ggtgcgatca cagctcactg cagcctcaac ctcccaggct caagtgatcc tcccacctca   34800
gcttcctgag tccgctggga ccatagacac atgccgccac atccagctaa ttttgagata   34860
agttttcttg cagtagagtc aatggcagtg ttgttctgac cttctgccac agcaaaacat   34920
```

```
ctctgcaggt tgaggattag ttcttgcaaa taagtgattt ctaaatgatt gattggttct   34980
tttcacacat tttgcagatt tcttttatta aacaagttat atctaatgga gaaatacagt   35040
gagttgatga tctccaacaa aactttaatg ccacccagat caatgccaac cagattatga   35100
gttgcccatt ggaaacctca aggagtcttc attgattttg tattctcaaa ctgcatgtgt   35160
gtgctaaaat ggttgcatag agattccaca tgcagccatg catgtgtgta ggtgctccca   35220
ctagactagt tccttgactt attagggaac aagttaagaa ttacttcatg tcatgatcgg   35280
ctagttcttg taactaccca taagaaagct tataaggaat gtcacattgg ttttgaaaca   35340
atatcatctc ttttactgat ggagagaggt atgttttttct tttttttttt aaatagggaa   35400
caatgtgcta agatggaaaa aaaaaatcaa gtaggtttcc agggaggcat ttttttttt   35460 tttttttttt ttttgagacg gagtctcgtt ctgtcgccca ggcgggagtg ctgtggcgcg   35520
atctccgctc actgcaagct ctgccttccg ggttcacgcc attctcttgc ctcagcctcc   35580
cgagtagctg ggactacagg cgcccgccac tgcgcccggc taatttttg cattttagt   35640 agagacgggg tttcaccgtg gtctcgatct cctgacctcg tgatccgccc acctcggcct   35700
cccagagtgc tgggattaca ggcgtgagcc accgcgcccg gcccagggag cattttttaa   35760
aggcaccatc tcagaaggac gaggcaatgg taagtatcag gaatagttat tggcgagtcc   35820
agcacagcag tcaatgactg tgttctggac tgcaccgttg gactcgggaa ccactgtgtg   35880
gccaggctgt gggctccggc agttgttcaa accctgaac ctggagctca gaccagaggg   35940
ttgtatggga ggctcactgt cattcattgt aaccctaaga acctcatcct tccttgagcc   36000
cgattgttcc catctgatca gagcttagat gcaagattgg gaagaaaggt ggtggagttg   36060
gggtctgcct ggaggacagc ccaggtgagt catgcatggc tgggagagca gtaggttcat   36120
tctcaccacc tcattttct aaggggaaac agatccacaa gggagggtca gccccagatc   36180
attggccaca cttatgggaa acatgtgctg ctgttacgca ggccccttca ttctgtttgc   36240
atgctctcct tgtaacccct gggcctatca ggacgccagg gtgtctgttg gaagaggcat   36300
ccaagaagga tctttaggct gcaggatgga agcacacact acagcatgac cttaggtaga   36360
tggttcattc attaccttt aatatcttcc tctttctttg ctgtcaaaca tgggtaataa   36420 aataccaac ctgtcatatt ataagaagta attgaggcca ggtgcagtgg gtcatgcctg   36480
taatcccaac acgttgggag gctgaggagg gagaatcact tgggttcagg agttcgagac   36540
cagcctgggc cacacagtga gacttcatct ctacaaaaaa tttaaaaatt agccagacat   36600
ggtgatgcac acctgtagtc ccagctactt gggaggctga ggtgggagga tcgcttgagc   36660
tcaggagttt gaggctgtgt agctgtgatt gctccactgc actccagcct ggccaacgag   36720
caagaccctg tctcaaagaa aaaaaaatt aggtgaaaac aatgtctatg caacgctcag   36780
tgcctggtga tgtctaagga atgcccaaac tttctaggta aggggtaggg gatgcattgg   36840
gtgagagtcc cattggatga gcatgaatgg gaactcatca atattgctga aagtgcctga   36900
tccagaatta aaatatttca acagaaaatt cagaggaaac tttagaatgc tgaaaaatgc   36960
catattggtc agtcttactg gttaatcgac ttttctgaag tacatacaca ctttttttt   37020 atttgagata gaatctcgct ctttcatcca ggctgtagtg cagtggcaga atttcagctc   37080
actgcaacct ccacctccca ggttcaagtg attctcctgc ctcagcctcc cgagtagctg   37140
ggattacagg cacccactgc aacgctcagc tagttttgt atttttagta ggggtgaggt   37200
tttaccatgt tggccaggct ggtcttgaac tcctgacctc aggtgatctg cctgcttttg   37260
```

```
cctcccaaag tgctgggatt acaggtgtga gccacaactt ccttcccacc cagctaattt   37320 ttgtatttt  agtagaggca gggtttcacc atgttgacca ggctggtctc gaactcctga   37380
cctcaagtga tccatccgct ttggcctcca aaagtgctgg gattacaggc atgagccact   37440
gtgcccagca cacacttcac tttggatcaa gccccctta  gagcatctga acttcttttc   37500
cagtcccttg ttccacccag gcaatcccaa gcctggtgcc ttcctatctc tagcctttga   37560
tttaggctat tctgtctgcc tgtgtgcaac atttcctttc cctccttact gaagttctac   37620
cccatcctgt gttgcatgag ttgatggata attttgaaaa ataattatt  ggtaatcatt   37680 aacctctact gacttatttc attgatgcat ttttgagcct ggttaaacca agtctagcag   37740
tgctttcgga ttactttggt ggtgaaaatt gtttacttaa aaaaaaaaaa acaatttgaa   37800
acaaataaaa gtagaaagca gtggtttcaa gctcatttgg agtgtccaaa gtgacatgcc   37860
tggaaattta ggattttgaa ataattgtct gctcctcctc atggccacac ttcggggtac   37920
atctcataaa gtagacaaac acagatgaag gtcacctgtc tgactcactg tatgtaaacc   37980
tctcagaaat tcacccttgg ctgcactgct caccggaagt ccatttttctt ctagagtaaa  38040 gatttgcaat gatctaggac tcaaaaagtc catcttgggc catttgaatg acccagcat   38100 ctcattttac cctttgtatt tgtagcccct gcagagtggg gttcaaaatg tcagacaggt   38160
actactagta caggcagagg ggacactcag accatgagat ccttctcact gtctggacat   38220
tagaaagaga gcagagccca aggaaaagat atgggtagaa tacttttgtg atatacagct   38280
gtgagcccat gttagtggag atatttcaca attgaaaatc tggacccttc cccacaaact   38340
caaattttag aaaggttcat ctgatgcttt catacatctc aagtaaatgg ctctgtcttt   38400
tcatggttca gctgcaaatc tgaagtcttt acaatttgat tgcttaaata ttggttattg   38460
acaaattttc ttatcaattt gaatgttgta gcttccaaac ttttgtcaaa atttagacca   38520
caaaggcctt ttgagtatct ctttaatgat tgccagataa ttttcctatc catggctttc   38580
tctttacaga ataaaacttc agtattttc  cttgattcta gaagattgtc aaggtcatgt   38640
cctttatgga actcttgttt ccaacaaagt tgattttaa  acatctctcc atatttcctg   38700
ccataaacaa atactaggtt ttgtttttca aagataattt gtaatttata aagaaagatt   38760
aatgctgtcc cacctccccc atttgatcat taacatacaa attggaagaa atcatactt   38820 ggaaaaatga ttgatcagct gtttgctatt tttatctagt atagatttat ttgtcttatc   38880
aaaggtaaaa cgaataaagg tacacatcat ttttcatcag catatacagc taaataatca   38940
ataatgatac attatgtaaa tcccttggc  tcctgaatta cacgactttc ttttttttcca  39000 ttttctttt  tttcaacctg gatgagtctt aataaataat caaggcctga agtctaagaa   39060
atgtttgtct tctctctcac acttacagcc tttggaacag gaacccaatg cagcattggt   39120
tgtaattatt tcagtagctg cagtgcaaag cacattcagg tgaatataat cagactgtcc   39180
tagttccaag gagaagcagt agtaacaggt ctggcatcag gctcagagct atagacgagt   39240
cacagcttat aatatgatag actcacttta tgaaacccaa agggaacatt atataaagtg   39300
cacaatcatg agaaggaaat gagaacttct gaacctagga cttttttaaa attgttttac   39360
catatgcact taggttcaaa ctacatttga aaccactggg cattatcagt atgtctctgc   39420
aagagtcagc tactgctttt gcttaattgg tagctgcatt ttctcttaag ggggaatgc   39480 tttggagtgt gttttcctga taatttggag tggtctttgc tgaatggtga tcctaggttg   39540
gaatttccta cattgtacac caagaatcag ttggctggat gaaaacaag  tgacaaaggg   39600 ttttttcctt cccagtattc tcaaaatcct cagtaagaac tgaaggcatc atgactcttc   39660
```

```
agtgacatca gttgtccttg aggaggggtg gaggatttcg tggagacaca cataggcctg   39720
ataatgagga catctatgct gtaatccagc tctgctgcta attagttgtt tgcaattact   39780
aggttttttgg tatgtttaaa gactgcagag acaggcattc attccttttc actatgaaga   39840
atgtgtgaat gtaaattaag aaccacagct agctgagaag tacaaataat ttgtgaagcc   39900
tatttaatac tcgaaaattt caatttatgt cagttcattc aattttttcta catacagttg   39960
actgaacact ttctggtttt gtaacccccta ttagggaaaa ttcttttgcaa tggattttca   40020
tgataatctg gatagtctta gtgatcttat gttagaattt atttttattgc taggatgact   40080
tagtccaatt caaaactgat gatcaagaaa aattccttttc atggcattcc tgaaaacata   40140
atttttaagt caagggatga tcaggataat tctaggggcc tgtaagtttg aacattgaga   40200
ttgttgatac taagttctga acacatatta cccaaatgaa tctttttatta aacatttttgt   40260
ggtttcaaag gacatagagt agttatgcaa atcaatgtgg tgcagcaact acagtataac   40320
cttcagatgt tagggaatca acgactaaaa aaaaaaaagg acagtatttg aatgttatta   40380
caaagacacc tgcgattctt gaaggacatt tcaaaggcag acaatggggt aaattgtgat   40440
tgaaatacac gcgcaatctc tatgatatgc tccttccact tagaaagtgg gatgaaagct   40500
catcaattga agagtaattg ctaaaaaaga tttctcctct atctagcttg ggagtattta   40560
ggagctaatc agagtatttc gtcttctcgg aaattaaaag agatgaacag agttgtgcag   40620
acatggggaa aataaagttt agtttaatat ttagatttta aaattagtac ttgatggaca   40680
ttttaaaaag tgtacaatta tcaaaacttc aatatctaat ccttttatgt aaactatggt   40740
ggatacatgg aaacaccagg gacgggtgct ggttcttgtt aacttttctt tctctgtcag   40800
ccacaagagt gcctgtccca tagcagtaaa ctaataagta tttgctaaat taagaagtgg   40860
gaagggcgtt gtaggttatt gatcaaacga aaataaatat attttgttgt ttattcaaaa   40920
atttccccga cttaattttt ttaaaatgta acttaattttt ttaaagctca tctgtgtttc   40980
tttgttttgt gtcgagtcaa agattatttt atgtcaatta ccttttcatg ctgaggcaac   41040
agtttcagtt ttcccattct gcaaaactaa tttcctgatt cctctctcac cagggaccat   41100
tccccctccaa aatcctacaa ggtgggtcca tgacatctgc tagagaaaaa gagggacatg   41160
ttggagcgat aggattccca tgggcactga catactggcc tctggggata ggaagattaa   41220
tgcttagtac aagaaagaag gaaaagaagg ccttggcgag gactgttttta tctcagcatt   41280
tctcagaagc tccttcagtg gagacttcgc ctgggacctt cgccccacct tcttctaatg   41340
gcacttcctc cctgtggggc tccacgcggg acattacgtc ggtgatgcgt agggcatcgg   41400
gtgcggaaat gtgtgcgtgc ctcctggcgt gtgcgtgcct tctggcgtgt gcctgtgcgt   41460
gtacgtgcgc atgcgtccgc ctcccgggtt cacgccattc cctggcctca gcctccgggg   41520
tagctggggc tacgggcgct cgctttttttt ttttttttttt gtattttttag tagggacggg   41580
gtttcaccgt gttagccagg acggtctagg aaattttttaa gccactctga ctaaagaagg   41640
tggagttggc cgggcgcggt ggctcaaacc tgtaatccca gcactttggg aggccgaggc   41700
gggcggatca ctaggtcagg agatggagac catcctggct aacgcggtga aaccccgtct   41760
ctactaaaaa tacaaaaaaa ttagccgggc gcggtggcgg gcgcctgtag tcccagctac   41820
tcgggaggct gaggcaggag aatggcgtga acccgggagg cggagcttgc agtgagctga   41880
gatcgtacca ctgtactcca gcctggttag agtttatatt tcctttaaat ttctagaaa   41940
aacagattgt catgtatttt tatagagaca aaatactgat gaaggtgata tacaggtagc   42000
```

```
ttaattatga tttttctaag atttaattag atggtaaatt tacagtaatt attaatatgt   42060
tcactgcttt tattaaaaac catcaattct gaatccacaa tgacacaaat ggtgagtaag   42120
gcttatgtct tgtatctgtg ttctttcagt gcttaaatgt caagagaaaa acaaagactt   42180
ttaacatgat ttttaaggaa cgttttcatt ctatggtggt ttctaatgta tgtgtttgtc   42240
tttagacttc ctttatcctt ttcctttcat ctctttctca aactcataag gtttcctttg   42300
tgcagatact ttttttgcctg ttttttcctcc ctagtttatg ctgcttttct gtcaagaggc   42360
tatatttcag aatgggaaaa aagggcaagc atatatagtt aaatgaatca ttttacactg   42420
tttgtaagtt attatacata agctaatgtt tgatctctgg aggataaaaa tgagctcaag   42480
tttgagcaaa tgatggtgcc gcacacatgc cctaccttat ggtgagtcaa ctatggccta   42540
tgggtggtgg ccaattttttg taaataaaat gttttgcaac ccaaccacac acttaaattt   42600 acatttttcat atatggttct tttatactac agtgccagag tggaatggtt gccccagaca   42660
ctgcatggcc tacaaagcct aaaatattta tcatgtgatc ctttaccaga aaacattggc   42720
aatgcatact ttggcaattc atggtgatca tcttgggcct atgagttaat gcatccgtgc   42780
atacatttta aattagaaat atgtaataca ttagcattaa caacagagca tatgcttttg   42840
tattaggaat tctatgaatg catgcactac aactcttaaa cacagagcaa gtttaaagcc   42900
tggcatctgg ggtgtatgga tgagtggggc ctgggaacac ccttgaattt tacctgtaaa   42960
atttatgtgc accagggaaa gattcagtgg cgttcaacaa cacaagaagc tgcagctggt   43020
tcgtgtgggt tttcattggt ggtctctagc tgctcaagtg atggattcca gttgctggtt   43080
gatctctctt agggctaagg ttcattattg cacagattga tcttggagaa acatcttgac   43140 tgttttttttc acactccaat ccatttgttt tatgatctag aagaaaggaa cgcttaaatg   43200
caaacaatta ttgtgatttt tattccgctt cactgaactt tttaatgaag tgcattttgt   43260
acagttaaaa ccaggggggtt cctggattct atttttttgtg ggaattttttg agagagaagt   43320 aattctgact cagtacgctt ccttggagtg gataattaat attaatgggg aatgaaattg   43380 ttttgtctttt cgctggcatg ttgttctctg ccacacctgg catgctgtgg acctgtagta   43440
aatattaact aaatatattt tagacacaga tgattaagga tcttttgctg aaaaacattc   43500
tcttaatctt ttatacttcc ctttccacag tgcctgctga aaacatgaat ttcaattgtg   43560
tttctaagtc ttggtcaatt taagtgtgac atggggtgat ggggaaatag cagttaggac   43620
taaaggtaga aggtaacatg atccatgtga attgtggtca gtgcaaaggc ctggaacagc   43680
ggtcactctt tcctgtccat gaacctttgt gctattcctc tttgtacaca gtttaaaata   43740
taaataagaa aatgtcatgc tgccaagtat gtatcacagt gcaggccacg tagaagatgc   43800
tttatatgtg ttggatgcag gccagtgttc tcaactcagc agtttcagag gaagtgaaac   43860
aagccctggc tggaaaccag tagccgtaag gtctaagtcc tggctgagca gtccaaatgg   43920
gttccctaac ctattgccca tcccctcagc taagaagggc aggcagtgcc cctgggcaat   43980
gctggtttta tccaactctc agaaggcgcc attctttgcc tacgctctcc cgtgtattgg   44040
tccaaagccc accaacttcc tgagtggagt tccttcacat tctgcagaaa accttctgtg   44100
gtgctttaac attggatggg aagatgaagt tatcttgggc tctgggctat gttagtcatg   44160
ttttggtaaa cgaagcattc tgttttcacc aggggatgag taggtataat tttccttctt   44220
gagttttgca aacctgggtg gagaagaaaa tcagtgcaat gtcttatgaa tttttttttt   44280
aatagaagat agcaacttgg aagcaattga gtgttgagtc taagagattc cccaccccc   44340 ccagcatttg ttctgatctc atatatatgt acagaaaaat ataaattatt tagcattgac   44400
```

```
ttatctgtaa ttaagtcttc taaaaggact actgttttag ctgctatatt ttcttctcaa    44460
ttacttggaa aatttaaacc ttccttgggg aatgtttagt ctttcacttg tcctttaat      44520 ggtaattgat tggattgttc aaattatgct gttctgagaa gaagttaaca aataaaatct    44580
ggcaaagtaa taagcaaatg gcatcaggta aatgaaaaga acagcacact gtgtccagtg    44640
atatgtgtct tcactaattt cttacctttc aaaagttgaa gattgataat caaggtaaac    44700
tttaaaatgg aaaattgcc agctacagat tttaaagttc ataaaaggtg gttttttgat      44760
agcttttgtt gctactattt ccatttagcc ttttataata attagttaaa aatctcaact      44820
aattcttttg ataagatatc ataggttgta tttttcaatg tttaagccag atacttgctt    44880
aaaaatcagt taattaactg agagtgaata attgtcattt attattttat atttgaaata    44940
ttaggttata gtttaaacat tttacttaaa gtgtaactag aatactggac acattttgct    45000
aacactcagt gttttcaggt gttttttaaaa tcatcaccat ttctatggtt aagtcttaga    45060
acaacactct gaaatgatgt ggcatcaacc atctgagaaa gtaattaaaa gggataaaat    45120
agtaccacat gagttgggat tccttgacta tccaaccaaa aaattaccga ttttaggaaa    45180
cattctattt aatctaatta tccttcaaag tgagtggacc tttgacgtca ttttcaacag    45240
cagtgccatc ttgttttttgt gtagttgaag atcagttcat tgatcttatg tctcaggaag    45300
aaattgcagt atttcttttt tgtcttttttt tttttgaga cggagtcttg ctctctcgtc     45360
caggctggag tgcagtggcg cgatctccgc tcactgcaaa ctccgcctcc cgtgttcatg    45420
catatctcct gcctcagcct cccaagtggc tgggactaca ggcgcccacc accactcctg    45480
gctaattttt tgtattttta gtagagacag ggtttcacca tgttagccag gatggtctcg    45540
atctcctgac ctcgtgatct gcccgcctca gcctcccaaa gtgctgggat tagaggcgtg    45600
agccaccgtg cccggccagt atttattttt ttggtgttta aaaggttaaa ctgctttgga    45660
aagaaatttc aaaatgattt gggttttccg ggcttagaaa gcagactcca gctctaatag    45720
tatatgcttt ttttctacaa atgttttcca ctagatggtt atagagaatc gtttcaattg    45780 atttcttttct gatgtcttct ctatttggaa atgcagtcgt tcacatctaa tggacacttt    45840
ctagcagccc tgtttcatcc ctcctgtata cttcttaact aggattccag aaggagcagt    45900
cacatttgtt tttccttact ttccactcct tcttcagcat gttcatgttc tcagctgtaa    45960
cacataatca caaacttaat ggtttgaaga acactcattg gtaaacatgg ttctggaggc    46020
cactttctga aatggacctg gtggagctac aatcttagtg tcagcagggc tccttccttc    46080
ggaaggctcc aagggagaat cttttctcctt gtcgttttcc cccatggagg ctacctgcgt    46140
tccttagctg ttgtggcagg tcacatctcc ctctctgact ctgaccctcc tgcctccctc    46200
ttgtaagggc ccttgtaatg ccactgggct cacccagcta acccaggatc atctctttat    46260
ctcaaaatcc ttaacttaat cacatctgca aagtcccttt gccgtgaaag gtcacatatt    46320
cacagactct ggggattaag atgtggatag ctttggggac agtgcattat tcagcctcag    46380
gatgctataa tcgtatgatt gatgcatctc aggggtcatc ttagttggcc tctgcaacat    46440
ctttctccct cttgataccct ttcctgggat gctttcctca acatctttga caacactctt    46500
gttttccctt tttctccctg atggctgctt ttctctttat tttccttctt cccttgtctc    46560
tttccctcct ccttgctcca tctcccttgg gaatcccatt gtacattgta tactcgatgg    46620
aaggtatgtt tggaatatta tcacgtgtgt gaccaaagac tgatggccag tgaaatggtc    46680
ttaggtgatt tggccctaag ttcccttttc tatcccattt catgacatct gtctacatat    46740
```

-continued

```
cctgtgtctc aggcatgttg aaggacacac aaccttctgg taccagcagt gtttagccac   46800
agacctccgt gtcactgtta ttgctacctt cctcccttgc ctgactttc tccctgcagt   46860
ggaggtccta atgattccac attcacctga aagtcatttc tcaagggagc cttccatgac   46920
ctgctccccc tctataatca tgtatccaaa agagtacccc catgataacc ctctttcctc   46980
tcttgttaat ttcaatgcct tacttcccta ccagactaaa aattcccctg aatacaggaa   47040
atatcttacg ttattgtaat caccactccg tctaatgcag tgccccactg ctatggtttg   47100
aatatcccct ccgaaactta tgttgaaact taattctcag tgtggcagta ttaagaggtg   47160
ggcctttaag aggtgattgg atcaaggatt aatggattaa tgtgtaaaag gattaattgg   47220
ttaagaagaa ggagagagac ctgaggtagc actgagccct ttggctatgt gataacatgg   47280
gccacctcag gaatcagcag agagtcccta ttagcaagaa gcttctcatc agatgcagcc   47340
ccttaacctt ggacttctca gcccccagaa ctttaagaaa taaattcctt ttgttcataa   47400
agttactcag tttcagatgt tctcttataa gcagcgggaa acaggactac taagacacac   47460
agtcaaaaat tatttattaa attaataata ttaccataaa atcatagtag ttaaatctgt   47520
gtttagagat agtttcactc cttttagtct atcacttta aatctacgta ttcatgttag   47580
ttccgtggta tgagcgtctg tgtgcatagc tgtaattata gtgtaataga ttactaaagc   47640
agtcatgaaa cacttgaggg ttctttgtac caccgctcaa atttatttac atccatacac   47700
acttgtcaaa agaggtagag agtttcagat gcccttaact atccttattc cccacaggcc   47760
taccctcata tttctgatag cagctgatat accagggaga ctgaaaatta agttccatcc   47820
taagcacaga gacttaagag ttgctgtcac ttagagagag agagaagcaa actattggtg   47880
cctccgaatg caatattggt tttccccaaa gaatgcttta tcttcgcttt acttaaagaa   47940
aaaagcaggg cagggcagtg gaaatgaact gataaccttg tgtctgtgga tataactctg   48000
ctccagggaa gacattaaag ggtaatgctt tgaaaataac atcaagaaat gaaagttaac   48060
ataaaaaaaa aaaagctgtc agtactttag gtgttccaaa gtcctgtgga gagtggctta   48120
actggagttt atagcaactc tgagacattt tttttttagta cagttctgcc actactttct   48180
atgtttataa acaatgaaca gatgcattca gtgctagtta cctagaatca actctcatac   48240
ccagcattac actcgaacgt tgaatgttgt attagtccgt tcttgcattg ctttaagaaa   48300
atacctgagg ctgggtaatt tataaaggaa agaggtttaa ttggttcatg gttctgcagg   48360
atgtacagga agcataggggt ttttgcttc tggagagtcc tcagggaact acaatcttg    48420
gcggaaggta aaggggggagt gagctttctt acatggccgg agcaggagga agagagagag   48480
aggggcaagg tgctgcacac ttttaaacaa ccagatctca tgagaactca ctcactatac   48540
agtaccaagg gggccgatgc taaaccattc atgagaactc cgcccccatc atccagtctc   48600
ctcccaccag gccccacctc catcactggg aattacagtt cgacaggaga tttggatagg   48660
gacacatttt catcttaatt tgtatttttgg tatagtttca taggaaagat ttaggttggt   48720
gttctctcgc atggaaattc acttagagct tttacttgct tgttacttgt tttaaagcct   48780
ttccaattga accaatttat taagggcatc tatttaattt tctatggtaa atgtactaaa   48840
aactagaaga gatcttactg ccttgatact agttattgc ttgtttatta ggtgccctga    48900
aaagataact ttagcatcca ctgcttgcta accatccttg tcttcagcat cattagaaga   48960
tacgaaggag taaggaacgt gcttatgaga aaacagaagc tatggcatcc cccatcatag   49020
ccacatgagt cttgaatagg ccgcctgctt ctctgtcttc ttttttgcaag tgggttgcat   49080
cctagctttg gtggtgtcct tgtaactttg gaattgcctt tgagagaaga ccagtctgtc   49140
```

```
tctttccagc tgctggacct gagagattgg gctgcaggtg gcaaatggtc gctactgaga   49200
aaactgaaag caatgacagc catataatat ggtgtgaaca ccatatggat caaactggga   49260
catcacagtc agcacacact catccaattc tcagaccaag gcacaccatg aaattctgac   49320
atttaggttt cctgcctctt aggaattcca tcaaaattat ataagtagca ctattctaaa   49380
ttttaaccta ctatcatttt aaaaaatgac ttactcacag ccctaacact catcggagca   49440
ggttgatatt gtagaaaact ctagccctat gcaactggag tgatcttgat gctaagacaa   49500
tatgacccaa agccttgtcc tttcctcttg gctatatgaa tattttctaa cttttgtgaa   49560
caaaatatgc ctctttttcc tcatgatggt gtttcaaaat gagtcgatgg gtgtttttca   49620
gttattagtg gataggagct ctcttagctt agtccttcaa aagcttgtgt ttgatgttgt   49680
agctttgtaa attatctcaa tgtatgcata cacacatact cccctaccaa aaaggtcaa    49740 tagatgctta gaattccttc cttccttcct tccttccttc ctttttttca gggtcttgct   49800
ttgtcgctca ggctggagtg tagtagtaca atcatagctc actgcagctt tgagttcctg   49860
ggctcaagta atcttcccat ctcacacctc agcctctcct gggaccacag gcatgcacca   49920
ccacacccag ctgatttaaa atttgttttt ttagagacac ggttttccta tgttgttcag   49980
gctggtctcg aactcctgga ctctagtgat cctcctgtct tgtgctcctt ggattacagg   50040
cataagccgc cacgcccagc cacgtagtat ttctatattt tacttttagc ataagtccgt   50100
gaaagaacta tatttctcat gctttgttca actgtgcaca tcatgatgtt gaaggatttg   50160
cacgatggct atgatggtgg ctgtcactgc actacaatac tttttttgaa ataagtgaa    50220 atattcattg ttcactagaa tagtcttaca ggcatttgtt tctttagaat ttggaaactt   50280 cttttttatat tcatggtcgt atttcattct gctagcagtt taggcagatt caatctgtcc   50340
cactttccag tggtagaaac agtgtgaaga agtgaagtag ttgttggaaa atcactgtgg   50400
tttgcttccc aggggttgcc ttgtccactg attacaaaag tatcataaca catggcatct   50460
tcccacaagg agtttagagt ttgaaaagtc aatgtattaa tgtacatagg ggacccactt   50520
ccactcaaag caaacattga gtcaggtatc agagctcggt gggtgaacac gatggcattt   50580
aattatccta aattacttta tataatcaat atctactaac tgcctttgtt atgatgctac   50640
ccatcatttt tggagtcaca agcttcaac cttgtctaa ctaaaagatg gatatctgca    50700
ttttatatta ggtggtctgg aagccatagt aatattagag agcacatagg gaatgtttta   50760
gtccatttgg gctactataa ggaaatacca tagactgtgt agcttataaa caacagacat   50820
ttattgctca attctggagg ctgggagtcc aagatcaagg tatggcagat tcagtgtctg   50880
gtgagcaccc acatcctggt ttgtagatgg tgccttctcc ctgtatcctc atgtggtaga   50940
aggggtgagg gagctgagtt ccctttatg agggcactaa tcccattcat gaggctccaa    51000
cctcatgacc tcatcacctc ccaaggacct cgcctcctga taccatcatc ttggggtca    51060 caatttcaac ataggaattt ggaggggcac aaacattcag atcatagcag ggagagagat   51120
gagccttgcc caactccatg aagccatcta gattttttca gtctcagtcc tatttccatt   51180
ttttaatgtt gagttttgaa ctctattaat gtctcctggt attttcaaaa ctttgtagag   51240 cttttcatcat caatattaaa cctttcacat tcaaaggaca tgattatttt gtgtgagtag   51300
cgtgttgtta tttgacaaat gagtacaatt ataaataaat cttgaccatc ttgatagagg   51360
aaataaatgc acgtgtcaag atatactata atgcttttgt aatcaaaaca atgatggggc   51420
caggcgcagt ggctcacgcc tgtaatccca gcactttggg attacaccca ctgaggtggg   51480
```

```
tggatcactt gaggtcagga gttcgagacc accctggcca acatggtgaa accccatctc   51540
tactaaaaat acaaaaatta gccaggcatg gtggtgcacg cctgtaattc cagctactca   51600
ggaggctgag gcaggagaat cgcttgagcc caggaggcag aggttgcaat gagtcaagat   51660
ggtgtcactg cattctagcc tgggcaacag agtgagactc tgtctcaaaa acaaaacaat   51720
caaacaaaaa gcaatgatgg atagaacagg gtattattta aatgaaaact gtaaggggag   51780
ttgtatgctc tcaaatgtca ttatgcacag tctaatattt tcccttttac tttgtcactc   51840
tacctgctaa tttgcttcct taattcagag ttatgtcttt ggttattagt tataatatag   51900
gctgacagtt atgtagcgtt tcttctgtgc taggacctgt tccaagtgct ttttatatta   51960
actcattggt ctcaaccact ctacctgata gttaccatta gtattagttt cctatctgtg   52020
ctgcagtaac aagttactac agacttagtg gctgcttaca gctctagagg tcagaagtcc   52080
aaaatgagcc ttaggaggct aaaatcaagg tatcatcagg acaccgttct ttttggaggc   52140
tctaggagag acagatttc cctgcctttt ccagattcta gagacttctt actctccttg   52200
gctcataagt tcctttctgc accttcaatg ccagtagatt gagtccttct cattctgtca   52260 tcttctggt tcttcctctt ttcttttttcc cttttctact tataaggatc cttgtgatta   52320
tgtggaccca ctggataacc tggaatcatc tccccatttc gaggtctgct gactgggaac   52380
cttaattcta cctgcctctt tcatttgaat ctcttttcca tgtaaggtca cacaaagtca   52440
caagttcttg tattaacaca tggtcatccc gggggtccg ttattctgca gaccacacag   52500
ttgttatctt cattttacag acaagaaaga caaacagtga gagttaaatc acttactcag   52560
ggttgttggg ctgctaaatg gtagagccag ttaaaattag gagtgtacac agggaagcta   52620
ggcagtgttg tggtcaaggg ccttggcccc ctgaaggttc aatgaaaaat catggagaca   52680
aagtgatttt tactgtccac tcaactggat tgcacagagg gagagagaga ccaggagcct   52740
ggctggctgg tgagaaattc ttacccttg gccagcagtg tgggttcctg ggttctctgc   52800 actgtgcct ccaaaagagc agagcgtctt tgttgacccc gctcgctgtg tcataactgt   52860
aggggccaag gctctttact ccctaaaatt ttaatgaaaa atcactgact aggcagactg   52920
attaacagga gaaatgacat tacaagtgta tttaatgcag atacacagga gcctttggaa   52980
tgaagatcta ccctccaaat gaggtccaga agcttataca ccatcctgag gttacagaaa   53040
gagtgggggc ttgatccca gtaaaacagg tgatgggagg gggaggtgag gaattctgtt   53100
gaggagatta ttagaacaga gattaacttg taaagagttc tctttgaaaa ttaaatgatc   53160
cttggagaca cccttggaaa actgtctgct caggtgtggt tttatcttgt ttttttttt   53220 tttttttctg taatagataa tgatataact tgaagggggtt gaaaaacaac tgtaggttgt   53280
caaatgtatc ccatatccta gccctcactt ctggttccat cttactttc tatgtaagtt   53340 ttcacttcta gttctatttc ttacttagaa attgtgttaa tcactggtat aagtagcatc   53400
tttgccagat aaaaggaaa aacaaaaaca aatgctttat gacgatatgt gggagaaaag   53460
aatgtaatag tacttgagaa atattggaac tggttaaata ctagatggtg ttgggtagtg   53520
tttaataaaa tgattatatt tcatagagaa cattttctct acgctgaggc agaaatacag   53580
agataatttt atactatact catcctttct cctaatcata ttattttta aaattcaagt   53640 tagaatttga gtgattgtat tgctgctgtg ctgttttct cagaggaaaa atcatagcaa   53700
attatttcaa agatagatgg agaacatggt gtttctctat atccaggttg gattgaatgt   53760
tgtattagcc aatggaaacc ttcctcttca ccctctggag ggtcacggaa aatcatgtca   53820
caaaaggcag attaatagaa agcaatacat atttattaag ttgtagattt gtgtaacaca   53880
```

```
ggagccttca gaatgaggac acaaagatac aggggagact gtccaatttt ttttttattt    53940
caacttattt tagattcagg gggtacatgt gtaggtttgc tagatgggaa tattgcgtga    54000
tgctgaggta tagggtacaa ttgatcccaa tcaatggtgg taagcatagt gaccaccagc    54060
tagtttttca gtcctcaccc tactcacttc ccattctagt agtcccctgt gcctattgct    54120
cccgtcttta tttccgtgtt ttctcaagct cccacttata agtgagaaca tgcagtattt    54180
ggttttctgt ttttatgttg actcacttag gataatggcc tccagcagta tccatgtttc    54240
tgcaagggac ctgattttgt tcttttttcat ggttgcatag tattccacag tgcatatgtg    54300
gagaccacat tttctttatt tattccaccc accactgatt ggcatctagg ttgattccat    54360
gtctgtcttt gctattgtga atagtactac agtgaacata caaatgcatg cgtctttttt    54420
gtagaacgat ttatttcct ttgagtatat acccagtaac gggattgctg ggtcaaatgg      54480
tagttttgtt tcatttaagt cctttgagaa atctccaaac tactttccac agtggctgaa    54540
ctaatttaca atctcagcaa gaatgtataa gtgttccctt tttctctgca aactcactgg    54600
catctgttat atattttttt ttttgactat ttaatgatgg cctttctgac tggtgtgaga    54660
tggtttctca ttgtggtttt gatttacatt tccctaatga tcaatgatgt ggagcatttt    54720
tcagatgttt attgattgct tatatgccct cttttgagaa gtgtgtgttc atgttctagg    54780
cacagttttt ttttgttttt tgttttgttt tgttttgttt tgtttgagac agagtctagc    54840
tctgttgccc aggctggagt gcagtagcac catctcggct cactgcaacc tctacctcct    54900
gggttcaaaa aatcctgcct cagcctccta agtaggtggg attacaggtg cccaccacca    54960
tgcctggcta attattttgt atttttttag tagagacagg gtttcaccat gttggccagg    55020
ctagttttga gctcctgacc tcaagtgatc tgctgcctcg gcctcctgaa gtgctaggat    55080
tacaggcgtg agcgaccact accagccctt ggcacagttt ttaatggggt tatttggaaa    55140
ctcagttttt atgctaaggt tcaactaact gtggacaacc cagtagaaat agggttggac    55200
aaaaagggcc tgatctaaag ctaatggact gagtggggaa acccagccag gtctgtctgc    55260
ctagattctt cttggcctct ctgagcagca ttccttctgg gtgtgaggta ggaccctctg    55320
tggaatgggg ggtcttagga cctacagtca aaaaggcagg tcagaggatt tatttatggc    55380
cagtgtttac agaaaggcag gggaaagttg aggtcatctt ttttttggttt catgggtgct    55440
ttgtggggaa ggggtctggt ttgtatgacc tgctttaggg aggagggatt ccagttccta    55500
tggccagcct tcggggagaa tggaattgag agacaacagg tcagggagg gtcagagaaa     55560
aacctttgc ctctgaggct gctgaagcct tcattttgtg gtatcattct ctgagcccca      55620
acaacacaaa ttttttttaac ttcatgcaaa actcttaggt cagttgagcc tagaatacag   55680
gtttctacgc tgtgtggcta aagtacggtc cttccctcct ctccacaggg agcagatgaa    55740
atttattttg gaggaagtta actcagaata gaaggaccca gagatgtcag agagtggagt    55800
gggggcgaga gcccagactc cgtatctgtc ctgagaaagt taggacataa ggacccacag    55860
acatcagaga gtggagtagg ggtgagggcc cacgctctgt gtctgtaagg gaattgtcta    55920
cactctgcat actcacagcc atcagctttc ttgttcttcc ttccaagttg aaagtcactg    55980
gactccttca agtccatcct ggaggatccc tttcttggta aactgaactg gcagagaaaa    56040
gtattccata actggcattt ggaggccatt tgggcctatt acttatttac tgtacaatat    56100
gttcacctgc tgaggaagga cccctggcta tccacacaga cctgattctt aagtgagaaa    56160
agacagtctt acatcctaga tattttttgag aagctttcaa taagaaattc tttttaaaaa   56220
```

```
ttgaaaaaag aatcatctgg aggtagcaca gacaacacca accaagaaaa caagagacaa   56280
aatttctaat ctgtaacttg taggagatat gatgaaatag tgactcataa aaaacatggg   56340
aattctatta aaatgtgaca tattaggcaa attaaataat cagattggag aacgattatg   56400
aggatatctc caatgacaa aactttaatg agagagagat agcaaaatgg aaaggaacga    56460
atatggagac tctaggaatc tgacattcga agagtatttt caggaaggac aacagaatac   56520
aaataagcaa aagtgactta tgaataattt ttaaaataat cccagcattg agggatctac   56580
acttccaggc ttatgaaaca acactcaggg ctcaccatag tgaatgaatt gaaactccaa   56640
actacaaaag cacattgcga gatttcagaa gaacaaatat atagggaaga tcctaagagc   56700
ttggaggctg tattaggccg ttcttgcatt gatataaaga aatacccgag actgggtaat   56760
ttacaaagaa aagaggttta attggctcat ggttctgcag gccgtacagg aagcatggcg   56820
gctcctgggg aggcctcagg aacgtgtcaa tcatgacaga aggtgaaggg aaagcaggca   56880
catcttacat ggctggagca cgaggaagag agagagagga cgtgctacag cctttcaaac   56940
caccaggtct cctgagaact cactcactat acagtaccaa ggggtgtgta cagtaccatt   57000
caagagaact ctgctcccca tgatgccatc acctcccacc aggccccatc tccaacactg   57060
gggattacaa ttcaatatga gatttgggca gggacacaga tccaaatcat atcagaggca   57120
aagaaaaaaa acttattaag aatcaagaat ttgtaatgtc atagaatgct tcatgtcttc   57180
actgaacgtt aaaagataga aactttcaca attctaagaa aaaacaattt actacgtaga   57240
actcttggag caaactgtcc atgggcaggc agggtcaagg catttacact gatgtagcat   57300
ttccgaaaat ttacctttg tgcaccctt cttggaaagc tgtgtgatta tgtcttcctt     57360
caaacagcgg aataaatgac aaatagaaag atggggaatc caaggaacag tggccttcac   57420
agaagagagc tgaaagaatg caggtctcag attaatgccc agagcaggct gggacagctg   57480
gaatcctaga gtgagacttc aaggagaaag tacataaaag aaaaggaaat gagccatttg   57540
accatgtaga aatagtactt gagatgggct ttagttccct tggaacattc agaaaaattg   57600
aacaatagac acacagaaaa gcatgaaatg aaaatgtgaa gttgttgttg tctccagata   57660
aaacaggagg caattcaatg aaggagattt aattagagta gaatgcttca ttcaggagtg   57720
attattaatt gcacagttac aataaagtta aagagagaag gccaggtgta gtggctcacg   57780
cctgtaatcc cagcactctg ggaggccaag ataggcagat ctcttgagtc caacagttcg   57840
agaccagcct gggcaatgtg gcgaaatccc acctctacaa aaaattcaaa aattatctgg   57900
gcatggtggt gtgtggctgt agtcccagtt actgcagagg ctgaggtggg aagattgctg   57960
gagcctggaa ggttggggct gcggtgagtt gtgactgtac cattgcactc cagcctgggc   58020
aacagagcaa gaccctgtct cgaaaaaaca aaaaggcaga aggggcaaat agagtggtgg   58080
ttgcccattg ataatttata ggtaatatct aaaaataata tatcaagaaa aaatagcata   58140
aactattact tagaaaatatc atagagcata tatttggaga ggagaagcta agaaatctga   58200
aagcatttgc tttctaaagc aagtgtggtc atgggatgtt gtatgttggg caagaaagtg   58260
ctgtttgttg tgcaaataac acttgtagta gtttgacctt taaaacttca tgcatgcctt   58320
tctttattga aacaaaattt tttcaaaaga aaaatgataa ggccaagatt gaatggtatg   58380
tgaatgtgaa tatgacagtt aaaagcatga tttctcaaat gtacctgccc attggaatca   58440
cctggagaat gtaataggta ttaatgcctg tgctgtggtc ctccagagat tctgacttgc   58500
tcggtctgca atgcagactg ggcagtgaaa ttttcaatt ctccttaggg attctaagat    58560
gcagcagagt ttaggaagca tggatctagg tagctcagat tcttacttga atttaaaaat   58620
```

```
ctctagctgg gtgcagtggc tcatgcctgc aatcccagca ctttgtgctg ggctgaggtg    58680
ggaggattgc ttgagcccaa gagttccaga ccagcctggg caacatagcg tgcctgtgtt    58740
cccagctatt caggagactg aggtgggagg ttcgcttgag ccctggaggt caaggctgca    58800
gtgagctgag attataccgc tgcactcaag cctgggcaac agagtgagac cctgtttcaa    58860
aaaaaaaaaa aatcttgtcc agtgttctct tcaccaagat acagtggttt cagtaataaa    58920
ctactactaa catgatgatt tagattgagc caacttcatc actcagtcat ttctttgtta    58980
tctgatatgt tctttatgga aaggctttaa ttgcttgaaa atgacctaat gcttctccca    59040
agcttcccat tttttttttcc ctttcttaac tgaagtcaca gaatgttctc gtgtgtggaa    59100
tgctttgtct atcctacggg aagccaattg tgcatggctc atggcgccat gctggcttaa    59160
ttgttccaat tcctcctgtt tctccgacca cacatgaggt tgaattaaat ataatttcct    59220
cagtttgcat ttcccaggca gtcgtcctaa gtggcttctt ggaggagctc tgtgcattcc    59280
actggtctaa ttctgtgatg ccctttaact cgagggccaa ggacataatt accagctcta    59340
gaaattcgtt ccgtggtcaa ggatgcttgt gcagaggcca aattttcttt cattataatt    59400
tggcctttgc caagcttcaa agtgaagggg attgagttcc tactaaagag tattggcacc    59460
taggaagtga atgctttctc tatcttttgc agctagtgtg ttctacatttt cttcaatgta    59520 ccttctgcct ggtaaatgtc agattatttg ttgatcatcc tcagggtgta gttctttgtg    59580
ttgttaaata agaacccagt ggcttaaaag cattggcttt tgagaagtca ttttttatcct    59640 ggatgataac tcaaatccat gcagtgctga tatttacagc tgggaggtga catgatctta    59700
tcctttggtc tgttgctcaa attattgatt tcagtaggac ttactggctc ccttctgtct    59760
tggggatacc tttgatctgt cttgccttgg gggaccctcc ctctgacctg aatagcagc    59820 ctatttccac aagaagggac cctctgagag aggacagtct tcataccgcc tcttccgatt    59880
ttcctttatc ttttatgggt tttggcttta aactttact cttagaatgt ccttaaagct    59940
aatgattttt taatgttctc tagtgtatta ctaaaagctc ttcatctact tgaaagactg    60000
gggcaggaag attgcttgag cccaaaaggt cgaggctgca gtgagttgtg atcctgccac    60060
tgtattccag cctgggtgac agagcaagac cctgtctcaa aaaataaaa aggacaggtg    60120 cagtggctca cgcctataat cccagcactt tgggaggctg aagcaggagg attgcttgaa    60180
gccagagttc tagaccagcc tgcaacatag agagacccat ctcttcaaaa aataaaaaaa    60240
aaatagctgg acatgatggc acccctgt agtcccagct tcttgtgggg ctgagaccag    60300
caggaggact tctagagcct aggaattcca ggatgcagtg agcaatatgt atgtgttaat    60360
acatagtgaa accagttatt ggagaattag tatatgtcct cccacaaatt cagtatgttt    60420
tcctaattat ccaattaatt caagggcat aaacataata gatgcaaatt attttacgtt    60480
ttttgtttaa aaaccttttt gactgaatca gtctatgacg ctttagtatt tgaagttgcg    60540
gacagaactt agtcttaaga tagcactcgc tttgttgata gatttccatg gagggaattt    60600
ttgccagatg ataatttagc ttgaagatgt tatagatgtg gacagtcaca ccctctaagt    60660
tacacagtct ggggtgggcc aattgaaaag aacatgcaga aacacaggct tgttaaggga    60720
taattaaacg tgggggaaat agaacagtca tggcagagga tttaataggg tttaattggg    60780
ttaggaagaa taggccggag tgaaagaata gctcttaata ggaggtctag aaatagccaa    60840
ggaaagcatt aattgcagaa aatctgtgac atctgattac tgtagtgaaa gaaagatcca    60900
cctttaaaaa tcctatctat acagaaagaa gtgatagga gaaggaaatc ttcccacgga    60960
```

```
catatttaag aaaaacagtg gggaggtttg agatttcaaa gggccatggt tcaggttata    61020
attcaaaaga gaggcaaatg atagtcctac tcttcttgag tttcaggaag ggggaggatt    61080
ttgccacttg ctgtgaaata attttggagc ttctataacg ttgatccttt catcctattt    61140
tttcttggac ttgggatgtg gggagtggat aagatgggga tggagaagaa gcagggtttg    61200
aaatgcctct tttgattctg ttcattcccg gaattcttct ccatgggcct taaagagtag    61260
agactccttc ccggtgcatg acatccagtg gccaattaat gaaactttat ttcctcagat    61320
aagttccctt cctccattaa tttgtgggaa ttcagatgaa aacttacttg gactgtggtt    61380
ttctatgtgt ttgtgaatgg aaggacatgt ttgtctttga ccttcctta gtttcacgtc    61440 ttagtcttga tatttaagta gctttggttc agacagagaa ggaccatgtg tgcagttgct    61500
gggactgctc tctagcttgg aggttccctg gtcttgggaa agatctccct gcccatgca    61560 ggtggcatag atgtttaatt ttctacatga gagaagcgct agagttttt tattcattac    61620 ttgtgtgcac agctgtggcc tctagggaag ctcagctgag gtggtctcag gttccaccaa    61680
aggttaccgg ggagagatga ctaggaagac aggaagacct gtctcacttg ggagggtatg    61740
gcaagagcta ggcaagacct cctggtggag atatttgcct tttattcttt ctttttttt    61800 tttttttt tttgagacag tttcactctg tcacccgggc tgaagtgtag tggtgcgatc    61860
atggctcaca ccaacctccc cgtctcgagc tcaagccatc ctcccacctc agcctcttga    61920
gtagctaggg ctacaggcat gcaacaccat gtccagctaa ttttaaatt attttagaa    61980 acaaggtttt gccatgttgc ccagactggt cttgaactct taggctcaag tgatcctccc    62040
gcctcagcct ccgaaagtgt tgggattata ggcatgagcc atgttgcctg acccatttat    62100
tctcaagtac ttatgctcag ggcaggtctt ccaagggaag agaacagcca gataagactc    62160
gtatgagata gctgaggagg tggcatttca tccttccatg cacatgctcc ttatccacaa    62220
gcagaaagct gtaacctttg ctgtccccac taggtcatga taggtagata cgcaggtgat    62280
gaccacagac tggcaattag ccaaggattc tcagctgtgc acgctacatg tgtgagtgtg    62340
tgtgacagat cccctttggcg gtttggtgga aaattgatac attttgtaaa aatgatatgt    62400
ttaagtcata caataaggta aataacgcat aaaaggaaat cggttttatt gaaatagtta    62460
ccaaggtata ttaatattaa tatttaaagt tggtgcagtg gctcatgcct gtaaacacca    62520
gcatttgggg aggctgaggt gagaggattg cttgaggcca ggagttcaag accagcctgg    62580
ccaacaaagt gagactctgt ttctacaatc aataaaataa aaataaaaa taaaaagata    62640 tatttaaact gggctacagt aatacatgtg catctttatt gtgtgctaag tacctggatc    62700
tacttaagag gttcgtaata gtcacaattt caaagtacaa taagcgtaaa cagtattttg    62760
ggatatctgt gataacagtg ttaagtgtcc tacctcacg ggtaatggaa gcaaatacta    62820
aatttcagtg catggtagtg aaactaaaga tgtaattact tttgcccatt gcaatttgta    62880
gaacccatgg aatctatcta aagactcctg ggtggcaaag gataaatgct tgagggtatg    62940
ataccccatt cttcatgatg tgattattac atattgcatg cctgtatcaa aacaactcat    63000
gtgccccata tatatata tgtatatgta tatacacctg ctatgtactc acaaaaaaat    63060
aaataaagac acctgggtgg gattgggtt tttggactta gggtggagaa catctgcatt    63120
tagaattgtg tagaggaaag gttttgattt atttattata cctctgtttt ctttaaaaaa    63180
cctgcatgtg tagtaggaat tttgccagag gtgggaatgt gagagtcact agtttgcagc    63240
atagagcatt ctatactgag ataattattt ttatgtcaaa aagaaagtga agaatctggc    63300
agattagaat cttcatgtta ttttcattta aaaagcttgg aagtgtcaat atcaattaat    63360
```

```
attgactgct atttactgac attttttggca aaaaacattt cattttaatg aattttgtct    63420
tgtttgaatg tttgtaaggc tttggaggta gttttaggag atagttgcct ttgattcctg    63480
aggtatattc ttgggtctac cctgattctg tctcttgact ttgcacctct ttccttcctg    63540
aaccctgttt aaaagagcct tccttttacg actctttttct tccatcctat tcttccttcc   63600
catgctaatg tgagacacag aggttttat gagaagcctg ttgtctatat gctggatctt    63660
ggaagccttg gttatttcct agagatggaa ggtctgatct cagttaagtt ctgacccccag  63720
gacaagaagc ctctctggag taactgactc actgggatag agcctgtttt cacaaattaa   63780
tattcctgtc tggggagggc agaggaaaca ttttggggag tgggtggagg tgatgaggtt    63840
caagcctgag gatgaagctt gcctttcctg ggagcttgta cagtgtcata ctcaggaaat    63900
aaactgtgtg ggaaaggtgg tgtttagtaa tctagagccg aacaccttgt aaggccctca    63960
ccttgtcatt ctgcactgtc agaagcacat gagaaaagag tgtaggctgc cagagcaagc    64020
atcacaccga aataggaact tctcagatag agccgtctgc ctaaaacaaa gtaaccttag    64080
caaataggat ctgtgctaca gaaaatggag cactctagcc agggttgtga gatggagctg    64140
gtcctggggt cacaggtggt gtcttgggaa acgttctgaa gacactcagc ttttcggata    64200
ttgcacagtt cattaggaga ggtatgggca gtggttatga agctccttat gtaagagaca    64260
tagagataca ctcaacagta ttactccaga ggggttctggc tcctgtcttg cacttgggag   64320
tacacacttg ttcttgtcca cattaacctc caactgtcca catgatcaac catctgcaga    64380
cccactgcca gttgagggtc gtgccaggtc agaagtacta actgcaggtt aaactgtgct    64440
atttagaaat tgagtgtttt tttcttactc aaactgacag ttttcctttg tagaagaact    64500
cactcagctt ccactctggc ttaaatattt cctttacatg atcaatatta tctctgtcca    64560
tcagatacag caatgagaaa gccttttaaa ggaaatgagg ttaaagtga ctgggtatct     64620
agaattcttt attttgtttg ctaaattgca ggcaaatata ttcccagaac tagttgtgat    64680
acctttcag aaactggctt atttgacatt ggctgaaagt aatactctaa cactttactg     64740
ctgtgtcaat gagtgaaatt cctgcaggca aaaacaatag ggactacatc gtgaagccta    64800
tgagaatttt atggtggaaa catgagtgga gcaggtggtg gaagtagctc atcttctgtg    64860
gttgtggtac ccacaggaga tgagctaagg agaatgccct gaaacctaac cttgccaatt    64920
ttctgtcttc tgtgtcctgg ttccttctgg tttccttgtg tctcttttct tccttttaat    64980
ttaatagtgt ttactgaaga ccttctgtct tccaagttca agtattagtc atctctgggc    65040
tttgcccctta gatacttatc atagtctagc aatgaatgta agcattgagg aagtaatggt   65100
gacataatgt gaatgttcag tgtggtatca tcttccccac tctttgtaaa tcttggtggt    65160
cttaattctt gaatgtcaat gcttacccc tctatgctgt ctttacagaa gtcctctggc    65220
ctagctctct ctacatgtct aaaattgtag aagcatcttc tgggcactcc attgcaaagt    65280
ccattctgca gaagcccacc atcccacaga aggagcaggt gggaggcagt ggaccacagg    65340
ctggctgcat ggtagcaatt gaaaagcaat ggagcacagg ctggcttcat ggtaacagtt    65400
gaaaagcaat ggagcacagg ctggcttaat tgtagcaatt gaaaggcaag cttcatctca    65460
tcagctggag tgtttactac ttgaggatgg gtacttgatt ggtgtatctt tacatttat    65520
caaaatgggt ttcaccttgg aagcattcag tggtacctca gtgaataatt gtaattagct    65580
aggatttctt tggggaatac ttattgttct aaatttatat gtgtttacat atatgtactg    65640
tattagtctt ttttcacact gctgataaag acataccgga gactgggtaa tttataaaga    65700
```

```
aaaagagatt taatggactc acagttccat gtggttgggg aggcttcaca attatggcaa    65760
aaggcaaggt aagaacaaag gcatgtctta catggcggaa ggcaaaaaga gagagcttgt    65820 tcagggggaac tcctcattat aaaaccatca gatctcatga gacttactat cacgagaaca   65880
gtatggggga aactgccctc ttgattcagt tatctcccac agggtccctc tccctatacg    65940
tgggaattat gggagctaca attcaagatg agatttgtgt ggggacacag tcaaaccata    66000
tcacatacat atgcatatct ttatgtaagg tgtgtgaata taggtgtgta tattcatata    66060
ctcttgtact ttctcaaaca caaaccatag cacgtgcaat aatatccttg agttacatct    66120
gctactctgc ccatttttaca cataagagat ggaagcattg atggttatat taggtagggt    66180
tctctagagg aacagaacta ataggacaga tagatatata aaggggagtt tatcaagtag    66240
tatttgttca cacgatcaca aggtcccaca acaggccatc tgcaagctga ggagcaagga    66300
agccagtccg aatcccaaag ctgaaggact tggagtctga tgtttgaggg caggaagcat    66360
ctagcacagg agaaagatgt agacttagag gctaagctag tctagtcttt tcatgttttt    66420
ctgtctctgc tttatatttg ctggcagctg attagatggt gcccacccag attaagggtg    66480
ggtctgcctt ccccagccct ctgactcaaa tattaatctc ctttggcaac accctcagag    66540
acacacccag gatcaatact ttgcattctt caatccaatg aagttgacac tcagcattaa    66600
ccatcacaat ggtgtataca cccttctctg gttgctgatg gagttaaagt gagagccagg    66660
atttgaatca tagtcataaa actgcacaaa acctctgccc catactacct cccagataca    66720
taatacacac atgagtaggt gttttttgtgc ctgttatagt gcatttgagc ctgttgttct    66780
tagtttgctc ttatgtagga ccatctctct gaaaacagat gatcagcatc atatgcaaca    66840
ggtagtattg attatctgta gcataaaggc atggaacacg ggattttcag ggaatggagt    66900
aggaaaaatt cctgaaccta agcagcttaa tagtttaata tttcacttgg ttagttcgaa    66960
tatatatgtt catatgcaca tgcatgaaat gacatggata aaataagttt taatgtattg    67020
tatctatata aatctctta aacctcaaaa aatgtatata tccaaactaa ttatttgtca    67080
gtctctccct ctcttctcc ctctctctct ttccacgtat ttatatataa atatttctgc    67140
aaactaacca actgaaatat taagctccta tctatgtttt atatgtattt ctgcaaatag    67200
ccaaccaaaa tattaaagca attaaactcc taaatataat atttcttta tctattatat    67260 tatttcttca aactaaccaa ttgaaatatt aagcttctat gttttatata tataagtat    67320 ttctccaaat aaccaagcaa atattgagg tattaagctc ctgtgaatgt tttatattat    67380
tctatgtata tagaataata tatttttatat gttttttatt atattttata ttattctata    67440
tgtagaataa tatattttat atcctatatt atatatagaa taatatattt tatatcctat    67500
attatatata gaataatata ttatatatcc tatattatat atagaataat atatttttata    67560 tcctatatta tatatagaat aatatatttt atatcctata taatatatag aataatatat    67620
tttatatcct atataatata tagaataata tattttatat cctatataat atatagaata    67680 atatattta tatcctatat aatatataga ataatatatt ttatatccta tataatatat    67740
agaataatat atttattatcc ctatataata tatagaataa tatattttat atcctatatt    67800
atatatagaa taatatattt tatatcctat attatatata gaataatata ttttatatcc    67860
tatattatat atagaataat atattttata tcctatatta tatatagaat aatatattt    67920 attatattt tattttata atatattttg taatatatat gttttttata tatagaataa    67980
tatattttat attattctct ctctatatat agcaggttag tttgaagata tctatacgta    68040
taatatatta aaatttattt ttggccaggc gcgttggctc acgcctgtaa tcccagcact    68100
```

```
ctgggaggcc aaggcggggcg gataatgagg tcaggagttc aagactagcc tggccaatat   68160
ggtgaaaccc tgtctctact aaaaatacaa aaaattagct gggcatgggg gcatatgctt   68220
gtagtcctgg ctactcagga ggctgaggca agataatccg ggaggcagaa gttgtagtga   68280
gccgagatct caccactgca ctccagcctg ggtgacagag tgaaactctg tctcaaaaaa   68340
aaaaaaaatt attttataga tataatttca tatatgataa gttaaagtac aaactcttga   68400
aacaactcct cttatatatg aggggaaaga agaagattat ttgtacagta caattagtac   68460
agtgaattct gggaaaaagt cagtaaatac tcatttcaaa tcctcatgta caattcaagt   68520
aaagaaaaat ctggtggcat ttttatatcc tgctaataaa ggttatctgg tgttggaaaa   68580
catattttat ttttacatgt acatagtagg tgtatatatt tgtgggtaca tgagatattt   68640
tgatataggc atatgtgtaa aaatcacatt agaataaatg gagtatacat cacctgaagc   68700
atttatcatt tctttgtgtt acagactttc caattatgct tttagttatt taaaaatata   68760
cagtaaatta atgttgactg cagtcaccct gttgtgctat caaatactag atcttattca   68820
ttctgtctat attttgtgc ccattaacca tcctcacttc tctctctctc ccattaccct   68880
tcccagcctc tggtagccat cattctactc tctgtctccc tgactgcaac tgaaagaaat   68940 attttttaaag aataggctgg aaggccacac tgactctcac tgtttctggc acactaaacc   69000
ttgccatttt ctgcagtagg gattgtctcg cttcagttat gccttgctac ttcagtgaag   69060
gactttctgt tcccactggg ctcctatact gagtctgctt tggagataat agtctgagat   69120
gtcagagcgt cttagtggtg aaagcaactt aagaggtcac tggcacaagc cctcgttttg   69180
cagtggaggg agttgatggc gagggcactt ggctaattag tgaccagggc tatagcaggc   69240
tcaggttcca tgactgtgct taccatggct ggcaggatcc cagggctttt ctgtgtaata   69300
tgtgggtgga tggtctattg ccttgggctt gtcgcataat catggagaaa acagtttata   69360
ttttcccttc aatttttaaa tccaagatag tttgatagca catgggaaaa taaagtcatt   69420
gagtaaaact tatacggatg agaatctttt gattaaattt tcattgtaaa ataatcatag   69480
tcataaaaag tgtatcaaaa tgtgtatttg gatattcatt ttaaagagta aaaaataatc   69540
agatacatag tattgtaccc actgacagac aaggaaagag aacattccca ctgtttttat   69600
atatcagtgt gagttgcttc cctctctcct accttcagt gaaatctaat cccccaagat    69660
ttggttttca tactgtcctt gctgtatatt tcaggacaaa catagctctg agcaatatat   69720
tgtttagttt tactattatg taaataaat cacactattt gtagtcttct gtgacttgcc    69780
ttttatgttt gagattttcc cattttcctc catatatctg tattttattc attttttgact  69840 gttttgtaaa gccttctgtt ttaatatgcc aacatttatt tattcattat cctatttatg   69900
gatatctgga ttgtggcaat attttttgca attataattg gggcttattt atcctcagca   69960
aactaacgca ggaacagaaa accaaacacc gcatgttctc actcataagt gggagctgaa   70020
tgatgagaac acatggacac atggggagg gaaacaacac acagtgggc ctgtctgggg     70080 atgcccggag gggagagcat caggaagact agctaataga tgctgggctt aatacatagg   70140
tgatgggttg atttgtgcag caaaccacca tggcacatgt ttacctatgt cacaaacctg   70200
cacatcctgc acatgtacct tggaacttaa aagttgaaga aaaaaaaatg gggctgcagt   70260
ggacatttcc gtgcatgttt cctgatgcat gggagttcta gttgctccac atcgttgctc   70320
agtacttggt atcattgttt gtttgtattt ttattaatcc tattgtgatt tcatctgcat   70380
ttcaccaata atgaatgaca ttgagcctct tgtcctatgt tgaggctatc tgtagatttg   70440
```

```
aggactcctt cctggatgtg gatttatggt ggagaaacca caaagatgg ctttgagtgt     70500 aggctgaatt actagaaaag taatgatcta gttatccaaa tatgaaacaa aagcatggaa     70560
gcagtttggg gattggagaa tgagattttt aggagcacca taagatgtct atctgactat     70620
attcttgaag agaaaatagt catggcacta caggcatggt ggcacatacc atgttatcag     70680
ctggcactac aggtgtatgc ctccatgacc ttgaggacat atgactttga gttcggtgag     70740
agagatgaac acaaagccta gagagatctg caaatcattt gatttagatt tagaaattgt     70800
gtctggaaaa catttaattt cacacagaaa atcaagcatt aacgcacttt tattatttgc     70860
cagtccttgt gctagcttta gatatgcaga agatgaataa gaagaaaaaa tgcatcacag     70920
gtagggatag atacttcat gagaatgtaa gctcctagtg ggcaggaact ccttctttac     70980
cccattacgt accccttacct agcatagtga tctttacggg atacttctgt ggtctgaagg     71040
cttgtgtctt tccagaatcc ccatgttgac gttgtaaccc caaagtgatg gtgctaggag     71100
gtagggcctt tggagctgat gagatcatga gggtggatgc cccagaatgg tattaatgac     71160
attttaaaag atacccagg gagattcctt gccctttttcc cctttttccaa agttataagg     71220 aaaatacagc cctctaggaa gcaggccctc accatacact gaatctacca tgccttgatc     71280
ttggacttcc agcctccaga gctgtgagca atgaatatct gtggtttata agcccccaa     71340 gctatgatat tttgttacag cagcctgaat ggactaagcc aacttctaag ttttggtgtt     71400
gtcttatttc tttggtcggt gtaggatctt tctgtccaca tagtttactc tagaaagatg     71460
tatgccctat tcctcatggt atatttgtct ttcctatctg tggaatatcc tcttatccaa     71520
ttcgtcttgg ctgggcaaca tataagccat taactcttta cccttgggtt tagtttgggt     71580
tctgctgagg cccctgctga aaattctggt ttctacaatt atggctcatg catgttcctg     71640
acccattaaa cttcagtgga agaacagaaa tggtgaggga ggtgatggag ttgatacctt     71700
gagctgccat atggtgcaag atcatcttga agatagaaca tttggcatcc ttttttttt     71760 taagagatgg ggtcttgcta atttgcccag gctaaactca aactcctggg ctcaagtgat     71820
gctcctggct cagcctccca attacctggc aatacaggca tgtgccacca tgcctggcca     71880 cattttact ctccaattgc ttaatatata gtaaagataa tggttcaaaa tggtaaattt     71940
tttttgtgtg tataccaata acatttttt ttaccttaaa catattcaat ctttatttga     72000
caatttttta aaatttcaac ttttttttttt tattcatggg atatatctgc aggatttttt     72060
acctgggtgt attggatggt gctgaggttt gaggtacagt tgattctgcc acacaggtat     72120
ggagtatagc acccaacagg tagttttttct accttttccc cctccctctc cctgctgtag     72180
tagtcccaag tttgttattg ctttatgtcc atgagtaccc aatgtttagc tcccacttct     72240
aagtgagaac atgtggtatt tgattttctg tttctgcatt aattaactta aaataatggc     72300
ttccagctgc atccatgttg ctgcaaagga catgatttca tttgtttttt tttgtttgtt     72360
tgttttgttt ttttgagacg gagtctcgct ctgttgccca ggctggagtg cagtggcgcg     72420
atcttggctc actgcaagct ccgcctcctg ggttcacgct attctcctgc ctcagcctcc     72480
tgagtagctg ggactacagg tgcccgccac cacgcccagc taattttttg tattttttagt     72540 agagatgggg tttcactgtg ttagccagga tggtctcgat ctcctgacct cgtgatccac     72600
ctgcctcggc ctcccaaagt gctgggatta caggcgtgag ccaccgcgcc ggctgatttg     72660
tttttatggc tgcatagtat tccgtggtat atacgcatca catttctctt attcaatcta     72720
ctgttgatga actcttagat tgattccatg tctttgctat tgtgaatagt gctgtgatga     72780
gcatacatgt gcatgtgtct ttttggtaga acaatttatt ttcctttgta tatatacccca     72840
```

```
gtaatgtgat tgctaggtca aatggtagtt cctcttttaa gttccttgag aaatctccat   72900
actgctttac acaatggctg aactaattga cgttctcacc aacggtgtat atagccttct   72960
cttttctctg cagccgcaac agcatctgtt gttttttgat gttttatgaa tagccattct   73020
gactagtgtg agatggtatc tcattgtggt tttgacttgc atttctctgg tgaaaaatgg   73080 tggatttttta aatgggattt cattttttaga tttaatagaa actgcatagg tgactgtgca   73140
aagaactctt aagatttgac aaaaggcaaa ttagattgta atctccttta tgtaggaggg   73200
gaaataaaaa ccagaatatt aaaatatcta catgtacaaa aatagacaaa gtggcagatt   73260
gctggtgttg gatggatgtt gagcagggat ggaggacttg tgtgtgcatg catgcatggc   73320
catgcgtgga gagtggtcat tcattttggt aacagcatag agctttgggc ttcagaacaa   73380
aagataagcc acatcccact caggtaccct aaaatgttgt ctccactaga cacaaaagaa   73440
aaggaagcca gagatgtctg tagcttatgc agagttttgg gaatagctat tctagacttt   73500
cttagtgaac agtatagaag gattattgta caagcccagt aatttgggca aggatcagat   73560
tctgttgctt ttgttttctg gatgctccgt aatgaatgtg agatggaagc ggatgtctca   73620
agtgcttctt gttctcagaa acctcctggc agcagacatc tcagtgggcc cagacgttca   73680
gcgtggctgg aagtaaaaca cagggaaggg tgctcttttct cagttatcct atttttttt   73740 aaaagcatct acaaagcttc ctgttttcta atatattccc aggcctttga agacaaggc   73800 cataaacacc caggagatgt gactttattc ttttttaaggt ccagataccaa aaatgcctgt   73860 catcagggct caccttaatt aaaatacgtat cttaaaatta aaccaatctc aatttaagga   73920
atgtatactt tggggagaaa tttattacaa ttttttattca gaacactttta aattctgata   73980 ggcctgaaga gtgtgagcct caccttaatt gcaacctgag tcagaataac tgccctgcag   74040
agaatcattt aaaataccca atcaagttat aaattagtca aaatgccatt ctgagatatt   74100
attattttat gcagtctttg cagagaatac atgctatata gcccttcttc actcccaaag   74160
tatatgtata tatttaatga agttttcacc ttttttatta aaattttttaa tccattaaca   74220 attttagaat tcattttgta gcatatcctc tttatcttag agatattaaa tatctaccta   74280
tttatgaata actatcaata accacgtttc acccttttgtg aaatccttttt cagttttttga   74340 aactcacatg ggagatcttg tttttttttt tccccacaag gatgtaggtt ggttaaatttt   74400 acagtggttc tttaatgatg ataatgcaca tttgattgat atcaataata aatattgata   74460
tcttcaatat caacatttct tgtaatgcta aaaatttaca agttgccaat ttttttgaata   74520 tgactatatt ttcacacaca cacacataca cgacagcact aattatattc actaaatata   74580
cctacagata cttaatcatt tacacagcca ctataatttt tacttgatg ccttaaacca   74640 gtaattctcc cttgagggtg gttttggccc ctgggctacc tagcactatc tagagacatt   74700
ttccatagtt aaaactgggt aggaggtgcc actatcatct agtgagtaga ggtcagggat   74760
gctgcaaaat actgtacatt gtacaggcga cgccccccaca acaaagaatt atatggttca   74820
caatgtcatt tatactgaga tggggaaacg ctgggcttta attatagcaa ttttgtgcaa   74880
attagccaaa tttcaaaaaa caagggagtg aaaaaagata gctctcaacc tgtgaatatt   74940
gtgaatgccc aatctagacc tagtaagtgt acagatgccc ttgggcgcgt cttcttaggt   75000
tgctgctgct tcataatcgc tcactgccca tcaggacctt gtgggatgta gatttaggca   75060 gaggagggt ttgatcatac agctggatca gtcataacca ataagtgact catagtctca   75120
ttcacattga gtttgagaat ttaaggtgtg ggctggaatt ccttatggaa ctaactttat   75180
```

```
ataccttgga agaagtccac ccactgaatt ctacatttat tgagctctgt gtttcaggga    75240
atgtgcaata ccttgaggat acatactatc tcatttagtc ccaagtagct tttaaatatt    75300
tgagagtggt tttggccccc aggctgaaag taacagctac ctctggttaa aaatctttca    75360
ggaaagaagc aaccaaacag gacatcacct ctttgttttt cttgtctgtc tcttaattat    75420
tcagaaatgg gattgctgta tggcagacat ccaaatgttg tctacagtag aattcagaga    75480
tagaagcaaa cacctaaatc agtcattggt gagatgctat ttgtcacttt caaagttata    75540
atccagattt tcagtgcgtt ttcatccaac tctggtgaac ttttcccagg atgtcatgta    75600
ctatggaatt tcccccatt gtattattgt tctgtgatag atccagctcc aatatgtttt    75660
atttaaaaaa aaaagccat gtgatgtatt ctgttcaact gattacttaa atgaaatgga    75720
taattatttt ctgatgcaga tgctctgaat aacccacaaa atccttagaa acacatttgt    75780
atattttgag ttgaagaaca tgctaaaggc accctccttg caacacctag tgaaatattt    75840
tctgttccta ggggatcatt taacaacata atgtccattc ctgcacagca ttcttttatt    75900
gtcacaggag cagcgactta tgtagggata gttatattat ctatgtaaag acaaattgag    75960
gtggtgaccc tttaaaagtt gactccaggc tcaatgggaa agtaactcaa atgcagcctc    76020 agcttttttaa atgggctgaa gggtgaagag gatacccctct aaggcatgca gtggcttact    76080
ggaaagtcag gataattgta tcaacacttt taattatgaa tgaagtcttc aagaaactag    76140
cactacagca tgtacttgaa atgcaccatc ttgtatagtg ttttacaagg aaactgagat    76200
tcagagcagt gaagtgtgta gcctaaatat atatgcactt gaccagacca aggagaattt    76260
gtgtccaaag tctacactct tttcatttga tgatgttccc tttgtggcct gataaatatc    76320
cacatcatga tgccagattg acttggatgc atgcttccat ctttctccta ctggaaaact    76380
tttagagctc catgcatgtc tccttaggaa aatgtgacaa tttccttaaa catttgagaa    76440
acagtgtttt ggaagtaccc atgtattgat aaccagtctg gtaaacaata gcaaaactgg    76500
gaggtgttgt tactataatc tgcataacct gtataactct tgaacatctg tttgatcatt    76560
caacacagat ttgtttagtg ttttctaaat gtcaggcatt gttcatggtg ataggatgta    76620
cagaggaatt aagacaagtg gtggctgcta ggcatggtga ctcatgcctg taatcccaac    76680
actttgaaag gtcgaggggt aggatccctt gaggccagcc tggacaacat agggtgaccc    76740
aatgtctaca aaaaaatcca acgaattagc cggacatagt ggtgcatgct tgtggtccca    76800
gctactcggg agggtgaggc gggaggatgg gttgagccca ggagttggag gctgcagtga    76860
gctatgacag caccactgca ctgcagcttg gcaatatag caagacacca tctctaaaaa     76920
aaacaaaata aataaagaca ggtgatgttc ttgctgttgc ctactatgtg gagatggcac    76980
tatacacatt tctatacaaa tgaataggaa tttcatagag agatgttgtg gatttcgtgg    77040
aagagccagc cagtgttcta ggtggtcgtt gtgtggcttc attattcttg tctgctttct    77100 tcctcttttta ggctgccttg gagttttcat aagaaattgt ccctggaggt gttggatgat    77160
cacagcttcc ttggagcatt gcagttgctg gaatccagtt tcaggattaa gggagggctg    77220
cctccttgca atgggctgcc aagaaaacgg ctgtgcttgt tcttaacctc aggctctgtc    77280
tgtgatcagt ctgagagtct ctcccaggtc tactgctccc tggaaagccc tatctctctg    77340
caggctcgcc tctgggcttt gtctccttgg agccacatca ctgggacagc tgtggatgtg    77400
gatgcagatt tgaaccatgt cacggcccca gggactgcta tggcttcctt tgttgttcac    77460
cccggtctgc gtcatgttaa actccaatgt cctcctgtgg ttaactgctc ttgccatcaa    77520
gttcaccctc attgacagcc aagcacagta tccagttgtc aacacaaatt atggcaaaat    77580
```

```
ccggggccta agaacaccgt tacccaatga gatcttgggt ccagtggagc agtacttagg    77640
ggtcccctat gcctcacccc ccactggaga gaggcggttt cagcccccag aaccccgtc    77700 ctcctggact ggcatccgaa atactactca gtttgctgct gtgtgccccc agcacctgga    77760
tgagagatcc ttactgcatg acatgctgcc catctggttt accgccaatt tggatacttt    77820
gatgacctat gttcaagatc aaaatgaaga ctgcctttac ttaaacatct acgtgcccac    77880
ggaagatggt gagtacctca ctggaacaga aaacaatacc tcttgtgcag tgtgtagaga    77940
gatttgctag gagggtttta taatgtctca tgcatgatct cttctataac ccgtttattt    78000
tattttaatt tatttttcat attccaaatg caattcttgc agcaacttac cacatgttcc    78060
acttgtatgt attgggccat ctactgactg acaaaacta taaataataa ctttaattat    78120
tttcatatat tgccttctta acttttata atgcttattt gcagatgaaa ataaatgaa    78180 gcatataatg ttgcatgtta tacctgaatc atctgtaaag gaatgaatct atagaaaaat    78240
aatagaatta agtacactat tatgctccag tttgcaaact gaaagataga gaaaatggtt    78300 cttctgcct taatgactta agatattagc acctttttg agttttcaaa gaaaaacttg    78360 attgtttta atacaagt aggggatagt tcatacaatg gttggatttc attgtttaga    78420
atcggttttc ttaacgtaaa tttggatgtt cttttcttcc aatattcgct gcaatcaagt    78480
ggcaaaatgt aatcagatga ttctagctac attagagatg aatgcgtttg tattttaaa    78540 aatttccttt tttatataaa acaacaatga aagtctgtag acacaataac gtttaatata    78600
ttaacctaat gttagtaaaa catgaatagt tttatgtctg tatagatttc aaattcagat    78660
ttccttggaa gaataaccag actaaagtat gccataatgg tatcacattt cccagttagc    78720
atttccatat gccgttttta gatgaggaga aagaacaaca gagaataaaa tatacctgga    78780
aagaaaggaa gttaatttgt gggaatgata gatgtatcta atgtagaaac tagagtgtgt    78840
cctttgtata aagttcttcg tggaaagtgt gataaatttc ttttatggag aaatttcttc    78900 ttcttcttt ttttttttt taaacttcaa tccctggaaa acatttttca gtaagatttg    78960
gctgaaaata gtaaatcaac aacgacgtta atccactgat ctccaaaatt gttttgcatc    79020
tatcagatta ctctttctcc atataaatgc cagatagttt aagtagagtg tcatgaaaaa    79080
ccataccagg gttgtgtgtc actgaggtta caaattgtca ttgagattac aaagaacagc    79140
ccagagaaag aaattaaagg attctgcttc attatattag tggtttctgg catattgccc    79200
ttgtcgttat ggtgacagac ctctcaatta tctcataaag tccaggtctg aatgtgattc    79260
aaggagttaa actgacattt ggacgctgta cttccatggg gtgttctgag ctgtctccgt    79320
gcctaacagt ccctctttgt gtgtgtgt gagatgaata agagctctca aaagcaatta    79380
gggttctcat ttgagcagcc acctgggttg agatctttct cataatgaac tattcaaaca    79440 aaaccaaaa agaaaggaag acaaaaatgg ggagaaaacc ccccaaacag gacaaagggt    79500
taaaattgct ttcataatac tttggatgtg ctagagtctg gtgattttgt agagctagcc    79560
ttggcaacaa tgaatgcact tcaaatagaa ggcctcctca tataggagtt ggacagaatg    79620
agaccaccca tgaaaagaa tcaatagcct ccctgactgc agagccctgt atgtacaatt    79680
gtgtggatgg agaccacaaa cggtgtggcc gtttcattgc aattcggtat tgaattaaaa    79740
tttgaggaat gtaaatatgt gaaaaatgct attcagtgaa aaagtaatcc aaacttcata    79800
ataaacccag ttccacttgt ttagatcttt aggcttttg aagcaatatg tgcatatgat    79860
cttgacaagg gaatcagaaa tctaatagtg actgaaaagg tagaatcgat ctccccacga    79920
```

```
tgtgtaaact ttagaatttt gctggtgaga gttcaaagct acagccctgc atgtttgtac    79980
catccacaag tcacagccta tgggttagg agttttttatt tttggttgct tgcttgtttt    80040
cttaactcta tcaacgaaga accagtgcag gccaggcgcg gtggctcacg cctgtaatcc    80100
cagtactttg ggaggccgag gcaggcagat cacgtggtta ggagatcgag accatcctgg    80160
ccaacatggt gaaaccccat ctctactaaa aatacaaaaa ttagctgggc atggtggcgc    80220
gtgtctgtaa tcccagctac tcaggaggct gaggcaggag aattgcttga accaaggagg    80280
tggaggttgc agtgagccac aatcgcgcca ttgcactcca gcctggcaac atagcaagac    80340
tccgtctcaa aaaaaacaa aaacaaaaaa agaaccaatg cagagcttta gatgtttaat    80400
tattaattat tcactaaatg aatgaactcc gcatccacaa catattgaaa tgttggcatc    80460
atgctgattc tctccaaagg ccttctctta gggagtatct cagttcagat caatgctttt    80520
atttagcagg agagagagca atattattat ttggaattca aaattccact ctgaccagtc    80580
tgacaaagcc agaaagacaa atctaaacaa taacaacagc aaaaatctac ttttttttgtt    80640 tagctttgtc tttctgcctt gatcagattg gctcaaattt ctatgtttct actttcataa    80700
aatgtgtagg tatattaaaa atacaaaaat agactatttt agatacgtac ttatccttac    80760
atttaagaac taacttgcat gaggaaaagt gttggaaatt tcttcgtagt acaatagttt    80820
atgaaacata tatttttttt ctgtagaaaa caatactttt tataattccc tttaaaataa    80880
atcaggtctt gctgaaggtg agtctttttca tttaaactgg catcatgatc tactaaactt    80940
aggcttgggt ctttataact atttcctacc ttacaaattt ctttatttaa attttcatag    81000
gttattaatt tctctttgtt gttagacaac aggctaatta attaacttga attgcatatt    81060
taaccttttg ataggtgctc aaataaggtc aaagtcagtc aagccagtcg gaagctctag    81120
taggacacgt gggccattgt tgacaaggaa cagttggaga ccgattgacc gaatctgcat    81180
ggtgtgtgtg tgtgtgtgta tgtgacagag agagagagag agagagatag cagagagagt    81240
gtgactgagt gactactttg aggaagcaat gcagaatatg gcttggtagc ttgattaaac    81300
ataaattgtg aaagtcaagc cgagaagttc cagtctcaca tactaagtcc acttgagttc    81360
atacatgagg ggatggcagt acagttcgtg attcgtcttg gtccccaagg agactgaaca    81420
cagaaagatg agttatggaa acacttaagg tttttaatga gaaccagtga tactgtttag    81480
aagtgaggtt aaaagtaag ggaaaaataa agacacatt ttgaaggagt tgctcagaca    81540
agatatcata ttaaatataa agcttggagg agaaagagcc acaagtgagt ccagattgcc    81600
ttgggaaatg gacagaccca tggaaccact tcctgagtga cctacacctg tgctttttct    81660
ctggatcctt ggacatacat cttaaggtct tattcttgaa agatttcagg ggcgagaagc    81720
ccttccattc ttcatcatgg gactaaaaat actgggaaat ataaggaaa atataaatga    81780 aagtcattat cgcccaggca cagtggctca tgcctctaat ccgagcactt tgggaggtca    81840
tggtgggtgg atcacttgag gtcaggaatt cgtgaccagc ctggccaata tggtgaaacc    81900
ccgtctttac tacaaataca aaaaattagc tgggcatggt ggtgtgcgcc tgtaatctca    81960
gctacttagg aggctgaggc aggagaatga cctgaactcg agaggtggag ggaggttgca    82020
gtgagccgag atcgcaccac tgcactccag cctgggcaac agagtgagaa tccctctcaa    82080
aacaaaacaa agcaccactc attatcattg tattttcatt gtagcataac agcaaatgcc    82140
attatgattt ctagaaaagt gaaatttttgg gttgttttttt tttttgcta gcaatacaat    82200 tgaaaaagga agatattaaa aaagaacaga ttattggatg caaggtgtcc ctatcatctt    82260 tttccccccaa gatgacacct gactctttga atactatgac ttaagtaagc ttgctatgat    82320
```

```
tgttgattga ggacctattt ggtgaaaaca tggagcttta tgatgaaata taaacagaca   82380
cgacatggac aatgacctgt aggagtttgc acagttaata aacctagagg tagataataa   82440
gccagagcat cctagttagg gaacaaagaa agctctgtga cagctcaggg acaggctatt   82500
ttttgaggaa aaacttgatg gaagctgtta agttgttgag ctgtgccatg aagaatatat   82560
gggtgatgga agggattcat ctattaaagc atctgatgaa tggaacattt gaacacagaa   82620
atctatgtta agcagtttgg tgtcaatcgt tgctgttgtt actacttggg tgttaagtgt   82680
ggcgtggtaa cagaagctgt gctttagcat gggctgtttc tggcagtgcc atatcatgaa   82740
agttcttttt ttttttttttt tccttttaga aacaggatct tgctctgtca tccagggtga   82800
agtacaatgg tgcactcata gctccctgca gcctcaacct cctgggctca agggatcctt   82860
ccatctcagc ttcctgagta gctgggacta caggtgcact ccaccatacc tggctaatct   82920
ttttagtttc tgtagagatg gggtgtcact atgttgctct ggctggtctt gggttcaagt   82980
gatcctccca cctcggcctc ccaaaatgct ggcattacca gcataagcca ttgcactggg   83040
cccataaact tttttatgtt atccacagct gctgacccta tactttctag ggtagacaag   83100
ctacctaaga tgaaagggtg gcaggagaac aacagggaaa gaagctggaa agtcaaccag   83160
ctttgctagc gattttacaa aaaaaaaatg tattcgcttc ttttatagat accactggat   83220
ctaattcaag atataattta tagcatggtt ttcatccttg aatagctccc atcttttctg   83280
agggtcttac aaacttttct ggcattctgc attagtcaag agatatttgt gttcaaatgg   83340
tagaaggcaa cctagcctca atctgacttt gagggaaaaa atggaaattt attagaaggg   83400
ctatgggata tccaaactta ctgtaaaagt tgagaaatca gattggcaga atggcaggga   83460
tgcagctaga ctttagacac acctggaagc attgaatcca aggacatcac caatcttcat   83520
atctcgttct ttgcttcttt ctggaaatag gcttgcttta aatggcagta agagggttct   83580
ctgcagtttt tgttagttgc attttgtttt tctcagtacc accagtgagg acaaagttc    83640 cataattcca tactaaaaat cccagggcgg ggttttgatt ggcccacttg actcaggagt   83700
aagaagagat aaaactgggc tgttcttgtg tataccagtt ggcaggggga gaggacagt    83760 tctcaccata aggtgtctgg aatgagcagg cactacttca cttcactgtc caaaatattt   83820
ttgagcatcg attatatgcc agacatgcct tagaggctga gattgtgaga gatacaagca   83880
ttcctaattt tgagagatag gtacttgtag gcagaaaagt catggtccct gagagatgtg   83940
caagcaccgc cctccacccc taccccccag ccaactcgcc cattcctgga acctgggaat   84000
aggttggagg catggcacct gacttcttca atactctgcc ttaaataatg acttcaaatg   84060
gcaaagggga attaaggttg ccgattgaat taggtttgct aatcagcaga ccttccaata   84120
gggagaatct atcctggatt ctcatatata ttaacagaga ccctccactg tggatgcaga   84180
agactcaaaa ggagatcaga gttggtgtaa agcaacgtga gaaagagata cctggacatt   84240
gctggctttg aatatgagag agccaggaga aggaacgca ggtggcagtc tctagaagcc    84300
ggaagagaca gggaaacaga ttttccttta gagcttccag caaggagccc gacagccctc   84360
ctgataccct tgattctagcc ccatggaaga aactctgacc ttagaactgt aaaagaataa   84420
atgtgtgctg ttctaagctt actaagtttg tggagatttg tcttagtggt aatagaaaac   84480
taaggaagag ttttatcacc ctgtaatatt atttgaaatt cataatgaag tattactctg   84540
aaaacaaaag ttcagagtct ctgaagttgt ttggtttcgg gccttctgga cccctctcca   84600
ttctgggatt ctacttccaa gaatttctag ttgaaaacac ccttgggcac ttagagcttt   84660
```

```
ctaccttgct caagcatgct aaggagatca tatcaattct tattttaggg cagacatttt    84720
tcagattttt aaaaatgtat tttttaaaaa tttgagagat aggtaccctg tctctgaatg    84780
gggtcttgca ctgtggccca tgctgcagtg cagtgtcaca gtcatagctc actgcagcct    84840
cgaactcctg gccgcaagtg atcccccaac ttcagcctcc tgagtgtctg ggactatagg    84900
ctgagactac tatattgagg ttcagagaag aagcatgtcc aggtgtctgc aaattagaaa    84960
atggtggcag atttttttaaa aagaaacga tgaaaaatta tccctgatta gatttacatt    85020
acaattttca gccaccatga ctggctagtt tttaaatttt taaagagttg gagccttcct    85080
atgttgccca gactggtctg gaaccctagc ctcaagtgat cctttcatct caaactccag    85140
agttctggga ttacaggtgt gagccaccac gcccagtgac attttgcaaa tttgacattt    85200
tgcatcatgt taatatagcc tcatggccaa ttgtcctaaa tggtatattc aaagataat    85260 actgttttga cacagaaagg taccaaaggg tcatttagaa tttttcagg aagctataac    85320 agatttccag agtagatggc tttgaatgac atataacaaa ataccgaaat tgttctttcc    85380
tcatctgtct ccacagagtt tcactcaaga tcgcggctgc acctttacat gtcttatttt    85440
cctacttaca aacactgctg acaaaatcct ctgtgttccc cactccttcc ggctacacct    85500
taagctgtgg tctcttctgg gcaaagtgat tctctgacct tttcaagcta caccttgttt    85560
cctcctccaa ccaaaacttg tttgctggag ttgaaatgcc agtttagccc cttagcagat    85620
cagtcattat gggcaagtga cccagcttgc ttgggccaca gtgtccttat gtctaaaata    85680
gaggcggctg agaggtttaa ggttttaatc catataaagt gcttagtagc cagcacgtac    85740
aagcaccctg taatctgatg ttagtgcagc atcattaata acagaaaagg gaacccgaaa    85800
atttcagcaa aattgcatgt gcatagtggg tctggtatgt atattagtct aggcataata    85860
aatgttgaac gtctgtgaca taactattgt agtagtagag gggtaagctt aagaagtaag    85920
accaataaat agcccatcat ttctggcagt ttctagtatg gttttaacaa aagggaattt    85980
tgggaggaat aacattttta aaagagccc actattatca ttctgcttta ttcctaactt    86040
tagtcctttt gagcctgtgt tatcaaatgg attttgagca tatgtgaatt agagaaatta    86100
atcactagga aaggattaga attaacttt ttggaaaagt tccttaaacc gtgaaaaggc    86160
agtaacacca ttctttgtgt gtgagattaa agagaaatta attttctttc tcttcttgtc    86220
tagacacaca aagtccaatt gtacgcatac agtcacaaaa tataggtgaa aaacgaaaac    86280
tgtgttaaca cggtgagaca gatgttttaa ccaatcaaca tcaacatgca actaggtgaa    86340
aataattaaa ttactccagt tttcatctgt cagttggatg tttgacattg tgtagacaca    86400
gcttataagt aaagataatt atgaaagatt attaaataaa gatctccctg acacggatta    86460
attgaaaagt atttagtatt ttttgtaagc acagttaaac tggagtggat ttccgatagc    86520
atgtgtctct cccccagctc aaaaagcttt cagcaatttg aatactgagt aataatctta    86580
ttgagggttt agaaattaca tatgtttgga ataatactat ttagtagtat gaattatgcc    86640
tgtttgaata attaagaaat atcttttcct aacaaagaac attttccctt atgtacataa    86700
tcttccaata catgaatttt aattcaattc aatttgcaat ttagattctt gtcataattt    86760
gaacaaatac agattaccta gaatatatta aaaatcaaat tttcacatag tgcatatcat    86820
aagaattttt ttttagaaat tgtcagagat agaaacttta ggtacaacta gtccactgga    86880
atatttggcc atttaaaaca attagctcat tatttatttg tggagtcttg cttcctaaga    86940
tgttgtagtc ttatttgttg tcaattaata ttgctggttt gaacatggtt atttatttc    87000 cgtactattt tagccaagct attaattttt attatttatt ttttaatttt tatttttttt    87060
```

```
atgtttgaga cagtcttgct ctgtcaccca ggctggagtg cagtggtatg atctctgctc   87120
actgcagcct ccacctccca ggttcaagtg attctcctgc ctcagcctgc cgagtacctg   87180
ggactatagg tgcccaccac cacacccagg taattttgt atttttagta gagatagggt    87240
ttcaccatgt tagccaggct caaactcctg acctcaggtg atcctcctgc cttggcctcc   87300
caaagtgctg ggattacagg tgtgagccac cgtgcctggc ctagccaagc catttaacct   87360
ttaaatattt agtgtcctca gctattaaaa ataagagtaa tatgattata catcctatga   87420
atttgtttta taattattgt gatttgggag taaacaacta tataagaaat aattataaaa   87480
gagataagat tagtgcatat taagactttg atgtcaggtt aattgaatgt taatcccatg   87540
actttatctt tcattgcaag attctttgcc tgagtggggt actggaagcc attgttgaga   87600
gtagatccga tcttactaga ctgttggctg gttctcctaa aaccaggctg ttttcataat   87660
gagttagttt aacattttgt ctttatgttt aagcacccct ttccttggtg cagtcacagc   87720
caaactgcaa acagaaatcg agaagttgtg agctccagat ttgagagcca cagagagttt   87780
gtgagatcaa aaacatccac tctcagtaaa taaatcagag ctacctaaat cacacagtca   87840
gcttaaaggc aagggaacca gagggaaaaa ctccaaagga gtgatctctt catgcaattg   87900
ctactggtaa aataaagcaa agatgagaca gtgtagtctc caccttatta tttcaatcta   87960
atattctata ttgaggttca gagaagcagg tccagatttc cacaaattag aaagtggtgg   88020
cttgctcttg taatcctagc acttggggag gtctaggtgg gtggattgct tgagcccagg   88080
agttaagacc agcctgggca acatgacaaa accctgtcct taccagaaaa aaaaaaaatt   88140
agctgggcat ggtggtgctg gcctgtagtc ccagctactt gaggggatga ggcgggagga   88200
tcacttgtgc ttgggagatc aaggctatgg tgagctgaga tcacagcagt gcactccagc   88260
ctgggtgaca cagtgagacc ctgtatctaa aaaagaaata aaagagaaac atttccttgt   88320
tagactttac gtatctgacg atgacttttg atggtgaagg taggcattgg tatgtggtct   88380
gtggtgtgtg tgtgtgtgtg tgtgtgtgtg tgtgtgtgtg tgtgtctgtg tgtgaatgct   88440
attgaaggaa acccggtagg agaaatatcc acaattcagt taagatcaaa catgttacaa   88500
tttctcggga agtgccaagt tttacaacac ctaaactata tcctcttcct ctctgaaacc   88560
ccaaacatcc caaagtctcc ttcaagccag acatcctctt ggtctactgt gcatggtgtc   88620
tgcacggtcc tcaagtttgc ctcagggaaa gtgcctgttg ccatcagaaa gaagaatgc    88680 agcaggtact gatttatctc aggcaaagga gctcttgtgg tgggtttcaa caagatatga   88740
aaattgtagg ttcttgaaca ctcctttct tcttccttaa aatggatgtc tttagctaca    88800
ttctactctc ttctctgtct tttatgacat aatcagtcat tcactcaaca agggaacatc   88860
taatattcac ctaacatccc atttgcctgt cacatatgga ctttagcctc cagtcgggcc   88920
aatgacacta ttgatctcct aattccaatc tagactcttt gggtattttt ttctcttttc   88980
cattccttat tttctttaga ggcattttag ataactcatt taaaattat tagtaaataa    89040 atcattattt gcaatcagca tagacaaggc cttgggtgag tctaagtgga tatctggaga   89100
gatctaaacc cgctgctgga aaagtgagtg ggaaagcccc attgatatgt gacccaacta   89160
aaccaacgtt tcatcaaaag cagtgtcttc agggactgct ttaggattc agggaaaga    89220 aaatggaggc aaatctgaaa gtggatgttt tctatggagg atccttgata gaaaagtttt   89280
cacccagcct tgagtgaata tgcagagcgt aaacacatgt ttgtgcagtg aggaaatgct   89340
gtctatgttt cctaaaatgg aagttcttgt ttattgcttc tttagctgca cggagacata   89400
```

```
aaagatgcaa aactggggag aagggagaga taaaactaag acaaaactgg aggagggtgc    89460
aatgatgttg taatttaaca tgcaaaatac tcacttgggt attttttaaa ttgttacatt    89520
gtgacattgg agggttcata aatggaattc catccaaact aattctaatg cctatctttt    89580 cttttagca gactatagaa taaagttaaa tcaaagaaca tgaggtccca ttcttaccaa    89640
attcaaatat acttttatc acctggtgtt taaatcatta atacaaaagc tttcagtctc    89700
ctccaaattt ctattctagt aaagtactt cataatttta tattggaaat gtactaatcc    89760
agataactag tatgaaatca agttataata ctattttgca tgtttctaaa atgtttacat    89820
ttaaaaatag agaagtaagc cttagggaga aaacttcagc tttcccaaga atattaaaat    89880
gttaacaaat tatttcattt tgagctaaaa tcagataata atgagaacaa atttcaccat    89940
cgcacattct acagggatct ttgcatttta tacttttttt tttgttttgc tttataagag    90000
gggattttgg tatattgaat atcatactgg aaatttacct ggacggaaac gatagagtca    90060
acttagactt taatcacaga atgataacat cttccaagga aaggagctt ttgaggtcat    90120 ttcaccaaaa ctctttcacc atacagtatt ttcccgttca ttaacctttt ggcactctaa    90180
gcagagatga agtatcctcc cctgagttcc tagaagttga atttaatcac cattttacga    90240
gtctgccctc cccagtagat ggtaaaccct ttgaagaccc agagcatttt tgagataaaa    90300
gaatgaatca tatacttcag tacatggaac aaatgaataa acctgtagtg cctggccacc    90360 cagcttttt tttgaacctg accgataaag acgtttacag cttttaatt tcattatcag    90420 agaaagggtt ggcaatattt acctgagcac tctctacaaa cagagatgaa gaaatttgga    90480
atgtttcctt tctctcctaa tacatagctt tggaagtctt agaaaacatg ttggtatgtt    90540
ccttctaggt agtcttttgc aagcatcctc ttcagtgtca agcatctatt ctcatgcatc    90600
acattacagg ttatgaatat acccagagtt tatgtgagat ctttttttgt caaatgcatt    90660
aaacccttgg cttatatata ttgagctgga agccacaagt ttttgtaata ttttaaagt    90720 aatatatttt ataatatgcc ttagaaatta aaaagaaaat agaatacctc cacttcctat    90780
gacaaaatgt cagcatatac agcaaggcaa agccatttgt tgctgaagct cagttttcc    90840 caccggatgc tgaatgcaca acaatcacca gccaagccag gagtctgttt actgcacgtt    90900
tccctgaaat gccaagcccc tgaggtgtta caaggaggga aggcagcata catgtgtgat    90960
agaatggcca ataaactaat tggtttatag ttttgagaaa gcagctggtt gcctgttttt    91020
aaatgcagtg gtctataatt tgatagaatg cagaaggaat catttccaag aaattaatta    91080
aagttcatag gttggaaaat aatggagctc atcattaggg aaagcttatt ctaagactta    91140
ggataaaatg agcttcctct tgcatttcat tcaacttaag gttttgtagt tacttgtcat    91200
catcaaaaat atcatcagag tcatcgccat catcattatc taaatttgag tagctatgag    91260
aaggtattgt gaggtcctag ctttagagga atcaatttct ttgagatttg atattgttat    91320
tttaagactg cagagcatag gttagaatct gtgttttaaa aactttgaca ggccacgtca    91380
taggtagtaa agttttctct tggcatgagt tttgagttga cttgtgttat ggttgaattg    91440
tgtctctcaa aaaaattgtt tatgtcttaa ctcctggtgc ctaggaattt caccttattt    91500
gaaaatagga tttctgcaaa tgtaatcaag gtaagatgag ttcatactgt gttagggaag    91560
atcctaaacc caatataatt ggtgttcttg taagaagaga cacaacaaca aagacagaaa    91620
cagggagaac accatgtgag gatgaagca aacgttgaag tgattcatcc ctaagccagg    91680
gagcactgtt ggaaaccacc aggaaccaag aacaactcaa tccaagacag aagcatgaaa    91740 tggatttct ttaagagcct ctagaaggaa tcatcttaat tttggactct gccccagaac    91800
```

```
agtgagacaa tgcgttcttg tttcaagtca ccaagtttgt ggtaattagt tacaaagccc    91860
cagaaatgaa tgcagtctgg attaggtata ttctgcgtac atatgctgcc taagaatgcc    91920
agaagccaga agaggtgatg tctgcatttt tggttcctaa atcctctct cagtacccac    91980 tgctctgtcc agggcaaagc tcccctgaca catttttagc ctttaggcta tgtcctatct    92040
cccctgctca ccagagaagt aggtcttgga ttccagtctc tcagggctgg cattttccaa    92100
gtgaaagaca ctgcctttgt gtaaatcctt cccccttgag tgtaggcagg acattggatt    92160
tgtttgtgtc tcatggaata tggtagagat aatggaacac cacttccatg attatgttac    92220
ataagcatat aaattgtgtc ttactagtat acccttttg ttgcattctt ggtttccatg    92280
ctttgatgaa agagcagcca tattaaacag gtgcatatgg caagaagctc agagctgcct    92340
ctgaaacaac agccagcaag gaacagaggc tttcagtcca gcagtccaca gggcattgaa    92400
tcctgccaac aaccacataa gtttggaagc gaaccttcct cagttattca gctttaaaat    92460
gagaccccag ctcaggccaa caccttcatc agtgagagac ttcaaagcag tggaccctgc    92520
taaggttgtg cctggattcc tgatatgcag aaactcataa aataaataca ttacttgaaa    92580
ctgttaagtt ttggttattt gttacatagc agtcaataac taatgtggca taatatgcaa    92640
aacatggatt tcagctgagc acagtaatcc cagctccttg agaggctgag gtgggaggat    92700
tgcttgaggt caggaggtcg aggctgcagt gagctatgat agcaccattg caatcatagc    92760
tcatggcagc tatgagcctg ggagacagag caagaccttg tttctaaaaa aagacatgga    92820
tttcaaattt ggccagattg taacccaact tctacataga tattatgtct ccattggagg    92880
gatatatatt ttgagacttt gcaatcctta attacttagg aacaattagt tagcaagtga    92940
aagaaattca ggttgaattc acttaaggga aagaagaga ttttcgggtt ccatttacta    93000
gcggtgcatt tagtttcgaa aatggtgtcc tcaggtctaa tcattgctgt taggaatctg    93060
gcactttggc gccatgtttc ttctttggct ttcttagaga ggcttgtccg tgtgtggtgg    93120
taggcagtca acagcatttc ctagtatgtc atccttttct cagagaagca cattggccta    93180
gcaactatgc gtactggcct aattttagtt gcatgccaac caatgtctat atccagtgga    93240
aagagatact tgaattgata tggactgctt gggttatgta tactcttcag aaatgagaag    93300
agattgggta agtccagtag gcttagggta gatggaagta agattgctcc ccagaggaaa    93360
attgaatgct aggtaagcaa aactcattga tgtccattgt tgcttatatt acaaatagta    93420
ccaaacaaga aagaatggca tggctgcttc atggaagagg atgaacttg ggggcaaaac    93480 cttacctagg atatttcctt ttttcagcta aaaagaggaa cttggacatt cagaaatgag    93540
aaaacttgta tatcagttgc tgttgttgtt ggtttgtaaa cagctgtagc tcttagtgac    93600
atagagagat aaagtgacag gaacagatga ggatatttct attaggatgt tatccaggca    93660
gttctatgtt gggagtcacc ctcctgggac actcctgggt ctggaagctg tcagctggtg    93720
gcaaatcaga gatagtctga gatttaatgc cagatgggaa acgtgacctc aaatgaatga    93780
ggctgtttag gagtgggcgc aacatgctgt gcttgccatc tcttttaaga gttctaactg    93840
aaaggttagg tttactgaag gataagccaa tttggggagc tgatctggtg aacatgaatt    93900
tggccaaact tcagcctaag cgtttagcag ggtgaaagtt tgggaagagt ttcgttgtag    93960
aacattaggc aaatggctga caaaagagct tccagttctc tcacaaggaa ttcttcaaaa    94020
agcaaaggag gtccttctca gtcagcctgc tctttctgct cagtagactt ctttgtgaga    94080
ctatgctgtg agtgagttct caggctggtg atataacctg gtcttcaatt cttgtgcagc    94140
```

```
tctgtaagtc cacgtaggca ccactaaata tccttacgac attaagtgtc attggattgt    94200
ttgctaacat ttgcttccat atgggcccca ggcattagca aacatgtagt ttattcattt    94260
atttattcac tcagtgaata tttattgaac ttattctaat tgtcaggcca ctttgctaaa    94320
tgttgttcca tcactttcct tgcagaacat acagggaaaa atgcacaact aactggaatc    94380
atcatttagt gtaatccatg caatgatgca acaagttggg gagatgtgag aacatctggg    94440
agaagcatgt gtcccagact gagagggtga aaatgcacta aggagaaatt tgaagaatca    94500
gtaactgacc aaattgctgg gaggagagtc atttcagaca gacagaggag cacgttcaag    94560
gctgaagtcc acagcctgac attaatatcg attctcttag ctaagttttg ttaaagaaac    94620
caaatgacag tgaatttgaa gtcctgcact cagccaaccg tatgaagtgt agtcactgta    94680
tggtcagtta attacagggc agcatccttc agtcatcagt cgagctagag agaatattga    94740
cagatgtgct cttatgaaag ctgagaagct caaccaggac aagtatttag ctaaaagggg    94800
gtctgacctc ctttagaga tgggaagcaa gggtggacag cataacctgt agactaaatc    94860
tatcacactg ctgtttttgt gaagggttta atggaacaca aataagccct tttatttatg    94920
tattgtctat gtctgctttc acactacaaa gacgaagttg agtagttgca aaagagacca    94980
tatggcctgc aaagtctaca atatgtacta tcttacccct tatttttaaaa agttttctga    95040 cccctgatgt aaaggaccaa cttcatgaag tcgcatgtgg attttctagt taccatatag    95100
acatgaatgg aagagtacag aagttccatg tcagacagca attgttttca aacttgctat    95160
gaattttttc caaatgcaga ttcctgggct ccatccaggc ttccagtgac tcaaaatctg    95220
ggtatagatt ccaacaattt gccttttagt gaccttagag gtgatattga tggcaaaaat    95280
tttatatatg tacatattca tgaaacagaa aattggacgt gaaatatttt taatccacat    95340
ataaacagat actcctttct gtcattaaaa accaattagg aaaaaatgat aaaagcctga    95400 tttttaaaacc atggtccata tggcttatgc aagataattt tctgaagtga ccttcaagat    95460
gaaatagttg caaagtatat ctgtgttcag ttaaattagg aggtgtgtgt gcaacaagga    95520
attattagcc gtagatcttt aaaatcaaat caatgtaaac aaaacactgt cagcccagtg    95580
gccaaagaac acaatcaatc aaaatatgaa taaatataca caattataca ctactactac    95640
tagatgatga tgatgatggt gatgatgatg ttatgatgg tgatgatgag gatggtgatg    95700
gtgatagtga tgatggtgat aatgatgatg gtggttatcg tgatgacgat ggtgatgatg    95760
gtgatggtga tggttatgat gatgatagca atgaagataa caattattgt gatgataatt    95820
tatggcgata ataatgattg tggtgatggt ctgtttctat gcgtcaatct cagttgctcc    95880
cccagactcc atacaaacag aaccaccta gagatgtttc aaacttacca tgttcgaaac    95940
tcagctgctg cttttgacac aatgaatgcc ctcctgtctc cattttacc atcttaggag    96000 aactcacacc atcccctcat cactcagtga gccaagtgtg ctagctgctg atccacatgt    96060
ctgaatggcc gccttgagga attgacatta ccttggggac ctacagggag caatgatgct    96120
ggactggggc aaggatgaat aaaggaggga taagtccaag ttgttggggg aagacagggc    96180
agccaactct atctggagct ctcagatggg tttagcggtt gtggagatat ttccaatggc    96240
attttgaaga cgtggaagaa tgttattagg catagcagag attcttaact aagagcaatt    96300
ttggccccac tgtaagggac atttgacaat gtctagagat attgttggtt gtcacagctg    96360
gggaggtgct actgacatgg agtaggtggt gaccagagat gctgctgaac atggtaaaat    96420
gcagaagaac gactcacaca gcagagaatt atctagtcca aaatatcagt agttctgata    96480
ttgagaaact tggctctgta ttgtgcatgt gtaatcgttt tttacttact gattctagat    96540
```

```
tcagctggca agggggtgtc agcaatgtct ggagatattt tggattatcc catctgggca   96600
gtgtgtgctc ctgacatcta gaaggcagag gatgctgcta acatcctac aatgcacagt    96660 acagccctca caacaaacat aatcatccag cccccaaatg cccacagtgc tgatgttgtg   96720
aaaccctgct ctaagtcaaa gcattgtctt actcaatttt taattcctag tgtatatcag   96780
tggttctcaa ctttggggag gggacaggtt tgcttccagt gtacatttgg caatgtggga   96840 agacatttt gtttgttgtg agtatggagt gtgttactgg gaatggaggc aagggatgcc     96900
actagacatc ttaacagtgc ataggacagc ctccacacct cagaatgatc tggcccctaa   96960
tgtgaacagt actgaggtag agaaaacatg aggtagactg tagaagccta tagaagaaga   97020
gaatctgaga aaattgttgt gcttgggaa cactgaagaa tgtggagcaa ttgaacaaat     97080
gcttgtgcag acagattggc accaaattgc aatggagcac caatgggaca gtgaaaaggg   97140
acaagtccta caatgcacag ttcttgacca tccccaaagt gctccaaagc tacagaagtt   97200
ggtgtgcatg tattatctca ttgatcctat ttgggaatta tcatgttgac agctggagtc   97260
ccatgaagga acatttttaa gcagcaaagt gacaagctct gatttgcctt tgagattaa    97320 tgactcagag actgccagtt atttgttaac ttgcttgatt cagcctaagc agacatctag   97380
agggtgtaat ttgatttatt ctgcagaggg gtgattggcc cctacattat cttggcacac   97440
tgcctgaatt tctgaacacc aaagacttat ttatttagtg tatggccatc tcatttccaa   97500
gagtcaccaa agaagtgaga atggattaga tagggaacaa gctgaccatt ggattagttt   97560
atcagatgat tagcatgcca tgctaattta tcaagacatg gaacatttaa agaaggggag   97620
agtaacatat acagggaaga taggagatct ttgtcccaat tatttctttt tttttaatgc   97680
atgaatagtc ttttggtaaa tatagtttat gtttgtttct gctttctaag ttaggctgca   97740
aaatattatt tatcggtggt attctttgaa attgattggc atggcaagac tgtaaaagag   97800
tatccatagg tgtatttaaa aataaaagat cgtcttttca tctttgcaga aaaacatgta   97860
tttactattg cttggaatag aaagcagaat tttgctgtag ccattaggaa gtgacaaaca   97920
ctacgccata attatagtga gaagaaagca tcaaaaagaa atgttttggt ttttttttata  97980 tacagttggc acaaaaatgt ccacatatat gaatactcta agaatgcac cataaaaaga    98040 accttccacc actattaaca ggattaatcc gtgctcatta ccatgggatt ggggatacat   98100
ttttacatgt tcttgattag attcaagagc caaagaataa ggcctaattg atgaaagtgg   98160
gctctaattt tgtgctttta aaataatggc ctctggccaa atatgggcaa aagaaacagc   98220
acttgatttg ttactttaca tttgtttctt gcatcctgct cgaaaataga gatgatttac   98280
agttttaata tattttcat gcacaattaa catcattgtt gccagtttta tagaagaggc    98340
aggaaagtgg gccttctatg atttattgtg agtgcatgaa acagaagtaa tgctactagc   98400
aacagagttt tagtaggaaa aagttaaagc acacagtctt aaaaaggaaa ggttggtgtc   98460
aaaattatgt ttgctttagg taagctttat acctccatgg atggcttttt ttatagtaac   98520
aacaacagta actgtattta cattggggcc ttttctctgt ttcagaggct ttcatgtgga   98580
gtgccaaaat ggtaaaatat ataacattgt tatatgaagg agtgagggaa aatccaatca   98640
agattggcat ttttttaaaaa agaaaggag catgggaat atttttaaaga tttggggcca   98700 agcctcgtgg ctgatgcctg taatcccagt gttttgagag gctgaggaag gagaatcact   98760
tgatccagga gtttgagacc agcctgggca acatagcgag acctccacct ctataaaaaa   98820
gactaaaaag ttagctgagt gtgatggcac gtacctgtag tctcagttac taggaaggct   98880
```

-continued

```
gaggtgggag gatagcttga gcccaggagg gccaggcttc agtgagctgt aatcacatca   98940
ctgcactcca gcctgggcaa cagagcaaga cgctgtgtct caaagaaaaa aaaaaaaaaa   99000
agatttggta tctttctttc ccccacagtt tgcatataca ttgaaaactg tgcatttaag   99060
ccaaaatagt ttttttttt aaacatttca ctataaaaaa ggagtctggc tttcacatgg    99120
gtacatgatt ttgctttggc ttcttcaatt cccacctgcc ctgttgtgag acccatgaag   99180
taagcaaagc attcttttg ccacggaaat gaaactccta acatattgt ttattgtcac    99240
ataatggaaa ggagaaacgt ttcaaaaata aggatacatg aagcccttat tgaaaagcaa   99300
tcatacattg gtgaatttaa tgttttggag caaaaactgt tatgttggat acctattagt   99360
cttttagct agtgaaatat gtacaaggca aaatcaagca tcaatagaag ggtctaacta    99420
agcttgtttc tcatatggtt tctctgccag ctcacacctc aagggtgcct cctgcctgca   99480
atgtgtactc tctggtccac acactgattt ccccttttct gtttcatggg gtgacttgct   99540
gaccttctct gtgcatggct agtagtactc tattgactgg caagggttgt gtcttccact   99600
tgggtcttcc aagctgctga agaaagcaac acagaaagta tagctgacaa taattatctg   99660
tcaaatgtat gtgaatcaca gtgtggatgg tcgacctgtt gtttctttt tctctttgaa    99720
aggaagattt cagttttctc tgcagccatg gtactttata aattatttcc tcttccatct   99780
cttaaaagtc actgttattt accaccccat tagctgtgga tggggtgaaa tgcccactca   99840
tgcagcacag gaggatacac agattgtcac acatctttc aggagaccac acagcagtgg   99900
gtagtgtagt attaaataaa tgcctgaaat atgagctggg aatgcattgc acttcaagga   99960
attttatcca taggatgtaa ctgggaaagt gcagaagaat gcatatatat atagttgttc   100020
attgttacat gttttatgat agcaaaaaaa aattaaaaaa tattcaactt tcattttaga  100080
cacggatttg caggtttgct acatgggaat actgtgtgat gctgaagttt ggggtataga  100140
tcccattacc caggtagcga acatggtacc caacaggtag tttttcaacc cacatccccc  100200
tgtcttcctc cccttctagt agtccctagt gtggagtgtt cccatatta tgtccatgtg   100260
tactcagtgt ttagccccca cttataagcg agaacatgtg atattttgtt tgtttttcta  100320
ttcctccatt aagtaaccaa aatttttaac aatgtagaat ccattacata attagagata  100380
caatacaagc attgaatacc agctgttaaa atggcattac aggataatat ttagtgatat  100440
ggaggaatat tcagagtgta ttatatacaa acatttcat catatcgttt tttactagag    100500
tggactgtca ttttcttgtg ggctcccttg tattatttac tctattgcat ctcagttttg  100560
ttgcatatta tgtaaaatag aagataatga tagcttggcg cattctctgc tgagactatt  100620
tacagtggtg taaaagatg ttgccagggg tgtgtgcctc agtctgtccc agccttcgta   100680
gggcccatg tttcaactcc ctaatgaccc attgaagaca cacgggcaca caggggagaa    100740
tgctctggtt taaacagtca accataagcc agacacagtg gtgcaacctg tgttgcacct  100800
tgtggtagcc tcttgctacc caagaggctg agacagagga tctcttgagg tcaggagttc  100860
aagaccagcc tgggcaacat agcaaaactc ccattctaaa aaattaaagc aaactcaacc  100920
attttgagtt ttacatgttg taaatatctt ctcccactgg cacccaccca tcattcctgg  100980
ttttgattga aacaaaacca ttagttttaa tgtagcaaaa tgccatcaac atattttcct  101040
ttctaacggt ttctcctacg tagtgcctgt taaagaaatc ctgttctacc ccaacatcac  101100
aaaaacattt tcctataagt atcagaattt cattgttcat acagacagtt tttaatccat  101160
gcagagttta tttttatata tgaaatgagg tgggaatctc atgttatttt ttccccaat   101220
aggggaacat tgctttgaca catgaaggaa gcaatgtatt cttttttttc ttttgagaca  101280
```

```
gagtcttgct ctgtagccca ggctggagtg caatggtgca gcctcagctc actgcaacct   101340
ctccctctca ggttcaagcg attctcctcc ctcagcctcc caagtagctg ggattacagg   101400
cacacgccac cacgcccagc taattttttgt aattttagta gagatggggt ttcaccatgt   101460
tggccaggct ggcctcgaac tgctgacctt gtgatccacc ctcggcctcc caaagtactg   101520
ggattacagg catgaaccac tgtgcccagc tacaatgtat tctttcccaa tgatttgtgg   101580
tgtcagccag gaccttgata gggataaatg gcatgcaact tgagaaatgt aattaagatg   101640
gggacaggat agtggagtcc ttatgtgaag ttgctgatgc ccgctgaggt tgaactggac   101700
ctacctacca gggagggaac tggaggtcat atatacaggc cttactcgcc ttctgccctc   101760
cggattacct gctagtgtct tccttggctg aaacccagga gcagccagaa ggcaagagtg   101820
aacctgttta tttaccttcc acaccagaga ggagtggaga tgaggaaaag tcttgaaggg   101880
gacagactcc tccccccaca aaatagtaca agcttttaaa attcatcata tatacatcag   101940
ccaatccaag ggctttatat ttggtcttgt tgatttcctg atccattcct gcaagattaa   102000
agtatgactc aaatagtaca aatgcccata tatttttcat cttcaacatt ctcgttgctt   102060
tttgtagaat ttattctttc atatacaata tggaatcaat gtatcaaaat ctgcaacatt   102120
cttctgtctt tgctgggaat tgtatttatt gaaatgttgg tttgaggaaa ataaacatc    102180 ttccaagctc atgttatctc atttgtaaac tggcatagtt cattacttgt tgagatctaa   102240
tcatagcttt attaaagact ttgagcatta tgtgttaatt gattattatt attattttgc   102300
aaatgatatc ttcaattaca ttttctactc ctggtataaa agaatgtcga tctttttttat  102360 acattgatta tatgttcagc catcttttt gattccctat tatttctagt agcttttctg    102420
ttaaattaca tggtttccat aaaaatggtg acattatgta caaataatga ccatttttctc  102480 tcttttccttt caatacttgt aattttcatt tcctttataa cttgtaccat tgtatggccc   102540
actgacgtcc agtgcgagga tgaatactgt tggtacaaac ttttgttccc attcatgatt   102600
ttacaggaaa tgagtctaac atctttttg taaatgcagc gttgaggaga gattttaaag    102660
catgcagtca ttatcagata atatgaatta cttgcaattc ccagtttttt ctaagttttt   102720
aaaaaatgtt ttcttttgtt cataaatgtt gattatgacc aaataatcaa ctggcatttc   102780
tacagctggt tatatgattc ttctcttata attaatgtgc tctgaaaatt aatatatttt   102840
taaatatata ttcaatttcg ggaataacac atttttaatc ttaaaagaaa cattttttaaa  102900 atggccatta ttctattata gtggaatata ttgtatatga aaaatagcta ctattctact   102960
aagtttggtt tgtaaatatt ccacttaggt tgtctacatc taccttcata aatgaatttg   103020
atttataatt ttctgatgtt atacactcta tacttttgat atgaatgtta aactgtccat   103080
acaaaaggat ttgggtagct ttcttttaatt gtatatttc tgaagaaaac ttaaataagt   103140
agaattacta aaattttgt gaaaattatc ttgggtggtg agtttttatg tgggagattt    103200
ttagtgattc tttcattact acttatagct tttagtttat tcattttcttt gcgtaaagtt  103260 gcttgttttg tttttttcct caaatatttc aatttctttt tttaataccca gggcttatac   103320 tattaaaata gtattttgta ttttttataa cttttgttttat ttgttatttt aaaaatgatt  103380 ttcctctttta aagactattt gttctcatta tttgttgtat attatttgtt gtatattgtt   103440
gtatattatt tgtttcatta tttgttgtat atgttactct tccttggtca gtcttgccag   103500
aagtttgttt atattattaa gcttttcgat aaactagctt tcattttggt aattagctca   103560 actgttttttt ctctgtttcg ctaatttctg ctcttacctt gatcatttcc tattttcaga   103620
```

```
tttatttgga tttattctgt tttctcttct tcctgtttct tgacttgcct ccatggctcg 103680
tttatttcca attcttcttg ttaccttgta aagatatttg aagttttaat tatcccttt  103740
aagcacttct tcagtcccat ctgacaaatt ttcacatgtg acatttgaac tatcactgga 103800
ctctgactgt tttgtgttta tacggtagca taaaggcaca tgcacacata tacatacaca 103860
catagatgtg tgtgtgtata tgtttagtgt tctatcatta ttttgaatgc ttttactat  103920
tgatttctaa ttctgttgac cgatagaata tagtgctgaa tgctgctgtt tctttaaagt 103980
actctttatg aaaggcagat tttgtaaacg ttcggtgtgt gcttgaaagc tatggacaca 104040
tttacacata catagacata ttcacaaata caaatacaga tatacgtgta tatgtgagaa 104100
tgtgtgtttt gaggagcata ggtttccata gatacccacc agatcacatg tatgggttac 104160
ttcagtcttc tatatcttat ttgttttggt gggtggggct agggacagag tctcgctctg 104220
ttgctcaggc tggagtgcag tggcctgatc tcggctcact gcaacctcgg cattctggct 104280
tcaagtggtt ctcctgcctc agccttccaa gtagctggga tcacaggtgc acaccaccac 104340
gcccagctaa cttttgtatt tttagtagag acgcggtttc actttgttgg ccaggctggt 104400
ctccaactcc tggcctcaag tgatccacca gcctcggcct cccaaagtgc tgggattaca 104460
ggcgtgggcc actgcaactg gcctatatcc tcaattacat tttatttcct aagtttatca 104520
ctccaagaat gttgtgtttt attctactgt aacatttat  cttttcttat ctgtccttta 104580
tcttatatat ttaatgtata tggatatact atgttatata tatgtagtat gtatatataa 104640
aatgtactta tacccttt  acatgttttg aagctgtatt attaggatgt tacatgaaag 104700
tgtcagttac acctttttaa tcttccattc cttttctagt atttattatc catttttgac 104760
atttacaatt tttgtttgat actaaatttg cttcctgtga tattttttca tttatatttt 104820
gttttatatt taaaattttt agtgtcttca ttttcaagtt tatgtatcca tttatttaa  104880
atatatcttt tcaacaatat gttgctaaaa gtattttaat caatatttta tctttattct 104940
aattttattt ctgcagttat cattattata gatttcactt ctgacatttt atttatatt  105000
ttatatttat caatcatgct ttttaaattt taccttttt  ttttttttgct ttacctgact 105060
tccattatat aattttaaaa gtttctttta ctgaccttat tattatattt ttctttcttc 105120
tgttttttt  tccttatagt tgggattcat caaatttccc tcttcccatt ttatgctgca 105180
cttatatttt aatgaagatg tatctagtct tattagctat caaacatttc agtatcccata 105240
attttcctca aaacaagata ttgatttagc attttctcta ctcttcggca tctctctctc 105300
tcaatcaccc cacactgtgt tagattctaa gagaatctgg gctctagatc atgttaaaaa 105360
tttgatttta gatcattgtt tcttcggaat aattttttgt cgttacctgt attatgttgc 105420
tgtgttctgg gttcctctcc ttgcagaaat atattgtgtc aagatttctg tgatgtaagt 105480
ggatttggat ttaagctatc atttaaatga cagtttcact ggacataaaa tccaggctga 105540
ttttctttcc cttgtacttg ctgggggtga gaagccactg catttgtat  cctacgttgc 105600
tttgcaatta gcctggtttt cattcctttg cacatcgcct gcttttctc  cttggaaaaa 105660
ttagacatat tttgtttaca tttgaggtac tcaaaaattg gaatttgttt ttgctttgtt 105720
ctgttttaaa tcaacgtatt atttactttg tgagtacttt cacttttaag ccttttttt  105780
tctttcattc tgggaaattc tcagcctttc tgtctaatgt agttcttcct agtctttttc 105840
tctttgttct ctttctgggt cattttttt  tataggactg gtaacacttc tatttccatc 105900
ttccatactt tagcatttgg aggatgtttt tccaccattt ttcatcccag atccattttg 105960
ggaaaatgta tctctgtctt ttggctccta tgtgcattgt ttgtgggtat ccttccattt 106020
```

```
cagtctgttc tttgtgctct ccagttcaac aatttcattt cttctcccg gtatctcgtg  106080
tgacttcctt tgaaaccctt tgttccaact ttatatcgct atcattgtct ctctgtccat  106140
tggagggatc tgcttctttt gaatcccagt ttgtttactt gggtcatttt attattatta  106200
ttttttaaat aggatgttcc ttttcttta agtgctttgc ttttgactg gctcttaaaa    106260
atttcttggg agttcttta ttttcttgag gccggtagag gtcttggaag gtaccaagtg   106320
tccaatgggc aatcaaaagc ccacctctct gcctggcgcg gtggctcaca cctgtaatcc  106380
cagcactttg ggaggccgag gcaggtggat catctgaaga gttcaagacc agcctgacca  106440
atatggtgaa accccatctc tactaaaaat acaaaaatta cctgggcatg gaggcatgtg  106500
cctgtagtcc cagctacttg ggaagctgag gcaggagaat cacttgaacc cgggaggcag  106560
aggttgcagt gagcagagat tgtgccactg cactccagcc taggtgacag agtgtgactg  106620
catctcaaga aaaaataaa aaacaaaaaa taaaggccca cctctcgatt tcatgcctct   106680
gggtaaattg gagggaaaag agggtccctc tgtgaagagc ccttggaact cgagttctaa  106740
tttctaaacc aagaacttta tattctttcc tccctcccta tcacttccat ccactggctg  106800
gctcttatct gaaaactgtc gtgtgcagtt ataaatactc aacacttagg gaaggagaag  106860
gaattctgag agatttcgcc agcctgattc ttttcattgc cataaaattc cactgcttta  106920
ccagaaatcc ttggaatgtg cttttcctag ctttgcactg tgaccttctt cattcggaat  106980
aacgaagatg agaaaagcat tgatccgccc agacagtgag gagcgaagag caatacctag  107040
gtggaaagct ctatctcccc tgactgtcct gtgaaatgca cctgagtctc agaggactcc  107100
actgccatct gtctgtccag gaatttccca ttttgtatgg cgacttcaaa gtaggtaaat  107160
actttgatta aaggaataga gaacagaatt tgggtagctt gttcaaaaga tggcatggaa  107220
aattctgtga ctggagtagt tgtgaagcat cactcttccc gtaagaataa aggaggcatt  107280
tgccagatgt ctgaaaacac acagacacac acacaaagga attacttctg gctgcaagaa  107340
tattctctct cagcatcttc ctgcatctcc atgggcaaac agaccacaa cagcctggga   107400
tttttaatt gccaacagtt ttcattgcat gagagcctga catgtctgtt gcatgatagg   107460
gtgtgttttt atttttggct tcctattggt ttcaacatat ccctccttcc atgtcataat  107520
gacaattaca aagacctgag ttgaacctag aacgcttttt ttttgtcaga cacaacaatg  107580
cagtggatgt tagtcatagg gtaattcaaa cagagataat tttgtatatt ctagaatatt  107640
atgttttcaa acgtaggttt tgatgtacca taagatttct tctgccattg aggcgatata  107700
tatgtgtgt tgtgtgtgtg tgtgtgtgtg tgtatgtata tatatgtgtg tatttttaaat  107760
ttaaattaga tatttttag aggccttagc ccttaagcag aattccctcc taatttaatg   107820
attttggacg aagctcattg tgaatcattt aaaaacacat tcatgcttct tcaaacagag  107880
gtaacaaagg atacagcacc ttgacttgtt gactaagtgc tgtcatggta gatgttattt  107940
agcatagaag atgcctgcag ggtcagttct actctctaaa gtttcttgag gctgtgttaa  108000
atgaaatcaa acacctgtgg attttttatt cttgttcacg cttttatac ctctcctttc   108060
ttctccctgg gcaacctgct ttcacactag tgcctacctc tgttttccct tcagaatgtg  108120
atctatgcta cacaatctga ttaacaagct caacagagtt ctactggaca tagaataaag  108180
aaaccagtat agttttctct ctagggacaa ggcagtgagg aagccagttt gaatacaggt  108240
tcttgctctt gtaagcattg acattcagca ggttccttac tttctgaaca ctgcagttat  108300
atgatgggca gacagggact aagaataaca cctacctcaa cggggctgtt gtgaggatta  108360
```

```
ctgagataat ttatgtaaat ccctagcaca atgcctgact catgcgagat ctttaattca 108420
tggtagcagt tactaatttc atttatcata atgagctgcc tgagctacca aggagctctg 108480
ccactcccag tactgttcta cagttcttta attcaacaaa gaaattttc tttagttcca 108540 aataagtgcc aggcatcagg ctaggtgctg ggtgtatgat gatgatcaaa acagtgttcg 108600 tatggggta gtcatcattt tgtcgatggg ccatttttta tgatgtccct cttcattata 108660
ggtcttgatt cttgcctctg ttttgtatac atatgtgttg cggcaggggc ttgctataaa 108720
aatcagaatt gcccaggctg agcgcagtgg tgcaatcatg gctcattgca gcttcgggct 108780
tcagtgatcc tcccacctca gccttcttag tagctgggat tacaggcaca ctccaccaca 108840
cctgcctctg ttttgtgtag ctgtgattac gtagcaattt tctgaatcag tgacaagatg 108900
caatgcatat ttttttcagt aggttaatta atttatctaa tctacatttg gagctatttt 108960
ttggagtgtt agtcatcata ataaatatgg tggcactgtc aatagtaata taaatataat 109020
ggtaccttaa ttccataata caaagatcac gtcttcatga ctgatgggcc atttcaaacc 109080
cataggtaca tttgctcgct ctgtaaagta tacaaaagta agaattctgg acatctttaa 109140
aagttgtaaa ttttacatg aaaacttaca ttcacaccat cttttgaata ttgaaaagat 109200
ttgggaacat ggggcctata tgtgactgtg gatgaggtgg ggctgttccc tttagacaca 109260
gcactcactt tgccatagtc acactcccca ccgctcccta ttgtgtctcc aaccccagg 109320 ctgttgtctg tttcttttcc aacgttatta cccactcata gatggtcaac cttatgatca 109380
ttgttacttt cttttcctca gaatctttct agtatttgtg attttttca tgtggttatt 109440 ttgagctttt tgcattaaga atttgggatc acatactcaa aagtttagta tttaccagtt 109500
tgtattattg agcacttcag aaatttattt ctgttgctgt tatcaactca taaaatatct 109560
gtttaattat ccaactaaag actagatagg atagtgattc ctattttctc caagctcata 109620
tctgtgaact ccttgattgc ccaacatagg cattcaatca ttcattcaac aaatacccat 109680
tgaggaccta ctatgatctg ggcactttc taggtgctga taattgtagt gaaatagtag 109740
accacagtgg acagtgtttc tttatggaat ttaagtgaat aaggaagtta ttttggagta 109800
tttcagatcg tgattcctgc tacgaagaaa aataattcag aataaagtag ataaggaata 109860
ataggaatgg acccacacag ttattatttt tattgctgtg gtcatactga tatctgaagc 109920
aagtaagaga agagtttcct atgaggatgg aatagcatgt gcaaagaccc tggagttgta 109980
gaatccttga tgcgtccaag gaatatggag aagaccagtt gggctagagt tgacaaaatg 110040
agggtgaagt gggggtataa aatagagag gtgctggaca gtaggccgtt gagagggctt 110100
tagcttttcc gtgatgaata ttggaaccca caatgtaatt ttgagcatga aaatgagagc 110160
cttgatttac atttttatca gatcaccctg agttctggtt ggagaatgag ctctaaggat 110220
ctgtgggtat atttagggag atacttaggt ggcctttgca ataatacgct caagggagga 110280
tgctggcttc accagagagc tgatagataa gccatggcca gattctggga atattttaaa 110340
ggaagatcca acaaatcgat tattcctaga atgcagaatg aatgagaaag agacaactta 110400
tggccaaccc caattccttt ggccgccgta actggaagaa ttgcgttgcc atgtgctgac 110460
aacaggagga ttgtgagagg agcactttag ggtgagggaa ttaggagact gcttttgttt 110520
aagttaagaa caaccaagga gagatagatg tcttagagac agctgggtac agtagtgtgg 110580
acatgaagag agaggtctac gctggagata caaggtcagg agacatgagc atgtagatga 110640
tatttacagt tgtgagactg aatcgcattt ccaacacaat gaatgtagat agagaggaga 110700
agtaagtgta ctagaagaaa aagaaggatg aagaggagga gagagagaag acagtgagga 110760
```

```
agaggaaaga agcagcgtgc atgtgtgcac ttgtatgaga aagagagaga gagagggaga   110820
aagtggaaga tatagataga aggagagaga gagagactgg gggaagaatt acatccaccc   110880
aaaacccaaa ttttaatgac ttacaatatg aaagcttcat ttttttttc tcttatgttg    110940
cacctcactg atggactatc atcagcccca cttctcttcc aagtctttat tccagaatcc   111000
aggctggagg ccatgcctga actgaggaaa tggtgttcat gtacaacagt tctttcagct   111060
tctgctcaga tgtggcattg cacatccact catatgcgat tgtccaaagc attttctat    111120
tctctgggag atacttcaag gggcacaaca gtggctgggg attgaggggg ctgtgaatag   111180
actttcagga aaaaggatca gctgtgctaa atgctgctga tgagtgcagt aacacaagga   111240
tgagtaactt gagtagcttg tagagaggta taggccattt gtttcatgcc caggaacaag   111300
gcaggaccag gaatcctggt tgagatgctg cagtttgggc tagttggagg tgggggcaag   111360
tttttctctc actgctggga cttactcagg ttaacagatg ggacgttgtg gaggagctgg   111420
agacggagga gaaagtgtag aagagttaac taggagatgg attgagagtg tttgatgtga   111480
gaggcagtag agcatgcatt gaacctaggc tgtatggttg gagggttttt ttccagccat   111540
gtcctgtctg ctcaggttca gaggaggtag gaggtagatt gaaccagcca caggtgatgc   111600
tccatgagta aagaagggtt gagagtcagg aattgaggag tccaaggcat taactgaaaa   111660
gatggttcat ggaatttaac aaagatgcgg acaaatatga ggagaggagg cagtcaaggg   111720
agagagaaag agtagggttg ggatacaggg aatgaaagtg agctccttaa gatgaatggc   111780
taatcccaca aaactggcca attcccataa ggtgaacggc taatcccatt agtgcattgt   111840
tgacatgaaa atgtcctcac caaataatga agaaaaattt gattttctta tgtggaaaaa   111900
gcaggaccaa aagcaatcaa ccaaaatcgt atctactacc tggcagtcca ttagaacaca   111960
ctaaacacac acataaagag aaaaatgaag tatgttaatt gtgaaacttg tatctccaaa   112020
aactggaaag cttcttggca cttaaaagca cttcttggca cttgggatta cttgcctgta   112080
atcccagcac tttgggaggc tgagacgggc ggatcacttg aggtcaggag ttccagacca   112140
gcctggccaa catggtgaaa ccctgtctct agtgaaaata taaaaattag ccgggcatgg   112200
tggcgcatgc ctatagttcc agctactcgg gaggctgagg cagaagaatc acttgaacct   112260
gggaggcggg ggctgaggta gaagaatcac ttgaacctgg gaggcggggg ctgaggccga   112320
agaatcactt gaacctggga ggcggggct gaggcagaag aatcacttga acctggaggg    112380
cgggggctgc agtgaactga aatcgtgcca ttgcactcca gcctgggcga cagagtgaga   112440
cgctgtctca aaaaaaaaa aaaaaaaaa aaaaaaaaa aaaaaaaaa agaaagaaag       112500
gttcaatacc tacttgttga atgaaagtgg acgtgtgaat tcaaagtttc cgctctttca   112560
cagtgttttt ttttttttt tttttttttt ttgacagagt ctcggtctgt cgcccaggct    112620
ggagtgcagt ggcacaatct ggctcactg caaactctgc ctcccgggtt cacgccattc    112680
tcctgcctta gcctcccgag tagctgggac tgcaggcgcc caccaccacg cctggctaat   112740
tttttgtatt ttgagtagag acggggtttc accgtgttag ccaggatggt ctccatctcc   112800
tgacctcctg atgcacccac cttggcctcc caaagtgctg ggattacaga catgagccac   112860
cgcgcccagc ctcattcagt tctttattac atttgtaaag gtaactctaa ctccgtgaga   112920
gcactttctc gctcacctct taattcttga gcaaacagag aagctgtgca tgataaagct   112980
ggagaattgg gtggtgtctt cctattaagc ttacaggaaa gcactgggca tttgaacag    113040
atgttgcatc ttgagagcca cagagtcagg tgtgcacgtt aaaacgatgc ttctaattgt   113100
```

```
tgcatagaga cagaagacaa tcacaaagat tctgccttga cctccttacc tctccagttc   113160
taaaaacatt tctcccacta cagaaagcat ccatctatgt gttttttgcc tccacgtggt   113220
cctattcctg aaatgctcct tccaagtctg tacttttcca agagctacta tttctggatc   113280
ttttgcagtt gcttcagcaa gaatcagttc tggcttcctt ggttctacca tgccaacttt   113340
accttctcgt ccctcagtgg gatgctaggg cttgggttaa ttcatctctc tccttcaagg   113400
cgacatgaag cccctgagaa caggggcata ttttttgccca gccattacct acaatgatac   113460
aggagtcctg taatattcgt tagagaaatg tgtccactga acatgaattt cctatcctgt   113520
tccttctaaa aaggatgcat gagttatcct atattcccaa ggcacaacat gactttgttc   113580
tgatatgtgc caccgtgatc ctgtagaatt tgttttgttt ccagtcccta agaataaatg   113640
tctcttaaag tattgtagtc attcactcta catttttatg agttattact ggcccaccta   113700
caaccatatt tcctccgaaa ttcatccatc ctcctggaat tacctgattc tgaattatta   113760
agtggttctc ttggccattt gctcaaaaaa agagcacact tattccaaca cacaggcatt   113820
gtttctaaat tattattgtt ttttcttcct agaaaccatt tagagatgaa gatccacttt   113880
agaacatgaa cccatttagt ttagactata acaattgaag atatggtgac tactgtttat   113940
ttctgttagg gatatatttt ttgtagattt cacaaaagac agaacctgct gtgtgacagc   114000
ttatctgcag gacaccgatg gtttgtagga cgatggtgag gctttgtgac aaggcagaaa   114060
tgtggaaggc tggcaagatt gtttactgag cttcccctaa ggatggaata attcaccaat   114120
cccacaactc ctccaccctc agtcactacc aatagctgtg cctcagtgtt ttcttttttaa  114180 tgattgtatg tattaagaaa aaaatcctca tatgtagtgt ttagtttatc tgattttcgt   114240
tactaaaata ataaaggaga aaagtaaata attcatataa aagtaaactt tcttattcca   114300
agcaggtgta tgtgtgcatg tttgtgtgtg tgtgtgtgtg tgtgtgtgtg tgtgtgtgtg   114360
tttgccactt tgatggaaag aggctgactt tgcagagact attttttgtt aagaactttc   114420
cattaaatta gagctttaag ttataacact gattgcatag gccagggaaa atggtaggat   114480
gtggcttaaa aggcaatctc acaagaagta tgacttttat cttatattat aaacaacagc   114540
acaaccttgg aatttgtccc aataaattcc ataagtataa aataaactaa ataagtaaag   114600
tgactaatat cctactaagt cttttccttc acacatgctt ttttgcctaa agccatttaa   114660
agtctctgag gatttaaatc tatgattctt tcatggagta gaagaaaccc agagaatata   114720
gaaatttaga aaaactttaa gacttattgg tttaacagaa gtaggccggg tgcggtggct   114780
catgcctcta atcccagcac tttgggatgc tgagctgggt ggatcacttg aggtaggagt   114840
tcaataccag cttggccaac atggtgaaac cccctctcta ctaaaaatac aaaaattagc   114900
cgggcgtagt ggtgcacacc tgtagttaca gctacttggg aagctgaggc aagagaatca   114960
cttgaaccca ggagacagag gctgcagtga gctgagattg cgccactgca cttccagcct   115020
gggtgacagg gcaagactcc atctcaaaaa caacagcaac aaacaaaaca aaacaaaaaa   115080
cccagaggta gatctaattc tgcagactgc aatcactcag ttatggatgg ataagtcagt   115140
ccttaagtcc atctgctatt tgtgtatcgt gcattttttt ttttttttga acaagcacg    115200 ttcccacctg gattgaatgt taatattcac tgaaagccag ggcattgcaa cgagcccttta  115260 ggatgttata attctgggcc attttacag ttcaggattt cagatttatt gcaatgttgt    115320 aagttttttag tttcttgtct ttctctaaca tctagtaagt tccaaaactt aaagaactac   115380
aggttttctt gataaatacc tgtgtcacta ctttttattt ttagatttt ctttttact      115440 acatgatctg agttaaaagt taaatatata tgaattattg ttttgaaaaa tattacctat   115500
```

```
aatagttttt taaaagaaac tttaatttta gatttgtgct aaattggcga agattgtgta 115560
gagttttcct tataccccac cctcaaattc cactactaga aacaccttac atcattattg 115620
tacatttgac actattaatg agccaatatg tgtgcaattt tttactaaag cccacccatt 115680
cttctgattt cgttggtatt ttccttctgt cttttttctt tcctcaaatc ctatccagga 115740
tcccacatta catttagccg tcatgtctcc ttgagctcct cttgactgtg acagttttc 115800
ttcttttgtc tttcatgacc ttaacagttt tgaggagggc tggtcacggg attggtacct 115860
tgtttggttt gtctgatgtt tttctcatgg ttatactggg gggctatgga ttgtgcagag 115920
gaagaccaga ggtgaagtgc cactttcatt acattgtatc aagggcacat actagcacca 115980
tgacattgca gttgatacta accttgatcc catggatgag gtgatgttgg ccagatatct 116040
ccagtatcac gttcgtcctc ctgcacacac actttctata ctgtaccctg tggaaagagg 116100
tcactacgtg cagcctacac ttaagaaagc aggaggccgg gtgtggtggc tcacacctgt 116160
aatcccagct actccagagg ctgaggcagg agaatcactt gaacccggga gaaggaaatt 116220
gcagtgagcc gagatcgcgc cattgcactc cagcctgggt gatagagcga gactccatct 116280
caaaaaaaca aaaataaatt aaaaaaaaaa aaaaagaaa gcggggacta taatcccctc 116340
cttgagggca gagtatctac agaaattatt tgaagttatt ttgcatgaga gatgtgccta 116400
ttctcgccta ctcatttatt tattccctca tttacatata tcagtatgga ctcatggata 116460
tttattttat actttgggtt gtaatctaat gtgatgttgt ttatctgcat agattttgtg 116520
tttacgtaac ttttttttcaa attcctgagg atagcttttt tagaaaatcc ctgtttttac 116580
tttagatcca aggattacgt ctgcaggtgt gttacaaggg tatcttgtgt gttgctgagg 116640
ttcaggcttc cgttgatccc gtcactaggt tattctgtgc ccagataatg agcacaggaa 116700
gttttttagt ccttgtcccc cctctgcaac agattgtagg aaataatctg agactgatca 116760
tttttaattt tcaagcactg aacatgcagt tattttatct agaaggtaga ccagcaaaac 116820
aaaattatat ttgacatttt agcatataag tattttctag ttaactttga catacaagaa 116880
gccaggttat gaatgtattt gttcatgact ctagcttgtt tggttaaaat tattctcctg 116940
ccaaccaaat gctttttgc taccctgaat atttaaaaaa ttttacaat atttcatctt 117000
taagagctat aaatgtatgt tttaatatcc cagggtaaga tatagggata ttttttagtc 117060
tgtcgaggct gctataacaa aataccttag actgggtaat ttataaacaa tagacattta 117120
ttgttattat tatcattaag acagggtctc tttctgttgc tcaggctgga gtgcagtggc 117180
ttgatcatgg ttcactgtag ccttgacttc ctgggctcaa ctgatcctcc cacctcagcc 117240
tcctgagtag ctgggaccat acgtgtgtgc caccatccct ggctaattt tatttttta 117300
atttttagta gcgatgagga ctcactacgt tgaccaggt ggttttgaac tcctggcctt 117360
aaacatttct cctgccttga cctcctaaag tgttgggatt acaggtatga gccactttgc 117420
ccagctaaca acacacattt atttctcatg gtcctgggaa gtccaggatc aaggtgctag 117480
cagattcagt gtctagtgag ggcccattcc cccaaatggc atcttcttga tttatcctca 117540
catgttggaa gggacaaggt ggaagggcct gcagcctctt ttataaggac actcatccca 117600
ttcatgaggg tagagttatc atgttgtgta ttggatttca gcatatgaat tttggggagga 117660
cactaccatt cagactatat aacaagatac attaggtttg gggtgttctg cacttgagtg 117720
aatctatgta agcccttca catattttta ctttcactga aataaaacta aataaggaaa 117780
ccaatgctat cctatatctt aaaatgagaa tggtttgtaa cagctcattg ccttgcatca 117840
```

```
tggtctttta gggttagggt tcgggttagg gttaggatta gcttcgcttt gctgggcaga   117900
gtaggtattt ccgcctcgaa ccacctctaa gggcttcagc tttcagtaac gcacctgtca   117960
cttctaatgc aaaaccttga gtcctctgtc tgtgtgcaga ttcaggaaca ggtttgaggt   118020
ctaagaattt tcttattatt gccttccatt tcaatttcta gttcctccaa agtccttcac   118080
aatgatgacc gagaggagac actcaaaaat tgttagcca gagtctcaaa gtacatagaa    118140 gctgttctc ttgggtggat attacaagtg cctctacagg caactgcatt tctttctctt    118200
tccaggattt ttgcttattg tccagatatg ctcctcctag tgagagggac acttctgatt   118260
tttcctgcct ccatggaaca ggggcttcag agaagaaact ctctacagcc ccttcgttcc   118320
attaataatt tataattaaa tgcatttcca gcatgaaggc tgcctaggag tagagaagca    118380
tattagaaga accaatctgc tgcgtatctg cttatagggt ttgagcccag tcaaggaggg    118440
atgcacagaa actcaggatt ctgacagccc agccccttg caattgggag ggtcgccaaa    118500
tttctttctt gcaaggggta cttactgtct gtgagtggga gcctcttgtg gataaggagt    118560
gagggcagag agggaacagc agagccctgg gaagttctt ccacttgact ctgagcgtct     118620
agacagcagc ctgcccccac cccctagatt ggctttgtac ctgtgagcaa agtttctgac   118680
tgtgccatac atctctggaa tacatttagt tgctaatgga gatattacta taattccaca   118740
tatgttttta gtctctcctt ggggctgtgc ccttctgtgt ggcttggcag aagagaaagg    118800
agagaaagat tatacatggc agccttgctt tggagggagt gaaacctgtg attttccttt    118860
tctgtgtcag gaaagcgttt ttctgctgct tgactagcca cctcccaggc acattaacca    118920
gtcaggtgat gctgacattt gtacccccta atctggctta tttctgaaac cctccctttg    118980
agccctaact gctataatta ggagactgga tcctaacagg tttggaaaaa ggtttgcaat    119040
ctcaaaataa agtagtgatt tgaaagagaa atgtatagt agagttagct atggggtttg      119100
cacattctac atttatgttt gtttgttttt attttttcgc tcagactgct cacagatgca    119160
gtgagcacac ccaaatgcat gtgatcaatg catgtctgac ttctgcagct atggaaggtc    119220
tgggtttgta agatcactgc tgtagaccct tgtttgacct ttttggattg ctggatcaga    119280
aagtgagaga ttgcgaaagt tttcttaaaa gaacaagtca gtgaatcaat tcattaattc    119340
ttttgttcat taggattagt taatatactg ctacagtaaa acctttgtt attgtctgta     119400 ataataaaag ttggattatg gcatggctaa ccccaatctc catacaatct gctcatagtt    119460
ttgacctcat tctaatataa ccctgtattt cacgtgattg aatgttttgc accatattta    119520
taatattaca tccaggtatt acttggtttc tgaaggttta taaaattgta aatgcagtac    119580 ataggtatt agagattttg ttgttttatt tttttagaga ctgggtcttg ctctatcaac     119640
ccaggctgga gtgcagtggt gcaatcatag ctcactgtaa ccttgaactc ctgggctcaa    119700
acgaccctcc accctcagcc tctggagtag cttgtattat aggtgcatgc caccatatcc     119760
ggctaatttt ttattttgat ttttgtagcg atagcatctc agtgtattgc ccagattggt   119820
ctcaaaatcc tagcctcaag caatcttcct gcattggcct tccaaagtgc tgggattaca    119880
ggtgccagcc actgtgcttg gccattacct agagtttttg ttagagataa tgaaataaga   119940
atgagattaa aatgaggtta gtctcatgct gcttaaaaca gtgatatgct taggagcagc   120000
tgcaggaaca tctgatccaa tcttggaggc agcctggagg gcttcccagg ggaagcacaa    120060
tgtagtccaa aacctgagag atgagcaggg attgactaac taaagagcag acctacacac   120120
caaattctgc catcagttcc ttgcatggca tggaaaattg atttctacaa ctacgcagta    120180 ttttcttcc ttttttttg aaacagattc tcgctttgtc acccaggctg gagtgcagta   120240
```

```
gagcgatttt ggctcactgc agcctcgacc tcctgggctc aagtgatcct cccacctgag  120300
cttccctagt agagtagctg gtactacata tgcacaccac catgcccagc caatttttta  120360
tttatttatt tatttatttt tgtagaaaca gggttttgcc atgttggcca ggctgctctt  120420
gaactcctga gctcaagtga tcagcccacc tcggcctcct aaagtgctgg gattacaggc  120480
atgagccacc attttttattt ggtatgtgtg cattcatagt tattctacaa aaataatat  120540
ttaataataa ttcacagtat cctgcagatt ccaaaataaa gtaagcttaa gttctgttgg  120600
aaaatgaatt tctgtgagaa ggctttggtg ctttgacttg aagctgacat caacattagt  120660
gttgggcatt tggctacaca cctgtcacat tcaaaagcca attcactttg agtctttatt  120720
ttgttggcag taagggctgc acatttcgat ccactgtgta ttttcctagc ccagattcca  120780
ctcaaagcag aggtttagag aaacccttg tttattgcaa atattatgcc aaaaataggg  120840
atgaggaacc agcactgtgt tgtgggaagg aacgagaaat aatcactatt tacaatagcc  120900
gagttgtgga atcaacctaa gtgtccatca acagtgcatt ggataaagaa aatgtagtac  120960
atctacaaca cagaatacta ggcagccata aaatagaatg gaatcatgtc ctttgcagca  121020
acatgaatgt ggctggaggc cattatccta ggtgaaataa ctcaaaaaca taaaatcaaa  121080
tatagcatgt tgtcacttat aactgggagc taaacaatgg gtacacatgg atataaagat  121140
ggaaacaatc aacactgggg actcaaacaa gggaaaggct gggagggggt gagggttgaa  121200
aaattaaccct atgggtacaa tgttcactct ttgtgtgatt ggaaccctag aagtccatat  121260
gtcaccagtg tgcaatatac ccatgtaaga aacctgcaca tgcacccctg aatccaaatt  121320
aaaatttaaa aacaaacaaa aacacaaaaa agtgtattgg ccacagagga gtgactgctg  121380
cttgacccag tgaggttgtc tgaaaaccct tatgttatgt gtctccagac caccttacc  121440
cggtgaaaat ggaggaccca tattcacacc atctttcacc tcttattagt ttactggggg  121500
taacctctcc aggctgcttg gggagtgcta agtaggtttt agtgtgcatc cactgtgagg  121560
catcagagaa acttcaggaa atcaagaaaa aggcaagttt gcaggtatga agtgaggctg  121620
cacctgcgtg aagctggctg aagtctaggc agagcagatc accacaagag cggctggaat  121680
aagccatgtg gccgaatggc atccagcaca acgatcaagt gaaacagagc tcctccagct  121740
gtggtagaac tagggccaaa gtatgtgaaa gtgttcaaag attcttcgca ttgaattcaa  121800
gctcatcatt gtccacaaat caatgagacc atgtctatat tggtaaagaa agaataaagc  121860
ataaattcat atttcaattt ttaggttatc tgaataaatg aatttcaaga gtgcttaagg  121920
tttttgctag atgtttgcag gttttttgcct ggagaggcac aggcagttct ttgtcctatc  121980
attctagcct tccacttgta gggattccct ggaaagttga cataaccgct gattcctagt  122040
tctgtttttgt gggaagtatc aagattaaga gaccctctgg gtgaacaaga tgtctttcaa  122100
tagatgaatg ggtaaataaa ctatggtgta ttcagacaat ggaatattat tccatgctat  122160
aaagaaatga gctattaagc catgaaaaga catggaggaa aattaaatgc atattactaa  122220
gtgaaagaag ctgatgggaa aaggctacat acagtatgat tccaactata ggacattctg  122280
gaaaaagcag aactgggga caataaaaaa tccatcattg tcagagtttc ggttggggat  122340
ggggaaagaa aagataaata ggtggatcat agaggatttt tatggcaggg aagatattct  122400
gtgttatact gtaatggtgg atgcaaggag gttcttttg tctaattaac tgttcacatt  122460
catcataatt gattccatac agtatgcatg gattttcagg gtccaagtgt taaccaactt  122520
cagtggactt aaaccactct gtaaatgggg tgctctttag tgtttgtttt gtttactgtt  122580
```

```
ctaggactgg ttaatagaaa tcagaggaca tacagatcca gagtccctta tctacaattt   122640
gaaagtcaaa aacagttcaa aactttacag tgatatcaaa actcatttgg gggcaaaacc   122700
tgatctgaca gatgactatt tgtgttcttt cttttccacc tcagggtgga catttagata   122760
ttttcctgca ggaatattaa tgagtttgat ttgggagtga tgttccatat tcctctgagg   122820
gtgctgcata aaacagatgt aaaaaaatta aaaagttctg agtccccttc ctcttgtcca   122880
caaaagcata ctcattccca agggtttcag atccccattg gtggatctgt gatatcaaag   122940
gtctcattga taatgttggt ggtcagtgga aaatagttgt gtggagagag atgtgttagt   123000
ctggacctca tgcaatgact gcagaaataa ttttatgatt tccaaagaac aacagacaat   123060
ctaaccacct cccttacctt taaagactga catctgtgtt gtgttcatgg atgattatgc   123120
aaatcaagaa aagtggcttc catcaaaata atgtcatttc tttttggaga aaagagcctg   123180
ggactgagtt gtgttatgtg tgcagtttgc cagctaaact cctggcttaa tgattgggat   123240
gggtttccaa gggctggttc tgagactcag tggcagttag ttaggtggta atttccccat   123300
taacattaat gagaaatgaa ataagttact taagaaaacg tgctagacga tagtctctaa   123360
gtactgaaaa gtaaatgaac ccacctacgt ttgttcacat aaaatttctt agtatatttt   123420
aaatttgcta atctaatgta cttttttttt tgcttgtgct ttaactttgt taaattatgt   123480
cacgtaaaac attttattcc atattctaaa ttacataaat gtgtcacaca caatgtcatg   123540
aatcaagttt gtctaaagag gagataggcc aaggcaggtg gatcacttga ggtcgggagt   123600
tcaagaccag cctggccaac atggtgaaac cccatctcta ctaaaaatac aaaagttagt   123660
ggggcatggt ggtgcacacc tataatccca gctactcagg aggctgaggc aggagaatgg   123720
cttgaccctg aaaggtggaa gttgcagtga gtcaaaatca tgccactgca ttccagcctg   123780
ggagacggag tgggactcca tctcaaaaaa aaaaaggag ataatacact ttcacgtttg   123840
taaaataatg ttgattaaat ggtctaatgt gattttatct tgctaatcca gttaccgtcc   123900
cagtatctga attatgataa cagtttacgc agcatagttt tctaacagtt ttggttccat   123960
ctctgctatt aaattcaggc cactggatct gtttggttca acttggatta gggtgtgagg   124020
ttctgttttc ctacctctaa ctccatatac attgtccgtg ctcctgacct tccatgcagg   124080
aggcttgcag gtatctcctt aatctgtctg tcatctgttt cttctgccca tctcagggac   124140
tcctgatctt tccagactgc ccatcctctc ctgtcccttt gactcttcct ttttgttca   124200
ctttctgtaa ctccagtctg atcatctaaa tagtctgagg ggaagatgag gtactgaagg   124260
cactcttgtg agaatatttc tcaggttcct aggtccaagt ttccgttgca tcttggtttc   124320
tatttcagtc tgagcagaga gagagagaga gagagcaaaa aagatcttca ggataaaagt   124380
gagagagaga gaagatggag aaataaatat aaatgaacaa ctgataaatg ccttgagcta   124440
taactctgcc aaatgaacac agaaactcat gtgcagttag atattatcca cctgagaatg   124500
tagttgataa catatttcat cataaataat atcgtctaaa gcccttactt gggaagatta   124560
tgaagcaagc caaatcttat gcagtatgtc cttctgttct cttgacaagc ataagtttct   124620
atttctgtat tgctagaaat ttttagtcac atgcaattcc aacagtgctt taagctggtt   124680
attactaagt agaaggtaaa tgtttgatga tggaagaatt tgcggtggag gtgaaattta   124740
ggataaatat tagcaacttt gaaaagtaag gtgtagatct gtgcggtacc agaaaacatt   124800
taacagattc agaagttagt ttatgtgtac ctatatgtgc acacacatac acacacaatg   124860
catgcacact tatgcaaatc acacacacat gcctcacgca caagtgcaac actcaggtgc   124920
acccaattgc acatacgtat tctattacta ttctttgcaa tgctttgaat gctcatcatg   124980
```

```
taccacaaag ttatggtcta attcataata ccataaggtg cgtgtgcttt agagatactg   125040
tgtatttcct ttcaacatcg aactagtgac tattaatgtt ttaaaatcaa atttgataac   125100
attctgaaat aaaatactga tgtattaagt accaatgcgt tgacatcagg tttcataggt   125160
gttgaactgt agcgaggaaa acagttatca ggtgtcctac tgtaactcta cccagcagga   125220
aagctctatg taatgatggt agaatatcca aatgatggtg tccacatctg cacaggtacg   125280
atttgagatt cactgactta tttaggagga ttcagtaaaa tttcgcagat gttgttatgt   125340
agtaatattt ggctcattca tattctgcac tcctagacat tgcagaaaga catgcaactg   125400
tgatttccat ctcatccctt tcaccctatt ttgaaacatt tagttatgtc tactagttac   125460
cctaagttgt atttttttacc ctctaaaaag gaacaagaga agttggaatc catcccagct   125520
ttccttccag aaaatggagg ggaggaacaa ttggaatgga gaggaactcc agggagaaaa   125580
agacaaaagg cacatgagtg agtttgtcta ggctgggaga gtgggcgatc acatgagatt   125640
tgtgaactaa ttttgttctc cttctgtttc cactgataag cactttatga gtgccaccag   125700
tgtaagtaaa tattaaacct catctcaatt agtatctact cttttccaaa tatatgctta   125760
tgtcagaaaa tgagcagtag aaagcaacca caggatacca cctgcacacc cacgggctga   125820
gcattgcata cttttcaagga gtgctgttgt gttttcaaac ttagtaattt cccaaaacag   125880
agaattcaca gcttccctaa tcaccttcct cagaaccctg aatcttgtta attgagtcat   125940
ttttctgatg atcatgtact catacaattg actaaatgtc tcactatgcc ttcctgataa   126000
gtagtgtctc tacatgtgaa gtatctattt aatctatcta cccctctctc tctatctaat   126060
ctgttgattt cttatctatc taatttatat ctatcatctc tatgtatcta tgtatgtatg   126120
tatgcatata tgtatgtatc tatatatata tcgatctatc ttatctatat gtatctatca   126180
tctctatgca tctatgtatc tatctgtcta tgtatgtatg tatgtatgta tgtatgtata   126240
tatctatcaa tcctctctct ctctcttagt tcagcaaatt acttacaggt ttttgttatg   126300
taactgagca aaattatata cacacacata agaaggctgg aagttcaaga tcaaagtgct   126360
tacagattca gtgtctggtg gggacccact tcctgattca tagacagcgc cttctcactg   126420
tgtcctcaca tagtggaaag ggcaagggag ctctgtggga tccctttat aagggcactg   126480 atcccattca tgaaactcca ctgtcatgac ctcattacct ccaaaaggcg cccacctcct   126540
aatactgtcc cgttggggat taagattat atatttttc tttttaattt ctaattttttg   126600 tgggtacatg gtaggtatat atatttatgg agtacatgag atattttggt gtagacatgc   126660
aatgcataat aatcatatca tagaaaatgg ggtgtccatc tcctcaagca tttatctttt   126720
gtgttacaaa caatcaaatt atattatttt agttatttta aaatgtacaa ttaggccagg   126780
cacggtggct cacgcctgta atcccatcac tttgggaggc tgaggcaggc ggatcacgag   126840
gtcgggagat tgagaccagc ctggctaaca cagtgaaatc ccatctctac taaaaataca   126900
aaaaaattag ctaggtgtgg tggcgggcac ctgtagtccc agctactcag gaggctgagg   126960
caggagaatg gcgtgaacct gggaagcaga ggttgcagtg agccgagatc atgccactgc   127020
actccagcct gggcgacaga gcgagactca gtctcaaaaa aaaaaaaagt acaattaaat   127080
tactattgac tatagtattg actatagtca ccctgttgtg ctagcaaata ctaggtctta   127140
tttattcttt ctgactataa ttttttgtacc cattaaccac cccacttccc cacatcccac   127200
ccccactacc ctttccagtg cctgataacc cttttttgac tctctatgca catgagttca   127260
atctttttga ttttttagctc ccacaaataa gtgagaacat atgataacag tctttctgtc   127320
```

```
cctggcttat ttcacttaac ataatgatct ccagttttat ctatgttgta aatgacagga    127380
tctgattctt ttttatagct gaacaatact ccattgtgta tatgtaccac attttccttt    127440
atccattcac ctgttgatgg acagttagtt tgcttccaaa tcttggctat tgtgaacaaa    127500
gctgcaacaa acatggggt gtggatatct ctttgatata ctgattteet ttctttgggg    127560 gtttggatat aaacatatga attttgagag gacagaactt tcagactata gcatactgta    127620
ccatctatct atctgtccat ccatctgttt atctgtctcc cattcctgaa tattgcatgg    127680
catattttgt taattattte caatgtcata ttgagtttta aagtaagatt acatttctga    127740
gaggcctcac gtgggggcat cctgaaaagt acattctctt tatagtttaa atgttttggt    127800
ttttttcttt attttttca tatttaatta tatttctttc aagtgactcc tttgggagac    127860
atgattttcc tacctcctgg gactgccaca attcccctgc ctcttggaat gcaatcgatc    127920
tctagtctgc ctcaagtata aagatgatat tcatgttgat gacattgaga aggatgagga    127980
gaaaggagtt gatcagagat ctatattcat ggtatatatg tttatcgtat atatatttat    128040
ctgcttatcg tcttcagaat ataaactcca agactgtggg tctttgtttt cttcagtact    128100
accttgcaga gtctaggcct atttattcaa agcttaatat ttgtgaagtg catgaatgaa    128160
taaatgaatt ctaatgttat cactgccgtt ggtatggtat ctgtttctct atctgtattg    128220
tcctctctac ttttcattat ttgtttaatt cccactcatt gagacagatt gcagaagatt    128280
cctttgccaa ctacttctgg gtagagataa atttccctcc acggagctcc cactggactc    128340
tacctgcagc tatatgttat cttgtatttt ccaacactca gctgtaccac ataagacttg    128400
attgagtgaa gaccctgact tagctttgca taaaaccaaa gtaaatgctt tccacacata    128460
gccattcaca gacattttca cattttatac agcaactgat gaactaggct agtgttggga    128520
acaggccccc taaaatctgg ccataaactt gcccccaaac tggccaaaac aaaatctctg    128580
cagcactgtg acatgttcat gatggccatg accccatgc tggaaggctg tgggtttacc    128640
agaatgaggg caaggaacac ctggcccacc cagggcggaa aaccgcttaa aggtgttctt    128700
aaaccacaaa caatagcatg agcgatctgt gccttaagga catgctcctg ctgcagataa    128760
ctagccagag cccatccctt tatttcagcc catcccttg tttcccataa agaatacttt    128820
tagttatcta taatctataa aaacaatgct tatcactggc ttgctgttaa caaatatgtg    128880
ggtgaactgt ttgaggctct cacctctgaa ggctgtgaga cccctgattt cccactccac    128940
acctctatat ttctgtgtgt ctttaattcc tctagcgctg ctgggttagg gtctcccgga    129000
ccgagctggt cttggcaggc tataaagaca ttttctactg gcttaacaga gaagaaaaac    129060
aaagcttagg gagactgatt atgcagaatt taatttgcaa caagcaaaga caagtctatt    129120
gacttcaaat ggcatcatc acattgtcat ctgataattt ttccagcatc ctttgcctcc    129180
tctgtgttaa attataaatt aatgctgatt tatacagttc agttcagctt cacaaatatt    129240
taatgagcac ttgctgtgta ccaggtatta ttatataagt agttctttat ggtgtaagaa    129300
tggatagtag atactttttt atccattcaa ctttaaaagg ttgatgccta gtcatagata    129360
ccaggaaaca cttaagtgaa tgaggacaag ttttctgctg tcaaagagag agatcagaca    129420
ccaactagag tccaagaaag aacaaagtaa ttttgatcaa caaaactcat agaagaaaat    129480
aagcattctt tgttgttaca tatacttcag agccatttta gtgctcaaag tttgatagaa    129540
attgatacac aggacttgct gctctgaatt ggctatccca gaatattcta cgagctacaa    129600
ccagacctga cattaacctg tagttacttg tggtttattc atctatccat ctaaatgtta    129660
tgagcatctc ctatgtactc ttcatggtac tagactttag acattgaata cggagcaaaa    129720
```

```
aagacatagt ttcttattta atgtggctta tactctgatg tagcattcct tcaccagggg   129780
taattttgcc tcaggggaca tttggcgatg tctaaggaca gtgtaggttg tcatgactga   129840
gatttgttgc tgatgtctag tgggaagagg ccagaccccc ttcacaataa agaattatct   129900
gaccaaaaaa ggtcagcagt gccaaggttg agaaactctt ccagcagttg aagaaaaata   129960
atcatcagat cacccacaag tataattaca aactgaaata catgttagat gctggtagag   130020
ctggtttcca aagtttctga tccagttgtg aggatacata ttgatattga aacgggcgg    130080 ttgaaggggc agtagtaagt tattagggta agaaggtctt ggtgagcaga gggactttca   130140
tgcgaagact ccagggctcg aaggagccca gtgcagtcag gatctgaagt gacaggtgtg   130200
gcttgagaac agcggcaatg gggagttagg caggagggga agctggaaat gcaggcaggg   130260
gtagacaata aaagtacgca ggccgtttat attatacaat cctgtagact tctttcttct   130320
ttcattcttg atacttttct ataataacat tcaagcattg gatcagcacc ctttgttgtc   130380
ttctgtcatg tagcccaaag gtttaccttg gagacacaaa ggcaactaag acaatggttt   130440
ctgcactagg gagatcatat tctcactcag aagacatttg cagggtgtga ttagtgagtc   130500
tcacatacat gtcaatttct tcctaagacc ttgtgctttt ctagttttta tttttttatt   130560 attatttta tttatgtatt ttatttgaga gagcctcgct ctgccaccca cactggagtg   130620
cagtggtgtg atcatagata gctcactgca gcctccaact cctgggctca agcaatcctc   130680
ttccctcagc ctcccaagta gctagaacta caaacatcca caaccacacc cagcttattt   130740 tatttttgt agaggcaagg ctgtctctac aaattccgtt gcccaggctg gtctcaaatg   130800
cctgggctca agcgatcctc cggcctgggc ctaccaaagt gctgggattc caggtgcgag   130860
ccatcgcgcc ccaccctcta gtttttaatt ggtttatttt cttctcatat ttcagttgag   130920
cattattcat ttattgctgt tgaggtttta cttttttttt tcttcccaaa ggtagattgt   130980
agacagctca cctttgttac caatttgaaa tgctagatgt taattcttaa tgttgtagct   131040
gtaaagggcc atgatttgag gacgtgttat tttttaagc ctgagtttgg attggtctga    131100
gttgaatgca gttgctaagc catcgaatga gggagtgtcc ctgaactaat gagtgacatg   131160
gaccttttct tataggtgag agtccatttg tgataaaggc attgttttag gatacataag   131220
ggtcatggtg tatattctta gcaagtgtta tgaatacatt cgatctattt cttttgaatt   131280
ttagtgtttc tctactctcc atcttactaa accaggtgtc ccagatttcg ggttcagcac   131340
atttgtgtct gggttcacat agagggacta actaggtgga gtttagggta agggggtatt   131400
cagagtcctg ccctcctgca accacagcaa cacccccaag tctctctcat tagattgtat   131460
ttgttctcct acttatgttc tttggcctct gctataaaca ttttcaaaaa agtatccaat   131520
gaaaacaatg ttgtcaatga ctgtctttag taagtctgta gtcagattca tatctttaaa   131580
atatgtacac tgtgtgaata tttcaaagta tgtatcatga aaacaaataa ggaaaaaaaa   131640
aaaaaagcca agaaagctga gatggctcta ttaatatcag gcaagatac cttcaagata    131700 aggattattt ccaaaataaa agagagacat ttcataatga tacaaggaag aattcaccta   131760
agagaactaa taatgttaat ttgtgtacac ctaataagag agctgttaat tatacaatta   131820
gcaataaatg caaagaaaga ctcatcaata atgcagttg gagatgttaa gatgttacca    131880
caatagatga aagatgaaga tagaaaacac acacacacac acacacacac acacacgata   131940
tgaaaatttt caacagcacc atcaatgtcc ttggcaactt cgtacttcga gtccaacctc   132000
ccttcacaat ctaatacaga aacaaacaac ccatgatttt tctgcatttc gtggttaggt   132060
```

```
tccctgtggc tcaaggcctc tgqcgcaaat gatgttgtct tttagatttt catgctaaga    132120
agatactcat gttcgtatgt gtgtgctttt tcctctatag catccttaat gttggcctcc    132180
agatgagagt ctctgacaat ggggctttaa catcaaacag ccaaagtctc tcagcgagtt    132240
aacctctttg gccttaaatt tctcacataa tgacatacaa cagtccgctc ttcttcaagt    132300
ggcctttgag gagtctaggg acacttgtga attcacttcc acaactcagc tgcattgcga    132360
attcaattat tgtgctggga gatgttgtac cattatttt ttttaaaggt gcatattcta    132420
aaggttaatc ttgaggctat cacattaagg gttaacattt tatcgggggc attatagagt    132480
gcatttttga tggctgtgat ttcagataac aagcttgttg tttctatttt tcagctctag    132540
cttggcctct aatctgtagg gaaggctggt tcctaaatgc aggaaatgag gctcaataga    132600
acatgaaaag ccagtgttaa tacaccattc aatctcaaga aagagtggga ggaagaatga    132660
cagagctgtt ttttgacaga tgagtggtta ggcatccccc tagctctcca agtcaccact    132720
aggatgaact ttcaggatgc agtgtcctgt ggaatttggc tctgaaacat aacttcttca    132780
taaggcagat attgtaacgc agttctggat tttgtaccta cagacagctc tgtgttatgg    132840
taactgtttt ctgttggcac aacaaacaat tagttagctt catgctgtag aatatttcca    132900
gatgccctga tactccaaac cattggtcat tgcagcctcc atattcagat gtagcggcta    132960
taaacaggtg atgcatgcat cctggccagg gaccatttg attttccac cttttctttt    133020 cccaaattca gggtttgtcc acattagcac tattaaaact ttggggcgc ttcctgtgcg    133080 ttgtaagatg tttagcagca ctcctggcgt ctacccactc caagtcttta cacctaacg    133140 cccatcctta attgtgacaa ccaaaactac ctgcaggcat tgccaagtgg ctcctgaggg    133200
ggcagcattg tcttcattga gcaccagtat ggtaatccta gcctaatcta ttgtgttacc    133260
ttattgttcc ttaacatata tggggtagaa tcagaattac aggaacgtga atttctttca    133320
acaattattt ctttacaatt atgtaataaa atcataaaag gtaaaactgt atctttttag    133380
aagccaagaa gcaacagttt atgaaacaaa acctctttta gtatttcata ttaatcaata    133440
gatattgtgg aaaggctagt tcttctttaa ggtaacagtt gcttaagagt tgaagtgcag    133500
cttatgagtt ttacaagccc tgatttatgc acagcttgag gcattgttgt tttgcaacta    133560 ttgtttttcca gcagcactgc tatttataa agcatgtat cagcaatagt atagaattgc    133620
atatatgctt cagagtcaat gcaatcatta aatagcatgc aatctgagta gagtctaccc    133680
aaagctggaa ttcagagcgc atatttatgc acttagcaac attgccataa ttacacacac    133740
acacacacac acacacacac acacacacac acacacacac gcacgcacgt acttaaagcc    133800 ttagccatt aaaaatagaa ttcaacaact aaggctcgta cacatggaac tcttttcata    133860
gcaggatttc caatgtgcaa atttgataaa attactcttt ttaaaaaaaa aattgctgca    133920 acgttttca ttaacaccat aaacatttac acatgattca ccccaaattg cacctagat    133980 gtatttaccc tgacttggca atttcatact tcatgtctct acttcccttc atgcttcaat    134040
acagaaacag caaccgatg acttttctgt atttctgtgg ctcaagtcct ctggccaacc    134100
tgataaatgg cttaggctat tcgataacct gcagcagatc ctctgagatc ttctttagaa    134160
atttcctcca agatcctaac tacattcatt tgtagaaata tttgagatgc aatgcatacc    134220
ctgtctagta tccccccacc ccataacaga aatgtgaagt agggtgatct gtcatctttg    134280
tgcaggtcat tgccagctct agcaccagaa tctcctcacc tggggaatat ctcagtccca    134340
ggccaactgg gacttggata ctctaattct aggtgtggtt gaagcatcgg tgggttccta    134400
taacactggc acagggaaaa acattaacag tgggacagaa tagagagtcc agaagccaga    134460
```

```
agtgcatatg aatagagaag ctggtcccag ctgggaccag cttttaacc ttgccaaatc   134520 ttgctattgc atctttagct tttcttcttt ccttttata ccttcttcct tctactttct   134580
gtttagtttc ttctgttttt ctccactaat ttcttaagtg ggatgattca ctcattactt   134640
tttgcccttg tgtttgttac tgatgtcagt atttatggct ttaaattttc tctactgcta   134700
attttcctgc ctcctgtaaa ttctaaaaca cagtatttca gtatttgtct attaagtgtt   134760
aagtgagatt tgtgtgacgt tctaataaac agttaatttt taagtgtttt gtgtgtattt   134820
tctaatgatg agatacaaaa ttatgtaatt gtctatcaaa tcatcggtta actgtttatg   134880
gcatctgttt ttcctatttt ttgatctatt aaaattgaaa ataggtttct ttgtatcttc   134940
cattaatgaa tgaatttata aattcttcct ataatactac tgatttgggg ttttttaaag   135000
aacgtatgtg gcataaaata tataacaagt tatctccttg aagaatgaaa tattttacta   135060
tgtaatattc ttgctatctc ttaaaatgct ttctgtttta caatagatat ccaatattag   135120
tagaaatatg cttgtttctt ttttacttttt gggttggcta ttgctgagaa tatatttttt   135180
atattttcac ctttagtaat ttcagatatt atggttgtat catttcatat gacagatatc   135240
tataatttct ttttttcaat gtgacagttt cagtctagta attgcataac ttatgctatt   135300
tatgagtttg aagatatttg atataattca acgtatttta atctttcgga tttccttttt   135360
tatgcattcc ttttaataaa tgagtttgtt ctttttctgt attttcttct taatttgcca   135420
tttacttgat ttctacttttt caagaaaagc ttgcagttgt aaaactcaca tttaagtcat   135480
taaagtctaa aattaagcaa gaccttagct ccattctaga aaataccaat cacctgtctc   135540
cctagttaca ggctattatt atgtatcatg aatatttgtt ataaactctt tcagttttttg   135600 tttgattgaa tacctttgtt ccctgctcat tcctgaaaga taattttgct tattatgcaa   135660
atccaggtgg accattattt cacatttcac tgtcttctgg ctatacagat gtcagttggt   135720
tttgagttaa actttatgca caggttgtct ttggcaaggg ctaaaattta agatctcctg   135780
tttatttttg gcattcatca gtttcatgtc aatattgatt tttttttgc tttatccatt   135840 cttttctatgg tttctgtgcc tttggattca tatatttaat cattatttga agatcttagg   135900 gatcacctttt caaatactga cacttctcca ttcttcctgt tttctcaaat tttgatttga   135960
tatatgagat tctcattttt gcacccatgt ctcctaaatt gacttttata ttattagttt   136020
ctgtcttctg tttttttgtaa gattttccca gacatatctt ttttttattgt cttttcttct   136080 gtgtctaatc tctttagcta atccattaat ttctatttat ttcaacaaat acagttttta   136140
tttatttcat ttctatgtgg tcattttca aatcttcctt gtccttttcca gtaatttcct   136200 gttttttgtt tattgtttcc tgtttcaaac tttatttttt aaatagctat tttaatacca   136260
caagttttgt gtgcagcacc tataatacct cagtgttcat gggcttagtg atctttgact   136320
gtgaactcat gtttgtttga tcttaatctg tgggaatttt ctggcctatg ctggcattct   136380
ttccccaggc aggtaggttc gctttccttc tgatagaagc tagagtgtaa gacttgagcc   136440
ctttcaaggg tccaaattct ccaccttact ggaagccaag cttgggtttc tggccccagc   136500
cccttgtctt acacatctgg ctgcccttcc agctacctgc tcccctttgtc tgaggtcagt   136560 gctactatgg gtgtgttaca taagggcaga cttcccttag gtccagtttt cccttttgctc   136620 aggacaccca aatattcttt tgcttacact gttggaggag ctttatgtgg gaaagcttaa   136680
ttttggatat ttctcttact tccttgtgcc cagaagttca ctagcaagtg catcttatca   136740
ggaggtaatt gttttgttca gggaaggtct cccagagtga tgtgttacct gctgatgata   136800
```

```
ggagtggaag cttttccttt gagaaggttt caccaatgga aaaacaggaa ggaatgaggg   136860
agggagggag ggaggaaggg gggaagaaag aaaggaagaa aggaaggaag agagagaagg   136920
aaggagtaaa aaaagaaagg gaggaaggga gagagggaag gagtgaaaaa agaacaaagg   136980
aagaaaggaa ggaaggaagt aaagaaggag aggaggaaga agtactgagg aacatcttac   137040
tcaatggtga gacccagttc gtacatgttc ttatcctatg agctaatttt ttctcttttg   137100
tttttcttaa gagaattggc tgtctcttac tctgtaatac agatctgtga gaaaatagct   137160
tttataaaaa gagattttgt agtattacac acttggcagg aatatagttg tctgttgtaa   137220
taatgaatac taatctagaa taggaggctg agaagaaaaa tataattaaa atggtaatgg   137280
cttttttttt atgtgaatga aactcatcca gtattggttt tgaaagatat ctaagttcta   137340
ggagcagact gtagcagaat ctcctttaat actctaagga aaggacgctt ttagaaagta   137400
ggcattgcct ccttatgtga aaactgcatt cctttcatga gggttccatt ttctggaaca   137460
caggatgtaa gacaggagac ataagaaggg atcttgtagc agtgcagatg aatcaagtca   137520
ctgcactttc ttatttgatc ttattttaaa aagatgcttc cagggaagca ggaccttgga   137580
acccacaaag tctggagcaa gtcattgacc tcgcaaggta ttcacgtcct cacagtaaaa   137640
tgagaataaa aattgctagt ttttaaggat actcttagga ataaataact tgttatagca   137700
catatcagac catcagtcat gccagcctgt tttcctttct ctcttactct ctccctctgt   137760
tcattttctc catcttctct ccaactattc ctccctctct accactgttg ctccctccct   137820
ccctccctcc cttccttcct tccatttttt ccttccttcc tttctacatc cctccttccc   137880 ctctcttct tttcctttgc ttccttttct ttttcttcct ctctcttttt cctacaaaac   137940
agtatttgtc aactttggca ctcatgacat gtggagctga tcaccccgtc tttgttgtag   138000
gaggtgtcct atgcattgta ggaggtttag tttagcagca tgcctgggct ctgcccagta   138060
gatgacagtg gcaccactac cacaagttat gaaaaccaaa aatatctcca gacattgtca   138120
aatattgcct ctgaggcgaa accacccctg gttgtgaacc accactcaaa aatacacttc   138180
atatcaataa aaatcctgct ttatatatat atgttttttg ctcagttcag ggttattaag   138240
attgtaagac actagtgttt ttacaagatt tctaggatg ttctttgatt gagtcttaaa   138300
atcttactgt tgatgaaaaa ttgaaattat gttgttattt ttatattcct tcatatagca   138360
gcataaaact tggtatttta tgggaatgag tatgcatctt gttctgattc tatggtctac   138420
ttttatgtgt ctcaaaatga gattcagatc aaagaaaatt aaaacgagag caaaagtgaa   138480
tattaaggta aaggtatagc attctgatta tctgctgctt gtccatctca ggtatgcaat   138540
actgacactg tgccactagt agcttcttga cattcttaag atgaaaatag tttagttttt   138600
atctaaatat attaatagag aatatacaat atatatttat tcatatatta atactggaac   138660
aatagagtaa ggttaaacac tcaaaattta gctcaaccct gagattatta tgaagtactt   138720
acaaaaataa aaactaaaaa gacattagta gcgtacttcc cagcttcatc tctgcaggag   138780
gtgttacctt agctcagggc ttggagaata ggacatgtgt ttacgtgatt gactcttgtt   138840
gggattgttc tcagagctct cctgaccttg gtccacacac ttgggagcac atgattccta   138900
atactgataa ccacagtctc atgaatttt ctcattttgc agaggaggga attgaggcac   138960
tagatggtaa tatcttttc atttcacata gttgctggtg gctaagggaa gctggtgctc   139020
agcttgtccc aggccatatc taagacattt gtctggcccc ttgctttcct tcctttcatg   139080
catacagcaa gcatatccaa cttttctatg ctggtctatt tctagaaggt gttatttgac   139140
atggcatcac ctcctttgta gccctctgac tatgagaatg atagaatgac ctctctttta   139200
```

```
aacctatctc cttatccgcc ccaacacata cccctttggg gtggggtcat aaggggtat    139260
cccttctcca cactaactttt accgacttct ctcttcattg tctctctgca gcagataatg  139320
taagcaagaa aaagattaag ttaattacat gcacctcaag tttcagtagg aatatcccac   139380
aattcctctg tctcttaatt taactgttat ttattgaaca cctgctgtgt tcttgggaaa   139440
attccaggtg ctggatggaa ttagtttatg atgatagcta agacttgcag agacattaat   139500
gtgctgttct tcttcttctt cagaaagtat agccatgtac aaactactaa agggcgatat   139560
caaatgttgg ggagataaat atcaaaatac agagcttcca tacctgtagt tttggttagt   139620
ttaataggcg ttaacattta ctcattttca gctacctaca tttattgagc agtgcctata   139680
ccactcattg taatttaatt gcataataaa ttacactgta tttgctgttt atagaaattt   139740
agaaatttag tttaacgata tgtttataat tttcttacta ctatggataa tacatttaat   139800
gactataatt aaattcttgc aaaattttg aattgttttt agtaatttgc caatgatttt    139860
cccaggtatt aatttaatat attgaaattt tgtctttata gcatagaggt tttttatttc   139920
attcatttat ttaacaggca tttatcattc atctgcttta tgcaaggaaa aaaatggtca   139980
agacaaggat gccaagtctt taacctcagg gaacttacag tttatgtaca gggacacata   140040
cttatcaaat aaacagagaa aggaatgtat attcatatga actcggcatc atatattctt   140100
ctttatgtta tcattaataa catccaaatg tcaacaacac atctattgtt actttggtta   140160
aaaagctaca cagacagtag tagatatggt acttggatga agaaagctga agtttattat   140220
tttctctttc tagtttttaat ccctaagggt cattgataaa agacttacac aaaccccccct 140280
ttagtaacct aataatgtat aataatcctg ttcttaaaat ggtgatagag atttgcttgg   140340
tttctactac ataacaccat aataccatat taagacttga atctctttat atcatggaac   140400
aactcaggta gtgttacaaa ctgctgttac tgaataaatg cggagaagaa caagctctcc   140460
agagcagtgc catgcctgtg tctgatgttt cccaggatag aaaactgcgc agatgttgat   140520
ggtttgtttc aggtgctttg acagcctgat catgggctct agccgtggac catgaaaaat   140580
ggcttctgca ggggcttaag aaagacaatg aagagcttcg cattttctct tggcatttcc   140640
tgctattgtt taaaaggtca catatgcaat ttaaaatgtt ccatgcatgg agcatgacaa    140700
atgccacgta gaaatgaaa ctgctttcgt tgacattttt ggccaatttc caagggtac     140760
cattttccgc cttttccctt ttgtggattt gcaaatttg gcttgtgcaa aatgcgtgcc    140820
ccacggtgca ctctaggttg ggaagtgcca catgttaggt agaaaatcgt gtgtagatga   140880
gaatggcaca ttcagaataa aagtgagaaa ttaaatgaca tcaaaaaaat agagaaaaat   140940
agagaaaaac ttgtaaatga gtccatcaga actatcagaa gctcaaaaag aaagaaggc    141000
ttagaactca tcaataacaa tgtccagtct cattcatatg taaagaaagt gaaatcaact   141060
ttattttagt taattttact ttatttatt ttattatcct tttacctagc tgaatggcaa    141120
aactcagttc agttatcttt gggcatggaa aaatgagcac tctcacagtt tgctagttgg   141180
aggaagaatt gaagtagagt tttagaagac attgggtatt atacaacaaa atttagaaag   141240
agacccactt tactcctctg gaagcatttt tgcttccagg aatctatctt acagatatat   141300
acacaaagat atatgtacat aggtgatcat tgcaactgaa atttttctca tcaggaagat   141360
gagtgaatta ttttaagcac ttagaatatt aaaactatct ttcccttgaa attgaagagg   141420
cagagcaaaa tgtgaggaca cagagtaata ttcacataaa ctccttaaac ctatgtatgc   141480
acgtatagat acttgtatat atacatagat atgaatgcac aatagtatcc atacacatat   141540
```

```
gtgtacatat gtgtgcatgt gggtgaatgc ttatgtgtag atttgtatac aaatgtgtgt   141600
atgttgctgt attaaaaaaa gtcaaaaaat aaacaaatta ttaacaatgt ttgcctctta   141660
gaaggtgact atggtacggt gcccttagag agaggctttg attggcagag aaaatgaaaa   141720
accataactg cacctatatt taagatttta aaaaattctt tgtagtgagt ttgagtaact   141780
tttaaaagta cattgacatt tcatttatgc agatcttcta ggtgtgtata aaaagccatg   141840
agaaaaagat gatttcatgt gatagagaaa actagcacag gttagaattt ggactcagct   141900
gatgagacag tatctgccca aaccaattta atcaaagctt tgttgcatga gccgggtgtg   141960
gtgagtcaca cctgtgactg cagcgctttg ggagaccgag gagtgaggat cacttgaggc   142020
caggagttca agaccaggct gggcaacata atgagatccc ttctctacaa aaagtttaaa   142080
aaatctagcc aggcgtggtg actcaggcct gtggtctcag ctactcagaa gactgaggtg   142140
ggagggttgc atgagcccat gagtttgagg ctgcagtgag ctatgatcac accactacac   142200
tccagcctgg gggacagaac aagacccgt ccttaaaaaa atttgtttta aacacttcat   142260
tgtgtggaag aaagctgtat atttaaacaa atataaccaa acccgtaata ctggggagaa   142320
agattgatgg attgttgaaa ggattatacc cgttaggcca attttgagat gtaggcaagg   142380
aatctcagaa gttccaaaaa gttctgctgt ggttcagtgt tacagggaaa tctactcaag   142440
ggaataatat atggcttgca atcattttgc ttttttgtta catttcctat tattcattgc   142500
ttcatttggc ttgagagaag ccccacagag gaataagaaa taccctacat cattcacatc   142560
ttcttggctt ttgaaaatta aattttatat acttaaaagc agccatgaca catgaaaaca   142620
ttttctttct tcctcaaacc atctttacct agcctcaccc aaaccaaact ttaattttta   142680 cattaattt tcttttccaa agctatgcag ctgacactca tctgctcact tggcataatt   142740
catttggtat ccagtaagtt taagaaattc tgtctgggct tcatgcaatc ataacctaca   142800
tccaaatagc aacacttata ataacagtaa taatagtatt ttttagtgtt cacatggatt   142860 ttctcccta attttcatga catctcaaca aaatagacaa aatacatggg cttctcctca   142920
gccctgagct ttgcctatcg ttaaccccctt gaagaaaaat ggcgctgagc tatcagtcag   142980
tcattccctg gcagaaaggg aacagaatca gtatagatgg cttctgaag acattgactt   143040 gatttctgtc accaacaatg gcatattcag gctgtgctcc atgccaggtg ccgtgtgggc   143100
atggagtcca ccacaccagg ggaattctca gaagcagtat tgaaaacaca taggaaagca   143160
ttacttaagc ctgtataaac ataagctctg tccagacatg gaatacagtg ggagttcttc   143220
ctaggataat cccaaaaact aatacatcag aaagcttacc tataacatga gaattcaagg   143280
caaaggcatt tttggtatgt aagtaaaata ttaggttgaa tccatctctt aatgcggatg   143340
ttgaagaatt aatgttatat ccatgaagcc agtgttgact ggaaggactc aaaaaaatct   143400
gaagaatata aattccttga ccttctttat tgaagacttc agctccatta cacgaccacc   143460
tcacagtcct cattcggttg cctttttgcct gtttctgact tactgaagga caatggtgtg   143520
gagctacgat ttatcaccca gaaaatgatt actaaagtcc gtattctact ctgaatactg   143580
aaaactctga agtaatgacc ctaacctaaa cctcctcttc ttctggctat cacttcttcc   143640
ttcccacttt gatcactctt ccatgaatcc tggcaaacct cctagtactg agtatccttc   143700
cagccaccaa acgtctgaca tagatcgctg gatctgactt taattctctc actaagaccc   143760
tcaatttcct cctctgcttg tggtgggctc accctgttgt ttctcagcta agggtgcatc   143820
cagatatcaa tttcttgtgt cccatagcac tgctagcatt aagtgaatta ctgcatggtt   143880
tggtctcatt agtgtgtggt ttccagaaac acttgagatc ttactgttgg cttgtaatct   143940
```

```
gtcttagtcc attttgtgct gctataacag aatacctgaa actgggttgt aaaacatata 144000
aatttatttc tcctagttcc agaggctggc aagtccaaga tcaaggcacc atgatctggc 144060
aagaccttct tgaacatcat caaatggcag aagggcaaag agcttaagag agtgaaccca 144120
ctcctgcaag ccctttttat aattacactc atctgttcat gagggcagag cctttgttac 144180
ctaaacacct gccattgtcc cctctcctgc aacactgtct tactagggtt taataatatt 144240
catgtcaacg catgaattcg gggaacacat tcacaccata ggacaaccca tttacactct 144300
ctcctcatcg gggtcaaagg gcatcaattt aaggtttttt gaccttttt gttttcatta 144360 tatctcattt ttatactaac agattcattt gttcgtataa ctctcctgtc ttccagaatc 144420
tgggacagtt ttccacctcc caagtgggat ctaggagtta acccccacca tcaacccaag 144480
tactcctcct gtgtccaatg gccagtcagc ctcaatcctg tcttctcttg agttatgaca 144540
tatttttctc cttccattaa tagtgaccat tactgtaata ggaatttata gttctttgtc 144600
ctccagttct ccaaaactgg ttctctatcc tttcaatttt atgctaacaa atctcattaa 144660
agtatgacca gtgatttcta cattgccaaa acccagtggt gtcttttag tgatgatcct 144720 atatcaattt gatgggcact ttatcacttg cagaattctt attccttttc attttatcac 144780
tatgttctgg ttttattcta caattgtgag aagctcttct gtattttctt ctcttattat 144840
tcttaaatgt tgacttttcc taggatttgt tcttgacttc attctgtata ttgtatgtct 144900
aggtaattca ttgcatcttc ttatcttcaa ctatctgcct ctatgtggat gattctcaag 144960
tctttatttc cagctcaggc cactagcttc agttacagtg tttgtaattt tagcccctat 145020
tagaaatctc tagttgagtg tcacatagac actccaaaca caacacattc aaatattaag 145080
agatgctctt cctctaaaac ctattcctct ctgcaccctc ctgttagtta aaggtgcccc 145140 ataccagt gtgtccaaga tacaaactct gttggatttt acttctcttt tctcagcact 145200
tatgtaaatg gatgtctact tctcatttct gccctgcaga acattcctag ctatgtgctg 145260
tcttcctgtg gcccactgtg acagcttcct tatctcagtt tagattgtta tgcagtccat 145320
tactcttctg cctcctacct tcaagctact attggagtca tcttcctgat tctcacatct 145380
gatggctttc agtggctaag tgatgcattc caatctttct tagttcattt tatgctgcta 145440
caacaaaaca cctgaaactg ggttataaaa aatagaaatg tatttctcat agttctagag 145500
gctgggaagt ccaggatcaa ggcaccatca tctggcaaga ccattttgca catcatcaaa 145560
tggcacaggg gcaaagagct caagagagtg aacccactcc tgcaagccgt taaaaacgca 145620
tcatgggccg ggcgcggtgg ctcacgcctg taatcccagc actttgggag gctgaggcag 145680
gcggatcatg aggtcaggag atcaagacca tcctggctaa cacggtgaaa ccccgtctct 145740
actaaaaata caaaaaatta gccgggcgag gtggcgggca cctgtagtcc cagctactcg 145800
ggaggctgag gcaggagaat ggcgtgaacc ccaggggggcg gagcctgcag tgagccgaga 145860
ttgcgccacc gcactccagc ctgggcgaca gcgagactcc gtctcaaaaa aaaaaaaaa 145920 aaaaagaaa aaacgcatc atggcaaaat ctcttttttt accacctggg aaaacctaag 145980
acccttggga cagcacagaa gactccttaa tctgcccatg tgtccctttc cagtgttagc 146040
ttcttttact ttttcttgta caccctcgtgc ccttgcccct tggaacaaac agctcacagt 146100
tccctcagca cacccaccct tctacctgcc cgggagctgc cttccgataa gttgtatctc 146160
gatgacttcc tccccactct ccatctggga agatcccagt cattcatttg ttaaggccca 146220
gtgaaaaaga ttttatttat tttccttcat ataatatttt tatgtataca tatatatgca 146280
```

```
tatgtatgct atctatctat tagatacatc ttgttttggc ttattttat tttttatgtt   146340 ttgagacaga gtctcagtct gtcacccagg ctggattgca gtggcatgat cacagctcac   146400
tgcaacctcg acctcctggg ctcaagcaat cctcccacct cagcctcccg agtatctggg   146460
actacaggtg cataccacca tgcccagcta attttgtat ttttttttt gtggagacac   146520 agtcccacta tattgcccag gctgttttg aattcctggg ctcaagcaat ccacctgcgt   146580
cagccttcta tagtgctggg attgcatgcc tgtgccctg tgtctgacgt tatccttgtt   146640
attttaatgc ctacctcatt tgtctttttc aaataataat caacaaatga tttctggatt   146700
gataaatgca tgaatgaaat gatagtttgc caaaatacag aatattaaaa ccatagggta   146760
accttgagac aatttaggta aaaataggg gattatttta tattagaaga ttattcaatg   146820
tattattaaa atgtttgttt attgcatgtg ttttaagtgt tgagaattta acagagaacg   146880
agacatgaat ggtctaagtg tttatgcatc ataataaagt tgaagaaatg tagggttccc   146940
atggtgtttc ttttcaaact ttgataataa cacttcttta ttgatcgcaa ctgtacattg   147000
gcagcaccgc ctccagactg gaaaataaga tcgatttctc ctttgtgttt cttttataac   147060
cttgcaattt tattcctctt gggcttactg ttatgagttt ggtttctagt ttctagagca   147120
tgagttctaa gaagtggaaa tcaagatgga aggaagttac tatagtgaga gggtgtcatg   147180
ccctgcaggc taggtatctt agagtctgac tgcaactccc ttgacacagg cagttcttt   147240 tcttgcctgc agccctttcc aaacaaatat caccagcctc atattcccct cccctttata   147300
gatggagccc ctttgtcaag caggccagtt tactgggaaa aggcccttct cagacatgct   147360
ttctcatcct gatgctttgc ctttaccagg agtgaggcca gaaccttcag catgcattta   147420
tatcaaaaaa gagagatgtg ctgttttcat ttaaattccg catttccact gggcatagtg   147480
gctcatgcct gtaatcccag cactttggga ggctagggca ggaaaatcgc ttgagaccag   147540
gagatcatga ccagcccagg caacataatg agacccgtc tctacaattt ttttgagaa   147600 agggtctcag tctgtcaccc aggctggatt gcagtggcat gtccacagct ccctgcagcc   147660
tcaacctcct aggctcaagc aatcctccca cctcagcctc tggagtagct tggaccacag   147720
gtgtgcacca ccatgcctgg ataattttg ttttttggta gagacagggt tttgccatgt   147780
tggtcaggtt ggtcttgaac tcctgacctc aggtgatctg cctgccttgg cctcccaaag   147840
tgctgggatt acaggtgcga atcactgcgc tcagcctcta taattttttt ttttaatta   147900 gtgtgctagt agtctcagct acttagaagg ctgaagcaga aggattgcct gagcccagga   147960
gtttgaggat acaatgagcc atgatcacat tccaccctgg gtgacatagt gagacgctgt   148020
ctctattaaa aaaataaata aacaaattat aaattttcac atagtcgtaa acctctgaag   148080
atgtggatac ttcatttgtc acatttaggt ctttaataca ctaataccttt ctctgggaa    148140 acagtgtttc tcagtctctc ccgtattgat aatgtttcca ctttgcccttg aagattttg    148200 tgggttatgg ggaaacagtt tatggggtgt ctttcagcag aaccacaacc ctttttagga   148260
agaagctaat tatggtgtga aagggacagg tgctcttatt aggtagtgat agtaagagtt   148320
aaaacccagt tctcttgagc tgttacttgg attcttcaac tgagggtgat tttgcatctt   148380
tggcactaga tgtcattcaa ctgacagtca tggactccca ggggaccccc aaactctatg   148440
tcacctttat gagtaggcga gaatggattt ttcttggaga ggagtgtctc ctcaaagaag   148500
tctgtgacct agaagaaaag atgaaaaatc tctgctttgg attcggaatg tcaggactgt   148560
tcacttggaa cttaaggaga gtttcttcct agtatatacg agactgaacc ttatgggtt    148620 gccatttct tagacccaaa gctttcaaat acagtcattt tcatatgact tctacttaga   148680
```

```
caataagatc atcatgtatt ccttttttcc tctttcagca tctggcattt ttctcctctt 148740
gggcttgttg ttctggtttt ttttttttt ctggtttcta gaccataagc attcatgcat 148800
tcacattatg ttgcctccta agttgtaagc tctccaaaga gagggaatat agctgcttta 148860
tgtcttcacc caactttgag tagagatgat ggcaggaaac agagagcatt ttcacagaga 148920
agatggagtc catttgagtc aggggatctt gtttgaaatc ttacctgtgt gatctggggt 148980
gaattaatac agctgtctgg aaaatttaga acagagacct cagaggattg cagtaaggag 149040
tcctagaagt taggatctcc tcagtaaata taaatactta ttctcttggg taatgaagct 149100
gacccacagg atgatgccaa ttatttcctt ggtattataa gcacataaac aatagttcac 149160
atttattgag tgcttactat gtgtaagata caattatgtg ctttgggata tgggttcaca 149220
catgaaacaa gtgtttattt agtgcctact ctgtgcccaa cactggagat gcagctgtca 149280
tgagcactaa caccatccca atatcatggt gctcatgtac ccatgtggga aaaagtaaag 149340
acaggctcaa gcatataaaa tagggaaggt ggtcttagga taattcaagc tggattggga 149400
tcagtagtga ttgaagggct agattaaatg aggagtttag gacatgcatc tctgcaagat 149460
ggcatttgag caagaaacat aggcaagact tatctacttt aattttcaca gtagggtcat 149520
gagattacac tgtttattaa ctctgttaca gagatgtgga aactgagatt aggatgattg 149580
aataacagcc agattagtaa tagggctggt agtctttaat gcaagtctca tgggctatgc 149640
tgcacacagt cttaacaact tgccaccttc cgtggtataa gagaggaacc aacccaattc 149700
ccgttgcctg ccttccctgc tatattagtc tattcttaca ctgctataaa aaatacctga 149760
gactgggtaa tttataaagg aagaggttta attgactcac agttccgcat agctgggaag 149820
gcctcaggaa atttacaatc atggcaaaag gtgaaaggga aggaaagcac cttcttcaca 149880
gggcagcagg aaggagagaa gtgctgagca aggaggaaga accccatata aaaccatcag 149940
atctcatgag aactcactcg ctatcatgag aacatcgtgg gggaactgtc ctcatgatct 150000
aatcaccccc catgaggtcc ctcccccaac acgtggggat tacaatttgg attacaattc 150060
aagatgagat ttgggtggag acacagagcc agaccatatc acttgccatc taattacctt 150120
gatcaactac cctgcaacca ttccttagtg agtaataggg ccacactcag gaatggtttt 150180
aatagaattt aaaagttatc agtattgtag tttaattgta atttttaaaaa tggtgaacct 150240 cacatcagtg gctaggatca gcacatgata tgctgcatct tggggtcaat aattgccgca 150300
agcacattat tagagttgct gttaatagtc atggaaacca ccctgtacct tcttccccca 150360
gtgcaaccaa cctggcagtg attgacctac tcggtagcga gttgctagac atcaggaaaa 150420
gtcagaagta agtggaagaa ggccaggtgt ctagaagacc cccccactac ccatagcagt 150480
agcaacacat atgcatagga ataggttaaa tgagtcttca ctcattgatc cattcattca 150540
tctttcatcc atgaattaac tattcatgac ccattgttgt tgactctgaa gatacgatag 150600
caaacaggat gcacaaattg tcctgctgtt actttagtta tggggacaga agataaagca 150660
gtgatcaaat gcatgaagga cagaattgct gatggtgatc atagctttga gggaaatgaa 150720
gcaacgataa catctaatgt gggttatgag gatctttgag atggagtggc cagggcatgt 150780
ctttatgagg gtgaggaatt taagcatccc agacacaagt tctgactcaa acatcagcct 150840
tttaattatg tgaaagggtc tcgcaaaatt taataaactt agtggtagga gttcaggtaa 150900
cactacaaga aaccaagctt tctttgtgaa tggtgaggtt agaagggggtt tgttgctgaa 150960 aatcccattt gcaggttcta aggctgggga tgaagtagaa ggaacaatct cttgtcattt 151020
```

```
gccaatcaaa gaacaatccc tgtatctggc aaaagagaca tacctttcta tgaatcctgg   151080
ttttggtcat aagccaaact tctatattag ttttcccttt ttggttgagt tagtgaacaa   151140
ttggatgatt agctaaatgt tgctgaaata ggaggaaggc agattaaaaa tacagaaagt   151200
aactcttatt taatgatttg aaaaaatgag gttaatccga caaaatttta aggaaaagtg   151260
agataatttt ggtgtataaa actatgaaat tttaggctgg gcatggtggc tgacacctgt   151320
agtcatagca cttgggaag ctgaggcagg aggattgctt gacccagga gttcgagacc   151380 agcctgggca acatagtgaa accccgtctc tacaaaaatt acagaaatta gctaggcatc   151440
ctggtgtgtg cctatggtcc cagctatgag ggaggctgag gcaaggagaa ttgcttgaac   151500
ctgagagttc aaggcctcgg tgcactctgt cctggcttgt agagtgagac cctgtcacac   151560
acacacacac accacacaca cacacagaca cacacacaca cacacacaca caaaataaaa   151620
ttttggaatg taataacatt gatgctgaag tgaattgtgg aaaaatatca tataaaatat   151680
attttaatca catagtataa atttctctct gtgcattagt taccaaaatt tgaacataaa   151740
cattttcaaa tacacacttg tgcaaatgtc agggatagca ggtggtatat cactttttat   151800
atttaaaatg catgtaggaa tgaaaggaaa aaggtaaaaa tatgttaagt gtagaattct   151860
aatgaaagaa catattggaa ctatgaaaac attatggagg actttgttca tttatggtct   151920
gagcacagat gatgctaaac atggtccttc aactttagct ggcagccatt tgaaatgaac   151980
acactaaaca ccatgagaag caactgcatg aaaagcaaag agagttatcc aagtgaactt   152040
catatctcat catttgcctg tgtttatgta atagtaaaga cccaaggaat tggtctaatt   152100
aattggtatt ttattttagt gatgaaataa tgagtgcggt tgagcatgcc agatgtattc   152160
atctgataca ttcttccagt cacatggtag gctgcattag gtgataatgc ttcaccctgc   152220
attcatttat aagttagtga agggaagtcc acaactctgg tctcagagca tttatcccat   152280
tgttgatcag ctaagctgtt gctcttactt agctgctaag gaatgaagct aattggacca   152340
ttccagcatg taaaatatgt aaaatatgtc ctttcatgga actctgaaac aaacaatgag   152400
aacaaccaga aaaattgcca gagtcataca aaagctgtct atttctaaat gatcattcct   152460
caagctcttg tcatctactg ggagcccta gatggatgta tagttgttgc tgttgtggct   152520
gattttgata ggactaacat aggaccagtg tatggagctg tttattaaga tgcttttgtt   152580
gctgagtatt tacattttgg gtgttctcgg ataacatacg ttaattccta ctgcagtatt   152640
taataaagtg taactagtgc ctgtctcacc tgtctgaaga cattcaaata tggagcgttt   152700
gtttctttct ctagtgcaga tactaaatat catattgtaa ttagagctat acagagattt   152760
agcatatagg actggcaagt cttggaggcc aatttttatg atgtgggaag aggggggcgt   152820
gatttagagt ggacaaataa agtgtgggaa aattttgtgt ttctggcttg agtgaccagc   152880
tcttacctct cctccccata ttctcttcct tgcctcagtg caaattcaca ctgtcttcat   152940
tttgtatgat caccctctgt cttagtccat ttagttttgc aattaaggaa tctctgagac   153000
tgggtgacat atagaggaaa gagatttatt tggctatgat tctgcaggct gtacatgaat   153060
cacggcatca ggatctgctt ctggtgaggg tgtcaggaag cttccactca tggtggaagg   153120
tgaagaagag ctggtgtatg caaagatcac gtggcaagag aagaagcaag agaatggggg   153180
gaaggaggtg ctaggctctt ttaaacagtc agctcttggg ggaatgaaca gagcaagaat   153240
tcagtcatta ctgcaaggct ggcaccaagc tgctcatgag ggatccacct ccatgactca   153300
aacacctccc actaggcttc atctccaaca ttgggaatca aatgtcagct tgatacttgg   153360
agaggacaaa catccaaact atagcactct gtctccttag gtgcaccttt cttcttcagt   153420
```

```
gactaatcta gagttctctt tggaaaatgc aaatgtagtt atgtttcttt tttgctttta 153480
tgccttactg gttccctgtt ctttatagca tcaggttgca tcttcatcaa ctggggaacc 153540
agttgatgaa gagaagatca gcatcctgaa gtatcttgta acttcttgaa gtatcttgaa 153600
gtatcttcaa gattcagaat gcatgttacc ttctctgcaa agtgctcttt gcaccttgtc 153660
cagtgtagct gtgttaactc cagtgcacct tcctgatgat cttcctaagg ctcttacctt 153720
cttgtcatta gtcgtttctg tgaccatctt gcctatagga atgtgggcta ctgtgggcaa 153780
gtacaatgcc tggcatgcag caggctttcc agaaatgctt gtttggcttc tagagttctc 153840
tttgctgtta ccacatccat ccctttatca tcctttttc cctagtcatc tttcctctgt 153900
acctttgccg ttggttcttt ctccatgaat caatataaat aatacaagct tgtgcatag 153960 cagaccttca ctcttgtctc atgatttcat ttctttcttc ggcatactga aaggcaagta 154020
cctttctctc tctgactctc aatttactca tctgtataat tttgatggtt ctttcaattg 154080
tctgctattg ctgatgatgg cacgaactca gatatgcaaa gtatcagact ttcactcttg 154140
tctcatgatt tcattgcttt cttctgcata cttaaaggcc attccttcc tctctatgac 154200 tctcaagttc ctcatctgta taattttgat agttgtttct actgcctgcc attgctacga 154260
caatggcaca aactcagata tgcaaagtac ctctgggtta aatgtgaaca aaaccttcaa 154320
cctgctgcaa gataatctga cctctgcttg actgtctagc tctgtttttcc tggcagttgg 154380 atgaagaaca tggcaacaat attcttggcc acattgctta caatacaaac gatccctat 154440 ttgtaaatag catcatgacc aggagaaacc ataaagacct gaaagaacct agtggtaata 154500
ccaccccacc tcaggcttcc cggagggcaa gttttggagt cactttgcag ctgctctgtt 154560
cactctagga accatggaaa ctctgctcat ggagtattta cagggaatat ggctgctgt 154620 gaaggctggg acttcaatgc caaggaatac ccaattcccg tggatatgga ccttgtaggg 154680
atctttgcat ctcagctgtc ctttgtggag cagatggttc ccatatgcct gctgcagcct 154740
tcctgatgag ctgagcttct tgtctgtatt gttttgagtc ggttggcacc atggtaactt 154800
tgggggggtc ttgtgattct gcatgtttaa tggaacctga gaagacccct actgggcatt 154860
aaagaacaaa gacaaatgtc cctgtgacag aatactggct caacaattgg ttttctctct 154920
gatgcctctt ccctgcttgg aaagcccttt tcttttatcc ttcataatca cttcttacat 154980
ctggcacagc cttcagcttt gcattattcc ttcattatct tttctcatcc cacattaaaa 155040
aaaattcttt aaattgtggc caaatgaaca tgacataaaa tgtaccattt tcacatgtgc 155100
agttcaagag tattaagtac attcacattg ttgtgcaaac atgcttttt tcactctgtg 155160 ccctcatttt gctctttcct ggtttccaat gcagtatctt atatatgatc taataaatgt 155220
gtcctgggca tctcagtctt gtatattttg gtcctctgtt atatcaggta caccttaagg 155280
atagacattg tgccctacta atcttcctcc ttcatcacat gaaatattgt gcttgcatag 155340
tacattttct tcactccccct ccctgttatt ttttatgtat atcatgacac ttatttgcca 155400
aggatggctt tggccctcta tgcaaaatgt caccaatggg aacaatgcta aagtctgcat 155460
aaatcttaag tttaattcta attttaaata tttgaatata gtgctagtgt tgtcattcta 155520
taggattcat taattcatcc catcaacaaa cacttattga gttccaaatt tgttcaaaac 155580
atggccgtat gtgctgctgt agaaaaaatg taaaaagtca gtttctagtg taagggaaat 155640
aaaatatgga tatcattaag tcctggagaa ggcagggggt gactgatttc aggcttgtac 155700 cataggggatt cccaggagga ataagtaggt tgcagcattt aagaagggat catgaaagac 155760
```

```
atgccacttt aactagttcc aaatggaatt ttggaagcag agccattgga tgttatagct   155820
gaagtaatat tttaagcaag gtgtcagaac aggattgagg cataatttca gaagaacatg   155880
aagtccttgt ttactaatgc agaatatgtt ttatgatagg ctggaaagtg aatctgtgac   155940
tagatttggg agtgattcag tgtacaatga atatggcagt aaagagcttg gacttaattc   156000
gggctgctgg tctggtcagc ccttgtgttt ggagagatga gtaacatttg caaggtgga    156060 gagaaggaat tggagattct agttaggtgc tttgggcata tgttcagtga gggatgaggc   156120
attaatgttc atcaaggcag cattcacaag ggctatggcg gcactgaatg ggagagcaga   156180
cagacacagg tgtcatccca gaggtggact ccgtatggca cagcggcaag ggagtgtgaa   156240
gggttatgac agatgctgag taggtgctag caacatattt tttaaaatag tggcaaaatg   156300
tatgtaagat ctataatttt tgcatgtaca gtttagggat attaacaata ttcacactgt   156360
tgtgcaaaca tgcttttttc actctgtcct cattttactc tttcctcatt tacagtgcag   156420
tatcttatat atgatctaat aactgtcccc taagcatctc agtcttgtat attttggccc   156480
actgttctat cacgtacact ttgaggggc attttcagat aattccaggt aaaacgtaaa   156540
cctcacgatg gcagctaaga aaacagggc gttctctgca ttggttagtt gcagggctat    156600
tagtcaaaat tccaaatctc atatgcagaa ggccaggatc tgcagtctta agtagttcag   156660
tttgtttcac ggaggtaaat aaaagaaaaa aggcatgctg aagatacata tccctggcct   156720
ctagataatc agacagtaag atctctccca cacaccagag aaatctattt ccagcttttct  156780 gttgcagtcc atgaaaatga cagaaaatac atgccctgct tggaccacag cctagctcat   156840
gggaaaaaaa aggaaaataa aaagaaccc gagcttgctg tggatggttc ctatggagtg    156900
tttttggcac tgtcagagtg cacactctga caggctgggc atggtggctg acacctgtag   156960
tcgtagcact ccatggcact gaatttacgg tggaaggatc acattggcaa gtcaaatcct   157020
tgggctacag gaaagactcc catgtgctgc ttttatgctc cccagcagcc aggctgtcgt   157080
tcacaaagca ctctccaagc atcttcattt aatgttgttg ggcacaaggc cctggtgacc   157140
ccgttaaaat ttaaatcttg ctcatacaaa gtgagggcag gttttcagtt gacatttgga   157200
ggtttctcca gccatgttag aaacaaaatg catttaagtg atgagcctt gatacataag    157260 aaggtgtaga gccagctgga tttctccggg accatgaggg gatccatctg attagggctt   157320
ctgaagccga aggaaactac agagagatgt aacttggctg actctcagtt cattattttc   157380
tcttggtaag agcacttctc atattggaca atcttttctt cactgattta gatattattt   157440
tagatgcacc ttttctttt gttatggaag ctttatttta aaataaagtt aacctaaaat    157500
gggcgtatta ctctccccc gccccaccgc taatgattta gaacatgaaa ataatccaca    157560
agaccatggg tgctgtcttc agctacaatt actactttct taattgtcat ggaaacatga   157620
tttattattg gatggttttt tactgtctta tgcaaagatt tcatatgagc cgcaatacac   157680
actgtttcat atgggtaagt ctcaatatta tctgacaaag agagcttctc tgcccaagtt   157740
tatgaaaagt acatttttt ttaagtcact gtcttgccca ggctgcagtg cagtggtacc    157800
atcatagctc actgcagcct caacctcctg ggctcaagca gtccgctcac ctcagcttcc   157860
ttagtagcta ggtgttttgg tttggctttt tatccccact tgaatatcat cttgaattgt   157920
aatccccaga tgttgaggga ggaatctggc gggagatgat tggatcatgg gggtggtctc   157980
ccttattctg ttctaatgat agtgagtgag ttctcacgag atctgatggt tttaaaagtg   158040
tctggcaggt tcctccttcg cacattcttc tctctcttcc caccatgtga aaaaggtcct   158100
tgcttccatc ccgccaccctt ctgccatgct tgtaagtttc ctgaggcccc ccatgccatg   158160
```

```
cggaggtcaa ttaaacctct ttccttctta aattacccag tctcgggtat ttatttatag   158220
aagtgtgaaa acaaactagg acactaggac tacaggcaca tgccatcacg gccagctagt   158280
ttatgtttat ttttttaattt ttgtagagat ggggtctcac tatgttgctc aggctagtct  158340
caaacttttg gccttgagca gtctttccac ctagacctcc caaagtgttg ggattacagg   158400
catgatccac tgcacctggc tgaaaagttt ctattgaatg gaagaacaa tgctgtgaaa    158460 atatattta ttaatgttca ggaaattgtg gaacttgaaa aactctagct ttttagcagt    158520
tttaatggct actatgtgct tctaaaattt gtacctgctt ttttgaagtg ttatatgcat   158580
ttttgtttgt tgatggtggt gatgttttg ccgttgatct cacctgctaa cgtggaaaca    158640
tttcaagaag tggaaaaatg tcttatttta gtacatacta tggtgtcagc tacattaaaa   158700
aaaaaagcct taaagaatgt agcttgaatt gagggttgct atgacttttt gttgtagtag   158760
atttatgaat tgtgtatcat cattttcctt cagtggaaaa ttcagtaact agtatgttac   158820
tggttcctgg attccaaggg aggagaacat gaaacattgc aatggaatta aactccaatg   158880
agcttgaccc agctacgatg ttgaagtgag ggaatacata aagacttggg tgtatgtgtg   158940
tgatctgttg gtattaaagt gccaggatta caacattcta tgaaaatggc taatcatatt   159000
caatatttat ttgagacgct taagatgcat ggtttgggtg gaactagggt taggggctg    159060 ctgttttgaa cagccaaact agaattctgc tcaattatct cacacaggca cacttctgag   159120 gcattttta catgatgcct caagaaagct ttgctccatt ttgtatttca gcatgaatac    159180
aaatttttga aatttccaca gtaaagtgtt tagacttacc aaaaggtagg ccttgttata   159240
ataacaccag taggaccgat gtagtcattt ctaaaatgat tcaagcactt tatgtttctg   159300
gatgagctat tagatcttac cttatgtgtc tggataagct attagatcat tacatatttt   159360
aaagtgaatt tttgaaattg ttggttcatt gtttaaattt tcaattttgt ttctgttgca   159420
ttaatctctg agatttgaaa atgagaaaag aaaaagatg gatacacatt aatgcttta    159480 taccttcctt tgtaacagca attgattgtg cacttgcttt tggctgtagt tagtccttt    159540 cttaaattag tttctggtat ggatgtctac ttttatttaa ttttttttt ttttgagac    159600 ggagtcttgc tctgtcaccc tggctagagt gcagtggcgc gatctcggct cactgcaagc   159660
tccacccccg aggttcaagc aattctcctg cctcagccag ctgagtagct gggactacag   159720
gcacctgcca ccacgccagg ctaactttg tattttagt aaagacgggg tttcactgtg     159780
ttagccagga tggtctcaat ctcctgacct cttgatccac cgcctcagt ctcccaaagt    159840 gctgggatta caggcgtgag ccaccgtacc cggcccact tttatttaat tttattcaa     159900 ttttacattt tatatgcctt gttacttcat ttcttagcac cagaactaca agtttaattc   159960
ttcagacatc ttctctagca cctcataagg tattctttgt tacttggtga tagagaacta   160020
tgtaatttga ttttcttctt ttgcaatgga gtgttcaaat acgtcgttgc ttttaggtga   160080
gggatgtgat taattagaaa aatgagtgga tcttagctca atgaaattta atcagcagaa   160140
tggaattttc cattcagagc aaatgagttc ctaggactgg acacacctag atctgctgac   160200
ccaaaaccct ttatagattt catttctgaa tgagctatta gatcattgta tatttcagg    160260 tgaattttta caattgttga ttcatcgttt aattttagt tttattttct gttgcattaa    160320
tctctgagat ttgacatata gaagaaactc tcatgccagc cccaaacgct ttccctatct   160380
cctcctccca tgccttcctg gagtggaggg aacgtcaggc ataagcagag cccaggagac   160440
actcatagac attctgagaa agcttttctc tgtagaaggg accaacacat cttgcaccct   160500
```

```
ctccctctct tgcccctgc ctgcatgtgg gtgcaggtgc ttttgtcagg accccactgc  160560
ttatctcagg tcaggagctg gcaaacctat gaacaagatg gaaacccaac tgctgaccag  160620
ggtggtgttc tgacaggaga gaagacttga gcccttatag acactgttga atcactaagc  160680
tgtaaacaat tttctttggt cttcttgtct ggtaaaatca attctctttc atcctttta   160740
aagacctcag tttgggcttt agaatccata ctggcaaatg cttcctcact aatattgtga  160800
gatttaatta gagatagcat tttatgtgct cacctaaaac tatacggtag acacaaagga  160860
gtctgggtct cagatcccaa cacgtggatt atagagaagg cagaatgcta taatgccttg  160920
agggtgagcc atccattatt tggggatttg aaaaaggaca atttctgttt tatgtttctg  160980
tcctcctaaa tggagttgag agacagcttc ttttctcctt agcatttggg caagaacaga  161040
atccagtaaa accactgagg aaggtcatca ttgcagcgtt tatttaacat gagtaattct  161100
agcatgagct ggcatgccat ttacatccat ctgttttaag tgtttgcaag cagaatggta  161160
ataagaaact ggggtaagtg ttaaaaataa ttatatggaa tatagattgc cccagatgca  161220
ctatctaatg ctgatgggaa aggagagagc agggggtacc tggaacctgg acttctcctt  161280
ggaaacatgc catgaccggg tatgttactg gattgcatag gtgcagaaca tggaacattg  161340
cagtggaatt gaactccaat gagctcagcc caactacgat attggagtga ggaatgcatg  161400
aagacaaaac ctttattata agtctgtgtg tgtgtgtgtg tgatctgttg ggattaaagt  161460
gccaggatta cagcattcta tgaaaatggt agtggagaaa aggaaggta gaggaaaaga   161520
gaaaaaccaa agcaagagga aaaccactgg aagaaaagaa gatgggaagg agaaagggca  161580
tctctgaaga atgtaaggag tacaagatcc cttacaggca gtgaacacat aagaaggcat  161640
cattccaccag aaagtcatac cagtttatgt attaaaactg ggaatggcaa tgataggcat  161700
tagttagaga ttatgcttta aattgtatgc atttgcatat ttttatatgt tttatttaat  161760
tttgttttgg ggggggact gtatctcact ctgttgccca ggctgatgtg cagtggtaca  161820
atcctagttt actgcaacct tgaactcctg ggcttaagtg accctctcac ctcagcctcc  161880
caagtagctg ggactacagg catgtgctac tatgtccaac taattttgtt attttttgt   161940
agagacaggt tctcaatgta ttgcccaggc tggtctggaa ctcctgggct caagtgatcc  162000
tcctgccttg gcctcccaaa gtgctgggat tacaggcgtg agccactgtg accagccctt  162060
ttgcatattt attgttttg tttgtttgtt tgttttttga gacagagtct cactctgtca   162120
cccaggctgg agtgcaatga cgcgatcttg gctcactgca acctctgcct gctgcgttca  162180
gcgattctc ctgcctcagc ctcccaagta gctgggatta caggtgccca ccaccaaacc   162240
cggctaattt tttgtatttt tagtagagac aggatttcac tatgttgggc agactggtct  162300
cgaactcctg acctcatgat ccgcctgcct catcctccca aagggctggg attacaggtg  162360
tgagccactg tgaccagccc atttgcacat ttagtgttta ttttcttaat cagtatcgaa  162420
actgtgaaag ggaatgttaa aacggtggag ccaggtgaaa aagaaaatcc aagagtcaga  162480
agagagcatc caaagaagaa ggcagaggca ataacaagta gactctgaga ctgaaattaa  162540
actgtatggc tagaagatgg gctagcatag gacaagatga ggtaacatgc taacatggaa  162600
gattgagaag aattgcaaat gagaaatcac ggataaaaca ctgaccgcct aataggataa  162660
aagcagagga tgttcataag cagctgtcat caccaaggaa gaggaaaaca tgggaaaggt  162720
tttgccctct gagcagaaca atcctgcatg tcaggggga gcctcatata ccatgtaacc  162780
tcatgttaaa ccataaatac ttaccaatac ctcttacagt gtgacaggac acaaactatt  162840
aaacctgatg cagataatgc ctttaaaat gagtattata tttgattatt atttctaata  162900
```

```
atgttataac tatgtttaaa ccatccactt tattccctag atgaaatata attgaattaa   162960
atgttaaaca tatttgacat gcatttctcg gggcttttga tttaacatttt taaaatatgc  163020
aatttagcta ttttaaaaaa cagtcttaaa aataacata gtatatcaag ataggcagaa    163080
ggaaaattta ggcaccaaat aatagagtac atgtttccta ttatgtgttt tggttgggag   163140
atgatctttg gaaagtgctg attctgtttt tgtttccata aaacaaaatt tccagagatt   163200
atatattgga ttctgcttga aagagttcag tagacattgc acttctatca cactgatagc   163260
ccaggaggaa ttttaactat gtaattattt aaccgcaaaa ttttccacct tctcccctta   163320
aacatttggc ggataaatta tgataaaagc agtcatgata tgcagttcgg tttcatagtt   163380
tcctttctct tccttttttgc tatatttcct aaagttctat tatggagaga taccagtttt  163440
aaatgtcaag caatgttaac atctttgcat ctttatctttt tcctatccac tcttctctct  163500
tttcttttct ttttttttttt aagggccaga gagtgacact tagccaatac ttaaccagta  163560
ctctcttttct gtttgtttgt gggaatttta tatctatttt ttcttttttca attttttattt 163620
taggttcaga gggtacatgt gcaggtttgt tacatgggta aattgggtgt cgctggggtt   163680
tggtgtacag atgattttgt cacgcaggta gtgagcatag tacctgatag gtagtttttt   163740
gaccctcagc cttttcccac ccaccacttt gaagtagacc cttgtgttta ttgttcccct   163800
ttttgggccc gtgcgtcctc aatgtttaga tcccacttgt aagtgagaat atgcagtact   163860
tgcttttctg tttctgcatt agttctctta agataatggc ctccagctgc actcttgttg   163920
cttcaaagaa catgattttg ttcttttttat ggctatatag tattccatga tgtatattac  163980
accacatttt ctttatccag ttcaccgttg atggccatct aggtggattc catgtctttg   164040
ctgttgtgaa tagtgctgtg ctgaacatgc aggtgcatgt gtctgtttgg tagaatgatt   164100
tatattcctt tggatagata tccagtaatg agaatgctgg gtcgaatggt agcgacttgt   164160
ctcttaatag ttttttacttt gcctcgatct cctgattctc tccctttttt tcctggccat  164220
tcccgctgca cttgcctcat ttgctattga tgacatgctt gtcccctgct tccatagatg   164280
tgtccacaaa tgcatgtgca cacgtgcttc agctaaagat tcctcagcta aagattctcc   164340
ctctccatca gggtttctct ctttagctca cctgcccttc tctacatggt tttaaagtga   164400
gatgattgta aatgtgtttt tcacaatgga aattctccca gcgggcgggg aggaaaaaag   164460
acatcttgaa atattttctg agaactatga ggaccggcag agtttgacat gttttttgagg  164520
cgataaagtc atgtgtccat ctgtgaaaga caggcattgg ctttatccac atccacacag   164580
ccttccccgc tgtgtggctt cattattgat ttgctgtcat gtagagtcga taatgagaaa   164640
acctaggtag ccttgaaccc aactttgcaa gaacctttta ggactctggg acttctaacc   164700
ctctaggaag gtggagttaa ggggatatag gcacagaatg gggcagaagg gaaagacatt   164760
aagagacagc ctttagcaga ccagagaata catgccgttt atcaaattgt tagatgtctg   164820
tgcaccagga atgttgattc aattatggta tctaaaaata ggacagaaat aaggaggaaa   164880
taaaaggaaa tgaaatagca gtttacctct ggcaaaaaca aagagcccaa tcagaaaaac   164940
tagacaaagc cacctgtagg actggaagaa accatgtgag ttaggtatca ctaaccttgg   165000
aaggacaagg acttcctagt atttttgtat tttgtgaagc actttctctg catttttctta  165060
atttgtcctt aagtgattat ctctcaacca accccaaaat ttgactcttc aaatcattta   165120
ttctctaaga ttttttaagca ttcaactgta atggcttatg tatcagcata gtcttatata  165180
attctaaaac aacattcata gcatggtatc ttgtaatatt tgactttcac tattaattct   165240
```

```
ttcagttatt atttgagtgc ctgtcacatg ccaggtattg ttctaagctt cagggatgca    165300
tccatgtaca aaataaataa aatttcctcc cttgtgccac tgatattcta taggtggatg    165360
gaaaacaaac ttaagagtta aataaattag gttttattta aagacagggt cttgccctgt    165420
cattcaggct gggtgcagtg tttaatcata gctcaccgta ctctccaact cccgggctca    165480
agcagtactc tcacatcagc ctcccaagta cctaggacta caggtgttgc caccatgccc    165540
agctatttat tttctgtatg ttttttcttt tgtagagatt gggtcttgct atgttgccca    165600
agctggtctg gaactcctag gttcaagcaa ccctccctcc ttggccccct aaattactag    165660
gatcacagac atgagccacc atacgtggcc aaagttttgt attattttat aaggtgatga    165720
gtgctgtgaa gaaaactaga agaggataag tggaattaga attgctaggg aagttgcagt    165780
attttaagta gggtggtcaa tgacaacctc aatgaaaagg ggatgtggga gtagagaatt    165840
gaaatagcta agggaaaaag ccatgatgat atatgagaag gatgttccag gcagagggaa    165900
cagccagtgc caaggctctg ggtaggaac atccctgttc tgtttagggc agagcagtgt     165960
attagtctgt tctcaagctg ccaataaaga tatgctcaag acttgggaat ttataaagga    166020
aagagtttta gtggactcac agttccacat ggttggggag gccttacaat catagcagag    166080
ggcaaggagg agcaaagtca tgtcttacat ggatggcagc aggcaagaga gagcgtgtgc    166140
agtcccttta caaaaccatc aggttttgtg atacttactc actatcacca gaacagcatg    166200
ggaaagacac accccatga ttcagttacc tccatcagg ccctcccac gattatgaga       166260
gctacaattt aagatgagat ttgggtgggg acacagccaa accatatcaa gcagtaagat    166320
ccacattct agagtatcag agtatgccat cagaatggca ggtatcagag tagggtggt      166380
ctatcgagaa ctttgtaatt ctgagaacca gggagaacaa atggaaggat ttcaacagat    166440
aattcatgtg tcaaggtgtg ttttaaagga gcactttgct tagctgaggc ttgtctgtag    166500
gggcaaaggt ggaatgtggg agaccagtta aaggctgat gtaagagtca agataagaac     166560
ctacagctgg gaggtgagaa gtggttggag tttttatac atttgaagta agatttgcta    166620
gttatatgga tgtggagtgt gggagatcga aggaagtcca gagttttgg cctaaacact     166680
ggaaaaggta gaggtggtca caggtgacat tggaggatgg gctagtagag acattcttaa    166740
gttatcatca aagtttaaat gtttgagttt gaaatgtcta tgagacatca aacggaagat    166800
atcccataag gagatggatg tcagagtctg aagttcaagg cagaaatctg tgctgaagag    166860
aaaaaatgtc agcctagata gtgtcgatgg tatctaaagc tatgaggcgg aataaaatta    166920
tcaagagagt tctgtggaca gagaagagaa aggaccaagg ctggagcttg ccaacaattt    166980
gagattggta ataatacgag gaacctggaa aggaaatgaa cataattgtc cagggtgtaa    167040
aagaaagtct ggtaatgtgg aagtgaaggg ggaaaaagg catttcaatg acagagaggt    167100
agtcaactgg gtgtaattca aataggtcat aaaatgcaca tctgctgcta tggtttccac    167160
tacagatgca aggaaaaagt gtcctcgtcc ttttgtctgt ctgattgtgg cagttgagat    167220
tgaatagagg tagacagagg ggaaaaaaga atgaggaaaa ttgagaacat agcaatgcaa    167280
atgtcatttt tgacctttag tagaaaagta ataattttgg tggagtgttg ggggtaaaag    167340
ccccaattgg ggcaggtttc agagagaata agagcaataa aattggaatc aatatcaata    167400
aatattttca aggatatttt cagaaaagga acaatataga cacactttt tttttaagat     167460
gagaaaattg ttttattgct tttaagatgg aaaatctaac cacatttctg tgtgctgtag    167520
ggttgatcta gaggcgtggt gttatcaatc agtacagtgt atagtgtgct acattaacaa    167580
atatccctaa aatggcagcg acatccacag ccactaaagt tgatttctcg ctcatgttca    167640
```

```
aagttcgcta agggttgact gtggctgttt tctgtgtatt cttaattctg ggacccgggc 167700
tgatggagaa gactcattta ttcttattat tactaattat ttttgttatt ttagcaaagg 167760
gggaaaatgg gcagaaccac attatagctc ttaaggtttt cgcttggaag tagccccact 167820
aatttctgtt catgtttcat ctgccaaagc aagtcaatta gctataactg aagtcatgga 167880
agtgagtcag tgaaattctt tcgagttagg gacagggaaa gtcttgcaag tgtgtatttg 167940
tccccttgag aggtgtggac agttttttac acaataatac aacatacaag aggaagacaa 168000
ttctgaggat atagcaagag caaggtgttc tattgttggg ttgtcaagag ttgatggagt 168060
ttgatgggtg agagtcagcc ttatattggg ttcctatcat tattctctta tgaaaagagg 168120
aggcacaaaa gatggggcca ttattgtcac atgggtaaat gggttagtgg tggtttgtgc 168180
atgttttctt gagatagaat ttcttcagtg tagtaagaag ccaggtcata ttctaacagt 168240
gaagatggag cacgagggat tggggattag aagaggaaga agaaggtgct atttagcaga 168300
gcctttaagg gaattcatca gagaaattta gtatgatata caggcatctc gattaaccta 168360
ctggaggttt gtgttcatga atttaatgtg agataagtca gcatgattaa atatcttctt 168420
tcatctgtgc tgatcagtaa aggtgaggcg gatgcatgct gggtggggag gtggatttca 168480
ccagggttgg agttttgcca aggaagaatc aagaattaag gctggattag aattgagggt 168540
gtctaaagga tcgtggatct gctatgactc cacaactcta agaaaagaag attcggtacc 168600
accatcctca ttatggaaat aacaaacgaa tgaaacaaaa ccatttgtca ctttctacaa 168660
gattcagagg gcttgtatgt ctatgatctc aggcctcaaa aagagtaaat cagttacctt 168720
tttcccacat aactctgtgt gtgtgttagt acaattttgt atgtttgccc tagaatgtga 168780
accatgaatt tgtgaaatga aagcagtgaa taggaaaaaa ggtaaagata cagtttttgta 168840
ttatctgtag caaaaatatt accacagcta tgtaatccac aaaaatggaa gaaatttatt 168900
aggtatttaa ttttttatcca agagtagtaa aatgaaggca gctatataat tatgtaggtg 168960
actgttaaaa tattagactt tttgttgaaa tttttttggct cagaaaacag gtttcatgcc 169020
atgctgaaaa attacttagt ttgatgaaaa agtaaacaag acatgacagt gaaatcatac 169080
agtgttgaaa caggaaatag ctaaaatgta ttttttctcag taaataagtg gctggcataa 169140
gttgtcctca ttttggggtc aagatcttat tttggtgtct cagctgaaga tgacctcttc 169200
acaatccatt aggtattgtg acactgatta attattatca agcagaaagt atttttttgga 169260
agtactttgc actaggcagg taaggcagtc gctaccacag gggcacaggt ttcgaagcag 169320
ttcaggagga gccaacgtct tgctgagaaa cccaaggcag acagcaatta gaggataaga 169380
taatgtataa ttaactgcca ccgtgtgtgg ggtagacaat tagagaacaa ggcaacacag 169440
atgttgtaag gtgctgatta tgggttttaa caataatgaa aaatgaaga caacatcatc 169500
agcgtgggct gacgctgtca ggggtggtgt gttttctcat gtgctgttac cctctaatca 169560
gtgttgagtt ggatagtatt cccaggaatg gctgtttggc ttcgcttctc ttaccagaga 169620
attgctctgc cttataaatg tagagactga catgtagaca cacttggatc atgaatttcc 169680
attctactct acaagaagta cagctgcaaa gaaaatcaaa tcatgttcag taccttttctg 169740
gaattttccc aagtactcag tagtcattct agctcacatc ttaactctgc tagggttcaa 169800
taagtatacc aaatgcatat ttttttttag ctaattccaa aatctaattc actttgatca 169860
atagtcatct cctatgaatt ccttgtgttt tcttcactat aaaatatttt tgtgattcat 169920
ctttcagtag acgaaaggtg aggtactttg agattatatt tctactaaat catgaatgat 169980
```

```
tcattattttt actgaaagta aacacatcca tcatattaaa tccatatcat gttctgttgt    170040
atattgtcac ttaagtgttt ttattatttt taaacaggtt gtataattgc atagagcttc    170100
aggctatcta catagacaaa atatctgaat aaaagtacaa cgatcatatt ttatcttgtc    170160
agtttaaatt atgtttaatg atttaattc cagggaaaac tctaatgtac caagttacca    170220
actgaaatgt gcccagtatc aatcctttat ttttaaatat aacattgtaa gttgttaagt    170280
aagttgttaa ctcttatccc taaaaagaca taatgttccc ttttcttatc atatgctaaa    170340
ataaaaattt ctaacaatga atgtgccatt tttataagcc agcaaactat gcaagtaagg    170400
atctcaatag aagatttaaa caaaataatt attttgctcc atattctgtt gcttttgttt    170460
tttgatgaga taattaattt tcatggaatt ttaaatgatc aatttgtagt aaattttggg    170520
aaatatgtcc attatttaat cacagattta gtatcttaaa cacattgaca acgtcaaact    170580
tgtctgcagc aaatggttac tgttaaaaat ttgccatagg ggtgagaact gcaatttata    170640
ctatttctaa gctatcaatg cttcaattat tacatgtgtt tatatatata tgtgtgtatg    170700
aacatgtgtg tgtgtgtgtg catgtataca caaattttaa agtaatggct tactgaaagg    170760
cctttttttc tcttcatatg actaagatat ctgaaattct gcccaaaatt gctaagatta    170820 tataccctttc tgaaaaattg caatgtgttt atgacgtatt tttatgatat ttcagtaccg    170880
gatatgttca ttaccccatg tatgaagtct tatcttgtga tgatgagttg atcagaccta    170940
ttacattgag aatattttta ggtataaact ttatatagtc tctgatggtg agtgtgtagg    171000
taaattgctt tgggctcacc tgattgtatt ttcattgttg ttgactttca ttatttcact    171060
aatttgggag caagggcttc ttttttatgg tctatttcta gatcatcttc ccttagatta    171120
catcatgtaa tgaactggca gaagatatta agtagatctt attcaaacaa gaactttgaa    171180
cctaaatgga gatttatcaa gctaaattag cctaattgtc tgtaacaatg accacagcat    171240
attaataaaa cctgtgaccc ttacatatat acatgtgcat tttaatgttc ttccactatg    171300
aaaggcattt tgtgatttaa tctgcttgat gaacgattaa tatgatattc actaattttt    171360
actcatctta ttcttaattc atctaattta tctaattctt agtaatctaa atgattcaag    171420
cctcttacag attttttatct ctacccagtt ttttcatccag ctgtccgtgt ggtcatctct    171480
gccttggtgt gcttgagaat tatttctgat tctatgacac caatgcactt tgcagtcttt    171540
gaacttgaat tggcagaatc aagcttcctc tagacaaatc actgaatctc ttttctcacg    171600
ttaaggtttg taggaaccct attctcaaag ctgccaaaac actactgctt agtctatgca    171660
aatcaacaac tacaaatgca cgtcactcaa tcaacattat gaaactcctt tttggaatga    171720
ttgatgatca caaaatgtga tcttgtgaca atatgatata ttcatttaag ccacattgag    171780
gtttcaaatt ggcaccattg acaacgtacc tctttcatgc taagtgtaat aatttgttgc    171840
ctctcatttt cctatgctgc ttcacttcat taaatctgaa taattaaaaa ttttcgtagc    171900
atcgccaaag tcacttccca ggagctaggg aatgtgtcga tctgtacact gatccagttc    171960
ctgctgacgt ttgcttggat gcagaggcca tccatcgctt tccattgatt tttgtcaatt    172020
gatgcttttc ttccttcttt cctggtgact taggaaatgt tctgaaactg tgcattcaag    172080
tcaacacatg ttagattcat aactaggatt caccttcaca gtggactggt cccaatttgc    172140 tgtatttttta ttcagcctgt caactcacac tatctgacta aaagacgcta atgcagtgtt    172200
ggccagtccc ctgtcatctc tttctaattg tttggtctca aagcaatggt gcatgttaca    172260
catatccatt taactgtcca attaacgcat gtttctagac aattctgata gaaagggtct    172320 ctttttcttcc ttcagcccaa acaaagcaaa acaaaacaaa agggcactta cacgatgttg    172380
```

```
atctatgttt tatcttttt ttttttgag atggaatctc cctctatcac cctggctgga    172440
gtgcagtggc gcgatccccg ctccctacaa cctccgcctc ccaggttcaa acagttctcc   172500
tgcctcagcc ttccgagtag ctgggactac aggcatgcac caccacaccc ggctaagttt   172560
tgtatttta  atagagatgg ggttttgcca tgttggccag gctggtctca aactcctgac   172620
ctcaagtgat ccacacacct tggcctccca aaatgctggg attacaggtg tgagccacca   172680
cccctggcct gttttgttt  tatcttaaat ctcttaggct gagactcata tggtcccact   172740
tacccatctt tttacagcat gaaattgtcc agttaaaatt acagctcttt attaatggcc   172800
ttaagactct tcattttgaa tggataaaat agtaataggc tgtgagcacc aacagtatta   172860
atgtatcatt catgcatgat atagtagtgt tgacatcttt cttttccttt tctgttttta   172920
aatgaagttc aggaaaccaa tatgaaaggt aagaaattgc caacatcttg gactatcaaa   172980
tcatggcaga caatgaatta aagaattcaa caaatctttg gcagcatcag tttcaaaggt   173040
atttagatac aaccaccgtg taattctaca caatttaatt aaatcattta tcaaatcctc   173100
tacaacttga ataatttaac tgatatcaga ataatccatt tttcagataa ttattttat    173160
atttaatgtg ttaaatataa aaatatgaca cttctcttgc ataatttgca gaatgttatt   173220
tatttcatta ttttattatt attttaaaa tttcaacttt tatttgatac atgtacagat    173280
ttattaaatg gaaatattgc ctgatgctgg ggtttgcagg aaggatcctg tcacccaggt   173340
agtgagcata acatccaata ggtagttttg taagccccc  cacaaccagc accctatagt    173400
agttctcagt gtcttgctct tttgcccagg tgcaatcaaa gctcaccaca gcctccaact   173460
cctggactca agtgatcctc ctgcctcagc ttcctgagta aataggacta cagatgccac   173520
catggccaac taatttttta atttttactt tgtagagatg gagtattgct atgttgacta   173580
ggatgatcat ccactcctgg cctcaaatga tcctcccggc taggccttcc aatgtgccag   173640
gattagaagt gtgagccacc tcgcccagcc ccaatgcttg atctttaaga gcttcaggca   173700
gttgaagggt tttgtctgcc tgccacagcc ttccatcttt ttgagatgtg tttacctgag   173760
acagctaagt aggtgacaac ctgaactacg gttgctggca attggaaaac agaagattgc   173820
tctgttgatc cattgggaga agtacagtag tctgtagagg aacagaatcc cagggttttt   173880
ttctggcatg gaatcactct agagagccac attaaaaatt taattcctgc tgagcacagt   173940
ggcttacgcc tgtaatccca gcactttggg aggccgagga gggcggatca tgaggtcagg   174000
agttcgagac tagcctgacc aacatggtga acgctgtct  ctactaaaaa tacaaaaatt    174060
agctgggtgt ggtggcgtgc acctgtaatc ccagctactc gggaggctga ggcaggagaa   174120
ttgcttgaac ccgggagatg gaggttgcag tgagccaagt ttacaccatt gcactccacc   174180
ttgggcaaaa caagcaaaaa actccatctc aaaaaaaat  taattcccct ttgactgttg    174240
attttattta tttattatta tttttttaga gacagggtct tgctctgtct ttcagattgg   174300
agtggtatga tcatagctca ctgcaacctt gaaatcctga ggtcaagtga tcctcccacc   174360
tcagcttccc aagtagcttg gttgacaggc atgcaccact acacctagct aattttcta    174420
tttttatttt tgtagaaaca gggtctcgct ctgctgccca gtctggtctt gaactcctgg   174480
cctcatacga tcctcccacc tagttcttcc gaagtgctgg gtttataggt gtgatagtgc   174540
cgagccattt ggctgctgtt tttacattta taccattatc ttcatcctaa ataggaattc   174600
tgatagtatt gttggcagaa tagggtcaac tggaacacac attttgttc  tctaggtaaa    174660
gatgatgaaa cttaaaatgt agctaatgtt attcctgcaa tgaatatgtc aatttctaat   174720
```

```
ctggggacaa aaataaataa aaaaaaagtt gcacgtatta aacaccttct tgactaagtg  174780
gcagctgtaa tgatttcact tggggatagc cattgcttct taactcatgc taacagtgca  174840
ttaaagctat tgattttag tggctgctgt gctttcgtga ttgtagatca tttctctctt  174900
tggaaactct atttgatgac aaagctggct ctgttgcaga gtaatgataa aagaaaggac  174960
ctaccagaat ttcaagtgaa atgtataaca tatgtgataa tgcatggtga ctgcaatgat  175020
tatttcccga tgttgctgtt taatagccat gaaagcatcc tactgaaata gagtatttct  175080
gctttgaatg gcttagttag ctcaaaaatt ttgaaagctt tctcagtaaa gcatggtgcc  175140
aggcactgaa agattccttt tggaggagcc agagtcaatt tggatgatgt ttataaaatg  175200
ctgctggaaa attgggtggt gttttctaaa tgatcttcct agtaatgatt tatgctgtaa  175260
atcagaaagg ttgccatctc tctggatgga aatgcatagt catatgcccg taaatgcagg  175320
gatttgacct cctataaaaa agctctctct tcccctcat ttatgtgatg attgtatacc  175380
atctgagcgc tgagaaaccc attggccatc ttccacttgt gtgtggctgg aggtgcttgc  175440
tgcagctctg tgatgccctg agccagcatg ctcgtggagt tccagtctgc tgcatgaaca  175500
agtggagaaa catgatcttc ctaaactgct cacaagctgc taaatgagtg atttgtgttc  175560
cctttgaatt catgctgtaa atggaaatgc ttgctccttc ccgggttatt actctgtgta  175620
cacgccattt gaggatgcag ataattgttg catcttcact gaagcatccc atcttagtcc  175680
agatttccgt tttcacagac caaagggca aagtcagact tggcagacag cgcagcttca  175740
gtctcatggg gggatttctt tgtctcatca gcctcagtca tgggctttcc agccattata  175800
atttcacatg taatatggtg ggtgtccatc tgagcaagtg tggtgcctca gtagggttgg  175860
aggaggcact tggagctgat gtagagaaag gagagtgaat taaaagtgga aggaggcaaa  175920
ttaaaagaag cgaggaaaca ttctttttca caccagagaa acgttttcaa aacaccaggg  175980
aagcctcaga accaatccag gtactgcttt tatttctgaa ctctgttata atttgtgatg  176040
tcagaagctt ctatggaatc tactgatatg tgcagaaata atgtgctgct gtgcccattc  176100
tgtgttatac atttagaagc agttgcggta tcatgggata cataatattc tttaatccca  176160
atagggcttt caattctaaa tataacaaaa acagttggga aaggcacaca tacacaggtt  176220
ggcctgtaga gatggaggtg gccaatttgg tgtgttttga acagacgggg atgctctctg  176280
cgtactgccc ccacaccaca ggacagctga caggcagccc aaatgcccgt gcagactgct  176340
gaactccaga tggcttgctg gtgctggctg gcacgccttc aagtcctgcc tttcttgggt  176400
ccctaacaga attcacatta cctgaaattt cagggaattt gtggggctgg ctaaacagat  176460
tccttacata actggtgatg tgcggtcaga aagagaatag atgagtaaga ttgcattggc  176520
tgcctgtgtg tattagtttt cttttgctgc atattgaatt actgcaaact cagtggctta  176580
aaatcacaca catttattat gtcacaattt ctgtggtcag gcgtctgggc atgtctgagc  176640
tggatttcct cctcagtgcc acacagagat gctatcaagg tgtcggctgg gcagcatgac  176700
tctcgggagg ctcatggtcc ttttccaagg tcactcaggt attggcagaa tctggtttat  176760
tttggttgta ggattgaggt cccctctttc ttggtggatg tcagcagggg tcgatgtcag  176820
ctcctagagt tccccaggc agcttcttgc catgaagcca tctcagggac tgtctcccaa  176880
tacggcgaca cgtatcttca agtccagcag gagaatctct tacttccagt cggctaataa  176940
aataatctta gataacataa cctaatcaag gcaatggcat cccatcctat ttcctaggta  177000
atgtaataca ctcaagggat gacttctatc aacctcatag gtccggctca aattcaactt  177060
cctgggatta cgggagggca tggcttatta ggtccttctg agtcataaat gctctaatgt  177120
```

```
ataaacttcc tagggtttct ataatatatt aacactgggt ggtaaatggt gtaaactggg 177180
tgacttacaa caacagaaat atattctctc ccggttctgg aggccagaag accaaaatca 177240
aggtgttggc atggttggtt tcttctggag cctccgaggg agaatttgtt ccttgtctct 177300
ctcctactt  ctgggggct  gccggttaac ttttggcttt tcttggaagc gtcacttcaa 177360
tgtctgtctt catctttaca aggccttctt ctctccatat gtttctggat cctctcctct 177420
tcttaaaagg atactagtca ttgggtctag ggaccactgc aaatctgtga tgattttatc 177480
tccaaagaaa ttacgtgatc acatctgcaa agaccctgca gtagtacctt tttatccatg 177540
gttttgcttt ccagggtttc agttccctgt gatcatttaa tctctaggct tagtcagtta 177600
actcttgaga tattaagagt taatctcttg ctgtgtataa tttataaatt aaactttatc 177660
atagacatta atacatagga gacaacatag tatctataca atttgatact agctgcagtt 177720
tcaggccttg aaacatatcc tcatagataa ggatgtgggg tgttatatat ttccacatag 177780
gaacacattc tgagattctg gtggatgtga attttttggga cattattcaa cacagtacac 177840
cccgtcaagc tttgcccatg acctgacact gcccaatcct ctggtctcat cttgtgggga 177900
ctctccttca ccttttctgg aatatttcct tacaacttcc tttctaactc cttaactcct 177960
aattcagatc atcttgggct aggagtaata ttcagtactc aatcattaga gaagatgggg 178020
tcaccaggag ataaataggt aagcagatag gtaggttgat agatatagat agttagatag 178080
atagatagat agatagatag atagatggac agacagacag acatgggtga atagatgatg 178140
gagatggata gatagaaagg tagatagatg atatatgtgt aagaatagat agataaatag 178200
atagatatga ataggtggat agatgataga tcgatggata gatacatgga tagagatgat 178260
agatataggt agatagagat ggatagataa atgatagaaa ggcagataga tacatagatg 178320
catagacaga tatggataca tggatagatg atagatagag atgggtagac aggtagatat 178380
atggtagata taaagatgtt agagatggat agatgataga gatggataga taggtaggta 178440
aataagtaga tataaattta gatagagatg aatagacagg tagataggta aatagacaga 178500
caggtaggta ggtagaggac agagatggat agatagacag gtagatgata gatggtagag 178560
atggatagat agacctctta atccctatgt atcaatccat ctctatagct atctgtaatc 178620
acacatgtat atgtctacat gctcattaat aacattttca cagcaggaat tcagtgattt 178680
agtgattatt gaattaattg ttgcataagg ctccctgagg gcaacactgg gtcttcttgt 178740
tcactatcct cagtgctatc attttacagt gggaggaagc ttaccttcct accaaaagca 178800
ttctgtggct ctgaagtggg agaaagatag attctctgcc acctttccca aaccagggat 178860
cctggttcca acatcaggat ttacctggcg ctgaaaggat tcattccatt gcattaattg 178920
tattcatgca catgagtatt ttctgagcat ctctgaggaa ggcaacagtt tctatggtga 178980
acggtgtgga gagcacagtc actcctcatt acagcactgg aagtaatcac aatgatgata 179040
acataccctg cattctatcc agagccattt ttaagattta aaaaatttac ttggcattat 179100
tttcttcatt tgagtagctc tttaaggtat tttgtgaccg cccccccccc ccatttttatt 179160
tttcctttg tagagaaggc ataatttttac tttcaccctc ttaagagttt tttctgatgg 179220
tcctgagaat taaatggaca aaggacagat cagcaggaga aaaacataca aacccatgta 179280
atttaaggtt tctgtgacat gagaaaaccc tcagatggaa acgaagactc aaagaagtgg 179340
cgacacttca gtgctttag agaaggttga acaaagacag acgatgatgg aaaagtagct 179400
aacctatgtg gaggctaaag aaatatgtgg tttattttaa catggtcttt tagtacacaa 179460
```

-continued

```
ttctcttatt tcagcctccc cttctcaatg acaagaatgc ttttccttc tggtatagg    179520
agggcacagt ccatacagga gtttcatctc ttgctttcag aaaggaaaac aggatcagag  179580
cagcttttctt gtacctgctg ttttttttcct cccctcccct cccctccccct cccctccct 179640
cccctccct cccctttcct ggcctggagc ttaaatgacc atacaccaac atagcatttc   179700
tggggtggca gattctgcca gcctttcact ttacatcctc ctgttatcat ctgaattttt  179760
gaattatcac tcacaacttt tgtacatggt ttcttaatat tttacaaata tctatatgca  179820
aaaataatgt tcatttggca taccttatt cttttttaaa attttatttt attttatttt   179880
attttaagtt ctgggatcca tgtgcaggac atgcaggtgt gttgcatagg taaacgtgtg  179940
ccatggggt ttgctgcccc taccaatcca tcacctaggt attaagcccc gcatccatta   180000
gctatttatg ctaatgctct cccttccccc cgccctcccct gacagaccct agtgtgtgtt  180060
gtttccctcc ctgtgtccat gtgttccaat tgttcagctc ccacttatac gtgagaacat  180120
gtggtgtttg gttctctgtt cctgcattag tttgctgagg ataatggctt ccacctccat  180180
ccatgtctct gcaaaggaca tgatcttgtt ctgttttatg gctgcatagt attccatggt  180240
gtatatgtac cacatttgct ttatccagtc aatcattgat gggcatttgg gttgattcca  180300
tgtctttgcg attgtgaata gcgctgcaat gaacatacac ttgcatgtcc acattgagaa  180360
accatctcac gcaagtcaga atggcgatta ttagaaaact catattcttt aataacatct  180420
ttgaaatgat gattcttcag tcttgaatca tcagtgcttc caggccatac cttccccatt  180480
cttaacttga atcctgactt cattcttgag cttgttggag ttgccctgag cttgatttct  180540
tagagtgaat tatcctgtga tttttactct atgcctaagt tagatggact ttcttagcat  180600
gctaatctct aaaaatacct tttcaaagga gagattggga aaggttttgt accaaaacat  180660
ggtagatctt gttccattat caactgcgtc tcgtgtcaga gagttctaag gtgagtgaaa  180720
ttgtgcgtgt ttgtagcgtg gtcataaaga catttcacag agtggatcgc aaacaaacca  180780
acagagcaca gagggcttga gagcaatggc agctggtgga agcacaggac agggcacagc  180840
gggaatttca tgggaccacg aaccaagaac agaacccatg accaggctgt ttttccttcc  180900
aggggcccag gctttctcag ctcagccttc acttgcatgc tgctttgagc atgtttggct  180960
tctttgagaa aatgagccac ccaagaggcc tacatccaag tcacctgcac tcagatccca  181020
gccaggagta tggagggccc atgtggggtg gagtggtgca cgtcctcacc accttagaca  181080
cagggaccac ctacctcatt ttagatggag tgggcagata atctgcacac atacctccaa  181140
aggtgtcctc tattgtagag acaccttttg tttttctccc tcaatcctgg acattttgtt  181200
tgttttctt tatttcacta attttacaat aaactgccag gatatgtctc catgtctagc   181260
tcttttgtg aattattctg gaaataacag cctctgcaag gctgctaaag tgacaaaggt  181320
attttttcaat cgcgtctgat tcctttcaga tatttccatc ttcctactcc atcatccatc 181380
tcttttttaaa aattttgttt tgttttttgag acaaggcctt gctctgtcac ccagattgga 181440
gtgcagtagc atgatcgtag ctcgctgcag ccttggtccc gggcttaggt gatcctccca   181500
cctcagcgcc cccaagtagc tgggactgca ggtgcacacc ccacgaccag ctaattttg    181560
tgttgttagt agatactggg ttttaccatg ttgcccaggc tggtctcgaa ctccggggct   181620
caagtgatcc gcctgcctca gccttcatgt tttctttacc agttggttcc ctctctttcc   181680
cacacttgct aagaccacta ctggttcact gtcacgatgt cacttacttt tttgactacc   181740
ttcagtgatc tttctttct gatttatgta tatatttcct gagtaatgtc attctttatt   181800
aaaaatgtat atgtatatat gtgtacacaa aagtatacat atatgtgtat atatcctaaa   181860
```

```
tgattctatt atttattgaa ataaataatg tatgtataat tatatattta tatataatgt   181920
aagcattagt atataatgta tattatggat acattatata tacattttat acacaattag   181980
gttctgtgta tactatatat gtatgtatac agacatgtgt atatatatat gtgtttataa   182040
tatatacaaa tgattgtaac agtgtgtgta tatatgtgtt tatgtgtata tatagtatat   182100
atataacatt aatgtgataa aagtgtatgt gcatatatgt gtatttgtgt ttttgtacat   182160
actcatgacc acatttaaag aataccattg taaaagctga ccatataatc gtctatgcgc   182220
atatatatat gcagcaaaaa tgccatcatc ttcattaata aatgccttct ttattaataa   182280
atatacattg gttcacaata tcaacctcag cattatatac atttcaacaa acatgctcat   182340
tgttttaagc atacattatt aattcatatt tattttgttt taagttgaga ttgttataac   182400
tccctctttt ttcaaatttt tagctaatgg tacttttttaa aaagaatgac tttattgtat   182460
tcaaattatc actagtggga taaataatgt aatgatggga aaaagcttcc tttgttccag   182520
ctataattat ctgtagttgt ttatttgttt tattcaactt aacattcatg ttttattcaa   182580
atcatcaata tataatgatt ttgttctgtt accaaagatc ttattgggaa ttctaaagta   182640
ataaattatt ttgaagaggt atcgatacta ttacactctt gatttatacc tggatcaatg   182700
aatgttttta aatatgtaag cgttcttttta tgtttcttgt tattttatat attttatgta   182760
acatgtgctg tacacttctt agagttattg ctagaacatt tatcatgaat gtgcaaagaa   182820 tttttttcaaa tatatttatg tgcatatata tgacaaatca ttttgtgtta attttataca   182880
attctaaata ataagtgact cattctaaat tatttagctg attctctaga ttctctttct   182940
cttgttggat agtcatatgc aggagtgact ttattttgtc tccttctttc tgatattttc   183000
agttctcaat acttttttaat aaaaacatat aggcttcgag tctgtagaag tatcttgaaa   183060
tatgatggtg atgatgaaca tcattgccct gtttatactt ttagtgaaaa ttcacttagt   183120
gcaacatttc ttttcctatt tgttgataag attaaaaagg atttcctgcc aaaataaata   183180
ttccatgtac tctacttttt aaattaaata cattaatagt accagatact atttgccatc   183240
tttcaaatag ctttttttctc ctttgatctt tccctcagct atcacctgac ttctttcctt   183300
caactgtgaa tgagacaaag caaaacaccc tacttcttcc cattgaacca tcttactgta   183360
tttgtagagt caacctaatt ccttattagg tcactgcata gttttttttt aatttaatat   183420
tttacgctat ttattataat gatcattgga ggaataatca gaacgtgtta agattcttta   183480
caagtaactt ttacatttta gtgttcttgg cctttgaact gcgttttgga tgaagaactt   183540
ttaggatttt ctgtgcttgg gggtgctaaa ggtgtttaca cctgagtgaa tgcccagaat   183600
ttgatcatat agattttttct attgacagtc tcaccttctt atggttattc tcttgtaaat   183660
tatctttacc tcaagaccaa gatttgcaaa tatattgatt ttcagtagat gcagtgttca   183720
catagtatct cctgaaacaa tcactttttg cagtgtcttt tgtatatcac tggttgcgtc   183780
cctttactca gatctaaggt acatctgttt ctgtattttt ccttatgagt ggtctggatt   183840
ttaattcttt caatacactt tatattttat tggagtatgc tttgccaacg catcctttttt   183900 atctcagact gttcttatgt ctctgtaata aagaaactgc atcttatttt actccatgaa   183960
aaatcacaaa tgattcccta agtgttcctt tagagtgttc ctgagaggac tgtggttgtc   184020
ttttattcta cattgtgtgt ctttttttaag actttattag cgcagttttta ggttcacaac   184080 aaaatagagg ggaacgtaca gagagttctc atatatcccc tgcccccata catgacggt   184140 cttccctatt ttccacatca cccaccagag gggtgtgttt gttacaatcc atgaacttac   184200
```

```
actgacatct tcatcaccca aagtccgtcc tttacagtag gctacagtct tggtggtggt    184260
gtacattctg tgggttcaga caaatccgta ataacataaa tccaccatta cagtatcaca    184320
cagtatagtt ctgcaaccct aaaaatcttc cataaaaaaa cctccacaat tttagcagtt    184380
tgtaacaaca aaggcttatt tccttttcct gaagttcatg tcggttgtgg gtggacttgc    184440
ttgttactta ggtagactga tattagaagg tgggaaaaga ataatacctc tccaggaaag    184500
gataggaact attttgaacc aataatacag ctcactacac aaaatgagtg aacacagtca    184560
cactgaaaga gagatgagtg acatatgctt aagttatgct tatgttgaca aggtctcact    184620
cacctaaact ggagtgcagt gccacaatta tagctcactg cagcctgcaa tccctggact    184680
caagcagtcc tcccacctca gcctcctgag cagctgggac tacaggcaca cacctgtgtg    184740
attttgttat ttatttattt atttatttat ttattttaa tagaaacagg ttctcattat    184800
gttcctagac tggtctcaaa cttcagcgtt caagcagtcc tcttgccttg gcctctcaga    184860
gtgctggaat tacaggcatg agccactgcg cccagcctcc tttagtgttt aactgaacag    184920
aataaagaac ctcttcatta tggtgaattg gctaagttca aaagagtagc aaaagccttc    184980
gtgggcagta ataattactc tatcttccaa atacttgagt gaccttatgc ttcttaaaat    185040
atatatttta gggctcttaa ttgaaatcaa ttgcctttat agcctctatt acagcatact    185100
cagaaattga agagcgggat gattttgtat aaatctagac taattttgtt tttctggaat    185160
gactagaacc atttaccatg tcaggtacac acacaagaaa cgctaagggc gagttgtgaa    185220
tgatttgact aggaacaata gttgggctgc ttttagatgt ctccttttgc tacatagaca    185280
gcaaaaggag aattcaccaa aggtgccagc ccttcagaat ccttgtccca caccaccaaa    185340
aagtcctgtg acagaaattc cacctattaa tcagctgctg tgtcctgact acggagaaaa    185400
gtatgatgca acagaacgca aacttttcca caatctcata acaaggaaaa aatatatgta    185460
tgtataatat gtgtacatat ataagaaaat gtatattaca tatatagtaa atacatacaa    185520
atacacgtat gtgtgtatgt atatatacac acatattttg ttttgttagg tattttttat    185580
gactatttat ttaaaaaagt cacattgaaa ataaaattga cttttatttg ccctaagtta    185640
cctcttgaaa tattgtgtta aaaacctaat aacttctgac aggtatatat ataccctag    185700 aggttaatat atatacgtgt gtttgtgtgt gtgtgtgtgt gtgtgtgtat gcgcgtgcat    185760
agaagttatt aggttttgtt tgtttgatgg ttttgttgtt gtttttttgag atggaatctc    185820 actctgtcgt gcaggctaga gtgcagtggc gtgatcttgg ctcactgcag cctccgcctc    185880
ctggattcta gtgattcttg tgcctcagtc tcccaagtag ctgtgattac aggcatgtga    185940
caccatgtct ggctattttt tgtattttta gtaaagatgg gatttcacca tgttggccag    186000
acttgtcttg aactcctggc ctcaggtgat ctgcctgccc tggcctccca aagtgccagg    186060
attacaggcg tgagccactg cgccaggcat tattaggttt ctagtacaac atttcaagag    186120
ttatatgtat agatatgtgt acgtgtgtgt gtatatatat atatatatat atatatatat    186180
atatatatat atatataaaa cctctatggg tatgttaggt ttttaataca acatttcaac    186240
aagcatctta ggacaaatga aagtcaatta tgttctcaac atgactttc ttaataaaca    186300 tacatttaaa ataacctagc aaaatacatt atttagtacc tattttaaa cacactgtgg    186360 tttaatctca agctcataga ttcttcgaga taatattgtc tatcagctga aaattctaaa    186420
aaaaaaatgg gaaaggctca tgtaaatata ataggatttg tatttcattt ctgaggacag    186480
aaacatttca atagtaaaat ttgcaacaaa aagtgcttat ggaaagttag acaatgctct    186540
aggactctaa tagtaagcac aggaatatgt cagagaccca taaaatcttt agatttattt    186600
```

```
tgattcctac ctgtaaaagt gtgaaatcaa ttattgctaa atccagcaaa acagcaaagg  186660
aaaattacta ttcaccttt tctctcagtc tgtcttccaa agctactaag agaaaaacaa  186720
gaaaaataca gaaaatccta cttccattat tacaatgaag cattttgag ctagtagaaa  186780 attagaatta gaccttgctt ttactggcat cacaaaagca tttcatcctg tttttgaaa  186840 tgacaaatgg cagaattctt atatacaata tgctaaccaa aatcatgtta ttgccacgtc  186900
atgaattata atttaatttc tactctcaaa gttaaataag aagatacaat attgcatttc  186960
cctgcttgaa gaggagaatt agttacactt gttacgtaaa ggctgtattc atcactggtt  187020
gtcatagctg ttatgactgt gactcttata atagaggtgg gcttgcagcc aaaaatatat  187080
gattcatcca aaagatattt accatgtaac ttatattata tgtgctgaat attttggtag  187140
tcattgcaaa ttaaggaata tggtgttgaa aaatcacagg taacaccttt ttcttgttgc  187200
taacaatcta acagggagac cttatttaac aagatatcat attacacatt acaattcatc  187260
ttgtgaagaa aaatgccaac tacagtgaat aattgaggaa cccaagttca tttacgaatg  187320
gaaggttggg atgaacaggg aatgcctttc tgaggaaatg gaatttaagc tgatcagtaa  187380
aaatgaatct tccaggagca tatgggcttt gcagatggga gaaacagcag agaatgccca  187440
aaagttctaa aggaaacctg atgatgaaat gagttaagcc atgttcctgg tagtgtatca  187500
gttagctttt gctacataag gaaccatctc aaagccgagc atctcaaacc accttatt  187560 agctaagcat ctcaaacaac ctctatttag gttatgattc ttggctggac atctgggctg  187620
tgctcagctg ggaggctctt cagtctagag tcagcttcca ggtctgttgg gtgctcattg  187680
gccaagcact atcttaacag ggtgcttgac agtgctccat gtggaatatc atcctctaac  187740
aggctagtat agactcttca tggaagcttg tcagggttgc atgtaggtgt gttcaagtcc  187800
tcttataatg aaagctaaga ataaggacag tgtgtcaccc cccacatccg gaatgtccaa  187860
ataagcaaat ccagaaagac acagatgaat gggtagtttc caggggctga gagtgaccac  187920
taaatggtac catattttt tggggggat catgaaaatg ttctgccatt agatattgtc  187980
aattattgca cagatccatg aatatattaa aaaccattgg attgcatact ttgacacggt  188040
gatgtgtatg gtatattaat tatatctcaa ttaagcaatt atatctgtct atcatttatc  188100
tgtaaaccag ataaaataag acaggctagg tatatagaaa aatagaacag aacaaggtag  188160
gcagaaacag aatctagcag atataaaact tggcatgtaa gtaaagagct gtaataccta  188220
tgtagctgaa aatggaactg ttctctaagg aaataattaa aataatctct atgctctagc  188280
atccagataa ataaattcca ggtgagttat gacccagatg tgaaataaaa ccttaaaact  188340
gttaggagaa tatgtaagca aataaaatgt ctttatgttt ctggattaag taatccttt  188400 tttttaaaaa aagcagaaat tatagagaaa atagtgataa attataatac ttatgcattt  188460
taaagcatta gtttagataa ttaaaaatca ataaaatggt taaagacaac agactagata  188520
tcaccaatgc tcaactgtgt aaacttgggc aaattattta atatctgtat acctaatttt  188580
cctcagctat aaaatgatat tagttacaca tctcataagg tatttatgaa gattgcatat  188640
tcggagctgg acacagtggc tcacacctgt aatacagcac tttgggaggc tgaggtggga  188700
gacttgcttg aggccaagag ttcaagacta gcctgcacaa catagtgaga ctttatctct  188760
acaagaaata gaacaaaatt aaccaggtgt ggtggtgcac acctgtagtc ccagctactc  188820
gggaggctga ggtcgaagaa tcactggagc ccttgagttg gaggctgcgg taagctacag  188880
ttgtgtgact gcactccagc ctgtgtgaca gagcaagact ttgtctctaa aaacaaaca   188940
```

```
aacaaaatgc atattcaaca tgcataaagc ccttagaacc atacgcagca ctgctatgca 189000
ctgttaaatg tttgcttttaa catgctcaaa aagaggccag catccatgaa tataaagatt 189060
tcctacaaat caataacaga cattcagcca gtcaaaaatt ggattgctat tcaagatggg 189120
aatttagaat gggaatatag aaatgcatct gtactagttt taaggaacat gcaaattgaa 189180
atataaactg ttaatatttt atactcatca aagtggcaaa tgtattgtct gataatgtca 189240
agtgttggca acagggtaag ggccaggaaa ttttcttacc tgctagtggg tgtatagcat 189300
aatacaactt gtttggaaag aaatatgcca gtatctactg aagataaaat tagtattacc 189360
ctatgtatca gttagctact gctgcataac aaaggactct aaaagtcaat gccttaagac 189420
aataagcgcc tattactgct tatgagcctc tgcatcttgt tagctggaaa tttattttgg 189480
tcttggctgg gctcattcat gtgtatgcat tgttgatttg gagtgagttc tcttaggtaa 189540
ttgggggttg ctggaggtaa ttttgcctag gttagggcca atgggttctt ctctatgaga 189600
tcttttgttg tgcaacctgc tagtctgatt tttcacagga cagtggcaga atttcaagag 189660
agtaagaata ggtacagggg atttgagtcc cagtcttgga aacagcacat cattatattt 189720
tttcttttga aaaatgcaa tcttaaagcc actcaagatt caagggtga aagtacagac 189780
tctctatgta tgaggaatag taaattcatg gggaggattg tagaactggg aaccttttgc 189840
ctgtcagtgg actacaccct gtaattcaac aattgtctat ctagtagtta tgtgccctgg 189900
aactggggtc ttcaaactgg cagatgtctt ttcaaaattt tcaaagtat gactctgctg 189960
atgattttaa agaaactaat tttcaggtac tcagcccca gatgttctcc tttctaagcc 190020
ttcctggtca ccaaaagctt cttcccacat cacaaaagga tgaccttcag taggcatgac 190080
actttgttac caacctttc tgccagggtt tataatacaa gaaatatctt tttgaatgct 190140
gctttctgga aagcccttt gctgaaggct ccataaaata agcctcctat cttatacata 190200
tttccattaa gagtgaagtt tggtcctgtt caggtgttct gatttcagaa aaagaaaaaa 190260
gaagccatag gtcagctatg gcagttcttt caaatgcaga aactgaactt ttctgttgct 190320
aaccaatttt tcaaggtgca tatacattgg gtgaagccca tcggtaaatg atccaatccg 190380
aaaatcatct gaaggtcatc tttcaaattc attgtggtag tgttattcaa gtggaggctc 190440
aaatatattt caagtgtatg catggaatat tttccccagc tagagtctgt tctccaggtg 190500
tatggaggaa agaggagttg tccaggttgt gtacctgttc ttctcatctt tctgggctaa 190560
ttcatgtcct ttctgtgccc tcagcctcca acccatgctt ctgctcagag cagcctgttt 190620
tctttgctcc cataaatgta ttcctggccc cagatcttct gtgcatattt agaagcccta 190680
acccacttcc tcaccagcca cccctctatc cccagactct cctaccagga acagcagagg 190740
atcctaaatt catgcatgca ttttcctgcc ccgttggaat gatctgtgtg catgtctgtc 190800
tctgatgttc atctccttct tcagtgtggg tgtgtcatta cctcttttag ccaggactgc 190860
atggcattac ctgtcttagt cgggactgca tgttaaaagg gtcaacacat atttgtagaa 190920
ggaattggct tctgagtgaa tgaacccatg tgtcatgggc agtctgtgag gacataccag 190980
tcacttcctt gctgccgaga gctggggata ttgcattgga ttagaagatt aagcccatat 191040
tactctatgg ccaagtgaca aaataatcaa tcacatccac atctgtgata gccaggaaaa 191100
catttctttc cgtgcccctc ccccacccccc cgccgtatgc aactttccct gtgtggaaat 191160
aatgtactta gcttaaaaag tctctttctc tacttaacaa gactaagttg aaaattaacc 191220
ttgcccactt aaaagaaaac gaatatgcag taaactatga actactaata cagttcaata 191280
tgatatctca tgcagaacaa taatgctgaa ggttctttt ggttctatta tttccttata 191340
```

```
ttcttgctta gataagatca catttgtatc tattgacttt ctatgatgat ttagatacat  191400
aagtggcaat aattaatata tattaaaaat acagatttaa attgttttc tgacttgtaa   191460 tgttaacagc agtatatgtg actgtgaggt tttcctttga tgttaatttt cactttgaca  191520
atagtcttcg ttttccaatt tttttaatt tttttatttt tattttatt ttttttgtg   191580 ataaggtctg gctgtttcac ccaggctgga gtgcagcagg gcgatctcag ctcactgcaa  191640
cctccacctc ccaggctcaa gtgatcctgc cacctcagtc tcccgaatag ctgggactac  191700
aggcatgcac caccatgtct ggctaatttt ttgtaatttt catacagaag aggtttcacc  191760
atgttggtca gtctgttcca gaactcctga cctccgccca cctcgacgtc ccaaagtgtt  191820
gggattacag gcatgagcca ccgcgcccat atcatttcc aaattcttta caagttttt    191880 ctcttacatt cataacataa agtgctattt taaatagact aacttttgaa ataacatag   191940 ataaagcact aaatggggac atcagaggaa caggctaaaa aaagctgga atattcttca   192000 ggattaggga cattgagatt ttatttataa aatgatattt aaattttaat aatagaattg  192060
ttgtactttt gcttggagta tttaaatctt ctctttaata tttaaagcca gttctgcaca  192120
gaggttttac ggagatgcta attgttgtat gaaaaggaat attattctgg aattttgagg  192180
aagggtagac atagagaaga taaaggaaac tcacagccta cctaggtttt atttgggctg  192240
tgtgtgtgtg tgtgtgtgtg tgtgtgtgtg tgcgccagcc acaagctggg tttattcttg  192300
aataaactgt agacaaattg ttttcctga atcttctaaa acctgcattt acatagtcca    192360
tggttgtgtc taaactagat actcaagaga acttggtttg ttttaaaggc atttaattag  192420
ttatatttac atggacaaat agagcagcag tttattaaaa aagaatgaaa ggataaacaa  192480
attaaatata cgtagaacag gaaagacagc atctaattat gtttctgggt caggctctga  192540
tatacaagat taatttaaaa ttgggatttg gcaagtaatt tctatcgaaa tctcagcagg  192600 agttttatt gcaactaaca agctgatttg gaaagtttca tggaaaggca aggatctag    192660 agcaatcaaa aagaccttgg aaaagggaa gaaagttgga gggcttccat ttctctattt   192720
taaaaggtac tataaagata tagtaatcaa gatagcaggc aactcacatg ggtataaatt  192780
tagaccaatg aaatataatt aattacagtt ggcccttgaa caacgtgaag gttagaaccc  192840
ctgcacagtc gaaaattcac ttaaaacttt ttaccccccc aacacttaac aaccaatagt  192900
ctactgttga ctggaagcct taccaataac ataaacagct aattatcaca tcttttgtat   192960
gttatatata caatgcactg tattctcaca ataaactaag ttagagaaaa gaaaatacca  193020
ttaagaaaat cataaggaag agaacatata tttaccactc attaaataga agtggatctt  193080
cttaaagatc ttcatcctca tcttcaggtt gaataggctg aggaggacga gggagaggag  193140
aggttggtct tgcagtctca ggggtggcag aggcagaaga aaatccacat ataagtggat  193200
ctgcacagtt cagaactgtg ttgttcaagc gtcaattata agggtttaga aataaatcct  193260
tcaatttgta gtcaatagat ttttaacaat ggtgccaaaa caattaaagg aggcaaggat  193320
agtcttttca ataatggtg ctgagacaat tggatattca tatgtaaaaa gatcaatttc    193380
aactcttacc tcttattgta cccaaaaatt aactcgaacg acaggtggca atataagaat  193440 taagctctt aaacttttag gaaacttcag caacacagga gaaggtcttc agggccatgg   193500
attgggaaag atttcataaa tatgacctca aaagtacaat ccttaaaaga attgatcaag  193560
tgaaactcat caaaattaaa aacttttaca cttcaaaagg cactattgag aacataaagt  193620
gctatttgtt gagaaaacca aaagacaagc cataaactgg gagaggagat ttgccaacca  193680
```

```
tattcccaat aaaagactttt tatttagaaa atatgtaaac aaaccactta ctattcaata    193740
ataagaagga aagaaattat tttttaatgg gcaaaaataa attaatagac atttctgcaa    193800
agacagtgta catgagaaga tatttaatat cattagttac taaacattag ctaaatgcaa    193860
atgaaaacta caatgaggcc aggtgcagtg gctcatgctt gtaatcccag cactttagga    193920
ggccaagatg agtggatcgc ttgaggcagg agttcaagac caacctggcc aacagggcaa    193980
gacccatgtc tactaaaaat acaaaaatta aacaggaata gtggtgcatg cctgtagtcc    194040
cagccacttg agaggctgag gcacgagaat tgcttaaacc caggaggtgg aggttgtcgt    194100
gagccgagat cgtaccactg cactctagcc tgggcaacag agcaagactt tgaaaaaaaa    194160
aaaaaaaaaa cctatgatga gacaccattt cacatccatt agtatggtta taacaaaaaa    194220
ggatattagc aagtgttggc taggtattag agaaatagag acccttata ccaccgttgg    194280 tgagaatgcc aggtattgca gctgatttgg aaaatagtct gtcagtttat taaaacatta    194340
agcataaatt tgccttatga aacagcaatt tcacccctag gtatctatgc aatagagatg    194400
aaaacatata tccatgcaaa aaatagtaca caaatgttca tagcagcttt attaataata    194460
atcaacaagt agaaataaac caaatgtcac tcaacaaata aatggattta aaagatgtgg    194520
tatacccata caatggaaaa taatttagcc ataaaaagga atgaagtatt gatgcatgct    194580
acagtatgaa aggacattga aaacatatgc taagtaaaag aaaccagaca caaataccg    194640 catattatat gagttcattt atatgaaatg cctagaagaa gcaaatctta taaagacaga    194700
aagtggatca gcaaggctat cacacccacg caccacccag gtctggtttt aaaaggtatt    194760
aagcccccat gaaatggaca ttacttgact tttgtttgat atatgaaaac agcattatca    194820
agtcttggtt tcaaaatatg tttaagctct tctgagttat gtagaacaga ggagtgtttt    194880
ccattcacaa gtgttggaga tgacagtatt ttcccttgc cttaatccgc ttatcctaga    194940
accctatagg aaggcaaaga ctgtcttgat tgattgacgc agttaaagtt attgatagtg    195000
ggatatgcac atatgggctg catctgtcta tgagaaggaa gcaatggagc caattaatta    195060
attcaagcaa aattaaatgt tcacaccttt taaatgtgga aactataaaa accaaaatgg    195120
tgctctgtgc actaagagca taagctagtt ttttgctatc cttaagggcc tcttcctgca    195180
ttttgcctat attaaaattc ctatgcagat cttattgagg tgatcaaggt agatgacttc    195240 gattttatt ttcttcaaca aattcacgta ccaataactt tcaaatgata tttagtaact    195300 atttaaaca cagaggacat gatcttcaaa cgatatttaa tagctatttt acacacagag    195360
ggcataactt tcaaatgata tttaataact attttaaaca cataggacat ggtctataat    195420
gttttgtcct gacttaaata tttattgcat gtagtagatt ttaatagaag aaaacaagag    195480
tgaatagtgg gtagtgcttc tctaaacaca gagtagaggt aaatcttagt gatttaaatt    195540
agtcacaatt ctgactttt gagattgcat gtttataagt ttttaatgca tgaaattaat    195600
gtcaattata taatattttg aataaagtcc ttccatgttt actgtgtttt tgcttgcctt    195660
atgaaaattt ctaaccataa tgtgtcagta acatttcaaa aatttattta aattacaaca    195720
tgttaacatc agaggaccat tgaatacgcc ataagcattt cttaagaa tgtgggaaat     195780 gtcttttcta ataatttaat ttttcttt tttaaaacaa ctcacgttag cattttttt     195840 tttgcagtag catcatttta acccccaact gcatattcac aggatatcta atattttg     195900 caagtaacat tttgaatttg ttcttcttga catcttatg tttatatgca ttttgcattt     195960
ccctatctca tttttttgaa atccaaatgt aacaaatttc aacttttgt gttacattct    196020 tttcttttt tcttttctg ggtagcatct ctctctttc tgaatttttt gaaaacctgt     196080
```

```
tgtttttgaa ttctcttttt tcccttattt ttccttctca atatgacccc aggagccaac 196140
acaaagaaaa acgcagatga tataacgagt aatgaccgtg gtgaagacga aggtatttt 196200 tgttttttca aagctcaacc ccagtgcatg attttatatc tatctatctc tcttttttt 196260 tttcatttca atctgttttt tctcccctta tttaaaacta gtacactttg gtgtgcttcc 196320
ttaattattt tcttcttgta tagaaaccac tgtcatttt taatcccagt taccatgtac 196380
aggaaacaaa tcactgtgag aagtataaac attgtttcta aacatgaaaa gagtaatgaa 196440
ctactgttta cagagaagcc cttttttt tttttttggc ttggtcgcaa gaagagaaaa 196500 tggaattta aaacatgcat gtatagtcta ttttctccct tccaaatgtt attttgtaag 196560
ttaatatact actttggagc tttggtcttc ttaattattt ttatgaacta caaaactgta 196620
cagcacctta gaagaatttt ttttgggggg ggggggctg aaatatcagt tttttttc 196680 ttcacaaaca tattgattcc aacatagatt tctgataatc tgctcacagt gaagtacacc 196740
aaaaagtgtt ttaatgagat gctgttgtta acgagccctg atgcattcag gactgccttt 196800
tacagcattt aagggggggt ggggaagata agagtatctc agaactgaaa aaggacaaaa 196860
agctagctat gttcatcttt cttttcacac cacggctttt ttgaaaacgt ttttctcctt 196920
aaaatgtttt gttgctgtga agtttcttct taaggctacc aaattgctca acacattgtc 196980
taccagaagt gaaaggattt ttttttaaaa gatggtaggt ctgaggtact catgcagaca 197040
actcgcatgc tgttttctg cccttctgc acaagaaatg atttttttt ttttaaaga 197100 ggagaagcaa caaaaaagt actcaagcaa gcccttcttc attggtaagg ctctatagga 197160
ttagctaaaa gcacatttt cccatctggg tagcaaaatg catggaactc cattaaggtc 197220
ctggctggac cttgggtct ctgtctgaaa ggcaatttaa agcccaaaag tgagtcctga 197280
attatccttg ctggtcaagc ccaacgtcca tgacagggtc ttttgaccaa ttcttgtagt 197340
tgctcccctc cttgcttatc ttcataaatc aactgttctc caagaaaaga atcttgcca 197400 acacccttgc tgtgcccagt cttcccttaa cattttgagt attgttactt ttactgagct 197460
catagagctg tcactgtctc aagtagctct ctgagagatc tccattctga tggccatagg 197520
agatcaaaat ctacacctgc ttcaggtagc cccttctttg ataagggctt ctgaatgcct 197580
gacattttat cagtattgag caaatacata aaaatgaaat aaactttgt ctcatatctt 197640 atactgctct aatttgtatc ctgtttggcc ttctcttttt aatacatttc ctctcgataa 197700
ttagaatctg ttttcacagt gttcccagtg aatctttatt accattaaaa tgccatctaa 197760
ttttcatttc atattgttaa gttatgattt tttgactttg cattaatata acagctggtt 197820
attacttcca caagttcaag agagtcttgt tctatatttt atgaaggta agagatgtta 197880 atctcacata ttttccaagg gagcacttta aagcagccct tcaaaatctc tacttactct 197940
tttttccaca atttactagg caaccgctgg taatggtaaa agaaatgagg ccaaaaacag 198000
caaattagga accagaaaga agcagtggat catgagaaaa gccatttctt attcatatag 198060
cagaagacat ttcccgtagt gtatgatgaa taaatgatta atagaagatt tttacttcat 198120
atttgaattt tatatgagaa aacaaaagac acttttctgc cgtggattaa atatctgcaa 198180
ataaatactt gggtaacttg acactctttt gtgtgcttta ctgtgaccaa tgggtatgtc 198240
gtgtcttctg tatgcaccca gtaaaattgt gatcataatt cattcaaatt ggagccacca 198300
tccaaacgat ggtaattcat atcctcagaa ttcctttgtg gtatttcaaa agtgtccctg 198360
tggattatga ggaaaaaaaa actttattga tgaagaaatt gaaataaat atgcataaat 198420
```

```
acttgagttt tcttttagtt acaaagatat ttaaattgta cacacacaca cacacacaca   198480
cacacacata tctgtatcca gaaatattta tacgtgaggt cagtcttcca aagattaaat   198540
gcagccctaa tggctgatta atgttataaa acaggtcttt ttcacaaagc aggccctaca   198600
gatggtctcc aactttctat catcacagat cattgttttt acatcattgt taatttaaat   198660
aataaagtaa attaccaaga ggaatcattg gttgcaagtc acaatgggag tttatattcc   198720
ctgtgaaaat ataaagcatt taaatagttt ggattctttt gccatttttt attacatctc   198780 ttttatttt gtcacctaag tatgttagta tgttactgta atcactggaa caaagacatt   198840
tgcttggaca tcttttcttt tttttcccta tttctgttca gttaataatt tttaactgtt   198900
gattttgctt tcttgtcatt atctgtccct tattgatagt ttatagcttc actactactt   198960
ttatgttttt attgttaaat tgaagatgaa tctgtacact cacctgcgaa ttaagatgca   199020
actatattaa aattaattat aattttgaag ttgattttat acttaattag aagataaaat   199080
atatttcatc aagggtccca tgtgtttatt caatttaaat cacattttag ggtttgagca   199140
aaatttagga aatgtgtact ttacctaaaa ccatttcttt tagtgcttta gatatatata   199200
gaagcttaga tgagcagagt acgctaaatg tctgtatgct tcttaaaata ccatttccat   199260
aaatagaaaa cgtaatagca ttgatcattt tccttagaca ctcttatcaa gggtcatatc   199320
atccataaaa ataaatgtgc ttaattcaag tcaaaatagg gaaatcagtg aatctccttt   199380
tttcttaatt tagcattggt gagtcagtgt gattctttat tgtgtttcct tacttggctt   199440 tttttttccag atattcatga tcagaacagt aagaagcccg tcatggtcta tatccatggg   199500
ggatcttaca tggagggcac cggcaacatg attgacggca gcattttggc aagctacgga   199560
aacgtcatcg tgatcaccat taactaccgt ctgggaatac taggtaagtg atttcatcat   199620
gtgaatgact gagcaagagg aaacatgaaa agtccacttc tcgttttgac ggggctcgtg   199680
gatttgaatc ctgttattcc agttcctggt taattccact tcacggtatt tactttatgt   199740
gattggatat gtttattcct tttactacct ttgtgcaaca tggtcatgaa tcccttctca   199800
aaccaatgca gactttaaga tcttaaagat gaaatgaaat tttatttata gcatgtttct   199860
cccttggagt tcaatgaatg tatgtttgtc tacatagacc tgtacaatga acacatattt   199920
ggtgatatta tagttgggaa tggccataga tcttagcttt cttttctgat tgtgtcattg   199980
tatgaatcag tatattgtgt ggaggaaaag attttatcca attctctaac tgattatgtt   200040
gagcctttgg aagatctgtt gttttggttc cattgcattt gcatgcaggg aaacttagct   200100
gttagttgac ttttgtccat tgatgatcta cgattaaagg ctaaatacat ggaaattcaa   200160
gtttagttcc tccttgtttt gatgtttcat ttcttttctt tctttctttt tttttttttt   200220
ctttgagatg gaatctcact ctgtcgccca ggctggagtg cagtggtgcg atcttggctc   200280
actacaacct ctgcctcccg ggttcaagtg attcttctgc ctcagcctcc caagtagctg   200340
ggactacagg cgcatgccac cacactcagc taattttgt gttttaata gagacagggt   200400 ttcaccatat tgaccaggct ggtctcgaac tcctgacctc gtgatccgcc tgcctcggcc   200460
ttccaaagtg ctgggattac aggtgtgagc cactacgccc ggccatcatt catcttcttc   200520
taattgtagg ttgaaaaatt atacatcttc agagtcagat ttcagtacct tctgagatgg   200580
cctttcctgg tgttggttag tttgtgaata atattcctaa gacctatgta aaaacatttg   200640
ttttccaggc aaaaatgcat taaaatggta tagaagataa agttttaac aagttagcca   200700 tgagagagat gtgtatattg gttccagtgt gattatgata caatatgaaa tacaaaacaa   200760
aatgaaggcc aggtgtggtg gctctcgcct ataatcccag cactttggga ggcccaggca   200820
```

```
ggcagatcac ttgaggtcag gaattagaaa acagcctgac caaagtggtg aaaccctgtc 200880
tctactaaaa atacaaaaat taactgggcc tgatggcagg cgcctgtaat cccagctact 200940
caggaggctg aggcgggaga atctctggaa cccagtaggt cgaggttgca atgagcagag 201000
atagcgccat tgcactccag cctgggtgac cgagtgagac ttttctcaaa aaaaaaaaaa 201060
taataataat actagtaata aattaattaa aataaaaagc aaaataagat ggactaaagg 201120
aggtctgtca aacaagaaat atgactgaaa atgttttctt caaatatggc caagaatatt 201180
ttcttttcaa tcagatgact tcatttcatt ttgagtgggt ttttttttt cctatgtgaa 201240 aacattaacc tgtaagaagc cctaaaaggt ggtgaattgc tgagaaaccc taagaggtgt 201300
tgtaagaaac cctaagagaa atgcatttct tactttgaaa tgcaaatcag tcacaggtgt 201360
tgctaaagtt gtatcttttg aaacattgat aaagaactca aaattccagg ttggtttctg 201420
cattaaagaa aataaacacc accaaaaaac cttttagtgt caaaaaactt attatgtcgt 201480
tggctttatt tcctatattt tttgtagttt tctgtgagcc acatcttggc ggaataatgt 201540
ctctgaactt ttgcatagca gtaattgcac gcttcactga atagttttca gaggcgctgg 201600
atagttgctt tggctactag tgttggaaac aggaaattgt gcttcttgat gttttacaaa 201660
aggttcattc tgacaaagag gtggaaggag gaaagtatgt gtgagggcat tgcacaggcc 201720
ctcttcaaag ggagcagtgt gtgcactgcc tgtagcacgg ccacacgaaa gaaagcttgg 201780
gcatgctttt ctgagggaag cagtgggcat caagaaaatt cttgctttgc tggaaccaca 201840
caatattctg ttgcatgcgt gatgaattga tgtgtctgat aagatagagt ttcaaaataa 201900
attgatctcc ttttcccct aaagctcagt tgtatcaagc aactctacac tatgattttt 201960
tttttatcag ttttgtccct tcgtgaatca attgcacatc ttgcaaatta gcctggaaag 202020
tatacacact ttttttagag gaaaaaaaa ctaattgaaa aattgttaag tctactttt 202080 gttatggaga gttttaaaa gtcataagat aacagagagc tgtaaaattg gtggggaaga 202140
aataaaagaa gcgatttagc atctctatgc cggtctattt acattcctcc aatgagctag 202200
tgtggaacag ccaagcacac tacagacccc cttcatttg atggaatgaa atgtgccaag 202260
tttgccgatt ttacaggacg atagagactt taaaatgtga ctgcgttggt ttttatcatg 202320
gatcttgcat ttactattgt cctcttgaaa acagctaggc ggcatttact ttttgcttgc 202380
aggaaactcc tattatcggt cttgaaaaaa tgtttttaaa cctttggcat ccagatattt 202440
aaaaagatga tcaaataaaa tacacagcag gcactgcaat gatcatttca gtgagtgcat 202500
ttcatacaag tagatacaat tttaggcaaa aagttgaaat attctttgag ttcttttct 202560 tccagtaaaa gtcataaatg cataaatgtt atcttcctac ctgaggaatg gaaaatatt 202620 gttttaagat tttttttttt taatggagta acaaatgcta ttctctgtta cccaaaagag 202680
aggattaaaa agatgaaaca tgcccataat ggaagcggaa tgctggcatt ggaaagaatg 202740
tagatcgcag ccagagacag acaggagcta acaactttcc tctacctctg ccttgagaaa 202800
gtcagctagc gtttcctcag actctttcct tagatgtaga aggcagtggt ctctcccttg 202860
caaggttgtt gtacagtata aaagttccat ggttcaaaat accacacttt acctcattaa 202920
tatataatct gcttgtcaat aaaaaaataa cttttttctt ttcttttttt ttttttttga 202980
gatggagtct cgcttttatt gcccaggctg gagggcagtg gcatgatctc ggctcactgc 203040
aacctctgcc tcccgggtcc aagcgcttct cctgcctcag cctccgcagt agctgggatt 203100
acaggcgcct gccaccacgc cccgctaatt tttgtatttt tagtagagac ggggttttgc 203160
```

```
cattttggcc aggctggtct caaactcctg acctcaggag atccacctgc cttggcctcc 203220
caaagtgctg ggattatcag catgagctac tgtgcctggc caaaaaataa ccttttaaaa 203280
aagatttaat ggactcatgt agatgaagtt tcataggctc tcagcagcaa ccattatacc 203340
cagtcacact acaatttcta gtgttattaa taccattatg cattgtatta atactactgt 203400
ttatccacag taagaattgt agctgaccca acctgtaatg gctaactaat atctatcaaa 203460
tattggcatc cagactgaac catgttaatt taaaataaca ttacaagaca cttgtagaca 203520
ttaaataaat cagaagatca tcatgtttgc tatttttaa aaaataatca gaactgtgct 203580
acacaatctt gctagccatt ggccatataa tttatgatcc aatccaggac atgtttgaga 203640
gttgctcatg tgctatgaat aaactgggat tgtcccaggc aaattgagat gtatcattat 203700
agctataaag taattattta tatctacatg aagtgtcttc tgattgaatt ggtgttcagt 203760
ttgtttttaa agaagctgca cttctataaa cagatttcct atgtgttctg ctatacaccc 203820
ttgtcactag gaaggtgtat atgttaccag aaagggatcc taatccagac cctaagagag 203880
ggttcttgat tctcgtgcaa gaaggaattg gaggcaaatc cgtaaagtga aagtaagttt 203940
attaggaaag taaaggaata aagaatgact gctccataag cagagcagcc cgagggctgc 204000
tagttggcta tttttatgat tatttcttga ttatatgcta agcaaggggt tggttattca 204060
tgagatttcc gggaaagggg tggcaattat tggaactaag ggttcctccc ctttttagac 204120
catatagggt aacttcctga cattgtcatg gcatttgtaa gctgtcatgg tgcttgtgga 204180
agggtctttt agcatgctaa tgcattgtaa ttagtgtata attagcgtat aatgagtagt 204240
gaggatgacc agacatcact ctagttgcca tcttggtttt ggtgggtttc ggctgttttt 204300
ttttactgca tccttttatc agcaaggtct ttgtggcctg tatcttgtgc tgacctcctg 204360
tctcatcctg tggctaagaa tgcctaactt cttgggaatg cagcccagta ggtcccagcc 204420
ttacgttacc cagcccttat tcaagatgga ggtgctctgg ttcaaacgtc tctgacatat 204480
atattcaaga atttggaaaa cctcaagttc accaatgcct ctcagattag tcattgccag 204540
ggtgtgtggt gttcctatct gctcagaagc cagaagccag caaaatcctt gctgagctgt 204600
acgtgccagg gcatttgcct ggtctcacct acccacttga gtacctatgc cctatcaccc 204660
attcacctca caacatccat acgtatcatt taccccctaag aagattagac attaatccag 204720
gtaataaact ttcagaacaa tcacctccag acagaaactg cagaggataa tctgataaat 204780
ctgaatccct gtaaggccat tactgaatca ataaatactc ttttctccat cttagttcct 204840
tactttagta taacttgagt tctccccaat ctgtttttt tttgttgttg ttgttcatga 204900
tagtccaaag accttcgatg taaaagagaa tgcatcttgc tcatgctttt tgatggaaat 204960
acctggaact tatttattcc ttcccctttc cagttgtctc caagtgcaag tctgtctgta 205020
cctgcagtgg atttcatcta cctccatta aatatgtatt tccgtttagc tcacatggta 205080
ctatcacctt tttggtgatc ctatgacttc atgcttcatg tatgctgaaa ttaattgttg 205140
cttcaaaaga gtcccaacta tgtaacatca actcattgtg tgcctctatg tggctggcag 205200
atattacttc atttaatctt cgtaaactcc cttggaagag ttaaccttat gtcctaccta 205260
tgaggagatg aatgctttga ggtaatggga tttactcatg gcatcacacc ttctagcagt 205320
cagagcaggg actgaaaccc gggtgtaact gaagccagag ctctgactta ccactcagaa 205380
ctcatccaca gccttcttaa ttaatgtcaa gtatgaatta gtaaaccatg gaatgagtga 205440
agaaattgag tatcacttta gcatcagatg tagcttttat cattatgcaa aaagttctt 205500 actgctgatc aagatacaca attgtgataa gatgcttaca gtgtatttt aagttcctca 205560
```

```
aagtgggtcc ttgaaggctg attcatttcc attcaatcga tactggtttg ctttggttca 205620
cggtgatggt ggcattaacc acaacaatgg catttgtcac atcaaagctc ttcggtgcag 205680
tagaactagt gtttcatcag gaaatttggt gtcctacccc cagttcccat gtcattgctg 205740
gcttgctgtg tcgtgtgcat aaattgagtc aaatgatcat ttcggtgcat ttcttacaat 205800
ctttcacata ttatagctat cctgaaaatt ttcatctgag ggtagattgc gtcatggtct 205860
tctgaagttg tctttctctt taagaccatt cattgaataa acctattaga cgctttggag 205920
tcataattga atataagaca gaaatggttt gatataaaag caaccaacat gcatagcaga 205980
aacagcattt gtagtcataa tttgggtgac ttaacccata tgcacgtgct cagcctaata 206040
atgtggtcac tttccctgtt ctggtgtccc ttgtagggtt ttcctctgaa attgagggag 206100
ggtgggctga gctctgaagc attcttgcaa catcggccag agtggtctca cctttatgct 206160
tttgtgatat gtgtgagcca tgtaatattc cactcaacaa agaagcctg gaaatcatta 206220 gaagagagga ccaatacgtt cttcccaaga gttacagcct caattccatg ggtgtgcatt 206280
tatgtgacat gcatctgaca ttagtgggag ttcaatgggt cactataatt tccctgaagc 206340
acacctgctg aaaaatgtca agctatctta taaatgacct gtatgttctt ctcccctttg 206400
gaagttagag gagttgctct attttggta catttgctat tttatttctt tttttctaac 206460
aatatttctt ttcttttaatg ctttatgaag gattttatt gaaatgataa atggaacaca 206520
tcttatgtat caagtcaaaa gttcataagc gtatatatta aaaagaaag catcatttcc 206580 tttttcgaga atcaacacac cttgatgcca gtctcctggt ttcattagaa tccctctctt 206640
ctcttcctct aaccaaaatg tctcagattc ccccgatttg atttctgtaa atggcctact 206700
ttgactggaa gaattgcctc tctctgtcta aaacaggacc caggcgttac taaaacaaaa 206760
cactgcaaaa agttaaatga ggagaaagga aagttaagca ttgtacttag tgagaaatac 206820
ataaacaaaa gtagagacgt aaaagaagca tgagagaagg gtgagaaagt gaaatcctga 206880
gacaagatga atggtgtgtg agcactcaaa cccaggaagt agcaaaggt ggaaggaaga 206940 atgggagcct ttagaataag attctttgtg ggctgggtgg cagatgttat cggtaaagcc 207000
agcctgggga gttggcaggg gtccatgcag tagataacac agcaatagag tgaacacatt 207060
gcagaagata gggcaacctc taatccagaa attatcagat aaagaaaaac caagacactt 207120
tgcaaaacaa aaaaaaaaac aaacaaaaa acacaacaca atgtcttgtt tttcatcatc 207180
atcttcttta taatgaggtt tccatgcatt gaatacacac ttggaaacac tgtaatccca 207240
tggttgttgt ggctgcagat tgataggtgt ggacaggtct ttggtggggc aaacaaaacc 207300
aggatcatgt tttttgctct cagaatgatc gtttgcttgg actttcctct tctgcctcct 207360
agtggctcaa aatgcccact gcattcattg gatttattca ggatgtgaag aaggtcaggg 207420
gaaattaagg atgagtgctt tgtcattagg acctgagagg caaatggagc agagatgggg 207480
acgactgcag tgggataagg actctctcac caggaaggtg ccattgatgt aatagttgat 207540
gggaacagca gagcaaagag gctccctcgt cctcagctga ctcaacaaca agcgagacat 207600
cagatggaac ggtatttatt gggcaaggaa aatcagggga aggctaggtg cagtggctct 207660
cacctgtaat cccagcactg tgggaggcca aggtgggagg attccttgag gccaggagtt 207720
ccagatcagc ctggacaacc tagtgagacc ctgtctcaga agaaagaaa gaaagagaga 207780 gggagagggg gagagagaga gagagggagg ggggagggag ggagggagga gagggagaga 207840
gagagagaga gagagagaga gagagagaga gagagagaga aaagaaggaa ggaaaaagaa 207900
```

```
aaaattagcc agatgtggtg atgtatgcct ggtgtctcag ctacttgaaa agctgaggca   207960
ggaggattgc ttgagcctag gagttcgagg ctgcagtgtg ctgtgattgc actccagtct   208020
cagcaacaga gtgaaatcct gtctcaaatt tttaaaaaag actcaaaaga aaatcaaggg   208080
agggagtgga gacaaggtag aaaagaattt tttttatttt gtgcttttt ccctaatgta    208140 ttcatttaat catcaaataa aaattgaata tattgatcat gtacaaagtg atgttttgaa   208200
atatgtatcc attgagaaat ggctaaatcg agctaattca caagtgcatt acttcaaatg   208260 cttattttc tggtgcaaac acttaaaatc tactttctta gagatgttca atattcaat     208320 tccttgtgat tcaactttgt ttgccatatt gaacagatct tttgaacttt ttcctgccaa   208380
ctgaaacttt gtaacctttg gccaacatct cccgtttcct ctccacctcc agcttcaagt   208440
tctgtaagag aacattctac tctctgcttc tgtaagcttg acttttttt agattccaca    208500 tataagtaag aacatgtgat atttgtcttt ctgtgtctgg cttgtatcac ttaacataat   208560
gtcctctggt tcatccatgt agtcccaaat gacacaactt cttcctttt ttttgaggta    208620 gaataatagt cccttgtgtg tataaacccc attttcttta ttcattcatc taatgatgga   208680
cattcaggtt gattccatat ttcagctgtt gtgattagtg ctgcaatgaa catgggagtg   208740
cagatttctc ttcaaagact tctttttcc aatcccaaat acacaaaatt atcatctggc    208800
atctgtcatg ctatgagac tctccttgat ctatttataa acgattcagg atttctttaa    208860
agaagctgaa attttatttt tacatgcata accatattta gaaatcaaaa tattcaaaca   208920
gaaatcacag aagaatctat tccatcaata tataattccc agttaattga ttatataatg   208980
tcatttaagc atgagttagt agtcacagag aatatgcctt aaaaatgttc tgtctttgaa   209040
agttttacat tcaaaacagt ctcttaagat tattaattct aaaagacacc atccctttct   209100
ctcttcagcc tgttttcttc attttgcttc tcatccagta tgtgaaaggt tgatgatttt   209160
tagttgatga ggttgacgtg ccctctttct ccttgggac agaaggacat aagttgtgct     209220
ttaaatgaaa ataagagtat gatgagtatc ccaagggatg atggaaagtt ccagggagaa   209280
gcattgaaat tgagagccaa attcaagtac attggaatta gggttctggt gataattctg   209340
tcagtatcta catatattca aggaaattag tcctttcgag taggataatg gaaaaatctc   209400
taaaaggcaa tctgagcggg atgtttaaag actacgtgat tattatgcag tgcatgcctg   209460
taccaaaaca tctcaagtac cccacaaatg tatacactta ctatgtaccc ataaagttta   209520
aaaaaatgta agactactac acatattctg gcctgcagct tttttccc tgacatttgc      209580 ctacccgcct gtaatagcac aggcaattct acaagaagca tgaatatgca catatgtaca   209640
tgcatgacag cagtgataca aagacagatg tgttgtgttc tagtataatt gtcttatttt   209700
tgtccattcc aacgttaata agtcattagc tttatggaaa tgaaccctag gggatgaaac   209760
atacaggtgc aaagtaaatt tcctagggac taaattataa ccaaattatg gcaggtacac   209820
cctgcattta gcgatataaa tatatgtttc aaataaaatt gtaacatatt gattggcacg   209880
tccagccata ttcttaagat actttatcct tggactaaaa ataataataa tcgcttttt    209940 gaatgaagtg tttaatttc agtgtaaaaa gtcaggaata ttttagaatg ctcaacgcaa    210000
cattgcttca atgagctagg gcctttatga agataagtca ctagaaagtc tgtgttgatt   210060
cggttaatta tttgagattg tatgcactga ttttcactgt gttaagtata gtggcattta   210120
ttagaggctc agatgttata gagagaaggc tgtgtccagt tatagggctg tagtcataaa   210180
cagatgggta aaatcaacac atcattgtaa atcataaaca ggcaggtatg ataaacacat   210240
aatgataagc atttcagcac tgggtgcagt gttgcatgcc tgtagtctca gctactcgcg   210300
```

```
aggctgacga tctttggagc ttaggagttc aagagcagcc tgggcaacat agtgagaacc 210360
catctttaaa cattaaaaag aacaacaaaa aaacatcatt tcagtgtaga caggcataac 210420
atgatctcac agagaaacac tacgatttgt acacaagaaa actaagcttt gcactggtgt 210480
tgggagaaca ttttggaatg ataaactatt tcctgtttgt tttaagaaat atttggtaag 210540
gtttaaagta gtgtctgcct ctttactaaa atattccagt atctgtttag atgtcccagt 210600
tggtcttaga tacttggtgg taaacatata tatacacata tatagcgcat atatgtgtat 210660
atatgtgggt gtgggtgcat atgggtgtgt ataatctatg tgtgtataca tacatatatg 210720
tgtacataca tacatatgtg tgtatacata tacatgtatc agttgtttgc ccttgtgatg 210780
cacacacaga tctatatgtg tgtatatata tgtgtctata tatgtataca tgctaatgtg 210840
tatgtataca tatataaaat atgttccttg attcacagtg ggattatatc ccaataaacc 210900
cgttgtaaat gtaagatgtc attagttgaa aatgcatcaa tacatctaac ctaccaaaca 210960
tcatagctta gcttggctga cattgaacat acttataaca cttacattag cctacagttg 211020
ggtgacatca tctaacacaa atcctatttt ataaataaag tgttgaatgt ttcatgtaca 211080
ctgcagagta gcagttgttt gcccttgtga ttgtgtggct gactgggagc tacagaccgc 211140
tgcctggcat ccaaagagac tatggtactg catattgcta gcttgggaat atatcaaaat 211200
tcaaaatatg atttctactg actgaatatc attttttgtat catcttaaga tcaaaaatca 211260
taaatcaaac cattgtaagt ccgggaatgt ctgtgtaata atttggctat agtcttaaac 211320
aggtgggtag aataaacaca ttattataaa tccatcctgt gcttttgaac acatggaggc 211380
taccccacca aaatgcctgt gttcaatata ttgcgaacct ctaggtatct tttccttca 211440 ttgctgttta attttttcctt ctaagcatga acttacaaga ttacttagga atagcattca 211500
tccttcttca ttcctctttg tttaaaacat gcttagcatt tctcatcttg aaagaaatga 211560
gtagctttct tcttttcaat catatttcat cagaactatt ctcttgaggg ccacagaaat 211620
gtcataagca ttttctctgg cacttctgat acttttaatg gcttttgata catcttcatg 211680
tttcttaatc ttccttgtgat ccttaccatg taagtgaccc gttgagctta tctccaactc 211740
ctatttttca ttgtctcctt cctttatttg aaacaactta catccagcgt gcacgtttga 211800
agtgtgcaat tcaatggcct ttagtatatg cacaacattg tgacaccagc aacaccatct 211860 aattttttgaa cattgacgtc attccaaaga gaaatcccat acctcttctc tcccaggtcc 211920
ccaggagata ggcttccact aactatctac ctgtctatat agatttgcct tttgggggca 211980
tttcatgtaa attaaatcat ataatacatg ctttttttgtg tgtctgactt cattcccttta 212040 atgttttttga ggctcatcca tgttgtagca tgcatctcta ctcttttatt ttttatggtt 212100
cggtaatatt tcattttatg gataccac actttgttta tccatccatc tgttgctaga 212160
cattgggatc atttccagtt tctggctgtt ctcaataatt gtgccatgaa cgttcatgtg 212220 caagttttttg tatggacata tatttcattt ttccttgattg gggatatagg agccgaatcg 212280
ataggtcata tcatgaactc tgtgtttaaa tatttgagaa tctttcaaat tattttccaa 212340
aataggtgta ccatttttaca ttttcaccat caatgcacaa aagttttaac ttctccacat 212400
cctcactcac acttgttctc atctgtcttt ttaattatag ccatcctaat gggtgtaaag 212460
tgatatcatg tttgggggtt tatttttgaa tatttacatc attccaaaaa gaagtcccgt 212520
atctcttctc tcctacatcc ccaaaaagta ggcaagaggt aatctactca agaaatgata 212580
ccagcttaaa ccagggcagt accagtgaga atgcaaagaa aataaaaaag aagaggttgt 212640
```

```
tctgcgtgtc ttacagatgc aacaggattt gctgatggat tggatgcaag gtggcagaga   212700
atgagaatgc attttttcctg atgactaatg atgttgaaca cctattcatg tgcttattgg  212760
acatgtgtgt aaatcctttg gaaaaatatc tattcagatc ctttgcctat tttaattgga   212820
ttatcttttc attactgagg tttaggaggg gtacttttaa gtagtataat gtggatacat   212880
gttccttacc acatgtggga ttcacaaaca ctcccattct gtgtcttcca cctccacttt   212940
cttgatggca cattcttatt actcatgttt ctgaaaacat aatcttcagc ctcattgacc   213000
aatgactctg aatattgact catatatgtt taagcaggct tgtccactta ctatatctca   213060
caagtcccat ggttatcgtg acagtccact gctatcccgt cccttgtggc tgtctcatca   213120
ttgtatggag acaatataag gatgccggga cagataaagg gtattaggat agagtgccat   213180
caatgtgtct gtgaagaagg gttcgtttca atcagttcac catgactggg gatttgattc   213240
tgtcaattgc tgactcagga atgtaaatgc tgagtaaggc aggacttgat cagtctattg   213300
ggggaaggca tcattgacca aagtgcagtg caaatttatt cattgactat gaggcatata   213360
actctttata actgtcaata gaaaatggac aaggcatccc tccgttcctt acaaggtttt   213420
gtaatgagcc ctggatttaa aaaaatacta gtaataataa gagaaagaga gggagacaga   213480
gagagagaga gtgagataga gtttctagtt taagtgaagt taaaatgttt tttctatata   213540
tacaaaacta gctttgccaa ggaagatgta gtagtggttt tcattcattc attcttcttt   213600
cattcaagaa acagatattg acaacctgct gtttgacaca tggtataaca acttccattg   213660
aaaatggagt agcaaacaaa acagagaaaa aatccccaat cctacagcat ttctatccag   213720
taggggaaaa aacaacgaca gacaagtatc gtaaaataca cagtagaata tgatatcaca   213780
agtgctatgg agaaatattt agtagagaag ggtgctaaat tagaaatttt gtgccaaaat   213840
tttgactaag gtggttatgg aaagtttcac agataaggca aaactgatgt gagggagtga   213900
tccatacagt tacctggagg aacagcatct tgggctaagg aaagatccag tgcaaaggcc   213960
ctgtggccac agagtccctg agaatatcag tgcagctgga aagtagtggt gaaggggata   214020
gtagcacctg atttcagaga tgtcagcatg agccacattt tatatgcctt taaaggacta   214080
gtgtattgtt cttagtgaga aaggaaatgg ctgtctatgt aaaggggcat taggttagaa   214140
ggttgttgca taatccaccc aagaaataaa aggcatttcg atcagaattt agctcttcta   214200
ctccatgaaa ctacttatca gttccattaa tgccttccac tctgcactct cagggttcga   214260
ttttctggaa aattttgaat tttgattttg attttccaga acatttagag ttctcgatga   214320
ctctctcctt cacgaaaaac attccttact tggtatctat atttgtttct ttccattgc    214380 tgctaaaaca aggtatcaca acttgttata actctaatgt taactctagg gaattaaaag   214440
caatgcagat ttattatctc acagttctgg gtgctaaaag tcccaaatgt gttcacattc   214500
aaagagagaa tccatttcct tggtttgtct gtttgtcttc ttttgaagac tggctacata   214560
tcttagatct cattctctgt ttctaacctt ccattttaaa aaacaaacaa acaaaaaaca   214620
ttatgattac ctagattcat ccagatgaac cgggttaagt tctcatctta agatcctcac   214680
tttttttttt ttttctctct ctgagatgga gtcttgctct gttgccaggc tggagtgcaa   214740
tggcgcgatc tcagctcact gcaacctccc cctcccgggt tcaagtgatt cccttgcctc   214800
agcctcccga gtagctggga ctacaggccc gcaccaccat gcctggctaa ttttttttgta  214860 ttttactaga cgggttttt caccatgttg gccaggatgg tgttgatctc ctgacctcgt    214920
gatccgctct ccttggcctc ttaaagtgct gggattacag gcgtgagtca ccgtgcctgc   214980
ccaggatgtt cacttttttaa aattgattta ttcttatttt attttagaga tgaggttttg   215040
```

```
ctctctcaga taggttggag tgcagtgtca taatcatagc tcactgaagt cccagcctct    215100
tgggtcaatt gatcctccta tctcaccctc ctgagaagct gggactacag acatgccacca   215160 ccacgcccag ctaagttta  tatttgttta cagaggggggt ttcaccatgt tgcccaggct   215220
ggtcgtgaac ccctaggctc aagtgatcca ccggcctcag cctcccaaaa tgctgggatt    215280
ataggtgtgc ttcctgacac cagtttctga ggtccttgac ggctgtggtc atagctcata   215340
ctacctctct ctccctagtg tctaccggac aataagcagt ttctgaatga ttagccgttg   215400
cagggttttt gactccaaat tgcaaaatgc aagctaatta aaaaggagt  gaatctattt    215460 actcattttt ttttttttt  agtttgagtg aactgattct caaaatcagt gaatgcccag    215520
tttcatgtaa accgtgttta tttccactgt ttacactcag cagctgtttc tttttcacaa    215580
acactggaga ttccatgttc cccgaaatat ctatgtatac ctgtatcata attcattaca    215640
cataggttag ctggaatgga gatatttat  atttgtggca tgcatttgat cttgaattga    215700
aacctgtagt ttagaaaaat ctacatatct ttatattttt aacagatttt gagaattata    215760
aaagcaaaac agtagagctc tacggtagaa ttttttttc  tttaggtctt tccatgggta    215820
ttttaaatgt ctcattatga aaagaccata aaccatggtt ttctaagagt tctgctgaat    215880
tttgcaattg gctggcacat tttctaaatg atcctgtaat ctccatgtat tagttttcta    215940
gagcggccat aacaaatgac cacaaatgtg atggctttaa aagagagaaa tttactcttt    216000
ctcatagttt gggaaaccag atgttcaaaa taaacgtgtt ggcagggctg cctttccctg    216060
ggtggttcca gaaaaagatc cttccttgcc ttttcagctc tggtggcctc ggtgtttgtc    216120
tctatcttcc caaggctgtc ttccctctat tgtatgtgtc gtctcctttt cttataaaga    216180
taccagtcat tggatttagg gttataccct caattcagga taattttatc tgcagatcct    216240
taactaatta tatctgcaaa gaccctattt tcaaataggg tcacattctg agtttccagg    216300
tggacatgta ttttttggagg atattacgca acccactcca cccaacacat cattattgca   216360
atatatatgt atgaatatag gtgtttcaga tatttacact acacatgtgt gtacaaccaa    216420
tgtattcagg atgccacctg gctttctcct tactaggcca cactctggca agaagatcta    216480
aggacaatct gggattcttc atctccttct tgcatcctct ttgcttccaa ataatgtagt    216540
catgcagtat ctgaaagttt atttcctgag cctttaaaac ttctccatca gtttgacaag    216600
gagtaaaagc gttttttcccc gttggccaca aaacttgtgc ttttgctcca gcaatacgca    216660
aagctatatt tcacacttcc ttcttaaatt acaggctata aatataaagc aaaaccttt     216720 accttggata ttctttctgt cttttccctc tgtgattaaa tctgattaca aatgctcatt    216780
aatgctctgc cttggaattg caatttgggc atgtgccatg tgaaaatgga ggttcctaaa    216840
aattaaaatc aaagattaat gcaggtttta aaaagggtc  ttattcaaat atatctcaag    216900
ttttaaaacg actcatggac ttttaatgaa atcaatggcc ttgtaatgcc tcattttttt    216960
tttcaaactc aactgtttca tagccttctc tttagaacat atctgattta ccagaaccca    217020
agatttgtga gatggtgtta tttttatct  ttacttttc  ctcaccccac ggtaccatga    217080
agagatcgtg taacatcctt tcctggtttt aaagacaggt gagtaacgat tacataacgt    217140
tcaaacaagt caggtgttct ccagaagatg gtgttaatgg tgtctgattc acagatgctg    217200
ccttgacccc tggcggtggt aggacctata ttctggtgaa agccaatttt aggccatgga    217260
ttataggacc tagatggaga aaaacgatac ctaaacctca tgagatctta attcactgat    217320
cggtggagag atatttttct ttcagatggt atcatcttat tgcatctcca gcagagtgtt    217380
```

```
tggccggtga aaataaaaat ggccattata aagaagttct ttagactttt aaaaatttta 217440
ctaggatcat gccagaaatt cctgctgtag aagtagatat gtatgtgtgt atacatatat 217500
atatatatat atatatttct gaatttgaga tgttgggtat tggtagagat tcattcattt 217560
gaatggaaat acgcttgctt tactttggc cagcatgaat gctctcattt gccacaggtt 217620
ggcaagctta ttggtttaaa tataaaggat cttgtgggta agactaacag caggttttca 217680
tagtgccaac atttctttct tttttattat catatttagg aaagtctctt gactctgaga 217740
tactttatat tgtgaaataa tagttctggt gcaagtatag attaatagat tattaaacac 217800
tttaagatat ggatggaaga gtacaactag gatattatta atgagtccca tttactattc 217860
tttaatttgc agtggaattt tcatttaact tttgaatata ccaatgatag gaagttagta 217920
gtgtttgcct gtaatttatc ctgagctcat ttatttgaag ttcaaatttg aaagcttcct 217980
tttgttgttt ggtaaataga gattattgtg attcaaaatg agtaatccct aaattgatgt 218040
agaaaaagat atttgaggct gggcacagtg actcacgcct gttatcccag cacgttggga 218100
ggctatggga ggtggatcac ttgaccagga gtttgagacc agcctggcca acatggcaat 218160
accccgtctc tactatgaat acaaaaatta gctgggcatg gtctcacaaa catgtaatcc 218220
cagctacttg ggaggctgag acccaagaat cgctggagcc tgggaggcgg aggttgtaat 218280
gagctgagat tgtaccactg cactccaccc tgggcgacag agcaagactt cgtctaaaat 218340
aataataata ataataataa taataataaa ataaaaagaa ctttgagata ttcatattgt 218400
ccaaaaagta taattcaaat acttaatgca gaaggcagta ggatcactaa actacagact 218460
cattcatcaa ttataacaga tggaagggtc tttgttagag tcctggaggc tgattgagca 218520
ttttaaatgg caggttcata ggggagatcc aggaggtcta aaggtgaggg tctacaagca 218580
ggaagcaccc ccactcccac ccccaaattc atgacaacaa cactaactag gcagcaaagg 218640
gatatttcct gatgtcagca gtcagcagaa tggtactgaa ggttgctaga taaatgcaag 218700
ttttgtagtc actcacctgc aagttatagg caagatattt atctgtactc ctacaggaaa 218760
ttagccctaa ttgactgctc ttaatcagaa caagacattc taacctctta ttcatggtta 218820
gcagtatatc ccacttgctt cactttgtga ttctccatca cattggaata actgacgtg 218880
ggatacattt ggaattgagt ctcaaattca aatcgccata gaacctgaaa agaaaatgta 218940
agaagagaca aaacagaaga aaaatgcagg atagagagtt atgatttaga tgtgttcatt 219000
ctgtgaacag agagcagatt ctcttggatc tggctgaaac aggggccccc tgtgttgtga 219060
aagtggtgta tgtcttcata cgtgttccca cgggcctgga caaccaacca catttgaaaa 219120
atgaagaaat gaaagcttgt ggtcagggtc acaaaacttg acagtggcag aagtggatcc 219180
aatttccagt caaatctatg actcgttcca tcttggccac aattatactg caactcaatt 219240
gcttttcttc cagtcagtac ccacccaccg aaatgtcagc tcttcaaggg cattaattgt 219300
tgtttgtttc attcattgtt gagtcttagg agcctgggac agtacattga aaatctcaat 219360
tgttgacatt ctcaataata cacaagaaat catgttttca gatcatggaa atcatatcca 219420
ttaggatggc tgttaataaa gtaaacgtaa aataagaagt tgtaatggag atgtggagaa 219480
actggaactc tttcacattg ctggtgggaa tgtaagatgg tacagtcatt gtggaaaact 219540
ctttggctgt tcctcaaaaa agtaaacatg gaactaccat atgtgatcca acaattctac 219600
ctccgggtat atactccaat tctacctctg ggtatatact caaaagaatt gaaagcagga 219660
attccaggag atatttgtat acgcagtcct taaccatgtt attcacaata gctaaaaact 219720
gaacttttga actagccaac tatccattga tggatgaatg gataaacaag tgatatatat 219780
```

```
gtatatattt atgcgtgtac acacacacac acacactgct gaaatggaat attattcagc 219840
ccttaaaaga aaggaaattc tgatacatgc tacaacataa ataaaccttg aggacatcat 219900
tctaagagaa ataagctaca tgctagtcac aaaaggacaa aagctgtatg attttaccaa 219960
tatgaggtac gtagagttgt caaattcaca gaggcaaaaa gttgaatggt gtttgtgtgc 220020
ggctgagagg cggagagaat ggaaaattat ttcctaatgg atagagtttc agtttggaaa 220080
ggtacaaaat gttctgaaga tagatggtgg ggacagttgg acaataatgt gactgttctt 220140
aaggccactc aattatacac caaaaaatag tttaaatgat caatttcata ttctctatat 220200
cacagtaaaa taaacatta tggtatctgt gatttaattg actatttgta atcatcacca 220260
tgttagagca tgttcagtat ctcatatcct gcaatattgg aatggacatg gtaattttg 220320
agtggtagaa aataaagtaa cttttaaaaa cccatctcta tgtattcaca taatcttaca 220380
tttcatataa gtgaaatcat acactctata tctcatttct ttctcctaat aaaatgttta 220440
caaggtttac aaggttcatc cacattgtag catgtatcaa tcagtaccgc atgctggttt 220500
atggctggat actattccat tgtatgatag accgcattct gttatgttta tctattttc 220560
atttgatgga tatttggatt caattcatag agacagaaag tagattagtg gttgctggtg 220620
cttggaagag gactataggg aattagcgtg tcatggttac agagtttcag tttgcgaaca 220680
tgaaaaattt ctagagatag attcacaaaa atgcaaatat actaaatgac attgaacaga 220740
acagtacact ttaaaatggt tcactttatg ttacgtgaat ttcctcttaa atagaagaaa 220800
aataaagtct gaagttgtca tatccttcac tgggatgctc tctttaaaag tgtagaaagg 220860
tcctgaaagg agcatataaa caaactaaac aacaatcaaa caaaacatgt catcgtaccc 220920
cacagcatcc tgacatggaa gactaaaaac tgtcccaggg ctctcttctt ccttatctgt 220980
tactttcagg ggcattttag cttaggattt aatttgacta ttgacaaccc cagtgtctcc 221040
atttgatctc agagcaaact tgaattgata attaaatttc catgcttttg accagggaaa 221100
gactttagga aatgtctttg aaactgtgaa cttgcagaaa ggagaaaatt ttatatgtat 221160
ctagcttcta tccattccat ttgtcatatg gtcagaactt acatgatgca agcaggccat 221220
ttacagggcc ctgggctgac agctacatgc tatattttgt atttgcttcc actattttgt 221280
tagcaaatgt atgtacttac taacaaaata cgtgttttaa gaaataaaat tattttaaga 221340
acaaaataat acaatgtttt aagaaaacct gcttttattt gctttttatt ttttatttaa 221400
aaatgtttat aaatttatgg gtgttacaaa ttcagttttg ttatatgggt atattcatag 221460
tggtgatgtc ggggctttta gtgtactcat cacccgaata gtggaacctt tatccagtag 221520
gtagtatttc atccttcatg ccccttcctc ctccttccac ctcctgacac tttatagtct 221580
ccagtgtcta ttattctacc ctgtatgtta atgtgcacct gttgtttagc tcccacttat 221640
aagtaaaaac atgcagtgtt ggactttctg agttatttca cttaggataa tggcctccac 221700
ccagtttcat acatgttgct gcaaaagaca taatttcatt ctttttatg actactactg 221760
agttgtattc catggatata taaaccatgg tatatataaa catttatata tccagtcatc 221820
tgttgatgga cacttaagtt gatttcatga ctttgctgtt gtgaatagtg tagtgataaa 221880
catatgagtg gaggtgtctt tttgatagaa ccatttcttt tcctttgagt agaaacccac 221940
aagtgggatt gctgggccaa atgatacttc tatcttaagt catttgggaa atctccatac 222000
tatttttccat agaggttgta ttaatttacc ttcccaccaa cagtgtataa ctgtacccct 222060
ttctcagcat ctttgccaac atgtgctgct ttttgacgtt tttcaaaatg tcattcattt 222120
```

```
tcattttat  tataattact  taaaaatgat  gacttttaac  agagaaggga  aaaataaagt  222180
tggtaatctt  ttgtagtgcc  atataatttc  tagttacaag  accacagata  agtcccatgc  222240
tgaagagagg  tgggtaaaat  agctcgtttg  aaatgaagca  catttgggaa  gataaaattg  222300
tttttaggat  gataacgatg  tttgatgtct  aactttggtc  tagttttct   aatgttaagt  222360
gtattcttaa  catctgccca  aattattcac  tctttaaacc  acatgccaaa  acattactta  222420
catttacttg  gttataata   aaatttggga  ctattagtgg  atgatattta  ctgcaagaat  222480
tgttaatctg  gcgtttggat  ctagtattta  gattacttta  tattttcagc  tgcatatgca  222540
actattagat  atctgcccac  acttttcct   tcccactgtg  aaaatacac   actgtattaa  222600
ggtgacaggt  tttcctattt  tcacccctta  gacttgagtt  attttctcat  cattattaac  222660
tcatagaacc  tgtgctttgt  tcctggcttc  agcttgagca  ctgtgcaaaa  atttatctta  222720
taagatttgg  tcaaaactgt  tggctgtgta  ggcacttccc  ctagtagaaa  cttcccttt   222780
cccctctgag  ggttcactga  aaaatcaact  taaaaaggca  gattaattga  agaaaaggca  222840
tgcaaatttc  cttaatgtg   gatagcttgg  caggaaggat  taggagactg  attacccaat  222900
atcttaatgg  agtagatatg  cttatatact  ctacttccta  gaggaaaggg  aggtgaggac  222960
tcctggatga  tacttagggg  gatagtaaat  gattttagg   ggaattaagt  gggcttgaag  223020
aacatacagt  ggcttagaac  aaagtctgtt  gggcttgcag  agcagacagt  ggtttgtcac  223080
aaaagtctgt  ccaggtgtgt  tgacagactt  cattctttct  tcctgcgata  tgagtccagt  223140
tactagaatc  tcggggaagg  gaccagaggt  cattgttttc  ttctttgatg  ggtccagact  223200
ttaggcagat  aaacaacttc  agaaaacaac  ttcctcctgt  gctttggggg  tcacagaggg  223260
ttgagagaca  agagggagtg  ggagaagatg  agagagacgt  tgaggcttct  tcttcagttc  223320
agcacatcaa  agtgccatat  tttgctgtat  gggtttatga  gtcccaacaa  ctgggtagtg  223380
aagacaaccc  agggctgtgt  gttgatggtt  ccgctgcaga  cagtcaaggc  tcacttctct  223440
gggaggaagc  taaatgccac  tcagagacac  atccccatct  cagatgtctt  tgttatattg  223500
atgacagttg  gcacccagat  ggcatgtatc  ccttgtggtt  tcaaccattg  gttgacatga  223560
ccttaaaggc  ccaaggtatg  tattcgttgg  tccatttttt  ggaggaatgc  cattttactt  223620
ccacaatgca  gcatagctgt  taaccattca  tcatgccagt  aagagaatcc  ccgggatctg  223680
cattgggaca  gaatccccat  tcactgcctt  gtctcacttt  tgtagtttgt  tttgttttgt  223740
ttgaatttgt  tttagttttt  aacaaataat  ctgaaggtaa  aatacaattg  aaagaagcac  223800
ttatcttatg  atatcaggat  aagtaaacta  gtgcagtttc  agaaacatct  aaccaagtgt  223860
tgttttcttg  ctggattgca  atattgatag  gcacatggga  taatatctca  tgtaaattct  223920
gaaacatcta  attgcatctt  gatccttcat  cttgacccte  ttctcagtgg  gctgcattta  223980
tccctaaaca  gcaacattct  gtcaattctt  aggaacgtga  aacgttacag  tctgcagagc  224040
aaattaccag  caggagaaaa  tattactgaa  tattcaaaag  catgcctttt  gtgtgaatga  224100
tcttgaagcc  ccagggaatg  ggggaaacag  ggttgggagt  acataagcca  agaaccttat  224160
ttgatccagc  agtttccggc  ttctaaaacc  ctacccatgc  agttccaaga  agaaaataac  224220
aaattggcat  cacttaatgt  ttagtgatag  aagaagaaaa  gcatgccttt  gttcattttc  224280
tactcttctc  atttcctgct  tcaccattcc  tatcaaatga  aacatttcgt  tttcatttcc  224340
tctctataac  ttgtactatt  tctgtgaata  gatgatgtgc  ttaacatatt  gatgtttgtg  224400
agtaaagata  ctcttgctat  catcaaaaga  aatagtatcc  atttgagaag  catctagtat  224460
atgaggaaaa  gttttgtttt  cattttttccc  ttatgttgtt  ttttatattt  taaatgtagt  224520
```

```
tgtaaaatga cagaacatgg gatcacaaag aaacacaaaa ttcgtaatta ataaatgtga   224580
ttttgtattt attttaggta tgcaaggggc acgtttgtgt gggagttcaa aagcatttaa   224640
atattttaaa tctcctttca ttcatttaat aagtgtcttt tgaggtcaga tgtaaacaga   224700
caacttgtta cacatgtttc ttgttttttag ggaacttcca ccccaacatg ggaaataaac  224760 agagaccta ctagttcttt aacagtttct taatgaaaca ggatatttcc ctgacccctt    224820
cacaggtggg aactggagtg cactggtgct ggaactagcc ggctgcttcc aggccagcgg   224880
gggtgaaccc tgctcactcg ctgctctacc ccttgtggga ggggaagcac aggtgagcag   224940
gtacaggagc cagggcgaac aattttgggc accagcaaga atgaactcca taccagcccc   225000
acggcagcat ctagtagagg gtagcccgca accctgaag acccagagga agtgttacac    225060
tgcctgtttg gctttgccat ccgcagagac cgtaagtgtt aacagctcag tggagggtca   225120
atgtgacagc cttttgcacc cacactcatg gcacgcaagt ttttgtcctg aggtgggaaa   225180
ttaaagaaaa ataaaatcaa aaagaaagag aaataagttt tcctgtatta ggctgacttt   225240
tcccagaggc agcaacaggc acagcccaga cccaggaaaa gtcttgataa tattatctaa   225300
tgtgctctgg agactctccc agcactccct caacataggg agaaggaaaa caaattttcg   225360
tttgttttat ggaatgagtt tatagattcc tgttctctgt aactaatgac ttcaagtatt   225420
ctgttttatc taaaaagtac aacgaaggtc atgagaagcc tgattaggcc tgaactacag   225480
ctgcttgggc accatagtga aggttatgaa ataaaccagt gcaaggcact ttagagcaaa   225540
acctaggtaa cagacatctg gattgcttgg caatggtcat atgcggtcct gagtttgtcc   225600
tgcctctgta tccctgctttt cacgccactg taagcttact tcaagctagc ccaccccctt   225660
ttgttaagtg tgtatgaaag acaagtgctg tctttgttcc gggcccagtc gttggacgtt   225720
gagtctgctg ggtctgagtg cactcaataa taaagatatc ctcctgtata cacccgagg    225780 tctctctctg gtcctcctga tcccgcaaca gactgacgtc caggagcaat caggtcacac   225840
gaacaaattg aagatggtaa atgcagggga tttttttattg ctggttgaaa gtagctctca  225900
gcaggaaggg gaactgaaaa cgggatggag caggaagata atcttcccca ggagtcccgt   225960
catccccggc cagaatcttc tccaaagcta tgccatcaag ctgtccctct gaagtcaagc   226020
cacttctctc tgatgtccaa ctataatttc cgatgtccag ctgcttctcc cctttccaag   226080
ctatgcctgg agtttttatg ggcacaggat gtggtgcagg gcaggccatg ggtggttttg   226140
gaaaaggcag cagtcgagtg ggaaaacagg aatgtaaatt ctcactttgg gccctggttg   226200 cttttttggct tgagggtggg gcacttaccg ggaacccgct ctcttctgcc cagaatttcc   226260
ctgccttctg tccctatcgg ttttgtattt attttaggta tgcaagaggc acgtttgtgt   226320
ggaagttcaa aaacgtttaa ttatttaaaa tctccttta ttaatttaat gaatgtcttt    226380
tgagctcaga tgtaaacagg caagtacagc ttatagctgc agtgaatgct gagaatgaag   226440
tactcaaaca attccagctg aacggggcgg ggaacagctc ttctgagaga gtgctgcccc   226500
aagatccatc cacctgaata tttattgaga gagcttgttt aaactacagt tcagatgaac   226560
aaaagacatc caccaggtgg ctcttttgcgg ttgggtcatg aggcacatat gaccttgtaa   226620
aaaacactca aaccacattc ttaggaggct gtgttcagca ctccttatca cacatactac   226680
tccctgtcct gttttcaggg acaaggagtt ctagtctcat gcacaaacaa catgcacaca   226740
gtgcctcagt attttttccat gcctcgacct cacgtgtctt ctacattagc ttgaatatgt   226800
tgccatgcac cccccacagg aagtcattac acatgttttcc tgattttagg ggagcttcta  226860
```

```
ccctaacatg ggaattaaag agagatccta ctagttcttt caagtgtctt aggtaaccaa 226920
ttagatatat tctacacccc ttagtggcaa gtgctcatgt tgtcaaattt gcatttgttt 226980
tcaaatgaga ttaaaacaca acaacaacaa tgtttaaatg tttctactat tagaaaataa 227040
aatcaatgta ttctatcttg gattttttcct ttatttcttt atagagttct ggtttgcaac 227100
aaagttttat cagtagctta tttaccttcc caagagctcg ggcaggattt gatggtgaat 227160
gtacatttag tggtttccat atttaaaaaa aaaaaaaaat gactctgaat aagctcccag 227220
gctctcagtt tcttctagtt ctttctgaaa tggtccacaa catgattgtt ttgaaattga 227280
aaaattaaat gcttttattt caaaccccac cgatctaaaa ccagtaggtg tacctttcat 227340
gagcacactt cattctgcag gtgaaaaatt ttcttccaac aattgtctat gatagtgatt 227400
tataagtcag caatttgctc taaagaatgt gtctctttct aagcatcaca agaagtaatt 227460
taaattatgc tgtttcttag taagcatgtt gattgaacct cacatatttc cactgattct 227520
acactaaaca cagactctct tttagttgta ctccatttga cttggtttat acagttcaca 227580
tagtcacttt tgtatgtcta aacttgcctg accattttac tagatggcat ggtgatatgg 227640
tttggctttg tcctcaccca aatgtcatct tgaactgtag ttcccataat ccccatgtgt 227700
catgggaggg agccagtggg aagtaattga atcctgtggt ggttaccctc atgatgttct 227760
catgatagtg agttctcatg agatcagagg attgtgtaag gggcttttcc tccttttgct 227820
cagcacttct ccttgctacc accatgtgat gaaggacata tttgcttccc cttccgccat 227880
gattgtaagt ttcctgagga ctccccagcc atgctgaact gtgagtcaaa ctttttttcct 227940 ttatacatta cccactctcg ggtatgtctt taatagcagc atgataatgg aaattgctac 228000
tgagagtggg gtgctgctgt gaagataccc aaaaatgtgg aagtgacttt ggaactgggt 228060
aacaggcaga aattggaaca gtttgaaggg ctcagaagac agggagatgt gggaaagttt 228120
ggaactttct agagacttgt tgaatggcct tgaccaaaat gctgatagtg atatggacaa 228180
tgaagtccag gctgaggtgg tctcagattg atatgggtaa cttgttagga actagaataa 228240
aggtgactct tgctatgttt taccaaagag actggaggca ttttgcctgg cgttgttgtt 228300
ccatgatttt tttttttatg ttcaacagga cgatggcaca acctagctgc aaggcacaga 228360
ccaactccca gcattgccag ggcttagggt acattaccag gtcagctgct gaccagcagg 228420
ggctgctttt ctcttttgtg agtaactgag aattaaataa actaagtaac atgcctcaaa 228480
tcctgcagag ggttggagat aatactggag tctcaacata gactatatgg gaaagtctag 228540
cccattaatc tccaggcttt tttctaagaa accaaacgcc aatattttat ttgttgcaga 228600
aaagggacat cctgtggtca acacaatctt cagtgggagt taattttaat caggttcttt 228660
agaattcagg aaagctggaa aaagaggag ttgtgtaact cacatactgg gaggcatctt 228720
ctgtggccag tcagcagata ccatctccat ggagagatg caggcatctt aaggatggga 228780
gaattccatt tatagcctag gacttttgtc catgggcctg gcttggatag ggatggccca 228840
tattaatgtc tttgactctt ggtttttattg ttacattctg tatggctgat tcagatttgt 228900
ccacactgat atatttgttc tctgattctg atcattgtgg ccatctttcc ctagaacaaa 228960
gggcttaggt taattttgc ggagtaatga catttttctgt ggcagccaaa ctccgtagaa 229020
caatattgct cctacttctt gttttcttcc aatggtaatt gaacgtgcaa gccacattca 229080
ggagtagggt ctgaaattcc ccaagagcta gccagcgata atagtgcaaa tctaatacat 229140
gcccttgaaa caccaaggga taaactcatg tgcatttgtt cttttggggt ttgaagaacc 229200
agatgacatg caaaagaaaa atattgacaa aagatatctc atcgtttact ttcaattatt 229260
```

```
gagtttgatt tcatgcatt caaccttagt ttttttaaga ggtaagtgat tctagtttgt  229320
gagagccaga agcatgcaca aataaacctt atttaacaaa ttaatctcat attttcttgg  229380
ttctgatgat tgcatactgc ttatttaaa aaggttgtga gcaagccaaa gttatcatac  229440
ttatttttaa agtgacagca tggctgagct ttcaaaatat gtttaaagat tctaagagaa  229500
acaggttaga aaacaagatg attgacagct ttttgggtta ttagatacag aaaattatac  229560
ttagatttat ttaggttgaa aattaatcct acagcattta aaccagctgg gagagcttgt  229620
gcatgcacaa gagtgttcaa gctgcaactt aaggccattg ggcaacagta gaaagaaaaa  229680
aatggttatt tcttctcttt cagaaccaac tgtgactgat taaccacaaa agatcagtgg  229740
gggtattcag gcctaggtcg tcttggtggc aactggggtt ttagtttgct ttcaggctca  229800
ttgctggaaa aggctgttca gaagcttcct ctacaacaag ggagatgaca gtgcgtgagt  229860
acaaagcaga gaggtgcagt gctttctaca gcaccgagtg ggcaaattgt gcagatttt  229920 cagtagaatc tacttaacac caatccatgc atttgcattt tattaaaatg aaactgtgat  229980
catttcaact gcacattgca gacatgccct ataaaatgtt tgaagtcctg ttttggacaa  230040
aagttttgaa aacatgcacc ccgtatcaat ttctctactt atattttgta tttaatttgt  230100
ctaaagaatg ccacatttc aaagcaagca ggccaagaga atgatctttt tttcctcttt  230160
tttttcccca gtgtttaaaa tgcaactgcc atggggctgt gccattttag ctgttggaaa  230220
aaataatcta ctatgccttg gttgtatgtc tgagtcatca gagcttctgg gaatgattct  230280
ttggcacatt ctaccaacaa tttaacatga cacaaaatca ttttcatatc ttgtgatagt  230340
gtcagccaag tgtttcatac acatggtgct aggtgctgaa aaaggtgtct gaataaaatt  230400
gttttcttaa aggaaccata ggggacatga taaaaagatg cacaattata tatctttttt  230460
tttttttttt ttgagaagga gtttccctct tgtcgcctag gttggagtgc aatggtgcaa  230520
tcttggctca ctgcaacctc tgcctcccag gttcaagtga ttctcctgcc tcagcctccc  230580
gagtagctgg gattacagga gcctgccacc acacccagct aattttttgta tttttagtag  230640 agacgaggtt tcaccatgtt ggcctggctg gtcttgaact cctgacttca ggtgatccac  230700
ccgcctcggc ctcccaaagt gttgggatta caggtgtgag ccactgcgcc cggcctaaag  230760
atgcacaatt acatttcata aattgagaga gtttcctaaa caagagagag catacctgga  230820
aatatcagag aaaaatacaa agggcttaaa gatgttgtat taagcaaagt tagactaagg  230880
cagcttggat gtgcatctcc tccactttat gtttatacct aagtagagat taaaagcaga  230940
ggaatttcaa tttccacatg acttgtatat gagcaacaga tgggagttct aactactgac  231000
cacattggca catcacacaa tgttttcttt caggtttctc tacctatggc aaaaccagtg  231060
ctgtattaga gcctcgtgag ctgtgtgttg ttgattaatt gacttaacct ctctgggcct  231120 cattttctc acctttaaaa taaatgagtc ttatggtgtt ttgaggatca aaagagttac  231180
tgtacaaaca gtgctagtaa gagtccctgc cacatggaaa ggctattata tatatatata  231240
tatacgtgtg tatatatata tatatatgtg tatatatata tgtgtatata tatatacaca  231300
cacacacaca cacacatgta attttatata ttaaatgtgt ataattata aattttgta  231360 ttataaatgt aaatctgtga tatatattaa aactatgaaa tacagatcat gtaatatata  231420
ctacctattg ttttttttttt aatttgtaac catattttga aaattttatt ttgcttatag  231480
gtcttgaaag tcattcccca atcaaccttt attaaaatcc ctttgattca ttggagaata  231540
tcaatacata tgaggtatta atatatataa catatgtaac tcttctgagt ttataaatgt  231600
```

```
atgtataaaa cataaaaatt actaactctt catatatatg tttgtatcta tatataattt 231660
atatatatag atatatatac atatttgtat tacatatgaa taatcatcac agtgtgtctg 231720
catttgttaa tctaacctcc tccaacccca cccccaaaaa agcagaaact aaaaatagag 231780
gaattttaag ttccacatga tttatatagg agcaacaaat ggaactacta acttccgacc 231840
gcattagcta atcatacaat ttttttcttt cgtgcttttg ttgtaaatat gattttatt 231900
taagagggta ttattgatta tctacgcaag aattagccat gttctccata cttctacttc 231960
agttttttaa aaaaggatga ggatagaccg ggcataagtg gctcatgcct gtaatcccag 232020
cactttggga ggccgaggcc ggcggatcac ttgagggaag gagtacaagt ggcctggcca 232080
acatggtgaa accccatctc tactaaaagt acaaaagtta gctgggcatg gtggcgcatc 232140
cctgtaatcc cagctacttg ggaggctgag gcaggagaat ctcctgaacc cgggaggcag 232200
aggttgcagt gagccaagat cacgccactg tactccagcc tgggtgacag agcaagactc 232260
tgtctcaaaa aaaaaaaaaa aggtgaaaag ggtgaggatt gttatttctg tgggcaggcc 232320
cacacagcat cagattcctc agaaactgca ccggtaaatg ggaaagtctt tgagtccctc 232380
tgacagagct tcaaggggct ggctgttcat tatcccacag cctcctttgc tctgtgtaag 232440
tggaggctct gtgcctctgt tatcttgcag tccctaggtg accccggcag ggagaaaaat 232500
cagtggaatc aaactcggta gcacagaaaa acgccccaaa ggcaaggatg agaggaaagt 232560
tgtgatccca catatcaaag tcggactctt atctagatgg gcacacctga gccacaggct 232620
ggcaggctga gattctgcaa aggctctgga ccccagataa gcttgactga ttgcattgtg 232680
atctcttctt ttcatcaggg gaggcgctgc tttgaatgac taagctggat ctgactttcc 232740
agggaatcct ttcagggact gtgaccatcc agctatcttt ggatggcttt gatgccctaa 232800
ttattttca cttggttgag gatacttta ggtatctgtt catgtgtcat cttgtacaga 232860
aatgtgtgtt ctgggcttat aaaaaaagtt taattgtaag acaaagggct ctaggtttca 232920
tatttattca cagtctgatg aatggcactt atggatacgt acgtgtatac agtaagtgct 232980
cactgaattt ctcttgagtg ataaactggg atacaaaatg tcagaaaaga aagagtgagg 233040
atgggcactg gatccagatg tcagtgaact ctgagggtct cttgctggtt aaaagaacag 233100
ggtactttta ttttcattct aaaccctgcc tgacccttgc ccttatatca gtgaatcacc 233160
atctcgatgg cccctcaaac atggcatctt tgaagtagag cctcattgag aaggactcct 233220
tagaagtctg tcatggctac taaaattcat atctgtgctt tgtgcctgag cactagtaca 233280
tgtgtcagct gtttcttaag cctacattga accattaggg aaagcccagt gtgctcccag 233340
ttcctaaaat ctggtcaagt cttgatgttg gtcaacatct tgcctggccc cagtcagatg 233400
tctccagcta tctgtaacag gactcagtgt cttgtttaca aaatgcatta gtcatatggc 233460
ttcgttgctg gctttgctgt ataggtcagg aataagtcag aaataaccaa aatgctccaa 233520
atcaagttct agctgttttg ataccaacat cttccatcaa cttcgcttct ccctgactca 233580
tctgtctgtc tgttcctgtg ctcttcgcac acagaggcaa ttttgtgtat aaagctcccc 233640
aagggaagaa gaggacagtg ccttcatggg aaactccttt ctcttaaata ggatttgcat 233700
acttaaccag agcatttgct tcagttaacc aagtgagagg tggagaaatt cttgcaaaac 233760
tatagctaca ttgagaggga ttattaaaag tattgactca ttcattagag gagctgttac 233820
aaagattgta gcaaccaaag caaaataaaa aatattgcca aaagtattct caaacgtatt 233880
ttaaaatgtc caaatattg ggcaagacta acatcaaaga aggtatatgt tttgacattg 233940
atttactaac tacttatcag tgtaagtaaa tacaccttca agcacttatt taggattaag 234000
```

```
gtagtcaagt tatatgagtt gtatgagtat gtgcaggcca caagggttgc aaaacatagt    234060
gaattcaata tccctctgcc atattgaata tccttctgcc gaacttctgc atcacagttg    234120
tggcctgcaa acaggtaaca gttgtctgcc aatcccttag ggatcactgc attctatagg    234180
gcttgaccag gaagtaagag gctcttccca ataagcgata tcgttatggt ccttgtggtt    234240
ctgctaagaa tctcagagaa gaaatgaaag atacatgaaa ttgtttgcat gctactagct    234300
ctagtgggta ggttggtagc gtagttcttc atggcaaaag acagaatata tccaaaattt    234360
tcaccatttt gccctggtt tgagggatgc atattccttt agaccattat gttgaaaaga    234420
aagttaaaaa taacataaga agagacctcc taagttgttt aatccaagcc ctcaatctta    234480
gcaagtgcct ggtgtaaaat gtctcattag gtaattaccc atctcctgtc tacccactaa    234540
gaggttctag taaagtacat actggctgga ttcaataaag cacaaatagg cagcaaatgc    234600
ttcttacatc tcaatctaat cggtagcctt ctttatcctc acccttggct gactaacgtg    234660
cataaagcat aggaattctg gccactcaag gatcttaacc atccagttca gtctgttgca    234720
atttctcctc cattacaaat ttttttcact ttccttcct gggaaagcca cagacaggac     234780
aaccattcag tgagaaagga gtgtgaagct gacgtctttc ctcactaaga ggagaggggc    234840
catgagagga aaaggcaact tcttgcgtgg ctggtggtag agttaaagtc tgatgctact    234900
gtcttctggg agcagcagct gtacacagtt gaactttact ttggaggcat atatgatttc    234960
cagggttct gtggcaagtt ccacccactg cagttcattt gacttgggtt gaatctcttt     235020
cctccctcca tcacttcagc tgaacctctt ctgtgatcct cacctgttct ctagaggtga    235080
gaccagggca cagtcccttt ctagatgacc aaagagcact tctttctatg tggttcacat    235140
ttggctccat caccatcgta gctgacaggg ccaaccctcc ggcatcttca tccttcacca    235200
ctgtctttgc tgtgccccat aaggcctgaa caaggctgat gggccaagta tggtgtggcc    235260
agccccacag tctgttacta ggccttgctt tggtagacac acttcttgat ttagaaccat    235320
ggctctcagt catgggcagt tgtgccctgc ttggcaatgt aaggagacat ttccagttgt    235380
cagagtgagt ttgaagggtg ttaatgcact tagttggtgg agaccacggt tactgttcaa    235440
catcctacaa ttcgtaggac actcatccat aacaatgatc tgattccaaa tgtcattgat    235500
gctgacatta ataaaccctg ctctaagtta atgttttttt cttactcata tttaaaatgc    235560
ttcctctagc taaaccatta gcccccagtg aggtataagt tttcctctcc aagggacatt    235620
tgactatgca tgtacatact tcgggttgtt acagctggag attggtgatg cttctggcat    235680
ctaatggata taagtccaag atgttgctca atatactgca atgcagagga cagcccacga    235740
gaacaaggaa ttatcccatt cataatgcca ctagtattaa ggttgaaaaa ccttggttta    235800
gaatatgggg atacttattg gtgctcccta aggtgctatc tgaaagcagc tttgaagaca    235860
agcagaggct ttgaagacat actcacaggg tatgatatag tttggatatt tgtcttctcc    235920
aaatctcacg ttgaaaactg atccccagtg ttggaggtgt gacttggtgg gaggcatttg    235980
ggtcattggc cggatccctc atgaatgact tggtgcagtc ttccaggtga tgcctgagtt    236040
cttgctctat tatttctcag gagatcaggt tgttaaaaag agcctggcac cttcctctcc    236100
tctctctctt gcttcctctc tcaccatatg atctgcgcac acagcagctc cccttcctct    236160
tccaccataa gtggaagctc cctgaggcct caccagaagc agatgctggt accatgcttc    236220
ttgtacaccc cgaagaactg tgagccaaat aaacctcttt tcttttcttt tttattttc    236280
taattagaga caaggtcttg ctctgttaga ctggagtaca gtggtgcaat catagctcac    236340
```

```
tgcagcctca aactcctagg ctcaagccac cctcccacct caacctcccg agtagctagg   236400
actacaggtg catgcctcca tgcccagtta attaaaaaaa ttgtagggac agtcttgctg   236460
agtttcccag gctggtctca aactcctgac ctcaagcggt cctcctgctt cagcctccta   236520
aagtgctggg attacagatg tgagccacca tgcctggacc gtcttttctt tataaattgc   236580
tcagcttcag gtattccgtt atagcaatgc atatggagta agacattgta caagtcccac   236640
tttgggcacg tctagatctg tctgtgatcc tagacaagtt atgtaatctc tctttgtgtc   236700
taaacctgtt gtttgtttct gtctttattc ctcattaggt ccaactctaa agatagtaaa   236760
attataggta taaatggagt taagagggggt gccttaccaa gagtaaaccc tccaggagtg   236820
ttattctgtc agtatgactt ggttttttagc tttgaaactt ttagcatgaa actaacatgg   236880
caggaaaagg cctaaattag aattcttcac acacaaaact ccttctatca ggaggcagcc   236940
catctgttgt caaataatcc tactcgtaga aatgtattaa attttctttt ccttcccctt   237000 ttccccttc attaaatgga attagattgt gacactatga ggaaattaaa gtgaaggtaa   237060
aataaaacaa acaggaagaa gtctgtcttc agattggata tgcaattatc ctgtctttac   237120
tgctgatttc aattataact cattggtgtt accagcccac gatagatgtc ccctgcctat   237180
gtggtgttta aatcaagtgt tggcatcatt cacacttgtt tactgttatt agcactgatg   237240
gatgtaatct tcatgtcttc ctctgaacac tgcatgctga gaaaggggcc ttatttcctc   237300
gtggattttc taggcaagag aatgtcaggc cctcacctgt cctatttcca tctcactcag   237360
cagaaaacac actggctcat ggaaactgca agcatcgttg tcagctgcac ctgcaggcac   237420
catggggttg caagtcagca tcccctttca gaaatgagga tggaattaga ggtggaaaga   237480
aaattctcca cagtcctctc acttctctgg gcttagacag ggaggtttct gctatgtttt   237540
cattgattat gctgtggggg gaagggagag gaggaatccc ctaagaagaa caatgtctca   237600
ttggatattg ttcctttggg ggaaaaaaaa aaggaaagg aaatattttc attttttctt   237660 acttttttcta ccctagaatc tcaatgccac cttcaaacat ttgaatctca cagggagaag   237720
gcggccacat atttcacccc caaatgctag gccatgtctt ctcatgtcag aaatgcccta   237780
ttgtgcgtgt gtccttgttg caagccatct tagacttgtt gtttcaggga tagggaaacc   237840
attctgcaat ccaaataagg ttgcatttct tgcaattcaa aataaaaggt gtgcatgcac   237900
acacgcatgt gctggtatta ttgtacagct tgcgtggtgc aaggctgaag gctaagggac   237960
taatggaggc tgaaatttag ccctagatac actctgcaag ctgagtacct gtgggccgt    238020 attacctggc tagaggtgtg cctatttctc atgcatccag tatcaggtac ttttctgact   238080
tagagggtcc ctcaacccctc tcctccttcc cctccaccta tcgtacttag catactgtat   238140
atttgccctt agtctgtttc atccaacttg atcacttggt agcctgtctt tatccccact   238200
gtctaaatca gtatttggaa tgtagtaggg acacaaaaaa aattagttga ataaaggaat   238260
aaatgggtga aatagtgaat gcatgaaaaa ggaaaaaatg aatatttttgg ctgctgtgta   238320 ttcttgtatt gttgttatat ataattcttc tgcctgtctt tcttcataca tacctcatta   238380
ttagtataaa ctaccagcat tcgtgatatg caggtctttg cttttgcaga gagccatggg   238440
tttctctaaa aggcatcttg cagcctcccg cccagggtgt ctctgtgcag ctaacctggt   238500
tgctaatctc tgcaagctcg tacttttttct gcagcacgtg attctgttct catttactct   238560
tgtaatcctt ctgtttcctt ctgaccagct tgagcttctg tatctagtgc cttgacgttc   238620
tctttctttt ttggtctttt taacattatt atgtcagtta taatgttttt cagttgcttt   238680
tagtattcag aaaattcttg aagccttctt attgcccact ggtatttttgt cttcgccgct   238740
```

```
tgttgtttgg gtggatttag atatagcaga gagagagaga gagagagaga gagagagaga   238800
gagaggaaaa tagagacaga gatatgtaat cccccaacc aaccccgtt atctgtgatt    238860 tccattaccc atggttaggt tagtacagta cagtgatatt ttgagagaga gaaagagaca  238920
tcacattcac gtaacgtttt attagagtat atattgttac agttgtattt tattttaatt  238980
gttgttaatc tcttactgtg cctaatttat aaaataaacg ttatcatggg catgcaggta  239040
taggaaaaaa cattgcatat atagagtttg gtactgtcca cagcttgagg catccaatgg  239100
gggtcttgga aagcatccct cactgcccct ggtaaggagg agctactcca gttttgagag  239160
gagaaactaa acagatatga aaacataca agttgtaacc taataggaaa attttaaag    239220 tgttattaaa aaccatatct tatatatctc atatattaaa ggacttcaca atggacttta  239280
ggaaattaag atggaagttg caatagcaaa agtttagcaa tgcgtattct tacatatgaa  239340
aatcaaaatt aacctagcag tgttctgagc aacttcactt taagaagtaa aactagtgaa  239400
atgataaagg tatatgggtg ctgactgtta cgtaattagg ctgatataat ttagcaagga  239460
tatcagaaat catataccca aaatgagctt tattatattc aaattagtca cttcagaggc  239520
agtacactaa ttacaataag gtaagactgc tggaaacttc tttatttctc ctcacttaaa  239580
aacgtttcag agcccatagt aatttatttt taatatcttg ctgaggcaag tcttaatcct  239640
taaggaggca tttatatttg gatacagcca gggttctgtt gagtaaggtc agtgaccaca  239700
ttgtataaca caattttaat tcaaagacaa ggaacagcta taaataaagg tgagcttgtt  239760
tcaactaact ctttttttat tttttttta tttttttat tttttttatt tttttgagac   239820
agagtctcgc tctgtcgccc aagctggagt gcagtggcat gatcacggct cactataacc  239880
tccacctcac aggttcaagc gattctcctg cctcaacctc ccaagtagcc agaaatacag  239940
gcacgtgcca ccacgcccag ctgattttg tattttttt agtagggacg gagtttcacc    240000
atgttagcca ggctggtctc gaactcttgg cttcaagtgt tctgcccgcc ttggcctccc  240060
aaagtgctgg gattacaggc gggagccaat gcgcccagcc tcaactaaac cttaaggcac  240120
attgaaaaga aaatcaaaat gcattgagct aaatgccagg catatgcctt tccaaatgga  240180
cttgccatga aggatgtcat tcctgtgcag ccaggtgttg tcttctatgt attttagaa    240240 tgcccatcat atagtctcac ctttttaaagt ctgtttagtg gaatgttttc taactttccc  240300
atgtacctcc catgtcattt tttgccagtt ctgccttccc taataaccaa tgaaggtact  240360
tgcttcatgt taaattctag gtaatctggt ttctactgaa ttagaacatt cccacccgcc  240420
aatgtctttg aataattaaa ggttttataa tgtggtttcc atacaactaa ctgaatattt  240480
catgtggcta gataaatagg taaattgcag tacagtagca attggtgtag acacttagag  240540
ggtcctaata aattattgca cacgccaatg tgcaatcaga aagaataact gtagtgttaa  240600
gcctcagaca atgctataga cctgaggatg ggcctgtgat ggacggatca atggctcagt  240660
tcctattgga gtttcacatc taggaataag tgaattcacg actattcatc agctgctgct  240720
actgtacgga agtgtgtcca ttgagaagtt gcagaagggg ctgggagatt ggataaggct  240780
tttgcagtac ccctccttt taaaaaagca gacagggtgt aactctattg caggctggag   240840
tgcagcgttg tgaccatggc tcaccgcagc ctccaactcc tgggctcaag tgatcctcct  240900
gcctcagcct cctgagtagc taggactaca actaggcacc accataccaa gctaattttt  240960
ttaaataaat tcactgagac agagtcttac tatgttgccc aggtgggtct caaactcctg  241020
gcctgaagca gtcctcccat ctcagcctcc cagagtgctg ggagaacagg cgtgagccac  241080
```

```
ggtgcccagc ctcaatacct tttaaattaa caggaagtgg aaaacagaaa ttctgcagca   241140
tgttttctc attagcatga atcactctct ggtgatgtgt tcatggtttc taatggtatt    241200
ttcaagatgg acaatataaa gacaaccatt agaaaccaca aataataggg ccatatgaaa   241260
caatataata gatgcatgag gttaactggt caacatttat gctgaactta gatttacact   241320
gattaaaaaa aataatccat ttgaagtgta acacacagaa accaaagttc tgtgtgttct   241380
gttatcttat attatcaatg ctccatgcaa tgtgaaagct taaggcaagt gtttctataa   241440
ccaacaccca tgtgaagaaa tatagtttcc atcttcaaag cagtgcatgc tcttttccca   241500
ttctatctcc ttatcctcct ccgtgataac cattattccc ttttactact catttccatg   241560
cttttcttta tattttccca atgataaagg catccctgaa tcacataatt aaattttgct   241620
tgtttggaga ctctaaatga atgcaacttt ctattacttt ctggtgtgtt tttttcatgc   241680
ataatactgt tttataaatt tcatatgtgt tgctgtgtat acatccattc cactcatttt   241740
aattgttgta tagtgttcta aagtctgaac ataccacagt ccctatgtcc attttattcc   241800
taatagatat ggttattatt ttgagtttga ggttattata aattcgtgtt attaacattc   241860
tttttcaggc accctccttt ctcacaagca ttggttttct gagacatata ccattatgga   241920
attgctggtt caaatcttca actgtatagt ttatataagg atgaactgtt ttccagtaca   241980
gaaatgcctg ttttcaccag gagtgtgcaa tcttcaacat gtggcagtat aaaagttcta   242040
ttttattttt ctgatctagc gtgtgtacat ggaaacccat tgtgtgttca ctgtgtttac   242100
tctgaggttg agacatttcc atatatctct tggccattca tatgtcctgt ttggtgaagc   242160
gtctgttttt gatctgtttt tctactgggt tgtgtgtctt attgctgtat ttcgattaga   242220
gtgcttcact gattatatat gttgcaaata tcttctgatt ttccttccat gtttttaatg   242280
atttatttaa ataagctaaa gttcttaatg ttagtttata gactttacaa tattttcttt   242340
cagattagtg ctttggaatt tttgtttagg atatcttttc ctaccaagag atatgaagat   242400
ttcctttat tttatctgaa aaaagcttaa tattttatct ttcatattga aaccacacag    242460
ggaatatatt tattgcattc tgtaagaggt ctagtttatt tttccttaga atatcacaat   242520
acaatttatt ttaaacagtt tgatccatgt cactaaagtt caagtgatct ctttgtctac   242580
ctctgtgcca atcatcacat ttttatcttc atgattttat aataatccgc aatttatatt   242640
tttatacttt gtttatttct tgccaatatg cattgcatcc ctgagaaaag tgtttatttt   242700
gcgatggttg gtgcaatgtg ctatatgtct aatatctcaa actgttgaag tatgttgttc   242760
acatactcta tatagttttc caggtggtag tttacatatt ctttcagtaa ctaaaatagg   242820
tctattaaat tttcccacga tgtttatgga tgttttaaaa tcttttcgta tattttcca    242880
aaatttagtt tcttgcattt tatatgctta tgaattttag tggatacagt ctagaatttt   242940
tattgcattg tggcaaatta aggttcttct cattataaag tgatcctctg taagtctgtg   243000
gtgcttcatg ccttaatgtc tgtttagttt gacgttaaca ttacctttgt tttgttagta   243060
atccaattgt gtatagttcc catgtgttta cttcaggcct ttctgttgac tcaggttttg   243120
agtcttttct acatagcgtc tatttgggtc tcataatctt tgattttcaa ccgcagatcc   243180
actgatattt acttttattt ttgatatatt tgtgtttaag tcttctatcc taaattgtgc   243240
tactaatatc ccacttctac atcttgcttg aattgctttt taaaaaatca ttcaggccag   243300
gcacagtggc tcacacctgt aatcctagca ctttgggaga ccaaggcagg aggatcactt   243360
tagaatcctc caggagttca agaccagcct gaggaacata gcaagacctc atctctatga   243420
aacataaaaa aaaataaata aataaaaaaa ataaattagc caggtgtggt ggtgtgcacc   243480
```

```
tgtagtccta ggtactccag agataagagt tgacaggaga gtctgatccc atgagttcaa    243540
ggctgcagtg acctatgatg gcaccactgc actgcaacct ggatgacaga acaagatcct    243600
gtctcagaaa ataaagaaat aaaagacaaa taacattact ccatttcctt cactcccact    243660
tctccctcta cactagatgt taaaagactg tactagtttt agtaaataac cctagaaatt    243720
acaacacaga tccttaatat aatcactaat tttaattaat acattttcca cttctctgaa    243780
aatacccagt agtcagtgta ttttagctcc atgtttatga cctaacctac ttgctgttag    243840
tacctttcaa tgttttgtgt tttttaggaa tctttttcag atatgattgc ttatcttatt    243900
atttcaatat taatttttgat tttctgatga ttacactatt ttatttatgt ttcattactt    243960
tttgtacctc ctacttttat ctgtgattat tgtcttaaaa gaatctatcg gtgatctaaa    244020
atatattttc agagctaaca agctgttgga aactctgttt gcatggctaa atgtgtcttt    244080
atgacatcct cttcttgaac aatattctca ttgaatttta atttgcaatt acttctttca    244140
gccatctgag aaatcattct cctattctct ggattccatt attggtatgg agaatttagc    244200
tgtcagttta agtgttgctc ctttaaaaat aatatatttt ctgcagatag tttgtctata    244260
tccccctgat acctttaaga tagttttttct ttgagtttct gccgtttcac tgtgatacca    244320
ttaggggttt attaatctga ttggaattcc ttgatgacct tgaaatttgc aatcgtggtt    244380
tcttccattc tgaaaatagt cattacctct tcaaattttg gtgctgtttc tcttgttttc    244440
actctgtttg cacataattt agattttctc cctctggctc cttttttagt cttttttttt    244500
ttgtattttg tattaaattt tactttcaag cttcattctg gattactttt tctcaagacc    244560
tataatctat ttcattaatt ctcttttcta ctgtatctaa tgcatggtta aaccaatgca    244620
tcaaatcttt atgtttgata tatattttca ttacatttca aggattaatt ttagtttctt    244680
cttatagttt ccacattttc gaagttctca attttatatt ttctggaatg cattcttcct    244740
agttatttta aagtctgcat tttgtatttc tatttttttc aatcacccct tgtttcttt    244800 ctctttttg ctttttggtt tcattgacta atatcttcat ggtctaagta ttataattat    244860
gcatatatta gatattctca tattgttttc cttatttcta actctctatt ttatatttt    244920 tgtatatgac agctccctgt gttgcccagg ctggagaggt tgtgctctgt gcccagtggc    244980
acaatcatag ctcactgtag cttcgatctc ttgggctcat gtgattctcc tgcctcagcc    245040
tcctgagtag ctgggactac agtcacatgc caccatgcct agctactatt ttatacttta    245100 aaatttttt agagactagg tcttgctttg ttgcccaggc tgttctctaa ttcctggcct    245160
caagcaatcc ttctaactca gtcttttgaa tagttgggat tacaggtgtg gccactgca    245220 cccggttttcc cagcttttttt cagatttcca cgatactctc tggatcgttt cttctcacct    245280
cttctcaagt ttgtccattt ttctcttcag ctttgtttaa tctgcccta ggtggaccca    245340 ttcattttct cattttgttt atttctctga tctagaagtt tgatttgatt tttatttttt    245400
catttttaat acttcttat tccctgcaga tgttttccaa cttttttgttt tcaagctttt    245460 tgaacattct tcaaaaaatt ggttatcatg tatatatttt catggcatct taattccttt    245520
gggatttctg ctggctcttg ttggtgactt cttgtttctt tcttcatggg cttggtaatc    245580
attgtgaatt ggccattgta tttgcaaatg gattagtggc atcttctcc aaagcagata    245640 acccatgggt agcgaaattc taggttcttt catccatggg gccatgctct tccctgaatt    245700
gttcatagat gttatgaagg tagactgcaa gcacttgcaa gactgaattt agttttgttt    245760
catgtttgcc ttgagggtga aacccatgaa ggtaggaaaa tgttaaaggc aagtatatta    245820
```

```
gattgggacc ttcaggcgtg actagggtct gagagttgcc ccattacatg gtgatgctgc   245880
aagaactccc acagtttctt ccagattgga acagtgcact agggcaaagg ctgctttgtg   245940
tgctgggcat ctagctggat catcatttgg tcgtcagtgt gttttttgttt gtttctttgt  246000
tttttgtttg tttgtattgt gttttgagac agggtcttac tgtgtcatcc aggctggagt   246060
gcagtggcac gaacagggtt cactgcagcc tcgaactcct gggctgaaga cttcctccca   246120
cctcaccctc cccagtagct gggaccacgg gtgtgtgcca ctacgcctgg ccacttttta   246180
aaaaatttt tgtagagaca aggtttcacc atgttgccca ggctgtgata atcagttttg    246240
aagctgtaat cttaaatatg attttagcac taaaatgttt ttaagagact aaaaaaatc    246300
acacatatta caatccattt tcaataagaa ggttggtttg aataatctac tctgttactg   246360
ctagatgtag gcttctgatt tattctaata tattacagaa atgagtaggt ggaacatgag   246420
tttataaaga taatgcaaat attttattag cactgtattc tcttaagagc agttcagagt   246480
tcaaagaatt gtgactttat ttcacaggca ttaaaataaa ttaaatcagc aatctcattc   246540
ctaacaactc aaacttcaaa gaaatttcag acagttaatc atcacctgac accacagcct   246600
atgcaacttg ggtttaatta ggatttatgt tactggtagc attgtggttg aaaagatatt   246660
ttcattaaca tttctctctg aagcactgag tcatactctt gtttattcgc aagtttcttt   246720
acacttttca atcaatattt gagtgttcct tgggaaatgt atgtttggct attttggtgt   246780
ttttgagagt gtttgatctt tgaaaatgca tgattaaaag ccattttaga aataaacatg   246840
agtgttttaa atacaaatta ctaaagccac tgttttgttt caaatttagg gatttaattt   246900
ttttaatgaa aatgctcctg tttatatatg catgaggtta tgtaaggtca tcaacttaaa   246960
gattgatgat ggatttagtg ccagctgttg attagtatgt ctgcaatcaa tctacaacat   247020
agcaataacg ctagctacct tggagagtta ctgggagaaa taataagac acaatgtatg    247080
taattggcct agcaaacttc tttgtatact ataattattc agtaaataat cccttgtga    247140
ttatttatct atcaatcagt cttagagcag tgaatttacc tttaaaatct agacacatta   247200
ggaaagaata atggtagatt ttaagacaaa attaaaattt cttggtgtac tcaaaaatat   247260
atattttctg ttaatgcaaa ttaggctttt atatttatta ttttttaatat ttgactctgg  247320
aatgttttca aaatttagtt gagtagatct taatgcaagt ctacttttaa aaaatctcat   247380
tatctagtag gctttactag taattaattt gaatttggta gacatgaaac acaccaattt   247440
cttgtacaca atcataaatc ctgtatacta tgtatactct gtatgcctgt atcttggtga   247500
agtgggaatt aaactttatc aaatttccat tgaaaaactg aagagcaaac taagatgtaa   247560
tcagaatgtt aataaatatt gtagaaatgg aaaagtttca gaatgtttag atttctcaag   247620
gaaatctcaa agcatgacac ttttcattgg tctgtcatgg ataattaggt cttttgctat   247680
ttttattat ttatttccaa tccgtcacaa acgtactttg gttgatgcat atatcaacta   247740
tagagtagta aatctgacaa agtctatgca ctgaaaacta tactctgtca ctgagggaca   247800
ctgatgaagg cttaagcaac tgggagacag actgtgttca caaacacaac accctcctga   247860
gaagatacaa tattgttaag atatttattt tgtacaaatt aatctacaga ctctttgcaa   247920
tcccaaataa aataacagta gacttttaga aaatacataa attaacaaga taaatttaaa   247980
attttaatga aaatacaaaa gatctacaat aaccaaaaca ttttttgtagc agtagaacat  248040
acttggaggg ctcctgctac ctgagctcaa gacttagtat agagctatat taattgaaac   248100
agcgtattat tgacataaag atgtaaaacc tgatcaatat catagactag agacaccaca   248160
tagaactgta catatatgga caatgaattt tccaaggaga ttcaaaggta attctatgca   248220
```

```
ggaatgattt ttttttcaag aaatggtgtt ggaaacatta agtatccata tacaaaagaa   248280
aagaaaaagt aaacaaaaag ctttgatcta taactcacaa tttgtacaaa aaacaactga   248340
aaagtgagtc aaatacctag atgtaaagct taaaattgta aaacttccag gagaaaaaaa   248400
aaaaaaagaa aaattttgtg actttagatt ttggcaaata tttcttactt aaaacaagaa   248460 gcttgattt taaaggaacc aattaataca ttggactaca tcaaaactta aaaaatgct    248520 tatgctacat gaaagacatt gctaagggaa tgtaaagaga attcacaaac tgggaggtaa   248580
gataggcaaa ttaaatatcg gatgaaggta ttgtaccagt ataaatgtat gcatacatac   248640
atatatatga tgcagtttcc tataaatata tagtatatat ggtattagac atatatgtat   248700
agacacgtac tggtacaatt atatactata tatacaatat tcatatatag tatatatgat   248760
acagtattgt atactatata taaaatatat catatattta ccatacagta tactacacat   248820
atgtatatat atgatatact gagtatcact attactaaaa attacagaat gtgaactatg   248880
aaaatgtaaa agcctattta aataaaataa atatttaaaa tactgtgttt tttatatata   248940
tagcacatgt agtatactaa attgtataca gtatagtata tatagtatac tgtatcatat   249000
atattgtcaa tatagtatat aatttaccc tgtgtgtgta tagatgtgtg tatatgtgtg    249060
tatatataca catatatatg tatgtgtgta tatatacaca tatatatgta tgtgtgtata   249120
tatacacata tatgtgtatg tgtgtatata tacacacata tatatattct aaaaggagaa   249180
ttaaaaagaa accaccccat aacaattgga cagaaaattg aacaggcagt tcacctagga   249240
aaacatacat atgaccaata gcccaatgaa aatgtgctca gcatcattag tcattggata   249300
aatgcacaaa tgaaaccaca gtgaaatacc actacacatc tgagaatggc tgaagccaca   249360
agactcgcta tgccagggct tggtgaggat ttggaggagc tagagtccac cccaagctgc   249420
tggtggggaa gtgatatgaa accaggactt ttgagaagag tttggcaatt ttttgttgt    249480 taaacctaca agtaccatgt ggttcagcca tttaactcct aggtatttac acaagaaaaa   249540
gaggagcata tgtccatacc aagaccaaga acctgaatgt attcataggc tggaatgctt   249600
ctgagcagta aaaatgaatg aactgttggt gcatgctaca acctgcatga atattaaaat   249660
gattatgcca agcctaagag gccaagcaat gaagagaccg taattctgtt acttcgcttt   249720
taatattttg gaagctgtaa ttcataatgc ctgtctgtaa gcagataact gtttgcctga   249780
gatgaggagg aggagcaaga gatatagatt ataaagggat atgggtaaac tttggggtgt   249840
gatatatata tatgtacatg tatatatatg tgtgtgtgta tatgtgtata aaatacacat   249900
atatgtatat tttaaacaga gtctcactct atcacccagg gtgaagtgca gtggcacaac   249960
ctcggctcac tacaacctcc acctcctggg ttcaagcagt tctcctgcct cagcctcccc   250020
agtagctggg actacaggtg catgccacca cgccctgcta tgtgtgattg atatttctgt   250080 cacctgact gtggtgatgg cttcataact gtatacataa gtcaacattt attatactgt    250140
atactttatg tacagtttat acttttacaa ctataacttc agaaacccac taccctattt   250200
taaaaaagtt aataattact ctcagccact gtgagacctc actgtttcct tatgctcatt   250260 tttccctta caacaatgg ggaactagta ttttatcaga taaaaataat gtttgatagg     250320
attttgtgca aagtctgttt tgcctactaa ttctgcctta tggcatctca gacatgtaaa   250380
ttagacaaga gccttcagta tgtctgatct gttgtcacgt tattttccac tagtttgtgt   250440
gatttagatt attttttaaag agctgataaa ggaaaggaaa ggaagagaga gatagaagaa   250500
agaaaagaga gaagaaagag aaagaaagag aaggaaggga aagaaagaaa gaaagaaaga   250560
```

```
aagaaagaaa gaaagaaaga aagaaagaaa gaaagaaaga aagaaagaaa aaaagagacg   250620 cctgtcttt  taattccagt tggaagcagc tttagttata aaatttccac tctctagaat   250680
attcttgggg aaaaaatgaa gtgtcaatta aattgatttt tttaacttgc atcctatgtc   250740
tctgaacatg attcttttc  aatcaggcat gtagttattg aggacccatt tatgagctgt   250800
gcatacatcc catccaattc catccaattc cgtccaatcc tgtccacaga catgttgaaa   250860
gcatgagctt cctgcaagag caatgcacca gccgttttcc tagagatggg tcttcaaaga   250920
gagggttctt tctcggagca cctgctcagg gaacaagact gactttaaac cagtgttagc   250980
aatatgcatg gtacactgaa ccatctgctg gaggacctcc ttgtgtccaa cacagtcctt   251040
ctgttgaatg tcatggaaaa gactgagggt tgaagcaaat cattttatgc agtgaggaga   251100
agaccgtgct catcttcag  ttttgagcc  acatctacct aatttatagt caggtttggt   251160
agcctcagca ctactgatat tgctgcata  aatctatgct ttgttggggt tgtcctgtgc   251220
attttaaggt attgaatagc atccccagtt cacacccacc agataccagt atataaatat   251280 ataccgttt  tgccaattaa aatgaataag aaaaaaatca ttgttacaga ttaataataa   251340
taataataat taataataag tggctggaca cagtggctca tgcctgtaat cctggcattt   251400
gggaaggcca aggcaggagg atcccatgag cctgggaatt tgaggccagt ctgggtaaca   251460
tagtgagacc ccatctctaa aaaaaaatg  aaaaattagc caggcatggt gatatgtgcc   251520
tgtagtccaa gctactcagg agactgaggc aataggatca cttgagccca ggtgtttgag   251580
gctccagtga gctagctatt gatggttcca ctgcactcca gcctaggcga cagagcaaga   251640
cctggtctct aaaaaataaa aataagtaaa taagctaaat gctcttgaac tgaaaaaaag   251700
aatgtattct atgagagata cctgataatc acctactttg accatgtttt tatccttcaa   251760
ggatttcaaa ctgttacaac aaacttctaa acgtgtatct cttagttca  gcttccttac   251820 atgaatttaa tgctccagta tgtgagacca attattgatt taaaaagggg tagatctgtt   251880
ttaaaattcc tttaccaata ttcctcatgc tcatgagaaa gatatgaggc agtgctgttg   251940
actgcatttg tattagtta  ataccacgag caagtgggaa aaattcagaa gtgacactga   252000
gttggtcatc tctcaattat catcatgaga agtacgcaca atgtgaacat tctgccatag   252060
ggcttgtctc tgtaaactgc tggtcaaggg gcatggacag attctactat ttttaaaaac   252120
atctttctga acagataacg gaggcttaat tgtagtgtaa acacactgat gtacaaatct   252180
cgaaaaacat aaaataaagt gtgttgagat tggaggtgct ctgttcaact ttcgagggat   252240
agaaaatatg cctatcagct gtaaaagcgg tgcatttatt ttcatttttt gagaccaaca   252300
ctagagcaga aagacacatt aacaaaaggg taagagtctt cagagcagat tactcccact   252360
tgaaaaatga gttaagtgat ttcacagcgg gagagaggga tatttgcagc aagaagtttc   252420
attagtcact gaatgaggtt tctctgacat atattttcac agaatgagaa gcatgatctt   252480
tagaagcaag agccataacc tttctatatt tttcttctgt ttattcattt tgctggaaga   252540 ttccttccc  tagccttctg gaaatttcag ccttctagtc tgatttggtg accttgttc    252600 actaggaaga acatagtccg tttctcttg  ccaaaggta  gttgcatgca tttgcaattt   252660
aaacaaggaa catccaaaaa aattagaatg tgtgtttgtt gaaatattg  tgattattaa   252720 agtcagagaa gatagctaaa acagaagatg cccatacttt gaaatcagat gattattaat   252780
agatgctgct ttgtgttgac tggagtttaa ctgccagtcc tttcttttgc caagatattt   252840
tcccaaaaga aacatttcag ttgtaggctc aataaggaga ctggaatctg ctttgtgaat   252900
tggtggcaaa aggaaaaggt gggggaaggta ggagaagaaa agagagatgg agccttcagg   252960
```

```
taggagacta cttttcttc ctttggtgtc tcatcttaat atttaaaaaa ttaaattgaa   253020
gactcagcta aggtatagaa aatatcaggc tttttctttt tgacatataa ccaacattat   253080
ctcttgtcaa gcaatttatt tttttatttt atttttttaa ttttctaata agactaggtt   253140
tattcagtac cctagtaaaa gttttttatta taagtatcca acagtataaa aagtacaaaa   253200
cagacctgta gatttctaat atattaatac aaagtgctta tttttaaac tgcttttttt   253260 tttttttttt gaaacggagt cttgctttgt cgcccaggct ggagtgcagt ggcgccatct   253320
cagctcactg caacctccat ctcccgggtt caagcaattc tcctgcctca gcctcctgag   253380
tagctgggat tacaggcacc caccactatg cctggctaat ttttttgtat ttttagtaga   253440
gatgaggttt caccaagttg gccagcctgc tctcaaactc ctaaactcaa gtgatccacc   253500
cacctctgcc tcccaaagtg ctaggattac aggtacatgt caccacgccc agctaatttt   253560
tgtactttta gtagagacag ggttttacca tgttggccag gttggtctac atgatgactt   253620
cctaaacaag tgcataactt cgattctaca aagatgaca gaattcatta gtactactcg   253680
tttgtcctca gttatacttt ctgcagtttc agttatctac ggtcaaccat ggtctgcaga   253740
aaattccaga aataaacaat gcatcagttt tacattgccc ttggttgtga gtagcatgat   253800
gaagtctcca gcagtcctgc tccctcccaa tccatcctgc ccaagaggtg aatcctccct   253860
ctgtctggca ttttcatgct gtagagactg cctgaccctt agtcacttag tagtctgctc   253920
agtgaccaga tcatctgtca tggtactgca gtgtttgttc tcaagtaacc cttatttcag   253980
ttaacaatgg ccccaaagtg caagagtagt gatgctggca tagtgttata attcttctat   254040
tgtattatta gctattattg ttaatttcct gtgactaatt gataaattaa gctttatcat   254100
aggcatctat gtataagaaa atgcacagca catataaggt tcagtactat ctgtgttttc   254160
aggtaaccac tacaggtctt ggtacgtgtc ccccgtgggt aacggaggac tcctattgtc   254220
tgtgttttat ttgaagggat tttgattcat ttgtgatctg tttcacgccc tcttcctttt   254280
ctcctctggc aaatttgagt tggcatgccc tccacttaat cttttaaatg cttgatccat   254340
tctattctgc agaagaatgt taaattttc attatgtcag tcaatatgct tttgaaaaaa   254400
gggacactcc tgtttgtgtt tcctctttaa attcatggtt tagagttttc tcctcttcct   254460
ttcgcttgag cctccccaac tgcagtgtct cctcagtcct ctaactccat gactgtggat   254520
gaaactccat cttgtttttc ttcaatgtgc tatttctcaa gtttacatct acaaatgtgc   254580
tgcaaatatc tggtactgaa tgatgtttca tttcagtgaa gcgtttgttt ttgtttgttt   254640
tgaaagttaa ttgtgcatgt ggtttaaaaa atccaatata acaaaaggca tacagggaca   254700
ccatttgacc atgccattcc ccaccccttc attcagttgt ttcagcgacc acctttcttt   254760
gttgtggctt gagaatcctt ccagagacgt gactaaacag ccatggaaat gccagtgcaa   254820
cagagcattc tttacatctt gctttttcca cttaataaca taactttgag gttgtcctat   254880
tttgacacat agacatccac ctcattcttc aggaagcctc tgtcacaggc acatatatgg   254940
acctaccata attcattgat tggactgcca tggttggaca cgaagattgt ttccaaatac   255000
ttgctaccat aaaccctagt gcagtgaaac ttccttcaca caccttttt tttcttttt    255060 gagagggagt ctagctatgt cacccaggct ggagtgcagt ggcacgatct cggctcactg   255120
caagctccgc ctcccgggtt cacgccattc cctgcctca gcctcccgag tagctgggac   255180
tacaggtgcc cgccaccaca cccggctaat tttttttgtat ttttagtaga cgggggtttt   255240
cgccgtggta gccaggatgg tctccatctc ctgaccttgt gatctgcctg ccttggcctc   255300
```

```
ccaaagtgct gggattacag gcatgagccc ttcacacacc tttgagtggg ggtaggattc   255360
catatctatt ttaaatgtat atagatgtta ttgagttta gaggactaaa caatttagct   255420
tccaagcata acctataaat gcatcttggc cactttcttg ccaacagagt gtgttataaa   255480
gcatgtcatt tttgtctgtc tcaggtcagt gaaactcctg taaaggacca gatagtaaat   255540
gtgagccaca tggtttctgt cctgactact caaatctgcc cttgcagtgt gagagcagca   255600
atagatgatt tgtccatgag tggtgtggct ctcttccaat aaatctgtat ttacaaaagg   255660
aggtcctggc caggtttgct tcctggatca tagtttgctg acccctggtc tatctaataa   255720
caacaataat aatctttagt ttgtttcttt tgtatgagtt aggctgttca tctgtttaaa   255780
aatctactta ggtattttt tcctgttaat tacatccgtt gctcattttg cataatgcag   255840
tttaactttc tcttgttggt ttattaaaag caatctatat atttgaaact taattacttt   255900
tatatattct gaaaaataat tgatctgtta gctgttgcaa cagttggctt tctgataaat   255960
ttctatttga catagaacca agtaaaaatt atgttacctt gggttgtaac agttactctt   256020
aaaaacattt agatctgcaa ggcacagtgt ctcatgcctg taatcccagc actcttgaag   256080
ctcctggctt caagagacat ccccgccccc accccgcccc cgcccccac cttgtcttcc   256140
caaagtgttg ggattatagt tgtaaaccag caggcctgac cttgtgtaga catggtaatt   256200
gacaagaatc ttgtagtcac attttcatag actatgcagt agatgcaata gactaacttc   256260
tgtatgaatc ttttcattt tgtattaatt ataatcattt gccaagtttg cttcattcat   256320
ttgtttagta aaagagtatg tgtaaggaat ttggtaggca attttagaa cttttagtga   256380
caactttgtt tttgattgtt tcttagtgaa agaaggatta caataagaac ttagccacaa   256440
aatacaagtt tccatgagtc actgcaaaat aacagggata gtttggaaag gcaaggagta   256500
accagaagct ttggggcata gttttcctta gttaaatcag tataataaat ggggtacaca   256560
ttgcaaatta tttattcata gtttggtagt ttgcattggt atgtcttaaa cctgaatact   256620
ttagagtgaa tgaagtaaat aggatgagat gatggggaat gcacacacac ccacacacat   256680
gcacacacaa acacacatgc atgcatgcat acatacatgc acacacacat atacatatgt   256740
gtgtgtgcct gtgtgtgcac atgtgtgtgt atgtatgtta cgtttacatt atttctgcat   256800
attaaacact ttcccctttc gttagatatt ctttattgag aaaatgcact acactagatt   256860
accattactt aaaagttgct ctcgcagcac aaatcaattc attatcttta aggataagcc   256920
catgtctgga ggtagggaaa tcattttta aaaattaaag tttctgtctt gaaatattgt   256980
catccttcac ttttctatg cactaggatg ctctttgctt tcaggaaaac acgttatgac   257040
tcatttaata ctgttgtccc tcttatccag aacagaacat accgtggttg cctaacagga   257100
aggctgcata taaacccag ttttgtctag tatcattttc cccaagtcca ttatgtgtgt   257160
tattgtgcag tgcatgtcca aatgaggatt tgagcagtag agaagaaatt cattaaagaa   257220
atgtgtcatc tccttgcaaa aaggaaagta ttgttgagga aattgttact gataagacaa   257280
aagtggtgaa tgaacatcta ccatttgaag gcatttctct gaagtgaaaa ttaccttgaa   257340
ttgtcttggg atcagttgtg acttgatcct tctattagga gctgtttcaa actcagagaa   257400
ggggtgatga ttcacactga tgactgaagg tttcttggag ctggtgtgaa taagaaggga   257460
aaagtattgc aaatgcatca ttgtggcttt cactgagact cagtggacag aattcatcat   257520
gatcttcctg ggctccagaa acacaggctt gaaatttagt agccagtctg ccaagcatgg   257580
agttaggcac agatgggatc tgagttagag aactctcctg ggactggtac ccagggaggg   257640
taatgtaggg tgaaatgtca ttgttcaaca tgcttattat tcacctgaac atgggtgaca   257700
```

```
ttcctttcct gagaaactct ggtctgacaa atgggttctt acaattattt ctgaaaatag   257760
aaaatgtatt tccaataatt attagttata tctatttatt atttctagtc atattattcc   257820
taataattga gctctatggc tattgggtga ggttcctcag ggaacagcgg attctctgtt   257880
actgaaggag tttaaacagt atctataccg agagtagtca agacatgcag agatgatttc   257940
catattataa gagaagttgg attgaattaa gtctgtgatt ccctgccatt ctgagatttt   258000
aaaagtccag gcctttaatg taccaattcc ctgtcatcat tagtctaatt attggcaact   258060
acattgaatt atacagtata gtatcagttg atgaatatag tatcaattga ttggtacaac   258120
actgtatcag gttgaattta actgagttaa ggtatggccc taccttctaa gagcttacca   258180
gttgacaata aaagcacatg ggtaggcaag agacacccac attattagat ataactatgt   258240
tattcatgtt acctaaagtt ggagagtaag aagaatgaat tcttgaggt agggatgaaa    258300 gtatatcccc attccaacag tttagatcca gagaagaaaa aatgtttcag agaggagata   258360
tgattttaaa aattgcttca gaggaaaaat tcagattggt aatggcagcc tagaaagatg   258420
ctaaatgagg aattctaagt caaaggcctt gcagaaagct aggaatgaac atgtcactgg   258480
ttctcatgga aaatgcttag agtcctgcag ggaataaatt cctttttttt tcttttttctt  258540 ttattattat actttaagtt ctagggtaca tgtgcacaac gtgcaggttt gttacatatg   258600
tatacatgtg ccatgttggt gtgctgcacc cattaactcg tcatttacat taggttatct   258660
cctttttttt aaatcattat tactattgta tttatttatt tattttttat tatacttttta   258720 tgttttaggg tacatgtgca caatgtgcag gttagttaca tatgtataca tgtgccattt   258780
tggtgtgctg cacccagtaa ctcgtcaatt aacattaggt atatctccaa atgctatccc   258840 tccccctcc ccccaccca caacaggcc cggtgtgtga tgttcccatt cctgtgtcca     258900
tgtgttctca ctgttcaatt cccacctatg agtgagaaca tgcggtgttt ggttgttttt   258960
ccttgtgata gtttgctgag aatgatggtt tccagcttca tccatgtccc tacaaaggac   259020
acgaactcat cattttttatg gctgcatagt attccatggt gtatatgtgc cacattttct   259080
taatccagtc tatcattgtt ggacatttgg gttggttcca agtctttgct attacgaata   259140
gtgacgcaat aaacatacgt gtgcatgtgt ctttatagca gcatgattta taatcctttg   259200
ggtatatgat cagtagtggg atggctgggt caaatggtat ttctagttct agatccctga   259260
gaaatcgcca cactgacttc cacaatggtt gaactagttt acagtcccgc caacagtgta   259320
aaagcattcc tatttctcca catcctctcc agcacccgtt gtttcctgac ttttttaatga  259380 ttgccattct aactggtgtg acatggtatc tcattgtggt tttgatttgc atttctctgg   259440
tggccagtga tgatgagcat ttttcatgt gtctttttggc tgcataaatg tcttcttttg   259500
agaagtgtct gttcatatcc tttgcccact ttttgatggg gttgttttgt tttttcttgg    259560
aaatttgttg gagttaattg tagattctgg atgttagccc tttgtcagat gagtagattg   259620 caaaaattttt ctcccatttt gtaggttgcc tgttcactct gatggtagtt tcttttgctg   259680
tgcagaagct ctttagttta attagatccc atttgtcaat tttggctttt gttgccattg   259740
cttttggtgt tttagacatg aagtccttgc ccatgcctat gtcctgaatg gtattgccta   259800
ggttttcttc tagggttttt atggtttag gtctaacatt taagtcttta atccattttg    259860
aattaatttt tgtgtaaggt gtaaggaagt tgagactggt agaagactaa gcttcttcca   259920
gactttaatc attgttatct ggaaaggaat tgaaaatagt ttttttctga atcattgtaa    259980
tcatgtgaaa tcactaaatg tcagtgttga attgaccaca aggaccaagc taattatgga   260040
```

```
agaaataggt gggggagaca ttgaacacag caatccacag gagtttgagt aagtctggag 260100
tgttgaactg gtgaaagtcc tccctgcaac agctccatcg gggcaattct gttaagtcaa 260160
gactcaagca ctggacggtg aatggtccag aaaaactatg tcattaaaaa tgcacatttg 260220
tttaaaataa ctaactgctc tttcgtggat gattggtact aagattttat aaactgttta 260280
gggaccacca tgattcctca cacacattaa ttaattcatg agagttgatt ttcttttcaa 260340
acacattgat acattattag tagatagcac cccaacacac acacacacac acacacacac 260400
acacacacac acacacacac acacagagag agagagagag agagggtac ttacaatcaa 260460
agacagccat actagatcca attggtagca acaaagtgag aaaagtacca gaacacacag 260520
gcaaattgaa aatacacaaa gccacatcca cagcatgccc tttaatggag gaagtgggaa 260580
gaaggttcca ttttccactc tgctcatttt cttccccacc acccattaag agtgtcaatt 260640
ctcattcaca ttccttttag agaagaacga accatcgaaa agggagctga gagttgtaat 260700
aaaaatattg cattacggat ttctccagtt tcctttcagt atgaagtatt tgttacttca 260760
ttgaaaaaag tagaagtatt gatcagccgc ttagcttgtg gcttctgctc tcaaggagtc 260820
agcacatagt ctgatgtgga ggaaaatcta taaatggatt tctgcaatct gcaggtaagc 260880
atgggatgaa atgttccttg acatccaacc caggttagaa atcagttttc aagactctaa 260940
atttgaggac ccctaggagc tcaaatgata aagagaagaa ggtttatagt ccatgatggg 261000
ggagggactg cacactacct gcagggtgag cagaaaggat gcaggggctt ggtatcacag 261060
gaccagcatt gtaaatatta caggaagtaa cctttcctgt gtgtccttca tgtgcttttc 261120
tttgtgcata ttcttgaggc ttaaaggaaa gggagccagt ctgtgtccat acttctctcc 261180
cgtgcacatc atcccggcat ggcactgctg atgcaaatta aaaaaataac ctttgactag 261240
aagcattttc ccagctacca gtttccttct ccccagtgca agacaatgtg acagcaaagg 261300
ttcatgcaca gaagcagaaa ggtagtggaa tgactcagct tctaactaaa ttccttccac 261360
cttccttagc tttgtggtct caggatttta taagaggtct ctcatgtgct gctacagaac 261420
cagcaggaaa aatcagacag ggccaagaca gagagaaaag agacaccttt ctcctatatt 261480
gcccctacct agggctccta tccaaagcat gttctagttc ctagatggtt gattccaata 261540
aaataacata aaaataaact gtgcaataaa aatttaaagg gagttgcgct gaccatcatt 261600
tttgaaatat ttaaaaatga gtcctcagta aattttggtg tgaacattag tattttgtca 261660
tggatagagg cacaagaaag gagtaaatgt gagacctaca ttgcatccaa tgcctgcatc 261720
agtagaatct aatctcttcc ccccatgata aaatggcctc attctgtcaa ctacaggctt 261780
tgctagcttt ttctcagaca acagaccaaa tttatcccca gcctgataag gatctttatt 261840
gcatttgctc ccacccacc tactgtattt agggtaatgg tgaaaaatgt acattgatgc 261900
tgaattttat agaaatagta gaaatggaaa tgatcttaca gagttgtcat ctactatctg 261960
gtgtaggttt ggttacaaag ctgtatttcc tcttccaagt tttaagtaat caagtttcaa 262020
aacaatcttt cctgacatcc agtttgtgtt aaagccaatt tcccaaatga ttttcatttg 262080
cattctggaa atgcagtgaa gccttgacat tttacaaaat gacctatctt ctactcaagt 262140
caatgaaact acagtaaaca ttttatgtgt agttgcaatg cttgtatctc cctcaagatt 262200
aaacacagaa aagcatcttt ggggaggata tttaaatacg atattaaagc ataaacatg 262260
tgtctgtatt ttttcagttt taagtatact tactaataat aacaggcaaa gtggtacgag 262320
gtaaaacact acttttcatt gttcagttta cagtagtcat tgactattct acatatgcgc 262380
ttagcataat atttacagac tatgtaatac aaatcacact ctgtgaattc tcatgtcctg 262440
```

```
tgagacacag gaacagaaga gctttgtaaa aaaacagcaa agtacaactt gaaaagttaa   262500
gccatatgag taagaaatca aagtgatgaa tttactaagt gtttattaat atttaagcta   262560
agtttacaca tgactcaaca tcatattcat actcatagtc tgttactgta ctttgccaaa   262620
ctgtctgtac tattttgtga gaggatatta tctttaatat tgctctcact gcaatgaagc   262680
ataaataaag tatatgtcat gttctacctt tcaggagct ccaatgaaca catgctatgg   262740
tttttaatga ctgtaaagaa aatttcaaag ccatatctta tctgtttcta tggagaagtt   262800
gatcaatgat caataccatt tgcaaggacc ccgatgtgtg acttgtttct ctttatactg   262860
tgacatgttt ccctgaaggt ggaacgtcaa tgagacattc attttctact aaatgaaaat   262920
gatgttaaag ttgcagtcta gtgataaagt taccaagatc tgcttcttgg atttttatg   262980 gggtttgggc aacacataaa gaaactttcc tctcattcaa gttgaacata tccaaccact   263040
tatatatatg ttgcccagtg aggtcagtgt tacatgaagt tgtagaacat ttactttgaa   263100
atgaggtttt ctcatttaat aaaagtgtca ccttgtgtca gtggcttagc tagttccagc   263160
ttctatttta tctcttatcc aatgagaata tgcctatcac ataaggagtg tggctgggaa   263220
gaatggtggt ctgtccttat ctcctgggtt tctctggtttc agaacctgca cagcggacag   263280
ttccaaacac tgcattccac catcatttca tcagcattcc tcttggaata aatgtgtctt   263340
gacagtctct cttagaagtg ctttctctga agctactgag gaccatgcca tgtgtaggca   263400
taactgaagc gtgcacattc tatagagtgc ctcgaagatg tgcacattct atagagtgcc   263460
tccaaggttt tcaagaagaa tggagcccaa cttggccaca ttggttacac acttgtgcat   263520
ggtccattta ttgactatcc caccttccaa gtaatttacc tgcacccgac ttcttgtctc   263580
atgtggggcc tttagagtaa ctccaaataa gaccaggtgg atgtgcagat gaaacgtttg   263640
atgcttgcat gtgcttgcct gattatgact gttaatcacc aggtgtgtca aactactcta   263700
gatgctcatt gtgtgtgtat gacaggtttt ggtgctcttt ctgcttttga taagccattc   263760
aatttaatag ggtgttctct gaatgcccag cttttcttta aacttagcat gtatattcac   263820
taccccacga tccacctaag acagttgcgt atcatttctt tatgcctgtt ccgtgttcta   263880
tgtatattag atgatttcat atagataagg agggaaagct catatttta acattttaac   263940 tattatgatg aaaaccttat ctagaagagg ttctcttctt tttgaagttg catagcatta   264000
gtaaagctat aggagctatc tcttgtatct gactagaaac gatacacatt taagataaaa   264060
agcatgggcc aggtggtggc atatgcctgt aatcccagta cttttggagg ccaaggcagg   264120
aggatcattt gaggccagga gttcaagact agccttggacc acatagcaag ccctccctcc   264180
ccaccctgtc tctacaaaaa gtgaaaaaat tagccagtca tggtggcatg tgcctatagt   264240
cacagctgct cgagaggcta agttgggagg attgctggag tccaggagtt caaagatacg   264300
ctgagctatg atcatgccac tgcagttcag cctgggtgac agagtgagac catgtttcag   264360
aaaacaagtg agtaaaataa aataaaaagc aataacaaga ttgcattatg ctttgagggc   264420
attaattttc aaatttaact ttacttgcat tttttttcctg tcattctttc tgtgtcggct   264480
agttcttatt ttagttgtaa tcttttttta gaatacttat gaatagaata aataccactg   264540
tattcacata gtatatttac tattattttt gtctccttgc attgtatttt aattatctat   264600
gtcagacact ttcctcagtc aaatgtacta ctagccatct aaatggagaa tttatcttag   264660
gaggagaatt cttctcattt atttttgcat acccagcaaa ttattcggga gtgagtgcac   264720
tgtttcatcc tgttgatagt cttccctgaa catttataac ccacccctga ctggctccag   264780
```

```
tctttacacc ttcctcaaga cctaacttaa atacactgaa ctgcctgaag tcgtctttga 264840
attttacatc ctttctctta actctcatac actttgcatt gttttcccat acagggcat  264900 caagaaatag accatattat aatgaatgta caataaagta ctaagagtaa taaaagtaaa 264960
tatattccga agcaggaaag agcaaatgct tgggtttttt atagaaggag agaaacgata 265020
atttgagaat gtttcatgga aactcttgca tttgagcaga actttacaaa ttaggcttag 265080
gcttcaatag ttaaaaatta gtgaagagaa catctctgca aagttgaatg ttctggtctc 265140
ctttctgttt gtttagtgag cagaattgat aatcgacatg caagtggctt ttaaactttt 265200
ccaaggacca gtcattgggg aattagtgtg gttcctctga acctttctag taatcccagg 265260
atttgagtat taagaacagt tagttgtgtt agccttaaga tgaaattctc ctaccttgtt 265320
gttttgaaga tgttacttag agggaaggag atgttttggt ctgttcgggc tgctaataca 265380 tcttttttctt ctcaaatttt actttaagca gtcaggagga accaagccat tccttcaaca 265440
cttttcttag aaatagcttc agctaaatct acttttatca ctcacacgat ctgccttcca 265500
caaattacta aaacatgaac acagttcagc caagttcttt gccactttgt agcaaagatc 265560
acctttcttt cattgtgcaa tggcatattt ctcatttgcc tctgacagct cataaaaatg 265620
gagcttcctg tccatatttc tagtgtcatt ctgttcaaaa ttgcatagat tttccctaag 265680
atgattgagg ctttctgtac agctcttctc tttttttttc tgagccctcc cctcactaga 265740
atcaccttca aaggtctatt catggcaacg taggctgtgt ctagcataca cttcaaaact 265800
tttctggctt ctacttatta cccagttcca gagctgcttc tgcatttttta ggtatttgtt 265860 atcttaacac cacactctca gtaccaattt ctgtcttagt ccactcagac tgctataaca 265920
aaataccata gtctgggggt gggggtgggg ggggtaata aacaacagac atttatttct 265980
cacagttctg gaggctggaa gcccaagatc aaggcagcag aagattcagt ctctgttgac 266040
aacccacttc ctggtccaca gacagtgact tctccctgtg tcctcacatg gaaaaagggt 266100
gagggagctc tttgagatct tttcttgaag gacactaacc tcattcacga gtactccatc 266160
ctcatgatct aacaacctct taaagatgcc acctcctaat accatctcct gggggaaggg 266220
agtttaggat ttcaaggttg aattttggga gaatgccaac attcagccca taaaggaga  266280 tagtatagga aaactacaga aatcaataaa ctcttctact gttttgatta aatatagca  266340 agtgcatttt tggtgtacat atttttacttt atctttgtta ttattcatct agaaaacaaa 266400
cgtacatagt gatagttaat tcttccatga cttttttgca aaagtgttgg tatgcattgg 266460
ctataagtct cctctctgac ttcataagac cttggaaagc tgccaaatat ctcagaactt 266520
gttgtcttga gtcttaaagt gactaaaatg accttagctc tacctgcctt ataggatgct 266580
ctgcccaatg atgcatgcag tatgcatgtt ctttaacaga gtatgttttg agactgcagg 266640
tttaggcgtt attagaatcc atttgactcc atagcccttt ttatggaaac atacatacat 266700
acttaatgtc aaatagttta tatctttttta ctagctaata tggataagta ctgtctcttc 266760
ccatttgact gtgtgtaact gccttctctt agaactcaac acaaaatgag ctttatgatt 266820
cacatttaca gtaacatgga gacagaacca cctcattcaa aacaggaaaa agcaggtata 266880
agatgccatg aagggaaatg agactgaatg tgttcaattt ttctttgttt ggcttatcac 266940
atatcgtaga gagatgtcct cttacatgca gtagaaataa gaacatcctt gaaaactcgg 267000
tttgagcagt tcaaaatcat atatttttta atgttgtatg agtttcaggt gataaatcct 267060
cttcaggata cctcagggt tcgcaaaaat gtaaaaatat gtttaaagtt tgaaatgact 267120
cacatttttt agtatccacg gcaaagaact gcttttccaa ccttaatagg atttcaaatt 267180
```

```
gacattgaca ttttagtaaa tcagaattag cttttctttt ttaagctcct gtgtcttatg  267240
taaatggctg tgctgacttt tatggaattg aatattccag aaaatgtcat ggaacctaat  267300
ataaaacaag ttaacattct catttttaga tcttaagggg atatggtgtt aaaatatagc  267360
ttttgatacc catccaacct gtgcaaggtt ttctgtgtat atgcgaattt caaatttgag  267420
aacttagcat gtcgatgaag gcaaatctat atacctgttg aaaacaaaat tgaaattctg  267480
aaggaattat tgtaatttac ttaaataaga actgtaagaa gtcagactgt taatggagtg  267540
tcaatagatt tcttctgaga gcttcaaaat cttttcactg cctttattac aagtctacca  267600
aaatatctgt tagattctga aagccaatct ctcattacaa aaagcattat tcacaatttt  267660
aacttatttc cacaatgaac attctacaga attattgtat ctttgtttaa agataaaaaa  267720
ttctccctcg ggaggctgag gcaggagaat ggcgtgaacc cgggaaggcg gagcttgcag  267780
tgagccgaga tcgcgccact gcactccagc ctgggcgaca gagggagact ccgtctcaaa  267840
taaataaata aataaataaa aataaaataa agtaaataaa taagtaaatg aataaataaa  267900 ttctccccccc gaggtctgaa atttattatt aatgtgaata ttttaagcat ttttagaaga  267960
aaataatttt gtaaaaaata ttgtaagtta tggaaaatat ggtggtgaag tataacattc  268020
acgaacttgc tagaaccttg ccctaaaaat gaactaatta ttggatcata tggcaaactg  268080
attaagaaga ataaggaact actttatatc atgaaaaaat acatgactat ccacctgcct  268140
tcctaaaact tcttcctctc atgtgccgct attttactta gagttttctt tcgggttaag  268200
gaacaatatc tttagaaggc tattcattaa agtactaatt agaaaaggta gttaattaag  268260
cttgtcacac acaatttata tattttctta tgatgtgtaa gagaaaacag cataaaaaag  268320
ataaattatt tattttcagt caaaataggg cactttttt gctttcctgc agctcattat  268380
acctaaattc ctttgtgaaa gtatttaagt aagttctttg aaatattgct tttaaaatat  268440
gtttactctt taaagttta aaaataagga aatgtataat atagtgaaat ttccccatca  268500
gtgtgttctg tgtattttct ccagctcttt cttgaattac aaacagcagt tctacaactt  268560
taccacccac acacacacat ttattcattt gcacatattt ctttttagtg tttttttttt  268620
tttgcaaaat tggcatcata ttaattatac tactctgcaa cttgctttat ttactgtttt  268680
taatatggaa attgactgaa gttaatttc aagcagttgt gtaatattga ttgaacttaa  268740
ttgatatact ataactgatt aaactacctc actgttattt ggaacactta tcgacaacac  268800
tgcagtgtaa aaccctcttt ctacttttgc agctttatga taattctata aataatcaga  268860
caccgattgt gatgcaatcg tatcacaaat tcaaagacac attataatgt cagtggaata  268920
agttagacat acagtgccaa ttaactcagg gttccagggg taattctttt cgtattgatg  268980
aaacgcaaat gcatcttact cattcagagt tgccagggcc ctggtgtaga aatctaaatc  269040
ataaccaaaa caaacagcat caccacgaag aaatcaacaa aaacaatttc atgagggttt  269100
tgagtatttg aataatattt cagtaattaa attttaaagc aagaactgac aggtttgccc  269160
accccatcca tcctgtgatg tcaaatgcac ggtatgtatc tggctgacag ggaaattgag  269220
gtaggaaaat agaatagata atatgctatt atgtacctgc gcttcagttt gaggaggata  269280
aaattgtttt aaccttatgt ccacattcct ggagtggttt gctagacctg catcagaaaa  269340
tccacatctt agttcttcag ctgttcacat ctcaatccac acagccttt gtcattagca  269400 tgccagaaat gcactacatt catgaaagga attactagtt acatcatggt gaatgttagc  269460
atgaactctc attggcccat aacattaaaa tattcaaaac atacaaattg gctaaaatcg  269520
```

```
tttagagaaa atgttcacaa tggcatgatg aaggtataaa aatccagaaa tgcctatgcc   269580
tttgacctgc tccagtgccc ataacttgaa gtctctttag tcctacgctc agccatggac   269640
taaggaaaat ttctcattac ctgatgctga ctgagaaaga taaagaaaca ccacttgttt   269700
tgtccttaaa gacttgagag gcaaagagct acatgataga agttgtacct ctcacaagtt   269760
tatggaagga gacatatgaa ctgttttctg tctgctgtgg aagtcagatg aatgactgcc   269820
tatatgtgta acacatttgg gcctgagaca cacatgatga ggggaggaat tacaaactat   269880
cactggtctc cttctttttc tgcgattact gttaccttac ctaacagtag gtaactgtaa   269940
tctaaaatga acctaaaaat tgtgcatgaa caaattagct caggtagctt gcaacattga   270000
ctttacagtt tgacctaggg gagccccacg ggctgaacct aatgaaactc agccaggtta   270060
tattaaaact gcgatagcct gtatctctac attttctgca acctggtttc tacataggga   270120
aatgctgctt gtgtttgctg taggcaaatc ttaaataaac catgactcag caagaagaag   270180
agaatgatgt gcagagatat tttagggaag ggataagatg gcagttttga atgggagccc   270240
acatggtaca agtactcata ttccattacc aacttcagga gcttttact ttggaaaacc   270300 atttttcacc ttatttcagt aatatgtcaa gcatttcagg tggtctgcaa aagccacata   270360
gctcagaggc ttagcaaacc tcctcagaca tcaggcagaa acactttcta aaccccttaa   270420
tgagtgtcaa gcaggaaatt gtgagtatat agtattaagg atgggactt gctattctta   270480 aatttacaga aaaaaattct ggattttctt cctcagtctc cacttaatga cagattttt   270540 tttaacaaaa agatgcatga cagtacctat ttaaacttac tctgataaat ttgatgaaat   270600
attctttttt taatccagac atctctatga gtttcagaat tattacccct gtcaaattca   270660
tctatgcttt ttttgtggaa atgttcaact tttgttctca ctgctccctg ccttccccca   270720
tcaacaaacc ctgaatatct gggaatttct caccagctat tatttaactc cattccacat   270780
gtccatcaga tgtcctacac aagattggtt aaatagaagt ttgttcgctg ggagaagatg   270840
acaacttttt atattaaatg cataaaaatt ttctcaatac tgcagggtga taagacaaa   270900 gaaaaggcca atttaaaagg aagtctttag aaaaaataca ataaagcaga aatgcttcac   270960
tttcctacac aatagggaaa aaattttaat gcttttgcaa aaattaaact ctaatgatgg   271020 aacaaagtttt atttatact gggtaaattt atgttaggca tgaaactaca taaaaatatg   271080
tggacaacaa agagtgattc agggctgctt aatcgctgtt gctcttggtg tggttttag   271140 gggattgcat aattggtgag ttccttacac gttgatttct cagattcacc aggcaataca   271200
taccagctgt cttggtaaat gcatgaaatg ttgcaatctt tgcaagtcct gcaattttac   271260
ttcaccagta actttccctg gtcaactaac agtatctaga gatcaggcag agggtgacca   271320
atggctgctc tgacgtacac atggagatac tgaaagatgt ggagttaagg atatttgaat   271380
aaatatttca tataatgaca actgtctttg ttagcaagca gaaatatcca ctgtgatgca   271440
aaggcatatc cttatgtcat atatatttgc tgtgaaaggt actgattcgt gcttatgtga   271500
aaacctctta aatcccgaat ctggggtctc ctctccccgt tttttctgga actcagatgc   271560
taaagttgat acaggaggag tggactgtcc caaataaagc agtcgggaa aggaggatcc   271620 attgcaaata aagggtaaaa aaggtacata tgaatagtat atctatttgc acgtaatgca   271680
ggttattctg gagggtatta aatatctatc agtaactatc atttgttaaa aaccagggat   271740
tcccaaggat gttagtggat gtatgagaaa gagtttctgg agatatatgt ttgggtgtcc   271800
actacgattg ttgcatttct tttcttcttt gtctctctct gtctctgact gtctctctct   271860
ctcagtttgc ttctctttcc ctttaaacac acacaaacac acacacacac acacacagac   271920
```

```
accacacaga atattcccaa cttcttaaca cacaacacca ataaaaaatg ccaataatca  271980
gattgtaaaa ctggcagttc ttttctttca atgtggcttt ctattctatt gtctctcaca  272040
tatcaaagaa acaagaggac aacagatcag gatacatttt gtcatgttta cattatgtag  272100
taacctgaaa caaatgccca gtgagtggag ggtttcttag ctttctgtca gttttcaaat  272160
gttttccctc ctcctgcctc cctggctttg ggttggtgat gcacgtgctg gtgctcagag  272220
atgccgtgcg ccctgacaag agattttgaa ctggggcata gatgattgtc cccaaagtga  272280
tctgctcagt tcccataatt ctacacattt caggcaatgg aaacacaatg agagagatag  272340
tttgggtggt ttttggattg caaacttagg cagccacagt ttcaaccagc aatactgatt  272400
tttctcagcc tttccatttc tacccagtgc ataacttata taaattttct tccaaaactt  272460
cacaattaaa ctattcctta ttttatgaag ttatcaatgt gtgtatgtct tagaatataa  272520
ttggtgtcat acaaaccagt ttatgcctct ttaactttag tgctatgatc ttaaaaattt  272580
tgactcccag gcaaatatag atataaatat aaatatacat gcattttttt cttgagagtc  272640
aaaattatat atttatatat atgtgtgtat attatatata tgtgtgtata tacacacata  272700
tagattaaat atatatattt catattatat attacagatt aaatatatat tatctatatt  272760
taatttcatt agtcatattg ttttctacag tttgatttcc agttttgcag gactttgtat  272820
tcatattcct gatatcagga aagggtgcat attgacacta cagctcaggt ggaatattta  272880
gaagacacat ggttgtaatt agttacttgc attttttcctg aatgctttttt atggtgttga  272940
ctgtttaaga atatcttgca ttgctttcca aacaaatata ctacacaagc agcatttctt  273000
gaatctcgtt gatctgtgtg gtgtgttggt gtggtcttat acaggatttt gtcttttttt  273060
tttttttagt gtggttgttt ctccttttttt cctttaatct aacaaatatt gaagtacttt  273120
aaaattttta atactggttt ttatggagaa tgagagtttc ctatcatttt cctggggtaa  273180
tgtcatacaa tgcatttctg aaaaaaaaat acttcttaaa ttttgttaat gttctgatta  273240
tttttctgtc attattttgc cactttgtat tatgttacat tactattcca taacctcctt  273300
tgattccagc attgggaatt ggttttcatt tccatggact cattactgag gtccttgttt  273360
ctttcgagat attaaacctg accctgaatt tttttcttc cctgtgagag tggaaattat  273420
aattcttttc tactggttca ggaaaaaaag aaactttact ttctaaagaa tatatttctt  273480
tttatggtca gatacgtttt aaataaaacg aaagctttca atatctgtct gtaaaagagc  273540
agggtttgga attctcattg gtgatggata tgtttatttt cttacctgac acgtcagcta  273600
ctgcagctaa agccagtgaa ctatttctat atcacttact gatgaagaaa taagggctc  273660
tctcatgata ctaagtgtat tgctgttcca ccatccggat attttttggct taaaccctga  273720
ggtgttacca gatggtaagg attttagaaa tgctaaaatg ataatagtag ggactacttt  273780
cgatattgtg aagtcagata tatcattgca agttttaaaa aaatggaata tttatatttt  273840
ttaagtatct gatttacctt aataaacact ttcatcaatt tcaagagcat ctacatgcta  273900
cattctggtc ctgaatttc atggttaaaa taaagcccca cccagagact agctaataac  273960
tatggtgatc aacagtggac agaaattcag agatactagt tatggtaaca tcctttaatg  274020
ctggagcctt actgtcatag aaacatgtga atgtcaaact aaaagtttaa aagccagata  274080
tttcaaaaga gtgggggagtg ggagagtata aattacccccc aaggaccctg gaagtgctag  274140
attctgggca agatccagat attttgcaatt tgttttaactc ccagttgacc atctgagaaa  274200
tattgagcaa gagagacaga gagagagaga gagagagaga gagagagaca gagacagaga  274260
```

-continued

```
gagacagaga cagagacaga gacagagatt gccagggacc aagggatgat gctagtgaac 274320
catttagcta caaagtgtca atgtatgagg ctggcgtggt ggctcatccc tgtaatccca 274380
gcacttttgg gaggtcgagg caggaggatt acttgagccc aggactttga gaccagcctg 274440
ggcaacatag tgagacctca tctcttaaaa aaaaaaaaaa aaaaaaaaaa agttagccaa 274500
gcatgctggt gcctgcctgt agtcccagct acttgagagg ctgaggctgg aggatcattg 274560
agtcctgcag ttgaggctg aaatgagctg tgattgcacc actgcactcc agcctgggtg 274620
acagaacaag accctgtctc taaataaata aataagtact atgtatatgc tgactctcca 274680
gccttgccta gtccccagaa gccttgcaac cttccaaaac ttgattgttt ttctcctaaa 274740
tttctcagat aattgagggg aaaatagagc tcagaatttg acaacagctg tccacatctc 274800
ctggaatccc tggcagaatg ctggtgctgt ctcttctctg ggtttcacag ggcgggcata 274860
aattataact ttattaggtt gagcacatat ggcctttagc cccaggagac cctccatggg 274920
gctagtctgt tggcagaggc agcttctgca ctttcattca aattcacaat ccataaggaa 274980
aaagaggcct tcaaggctgc agcctgcctt gggcttccgt ggggcatctc ctatcattgc 275040
caataatgct gtggtgaaac ccaggccaaa tattccaaca tcttttttgct gcttgtatga 275100 acacgatgca tattgcagtt caaaactagg aaaaagaag agcatattac aggcgaacac 275160
gaatgcatca gaatatggta cctttaaatt aaaagagaag gctcttgatt ttgaattctc 275220
aagtgtttct cttcaaatac acacaatgat gtctttcact ttaattttaa ctattatgga 275280
tacataatag atgtatatat gtatggggca catgcagtgt tttcctacag gcatacaatg 275340
tgtaataatc aagttagggt aattgggca ttcatcacct caagtattta tcccttctct 275400
gtgttaagaa cattccaaat ccactcttta gttattttaa aatatacaac agattatttt 275460
tgactatagt cactctggtg tgctatcaaa tagtagattt ttttttcgag gcagggtctt 275520
gctttgttac ccaggctgga gtgcagtttt gtgatgatag ctcactgccg cctcaatctc 275580
ctgggctcaa gcaatcctcc cacctcagcc tcctgagtag ctgaggccac aggcacatgc 275640
taccacagct ggctaattat tatttttta attttgtgta gattaggtct cactgtgttg 275700
cccaggctgg tctcaaactc ccgagctcaa atgatccccc tgccttgtcc tcccacagtg 275760
caacgattac aggtgtgaac ctgtgcccgg ctgataggaa ttttttgatgg agtttcccaa 275820 tatctgggct ttcaaagatt ttggatagtg aacgagatac tgcaaagatc tctctaaata 275880
tcaccagcct gaccagggac cttgtgttac ctatatgaat acactgaggt tgctgtctgt 275940
ttctctgtta atgtataagc agagaaagtt acattgatgc tcatcagatt ttcagtttaa 276000
tatcagagca ttgcaaatta aaatataagg tgcgggacat gtacaatttt actgcggggc 276060
atgcaaaacc tgagggcccc caaagcagaa gaaggcattc ggcctctagt ctgcatttcc 276120
tccctcctga gttgccagcc agccagccag cctgtcttac agattccaga cttgccagct 276180
cccacattgc atgagccaat tccttaaaat agatcaattt aataaattta acctatattg 276240
gtgaacaaat ttagcagaga actttgatat acattagtac cacttattat ttttagaaaa 276300
attggaattc gaataactaa cactaaagtc taattcgtca tctggtgtgt atgttataaa 276360
tgcacaccca ctcaccgaga cctattcaca gccacagcct catataaaaa taggcaatag 276420
atacaggaaa tgagaagcag ccatagaggg tcttacgtaa gaaaccccat ccttctcaca 276480
cctactcaag aacgttgttc ccaacatcta catcttttgt agtttatatc cactgggcgc 276540
acctaacatc acatccacat tcttttgttt atccgtttg gaaatacgtg cctgaccttc 276600
actttctctg cctgatgtgg ctgcatgttt ttgtttctct ggcaaccatc tcctcgtctt 276660
```

```
ccaagagtcc tcaccgatca catctcaact cctctccacc tatcctttct taaattcact 276720
ccaatcagta tatagcctca ccacttcacc agactcctct tgccaattat accattgcat 276780
cctaggcccc acaaaagtgg agttgctatt cctaatgttt ctaaaaaatg gccattctgc 276840
attttccctc gaatctccac tgcctctatt tttggaaaag agtttcatct ttgaaaaagc 276900
atttaagacc aactttttc ccactctgga gggaaatgaa atattgctga atgcagagga 276960
tatctccaag gcttcatact acttgctctg gcaatatttc cagatcctta tcctgcagca 277020
tttgcggtag ttgtccccct agaaatcata gttgaaacct actcctcaac tgtgtaggta 277080
tttggaagtg gggctttgga aggtatttgg agagtggagc ctcatgagtg gaattcctac 277140
cattataaaa gggacccccag agggcaccct cgtcccttttt atcatgtgag gacacagcaa 277200
gaaggcgctg tctatgaccc agaaagtggg tcctcaccag ccactgaatc tgccatgcct 277260
tgatcttgga cttccggtct ccagaactgt gagcaatttt ttttacaagc cgtggggtct 277320
gcagtctttt gttttagcag ccaaaagagg taagataggg catgttggga aggaatggag 277380
atgtccacaa acaccctgaa tcatatactg ctccccaacc ccccgtcctc ccagcagaga 277440
gagcaggaaa gagaaggctt acttcctcca ggttcgatgc tcttctacac acagttatga 277500
cagacagatt gccttatatt tttattcttt ttagttcatc tgaccaattg tcaaattgct 277560
caaatgtcag aaaaatggct caagggccg ctatggattt ctgcagtaga aaagaaaag 277620
acagaagact agatcccaat gtgttcctgg actggaagaa agttcttatt ttatggagcc 277680
ataaataaat atgacatttc ttgtgcctga gaatttgagg caggtagtac tcctgtgaag 277740
taagataatg tcttctgtaa aagaataaat tcattaaaaa ccatgggaat cattgtaagt 277800
ttcattgtca agaaagaaac agacatgatt ttggatgtag gtgaatgtta attattgaag 277860
atgattattg ttctcagaac aagtttattc tgattcgtag ccacagcagt tcaagagaaa 277920
agcaataaag gaaccacaac catatgaccc ttcttataat catgttgtgg tggggatgtt 277980
tcttctccgt cctacttcct gagaatgaca gaagggtttt gcaagagtga aggcagctgg 278040
gaatatattc cagccgcttc catagttcat gctgtggtaa ggagtttcaa ggtcacagtg 278100
aggcaaggag tttcaaggtc acagtgattg aacactagaa cttgtgcctc tgttctctgc 278160
tgaacgtctt ccatgactgc tacatcaggg cttggggttc ccactgacgt ggtgtttaag 278220
taacatttag agtccttatg gttatacact ttcatctcct tgtacagaaa gtttctggaa 278280
actgcccact attatatgac acatattaac ctgttgaatt tggttattta tgtgaggaaa 278340
ccacagaaaa ccataacaaa tcaaaatacc taagagccac aaatttcctc cagtgcagcc 278400
acatcccata gacaggtaat gtgcactaca tgtgtaattt taagttttct agtagttgca 278460
ttcaagagtg cccgaagaaa ccattgatac caattttaaa aatacattta atgtatccca 278520
atatttataa agtactaagt cagcagacaa tagagacaaa atatagtttg catattttt 278580
actacatatt tgatattcag agtacatttt acacttacaa cacatctcgg tttgaacaag 278640
ccacatttta tgtgctcaat agccacatgt ggttattggc tagcattttg gaaaacacag 278700
tgctagaaaa tgcattcttc ctgccatgat caaccattgt ctctcactta ctcctgggca 278760
actgtgttct aattgatttc cgggcattga ttattgcctt tcaggagaa caactgatca 278820
ccgtattata gtaggtcatt cctacacatg gccttcaggt cccaaacccg tctgatttgc 278880
taagccgttt ttccctcttg tcatgccatc ttccctttcat ttgctacatt ccaggttttc 278940
tagtctaatg cagtcactcc aggcactctg tacttgtact cagcatttac tgggtggtgt 279000
```

```
atatctgtcg taggctgttg gttgtaagtt tcatgacagc atacactatg cctccctttt  279060
tccacatgca ccaatccatc aaacctcatt gaggacataa aacacagcat ataaagcact  279120
ccatcgattg aattgaatta atgtgtgaac aattgcacct gcaagtgtaa ctgagggctc  279180
acgtggttgt catgtatcat ttttaaaatg tttaaataat gcgagttttc atctatattc  279240
ttattacttc tgtagaaatt aatctataat atttcaacag taacatggtt gaaattgagg  279300
ccttatgtaa tgtttgaaca caaatgataa cttgattctg aatcaacact gtatgtgcga  279360
tttgatgtct gatgtatgat ttggggcagt ttgagggtca gtcatttatt tgtactgagc  279420
ctctcaaatt ccctgtatgt gaagggaaca gttgagaata agtgtcttca gtggataaga  279480
cagtcgtctt tatccctgga aggcatcacc aactgatcac agcagtctgt ttttctgagt  279540
caagaggcaa cttcccctct atgtaggata ctacttttag tgtagtgtgc tcttccatat  279600
ctattggaat cattcaccct gatcaatcag gtttaagata aagggtgtga tagatagaaa  279660
tggatgcaga tgctcttgca aattgagttg aaccctttgt ctttgcatct tgtgctggcc  279720
tcagtgactg tcttcttgaa tagaatgttc tgggagtaaa gcactgggac ttccagggct  279780
ggatcataag aagctattaa gcttccattt agggcacttg gagtactgac cctcagggca  279840
ttctctcttg gaaccacat ctcatgttgc aaagtgttca agcccatgg agaggctatg  279900 catggtgctc cagtcagtag ctttagcttc actcccggtt gacaaccatt agtaccgcca  279960
tgtgagtcac ccattgtgga catcccagct gattgaggac tcctgtctct tcctatccct  280020
tagctgacta aggagatctc aagagagaac ttctcagcta agcccagtca gctcacagaa  280080
tcatgggaga tcctcataaa aggttgtttg aagccccaca ttatgggcat gtttgttaca  280140
caacattagc taaccagagc aggcactgaa actggaagtg aggttctgtt tcaacagaaa  280200
cctaaagtac atggtgttgg tgttggaccc tccatagggc aagactaaag gcttgaagaa  280260
caagggaaga aaattggagg ctggggaaat ggaatggaca agagaactc tttgaatgac  280320 tcactcacag ccttcagga cgagaagtaa cttttagcac tgtgcaactg caagcaaact  280380
ggattttgtc cttttaaaata gaaagatggc atctcaaaga acacatttgt catgagtagt  280440
tcctaataag cataatactt aacataaagt tcactggcgt atgttattta taatcttact  280500
atagtataat ttccattgga tagcaaaagg tcaaggatat aattacagaa atatattctt  280560
ttaaaatttc ttttggttac acttaaatgt aaattgtgaa caccattta ttttctattg  280620 tatcccatga ctttctatt gtttgggtca tattaaatct attttttacag tataaatttt  280680 gcagcatata ttcccacagg aaagaacaaa ttataaaaca cacagtttgt atatgtcttt  280740
cctttaaaag tgaaatttta actagttttt cttttttttc tgttactatg tctttccatt  280800
ctttggttca atacattccc acctactctt gaacgttttt tggaaagttg gcaatgaccc  280860
tttaaattct tttcagtctc tatctgccta acatatattt aggttccgta tatatttata  280920
tcatttccta cttaaataca catatttcca tttttgtgct catgctattc tgcaaatgcc  280980
tgcattttaa ggatgagaca tacatttaaa aagggcatct atgccttctt tcagaatttt  281040
ttttctaaat atctattact ttgatatttg aaattttgta cccacaaaca tacacataca  281100
cccatgtgtg cataatatac atctcacaga aatgccagcc atgtcgggaa aatgacagct  281160
ccatcagaaa tgtcttttaca tccacgtaat atatcttatt tccttgtata aggcacagat  281220
cctctgttac caatatcaac ttatccccag gctctaaatc acttgaagct acttttgatt  281280
ctctggagaa tttcagaata tattttttc ctcaaaattt catgaacttg tatgcatttt  281340
gtgcctcaga cttgaacgc cttggacaaa ttcctttatc cctgtgaatt tttaacgaat  281400
```

```
tctaaacaaa ataccIgact ccactttccc cccaaatttc ctgaccttgc gtgcattttg  281460
aactgcagac ttgaaaacac ttgtgcaaac gttccttcat ccctatgaat ctttaatcct  281520
aaacaaaatg cctgtatcaa tgctggcaag gttgtggaga aaagggaatc cttatacact  281580
attggtggaa gtgtaaattg gttcagccat tgtggaaagc agtgtggcca ttccgtaaaa  281640
agctaaaagc agaactacca ttagacccag caatcccatc cattactggg tatatactca  281700
aaggattata agttgttcca tcataaagac acatgcgcac atatgttcat tgtagcacta  281760
ttcacaatag caaagacaca gagtcaactt aaatgtccct cagtggtaga ctggataaag  281820
aaaatgtggt acatatacag aatggaaaac tatgcagcca taaaaagag caagatcatg   281880
tcttttgcag gaacatgaat agagctggag gccattatgc ttaaccaact atgtcggtaa  281940
cagagaatca aatactgcat gttctcactt ataagtggga gctaaagatg agaacacatg  282000
atcacatagt agggaacaac agacactggg gcctgctgga gggtggaggg taggagaggg  282060
agaggatcag gaaaaataac tattgagtac ttggcttagt acctgggtca tgaaataatc  282120
tgtacaacaa acccccatga cactagttta cctgcataac aaacctgcac atgcacccct  282180
gaacctaaaa taaagttttt aaagaatgcc agtatccact acatttatgg gcggtctttc  282240
tgagtttcac ctcagagaaa cactcctaaa attcaagtta tgactattta gactatttgt  282300
taatgatagc tctgtgtgtg tgtcttagcc ccctctctgt ttcctatgtg ttctacttga  282360
ttttTaaata aactatagga gctccacata ctaatttgat tctctacata aaatggtgcc  282420
atattctctt attttTccTt taggatttgt acagagactg tacaaaaTaT tttttgagtT  282480
gtgtaatggt atccaatatg gacaataaat gataagtaaa ttttggaaaa atcagttaaa  282540
agaagtgtaa tagatacata ggtgtcttaa ttgttttccg tcctcaagta tggacgtttt  282600
tgcaaagaca cgagcttttt acttcaggag acatttgtcg acgtctggaa aaaattttgg  282660
ttgccacagc tagatcatgg gggtgggtat cacttgcatc tagaggacag aggccaggga  282720
tgctttTaag ggacccacaa ggcacagaac agccccccat gacaaagagt cttTcatcta  282780
catgtgtcaa tatcgatgag attgagcaac ccaggtatag agtaatactg atgagcacaa  282840
agtatagctt gaagcctctt tTtccatatg gctgtgatag attgttttaa atgatcattg  282900
gaagaaataa acccttggtt ctatggaagt catgaggaat attctgccca tgtgcttgtg  282960
aaacctcagc ttggagcaaa gaggcgaata tcatgcaagt ggcttcctag aatcatgggg  283020
tttTgtacag attatttcat catccaggta ttgagccaag tacgcattag ttattttttt  283080
gatcctctcc ctaccccac ccttcaccct caagtaggcc ccagtgtgtg ttgttccct  283140
ctatgtgtgc atgtgttctc atactttagc ttccgtttat aagagaggac acgcagtatt  283200
tggttttctg agctggaggc cattatcctt agaatcttct atgttaaaaa caacagagca  283260
cctcctggct ttcctgggaa tccttgtttc ctgattccag acaagcgcca tggctgtgaa  283320
atcatgtatt tatgtgtatg ctgttggatt ttaatgtgaa atacctttc actgcgccaa  283380
gttcgcttcc aaatgtgatc ccgccaggct gaccaacaag gcattcagtc agcctacttt  283440
cttatgccgg gaccttTcac aaaatgaatc atatgtcact tttctttTca gaagcatatg  283500
ccattttatt ttattctggg agtttgaatc acaccatgca tctgttttag tgttgtTttt  283560
agtaagttca ctatcagtgc ttcctgagca tggtttctcg tatgggtac tcactgacct  283620
gtcccatcca tctttTcttc ctataaagcc tttactgcta tacttgtcta cttgcagaac  283680
ctccacactt tTTatgagct cccatttTTc tctcttcttg gtatttatca ttacttattg  283740
```

```
tgactcttgc atattggatg gtcaaaagag atccccagtg gttacactac aacaagataa   283800
atgtaggtat acttttctta attgttatta gtgttactta ttattttgtt ttattagaca   283860
ctactttcaa aggctttaca gcactgggta tgtgttctac cttttctttt cattttatcc   283920
tccacaacag ttctgtgatg aaagtactat tattaacttc atagtttaca cgacaaagca   283980
tggtttcata acttgtcagg atttcttagc cattatttga taaaattagg gatctaaatt   284040
ctgtcttcta gctccaaaca gatggttctt tccatgctat ttgctattat cttgtcaaaa   284100
gtaatgacaa aatagaactc aaatagtatt tttcttttgg ctgatttctt ctttcagacc   284160
agagaggttt ccaaggttaa agtagttcat taatttcaat ttcttcttct ttttttttt    284220
tttttttttt ttgagacaga gtcttctggt tcttttgccc aggttgaagc acagtgacac   284280
catcatagca cactgcagcc ttggcctcct aggctcaagc agtcctcctc tcttggcctc   284340
ccaaagtgct ggaatacagg ggtatgccac catgtcaggc tacttttat ttttattttt    284400
ttaagagaca gtcttgatct gttgcccatg ctggtctcga actcctgggc ttgaacattc   284460
ctccctcctt gacttcccaa agtgctgaga ttacagacat gggccaccat gcctggcctt   284520
aatttgggta tcttctaatt gatgtggact cttatgccct attcatttgt gttttgaagt   284580
gaactgactc tgaatgtcag tgatagggca ctgcttagtg ttggggtgg ttaggaagat     284640
atgcaagttt cttagagaat aaagcagctt gctgttcaca gcagaggggg tgtaactgtt   284700
tcaagaattt tagaatacta ctgtctgtga gttctgcaag aagttaggga agcctccac    284760
tcctggttag actggcagca acttttttgca ttataacaca acagacattt catgtccaag  284820
ccaggtaatc tgagctaccc ttgttcattc cagatccagg gttggtgagg caaaagggt    284880
gtccccaaaa tagatgggtc tctttattga acttctgggt tatctccatc atgtacagag   284940
atacagaatc atgcatttat aaactttatg gttgaagatg gcacccacag ttacagtttc   285000
ctcccaaacc tccctggcct atctcagttc ttaaagatgt ctggggattc ccagttaggc   285060
atagagtaac aaggcagctc tatccttaaa tgatcatggc aagctgccat atggctggta   285120
ttcatcctca gttaatgtgg atattctagt aggagggcac agtgacatag gaagaaatgg   285180
tcactctgtg ttcaaattat tccttttaact tagaaggcaa gtttaccacc ctgtgggtac   285240
tgagcattgc agacttcatg taagcatatt tttgagcatt ttctacaaac cctcatttct   285300
ccaaatccca tcctttgcaa cctcaagttt atccagggga ttcacactgc ctgcatgtcc   285360
ttgtatgcgt ttcttattgt tcctgtaaca aattatccaa cctgtagtgg cttaaaacac   285420
acgcatttgt tatctcacca ttctgaagct ctgaagtgtg agtagctcgg atggtttctc   285480
ttcatcatca cccaagggtg atttctgtgt gttggcagaa aggctgtgtt tcttcctcca   285540
gactccaggg atgcatccac ttccaggaac atttgggttg atggctacat ccagttccat   285600
ggggttgagg ttcctgcttc cttgcaggct attggctgag ggcaaatttt ggcttcttga   285660
gaaccgtagc attccttgac tcctggcctc cttcctcccc cttcaaagcc agcagtggca   285720
gcttctaatg cactgaatct ctccgacttc cttttctacc tcttgtctcc tttcccaagt   285780
tgcatggctt gtctggactg attgttccat taccattttc ctgcttctca gtatcatgga   285840
cccacttgga tattctagga taatcagctt atccttgacat cagctgccta gtaacctaa   285900
ttatatctgc aaagacaatt cacaacagta cctagattca tgtttgattt aataaccagg   285960
ggaacgagaa tctggggtgg atgactttat aattctgctt accacattcc tgtctataaa   286020
ctaatcttaa ggttggtgga caggccccctt acaactgact ttgagtaccc agaacactgg  286080
cttcctatct ttactcaacc agtgggctcc tccaggaaaa gcccaatcaa ggaagataac   286140
```

```
gccattattc tcatgctttt cctttcccct tccctcccct tctctcccct ccctcttct    286200
ccctttcct ttccttctct ttcattttga cacagagtct ttctctgtct cccaggcagg    286260
agtgcagtgg catgatctcg gcccaatgca acctctgcct cagcttccg agtagctgag    286320
actacaggac catgccacca caccacctaa tttttctatt tttagtagag acgaggtttc    286380
gccatgttgg ccaggctggt ctaacctcag gtgatccacc tgcctcagcc tcccaaagtg    286440
ctgggattcc aggcatgaat caccatgccc agcatgtcat gcccttttcga agtctgggta    286500
ataatcctca gatggtagtg cacatagtta tggagaatta gtgaaccact cctccctgat    286560
gtggctcgcc cccactgcaa ataatttgtc tattttatt tttattttta tttatttatt    286620
cttttttgag acagggtctt actctgtcgc ccagtcttga atgcagtggt gcaatcatag    286680
cccactgcag cctctacctc caggctcac gtgatcctcc cacctcagcc tcccgagtag    286740
ctgggactac aggtgcatgt cacctcgcat gactaatttt taaattttt gttgacgcag    286800
gatgttgtta tgctgcccag gctggtctta aactttagg ctcaagcagt tctcccacct    286860
aagcctccca agtgctgaa attaacaggt gtgagccacc cagcctggcc tatttgtcct    286920
ttttaattta aaagactcaa catgtagaaa ccattttacc ccttcacctt gtgcattaag    286980
agcttccttt ttcttaacat cctgctcctt gaaatcaacc cactctactt gtatggcagt    287040
tgttatttta atatttctaa ttaagataca gttttcattt taccttacag agacagtgag    287100
cgggtgctct tgaattccag tctggctttc tccattcctt tgggtaatca caggttaact    287160
tttttccttc atcagttttc agcagtcagt gaaaggtgca ttcattttca taaatcagcc    287220
atttggcaac atttgaatgt ttaatcagtt tgcgatcaca tcaaagaaca agggaagttc    287280
ttgggagatt tattacctcc tttggaatct gtgttcttag ctacaaaggt gcaatgactt    287340
tttctagttc tctgccccag atgtctgaac tgttaatatt tacagtgctc ctttcctgaa    287400
attcagagtc agcacctcat tttatcctat ttgtatccca acttacttta ttcaaagaga    287460
ttttacaacc tgagatagct ccgtaggaag agttcagttg tcagaagcaa tctgatccat    287520
ggaaattttc tggtgtttgt ttttccttga attaatttgc aggtttaaat tcttgcttag    287580
gccactctag gactttaat tgctatttct taggaaatat tccttagaac atgaagcagt    287640
ctgtctttca acacacacac acacacacac acacacacac acacacacac acacacacac    287700
accccctagc atacgatcca gaacaacgtt ttatctttt ttttttttt tgtaggaggg    287760
agtgtctcac tctgtcaccc acgctggagt gcagtggtgc cctcatagct cactgcagcc    287820
tcgacctcct gaacccaagt gatcctccag cctcagcttc ccaagtagct gggactagag    287880
gcacacacca tcacacccag ctaatttaat tttgaaaaaa cttttttttt tgtggagaca    287940
aggtctccat gttgctttgg ttggtcttga attcctgggc tcaagtgatt cttctgcttc    288000
agcctcccaa agtgctgaga tttctggcgt gagccaccac acccagccct aacatttat    288060
tcttttactg actgtgagat tttcattgac ttacgctatg tcaggcagac ttttcaagcc    288120
ataacctggc tttggtgatt tattattta gctcttcatg ttttaacagc ttctctgcta    288180
ccatgatagg ttataataag tgatagaaga aaggcatttt aaagtaattt atgaatgtgg    288240
atctcatttt gcttagctaa aaaaaaaaa gttttttttt tttctagaga atagaaccaa    288300
acagtgttca ctgtatcaca tattccttt agtgtattga gcattaatgg ggtatttttg    288360
cagcatcaga tcttcacaag gctggggttc atcagcagca cagtagctat taggtgattt    288420
tactcaaggc agcaaaattc gtttcttata acacagtctc tattgaagac acactctaag    288480
```

```
gcagtttgcc tcatctattt agcttttccaa aattctctct taaattgcag tttaatgaat   288540
agactaaaac acaaatttta agaaaaatgt agttataaga tatgaagtgt cttttaaatc   288600
tgccagtggt ttaagggata gtatacattt aaaataaagt tataggcact gatttagtcc   288660
tggaaaataa tggctttatt tcaataagcc agtatcagaa attagttttt gttttctttt   288720
ttttttccg tgatgaaatg tggtttctag tactggataa gaaatgcatg agaaataatg   288780
tatcccagca tatttaatat gcaacagtgt gatctcagta gccttgcaga tggctgagct   288840
gaggcactaa aagtgatgag atgacatttt gtattttttcc acacgttctt gcccattctc   288900
aggtgagtct gggctctcat cagtatttaa atgctgtttt accttggcaa gacatttagg   288960
tccagaaaat agtttaaaaa attaacatct acgcagaaag aacctccagg tagttaaaaa   289020
tagggcaatt gcggataca ccacatcctg aagacttagt gttgctaagt aaaccacatt   289080
attttaggtg tttcttcctg acattttat tttttcttg tgttattta attctggaac      289140
ataactggga actgagaata ctacatggga cccttatctc ttttctttgt tatgactgaa   289200
aatcataatt tgaaagatgc ttggaaaagg gaaagcttaa tatcttacac atattttat    289260
aagacaaaaa tatggaaaga tatgaaccat aaaatcagtt tagaatggga agggttagta   289320
aaacattttt tttgagcaga aaaggaatca tggaatggac actttataat atagtaattc   289380
agccaattta tttgatggaa ttcaaatgtc atgtcctctt tgtagctaag agtgcacatt   289440
agcattaacc ctaaaccaga ccacttggag ccaaagagat gtgtatgtgt gtgtgtgcat   289500
ctgcttctgt gtgtgtgtgt ttgccccatc tgagtgattt gattttttcac catctctcta  289560
tttttccact tccaaaattt aagcatttag acatttatta tattaaatat gtttgcattc   289620
tccctccctc cacatgcagt gttttacaaa tttcctatca gactgttccc atcctgcaaa   289680
ccccccagagc tctatggctg aggtactcct cttctgttc ccttctccat gcagatggaa   289740
tgtctgctgg gaactatctt caatctatat gtttcccatt cgtagaggtg gctaaatctg   289800
tgacatgcat ccatcctcat ccaatagtgt ctccacatga gtgagctgga taatgcaaaa   289860
ccaagcttcg acatcagtgg tatgaagtac acacacacac acacacacac acacacgcac   289920
acacacaaat acaaacacac ataatctctg tagctcagat tgggattgtc tagggttaat   289980
atcttttgtg ctaaaaatat ccctgtgcca cattgaagct tattataata attattaatt   290040
actgatatat ttcaactgtt atgtctccta aaaatatgca tagattatta agttttccct   290100
tctccttgtg tttttctgat tatgattttc tatcataaag gtgaaagtga taagggtccc   290160
atgtagtgtt ctaactctaa acctaatact gaccctaaac agaattgaac gctttaaact   290220
aacccatggc ctttgaccat tgcttcttga ccgttgagtt aacccataac cctgaacaga   290280
gaatgagaaa ttgaacccaa atttgaaccc aaacccctaac tagtgactgg atatgaaacc   290340
taatcctacc caactttgaa aaagaactca attctaaact caaaagcaaa gccaaccgaa   290400
cacctaatct aactttaatg taaacctttg aacttaccct taacttttgc cagtagccct   290460
tgactcttga cccctgatct gaacactgaa ggcatccccc aaattctccg acccatggcc   290520
tttgatccta atcttgactt ttgatcactg tccctaataa tgaatataat cccttgatca   290580
taacattgaa ctttgctcct accctgacat tcaattagtg atctaaccat accacaaacct  290640
gaacttgaac ccaaatccta acatgaacct tcctccatac ctgaaagcta tcctaaccct   290700
tgacctttga tctttatttt tctccttgac tcctgactgt gagatcccag cctggactaa   290760
aatgtatca cacactcaaa atcttttttg ttctgaatcg ttacccaaac ctgaacttga    290820
acccaaaccc tgaccctacc caattacaaa tctgaataca aaacctatcc ctattctaaa   290880
```

```
gttggggatt tgagtctctt agtcccgtag ggtagatgtg gtgtttgcag ccctgcagcc   290940
actatggaca ccacagactt ggacaaaatc tccaacgtat ttttgggaaa aaaggatgca   291000
accattagag aacaagatgt tgaaacttc atccataatc tctgtttgta cagacttcag   291060
```
(corrected line 3 kept as OCR'd)

```
gttggggatt tgagtctctt agtcccgtag ggtagatgtg gtgtttgcag ccctgcagcc   290940
actatggaca ccacagactt ggacaaaatc tccaacgtat ttttgggaaa aaaggatgca   291000
accattagag aacaagatgt tgaaactttc atccataatc tctgtttgta cagacttcag   291060
ggtgaaatac atgtggttgg aattgtgata tttccagcca caaaattgta ttatgttgag   291120
ataatgtggg tttccctatc cctgaaaatg tgttcatcca accaatagtt acttgtacca   291180
gcagtgcacc agggaccatt tgggttcct ggaggcagcc gtaagcaaaa gcatcccaga   291240
tccctgcttc tggaatccct gactatggaa ttggcatcct cataatgaat gtaataaaga   291300
aataaggtaa ataaagaaat aatctagact caaatgtgaa ctttagtcgc tctggaagtc   291360
caaaccctgt ccaaacatgt ccgccgatta cttcagagg atgggtgatg actcaggtta   291420
atatggttat ttttggagcc cgtcttacct attgtccttt atagatgatg tgttttccac   291480
ctcagatatc aacatgaaag actgggtcac ttctcaattc agaaatccac tcaaggttag   291540
gcactttggg aggtcgaagt gggaggatcg cttgagccca ggtgttcaag accagcctgg   291600
ccaaatggtt aaatcctgtc tctacaaaaa atagaaaaaa attagctggg tgtggtacca   291660
cctgcctgta gtcctggctg cttgggaggc tgaggctgga ggatacctga tcccaggagt   291720
ttgaggctgc agtgagctgt gatcatgcca ctacactcca gcctgggcaa cagagtgaga   291780
ccctgcttaa aaaaaaatt cattcaacta tgtgtaagag agagagagag gtgtttatta   291840
gatttaactg aggatttggg gagaaacttg ggggcatttt atcctatggg ataagaggga   291900
aaaataaacc ttttaaatta aacatctcgc ccttttgctg actacctttt ggctatccta   291960
acatgaaata ttcttctgga tgctacaact ctcagctcca ctgatcggct agagcagatt   292020
caccatcact tcttgttttt ggatttcacc ctctgccact cgtgatttaa caaataattc   292080
tctgaaaggc agttctcttt tgaaaagag ttttgcttct ctgtgttaaa ataatgtgtg   292140
ctgctgttaa aatagttttg tatacacgag ggaactcctt tagaagcttt atcacgtctc   292200
ttagctgtgc gtgcaatttg agtaattact atgtaccaat tccagtaaca tagccaatac   292260
atcagaactc tcaggggacg tagctgggaa cttcttgca aaacaactcc cacgtgttca   292320
ttcctgtctg gaaccacca gtaaaattta taatcagtaa taatttctcc aggcacagca   292380
actgagaatg gtagaacatt agttttaaaa accattttaa taaatgcct ttataaatat   292440
tgagacttaa ttatttagat taatttgttc cagttaatga aagatctctt agcacaagac   292500
tgggaaaaat tagaacacgt ataattttct tcattccaga taaacaatta ttttaatgtt   292560
tatctggtat ttgaccacaa acttaaattc ctgggtttcg taggattaga aatttaagg   292620
ttagtaatca ctcccgttgt taaactgctg gattttacct aaaattactg caaggatgta   292680
tcatttttt atacctcaag ctgttttgtg cagttctgct tccaacttcc atagacaatt   292740
ttaatcattt attttgttt tttcttatca gataatgttt cataacatgg atgtgaagaa   292800
ttaaatgaac atccttctgt gcacaaatta agattagaac acgaagattt tgggattccc   292860
ctcagttcct tttataaatt gtatttcttt ggacctgtcc taaggataac cacttttgtg   292920
aatctgattc attatttcct tcttttatta agtttatttt ctgcaaaatt gtcatgacca   292980
gcataaccca agaatatat tgttcgctct gcttttgatc ttttataaat aggatcatcc   293040
tatgttcttc ttgacctggc atttcccttt tcattgaata gtatgttttt gattttaacc   293100
atgaagatgc ttggagctgt agtttatttg tgttcactga tatatggaac ctcacccgat   293160
ggttatacca caagatattt aactctttca gaagctggaa atttgaattg gccttatgta   293220
```

```
aagagttcag ctattaggat tctgtgcgtg tctcttgttg aaaaaaaatg cagaagtttc 293280
tccaactaga aatgtattta ctggaccata ttttatgtgc atatttggat atacactctc 293340
aggttaaaaa ctgtttaagt ggttggacag ttttattcac ccaagaacag tatcagagtt 293400
ccctgtcctc tctgcattca ctgcactgaa tccaaaattg aatagaaatg aaattagctg 293460
tctttgattt gttctctctt tagacaaaag gcttccaatg ttgtatcatt atgtataatg 293520
tttgaagtaa gatataaata aactaccatt tcagataaa gaaatgttta ttctttcct 293580 taatttgata acatacaatc ataaattggt tcaaggcatt tttctttatc ttgtaagatt 293640
atccttgctt tgcatttaat tttttcatgt agcaaattaa ataacttaac tttcaaatgt 293700
taaacttagc ttgatattca gtatcttctt taatactgtt tttgtatttg ttgttagata 293760
ttaatcattt ttttctatct ctgtacaaaa caagatagac tataattttt ctttgttgag 293820
cttccctggt tttagcatcg actaatagta gctgtgtaga aagagtaaga gaacatttgt 293880
ttatgctttc tgggagagtt catataaaaa cacaaattat tcattcatta ataggtggta 293940
gacttgccat tcagtccacc ttggacagat tatttctttg ttgtacttaa aaccatcatt 294000
tatttcctcc ttgatttgtg gactacatta catattgact tcttgtatat atgaagaaaa 294060
acatgtttgt atgtctgcac atgtctgtta tcactctatt atgttccctt tctgcatttg 294120
tctgtctgct atatacattt tgctaaactg tcataacaaa ttatgagaaa tttagcagca 294180
taaacgaata gccatttatt acatcaggga tctgtaggtc agaaatcctg gtgcagtgga 294240
gcctagcttg gtcctcttct tagggtctcc catggctgaa atcaagagat tggcagggct 294300
gcattccttt ctgggtgctg tagggatgaa tatatcacaa catatagatt tttaaaatct 294360
aattatttgc actaacttct gattttacca cattagattc ataggtgaa ttcctgtcat 294420 attgatcatt cgagtcttat ggaagctttc tttctatctt acaacatcgt cagattgtta 294480
caggttttca tatgtattta ttcttatgct ttaaacaagg ggttttctct gttttatgta 294540
aagtttgacc taatattttc atcatatctg tgttatactt gagatgtata ttgtgaatat 294600
ataagcacac acaatgaact attcttcagc cttaaaaaag aaggaaataa gaaggaattc 294660
atgtaatttg tgacaagatg gatgtacctg gaggacatta tgttaagtga ataagccag 294720 gcacagaaag gtaaacactg catgatctca attatatgtg gaatctaaag aagtcaaact 294780
cagagaaaca gagagtagac tcatggttgt cagggactgg aagttgggtt catggggaa 294840 ttttggtcaa gaggcataga catctttctt cttcttataa tattatgttc ctatgttcta 294900 gttttttgagc tattaggatt tccatatcag cattttaggt cttatttatg cttgcatttt 294960
ttatattctt gataatttta gtctttctat atcttttggg tttaaatttg tctcttgagt 295020
tggatgcatt cttcatctta ggttttgtta caaacatgag attgtctgga aattttttta 295080
aattcatgag tttaaaccat ttatgtttgt tgaacgttaa ttttaccgat gcttattct 295140 gccatcttgt tttatatgtt caatttagtt acttcaggat aagcgtaact gtacattttg 295200
tttttgaaaa cataagtttc tacctgtcat ttaatagata tttaaataca tagttattta 295260
aaactctgtt atctattttt tatccttact atggttaacc ataactgatc acagggaatg 295320
ctgtttattt ttcccagttg ttttttataaa tttaacaaca taatattggt ttataccaat 295380
tttgttcaat ttctatatga aaatcaaaaa tatatagaat acatcaagga attcattgac 295440
agatctggga atttctaaca agataaactt ttttcaaaca tgcatctttt ttagtcccac 295500
ccctagtgct atttaagtag atatttccaa gaatttaagt tctgggctat tatccatata 295560 tgattttgt cttcctttt ctacccattt tagccaaata gaaattatag ttattggttg 295620
```

```
tgcttgcatt tcatatattt ttcagaattc ttaccaaatt agttatattc tttgataagt  295680
attttctcaa agataattt cagtctttaa atctttgctt agcaaaatga ttgaatctct  295740
ttttgatctt tttttttaac ttggcctata gtattaaatt ttttaaatt cagagttatt  295800 tttcttcaaa ctttcaaata tgactcctgt gtctgctaat gtcttgtgct atgactggga  295860
agtttgatgt caatctgatt cctattcatt catagctcac ccattttct ctctgaaggc  295920 tattagaatt ttctgtttgt ctttgatgtt cttaaattc ttagtaatat atctattcag  295980
ggcactcttt gagcccattc aaaataaggt ttttgttctt tttgtttgtt tcaagtgtat  296040
tttcattctt tcatcaactt agttcttcct ctgtattttt ttttctcttt ctgttacctg  296100
atcctggtat ctctaacaaa gtcatccatt tttccaagga tgcctttctc tcctttattc  296160
tttcctgatg ctttctggga atttcttcca tctgatcttc caatttggta attcattcta  296220
tgatttatct taactattag gttcttgttc atctttacta ttatttattc tatacctact  296280
atatttacca agttctcttt tacttcttat tataatctcc tatttgaaat atattcccct  296340
aggtgatcga atatatttat tttgtctatt gtaatttctt cattgatctg ttccaatcat  296400
tatatttaac gtagaagaat tttttttct gttgagagag agcgtttggt acctttgtaa  296460
atgttcaggt atatagctct ttgttaaaca tttagcctgt gttctcctta ggtgagtgga  296520
aactcatcca tcactctggt ttgtaattac gcatgtgatg ggacctaagg gcagacccaa  296580
gtctatgttt cttctatgag attaacattc aacaaacact tttagatcac tctggcgcac  296640
tgaagaagtt tgaaatttga gatttggctt taaactctct aaaggagcca gcattaggaa  296700
gaaacagcct ctttagcttc attcctgggg gtgtggaggg aaggggggtg aaacaggaaa  296760
agcccatagt ggccataagt gactggtggc cctgaaagtt tttaaccagc tcctcaacgc  296820
agctgagttt tccgtgggct tgccagagtc ccactacctg atggctgccc tcgagttcta  296880
agttgtatgg agaagagaag atgggaggga gattagacaa tgattaactc aaggcattct  296940
ttataagaga caagagtgaa cttaatactt tgtttttaaa ccagcatctt tctattacca  297000
cttccaccct ctgccagaag gtgcagccac tcccattcac catatataca tgattcatca  297060
gcttgtaatc tcctcgggat ggcttatagc ttactgattt catgttctat tattgctctt  297120
tccgcagatt gatgcctcgt cttatcctct gtagttttc aaaagtagat ttctgtggag  297180 gaagggggcat tatgttctat tcaccatctc aaaagaagca taactctctt tcttggatat  297240
attactattt ttcccacgtt gtgtatgctt ctcattaaag gtaggattct aaaccatcca  297300
aatgaatctg tgccaccacc tgcccctgga cttttggactg aagaggattg agaaatggtg  297360
aaatacttaa ctatttgata gcttccttca ttcccacaga ccacatcaga tgtagttagc  297420 taatataca attaacaaaa ttacccagga aatgcaacat atatacttat ttcattactt  297480
gtcaaaactt tctaaatggc tttcatctat ttctaaaaag aatcccaaat gttccaggaa  297540
caattcccta atgttctggt tttgaatatc acagctcatt tatcagcgta tatcatagct  297600
atgactatag acgccaaaat attaagtaat tcataatgac aatttggaca atgaagggta  297660
tattagaact tctttgagta ttttttattg caatatgaat ttttaaccaa agacttgtat  297720
gagctccaga gagcaaatcc actacatttc cccactctgc ctcccaaccc atcactatat  297780
agatccattg tggagctttt ttacttcttt gtggtgtatt aaaacaaagg atataaatc  297840 ccctgattat ggatgaaagt gatggaacat ttactgccat gagagtccct tatgataagt  297900
ggtagctgaa ctggaagttt aaagaactgt ggcagacagg atgggtaaa tcaataggat  297960
```

```
ccaggaccta ggaatgcatc aggaaagaca gcaacaggga aggatgagct agagcaattg 298020
aaagggtgat acatatattt ggagccaatt ctttttatgc tatcatcaag ataaaaccag 298080
tattcctcac ctggtagata tttctctttg caaaggtgga tattccacag ttcacttcca 298140
cagacctcat gcaaatgtca gattcagcgg ggagagggag cacccagtt tctttggcag 298200 cacagaatat aatgcatcat gtttatttgc aagcctggag atattcttgc atacatattt 298260
tatctagcag atgacactgg atccaattaa ttggtggctt tgaaatatat ttattggaat 298320
tcattatttt gggttatagt tgtttctgtg atccatgcaa tctaccagga tactcttcat 298380
gcttttgcat ttaaaagaat gacaccaagg gcttgtgaaa ggcacattct ggggtccatc 298440
ccccacaatt tgtgttctgt tgctttaggg gagggtgtga ggatttgtgc atctacctgc 298500
tttccacaaa gtagggtccc tgctggtata agggcacacc gtttaagtgc tactgcacag 298560
aagcatcaga tgtcattaag attgtgtgtt atctacattt cttattgttg ctcaactgcc 298620
agttactctt ttcataaaat atgtatctgt cctatatagg gctaagaatt aatttatccc 298680
agtctataac tacagagaga agcctactta atgagcattc ttgatggggc ataccaccca 298740
taaatatggc accttagcat ttgaaaaaac agaagaagca ggaaagttct ctctgacctt 298800
ctccccatcc ttctccccta aagccaggtc ataagaccct cctatgagag gtgactctct 298860
ataccaagag gaatagaaca ttcttatctc tgaggacaaa aggacacaga ggagaatctg 298920
aacacacagg ccttgctaag ttctccccag ttttttccca ttagataata acatttta 298980 cttcaatcat actttccaat gactgtccac tctttatcaa acctaagtat ctaagcacaa 299040
aaatccacag gtttccctgt ttcttttggg tcttcattgc cttatgaagg ctcctgtgtc 299100
atataaaact gttattaaat gaagtgcact ctttgcttaa tctgtctttt gtcataggg 299160 cctcagccat gaaactaaga taggaagaaa agatatttct tttccctat attattcaac 299220 aatattctag ttatacatgt aagcttaacc aaaagcttct agaatatcaa agtaataagt 299280
gtgaaatatg tgtgtgtgca cacatgtgtg catgcatata tatacacaca ctacattgta 299340
ggtgtgtata tatatgtata tacatataca catatatatt ttataagatg cgtatacaca 299400
tatacatttt tgtatgtgtg tgtgtgtgac agagtcttgc tctgttgtcc aggctggact 299460
gcagtggcgc tcactgcaac ctccacctcc tgggttcaag tgattctcct gtctcagcct 299520
ctggagtagc tgagattaca gccatgtgcc accatgcccg gctaattttt gtattttctt 299580
ttagtagaga tgggggtttca ccatgttggc caggctggtc tcgaactcct gacctcaggt 299640
gatcttccca cctcggcctc ccaaagtgct gggattacag aggtgagcca ccacgccaag 299700
ccggcacata atacatcttg taaaatatat ttagcaaagt ctatttaaaa ataattaata 299760
gtttattaaa tcttatgtag atttttttt caaaatgaac aagcttctgt ctttccaaca 299820
aagctttgga ataataatc attgcatttt cctctaacag gttaatcagc agatcaacta 299880
aaaccaaaat gagtctttct ctgggcacgg tggtgcatgt ctatagtccc agctactcag 299940
gagactgagg caggaggatc acttgagccc aggagttcaa ggaccagctt gggcaacata 300000
gcaagatacc atctctaaaa aaaaactaaa aattaaaaaa aaaataagt ctttctataa 300060 ctgtatgaca gggctaaggt gatttttatt gacagaggaa ttaaatttca atgtaccaag 300120
ttctatccgt atgatatctt ttctgatggt tggaagggca ccaaggggct tccatgaagc 300180
tcagtgacag catttcaca tggaagtcac tgcagcggaa agtagggtac acattcttgg 300240
taaataatat atgattgcac tattgatgaa tagcatttca aaagctctgc tatttattgt 300300
ctattgaaag ataaatgaat ccagcaagta aactgcctaa aatatttgta cactgttata 300360
```

```
aaatgtaaac acctctatca tactataaat ctccctcccc tccgctggaa aagacttcaa  300420
gctgagatca tcctcgtcct catcacatga ttgcttggaa tagagttgtc cctgaggcca  300480
cctgtcacct aagaggactt gtattcattt attcagtgtc catgtaatga aagaataaga  300540
cagacatact gtgaatataa aacacagag ttcaaaagac tattctgatt gagcagaagg  300600
aagatactaa acaaatatta gatgaacaaa gcttgtgtgt atggctttgg aagataagcc  300660
taggatctta atcttgttta taacacaa ctattaaacc ttcctgcgta aaatacattt  300720
taattgagac ttagcatgaa gatagaacac caagtctggg cattctgaaa agtttagacg  300780
cagaggaata actggcaggc agtgatttaa agtggataca gattttttgcc ctggagttgc  300840 agatgcgtgt aggaatgaaa aggaagtaat gggtgtgata accgatttaa acactaatca  300900
gtgagcccca aatattaacc atatactggg attctacaaa gagatgccat ggtaaaaata  300960
tgaattcaag tgttttaacc tgtatagctg gatacattct tgtgatatta acacgggaaa  301020
taagaaaaga gacgagtttg aatgagaaaa agatgtttag ctcaatatag cacacactga  301080
gctttaggct cgaataagac atctgagtgg tggaagactt agtcaagcat gggagaagtt  301140
agagctgaaa cccaggtaaa atccttcaag ttacaggcag aaatcattac cagatgtgtg  301200
gtggagtcac acggggatg tgagtcctaa tgcctgtgca gatgcatggg gaatgcagtg  301260
tctttttgaa ggactggttt tagcgctgca agaagtaaag taaattctct tttacctgca  301320
ttcttgttcc ctctggtgct tttatgagga cctaggcaag aatagtattg aaccacttat  301380
accatccatc tgttagaaga acctataata cagaaatatt tgctttgggc tgaactccaa  301440
acgtaatact taatgatttc tcttcaagtt tgttgacaca ttctacatct ccacatacaa  301500
tttgctccca gtcgtttctg agatatgcta cagaaagtac aattgatcaa acgttggctg  301560
tagggattca agaacagtcc tgtgactgca ttttcgttcc ttcctgaaac tattccaagg  301620
ccataaaaca cctttttttgt gtgaactgtc tttctgtatc ccatttcaga tgatatcttc  301680
tttcctttaa atacagtctt ttatattttt ctaattgtct gattgccaaa acaatatatc  301740
tgcattgcta taaatttaca gtatcaaaga tcatacagaa gaaaaatctt ttttaacaaa  301800
agaaaaccat tgttgataat ttagtttaca tacatacata tgtacataca tgtatcctct  301860
tagcactctg gggcccggag tagagagcaa acctgtgaaa cagatagata gatagataga  301920
tagatagata gatagataga tagatagaag atatagagat atgttagagc tatagagata  301980
tagtctctag atagatagat aagaatatct gtattctctc tctctagaca aatgattagg  302040
aaacagtcta taagaacgtg tgtgtgtgtg tgtgtgtgtg tgtgtgtgtg tgtatgctct  302100
ctagaggtag aatatatctc tctgtaggga gagagactta tgcatgtgta tgtatgtata  302160
aaacaaagaa acaataaaaa cacaaaggcc caaatatcaa ccagaagaaa ctgaccagct  302220
gtaatgggac aattagaaca tctgtaagaa tatttgtact ggatttaaaa tgataaagac  302280
ataaaagttc atgtattcat catgacaccc agaataaaac tcactggtta tattactagg  302340
ccacgatcgc attttcctga atcttgatca ataaagaat catgattttt tcccacttt  302400 cctatatata ttgaatttca gagtaactaa aaaattggtg attacaagta aaatttcaga  302460
taatatatgc agaaagaaca atactatctg aaaatcatta ttttgtgaaa ctccaaatta  302520
agtaagtata ttaatctgtc ctcacactga tctaaagaac tgctggacac taggtaattt  302580
attaaggaaa gaggtttact tgacttgcag ttccacatgg ctggggaggc ctcaggaagc  302640
ttacaattgt ggcagaaagg gcagcaaacg tgtctttctt cacatggtgg tggcaggaga  302700
```

```
gagaaatgag tgcccattga aaggggaaat cccttataaa accatcagat cttgtgaaaa   302760
ctgactcact accacgagaa caccatgggg gaaactgccc ccatgattca attatctcca   302820
cctggttcct cccacaacat gtggccatgg aactacaatt caagatggga tttgggtggg   302880
gacacagcca aaccatatca ataagagatc taggaaatta tctctgatta tttgaaaagc   302940
ttcgcaggtt tatatatata tatatatata tatatatata tatatatata tatatatata   303000
tgtgtgtatg tatatatata tatatatata tgtgtatgta tatatatata tatatatggt   303060
gggattcatt accaactgaa tgtaattatc aaccactctt aagataatta aaagtaacac   303120
tagcaggtat catgtaagtc cttattaaat tcagtataaa gtacagagca gttcctgggt   303180
gcgttgtttc ctacaaaggg caccataacc ctaaggaaga aaaacaagat gtgattagga   303240
aacattctgt taattctaga acatggggtg ttcttcagca gtaatgttca aaatgtggtt   303300
cacaaagcag caacttgtta gaaatgcaaa atttaagatc ctatacctgg gaggaggctt   303360
cctgaatcta aaattgaggg tgtgggttgc aaactattat ttctttccca aacccatctg   303420
tgatgtttat gcttgataaa atttgatggg acggttcatt gatttccata aggaattaac   303480
gatgtaagaa aatgagaaga agaattgtat tatggaaaag agggtgtcaa tattttcact   303540
tgctttctct ttaaatgtgt ggatcacaag atttgctttt cattaaaagt attcagatat   303600
atatacgtat ttgaaataca tgtgcctata cactaaccccc aaaacagctc attaagaatc   303660
tcttccactg ggacataggc atcagtattt gttaaaatat cactaagtgt ttagtgtggt   303720
tgatgagtgt agaagaata tattttcacc aagcttatga gatgggcagt ttggggccag   303780
gagaagaagg cagtgaaaga acttgggtga taagcagctg tctacttgca aaacaactta   303840
ttattaatga attgggactt taaatttttt tttttatttt cataggtttt aggggaacaa   303900
gtggtatttg cttacatgag tcacttcttt agtggtgatt tgtgagattt tggtgcaccc   303960
attacccaag cagtatacac tgaacccaat ttgtagtatt ttatcccccca acccctccc   304020 acccctttcc tctgagtccc cagagtccat tgtgtcattc ttatgccttt gcatcctcat   304080
agctcagctc ccacttatga atgagaacat aagatgtttg gttttccatt cctgagttac   304140
ttcacttcca ataatagtct ccagtcccat ccaggtagct gtgaatgcca ttaattcatt   304200
tctttgtatg gctgagtagc attccatcat atatttatgt accacagttt ctttatccgc   304260
tcgttgattc atgggcattg ggttggttcc acattgtgac ccaatgcttt taaaataatg   304320
tgtgtgtttg gccacgaaca taagccagaa cactagaaaa attgtttact gaaagccatc   304380
ttagtttcag gaacacaaag gaaatgaggt aatgtgtgaa aagaaccttta aaaattgtaa   304440 ggcattttgc ataaagatgt taggtgcttt ttgaagtttc tatttaaatg tggtcaatta   304500
gagaggtttt ttttttttca ttttatgttt gccttgaaag catttagaag tatgagaata   304560
tataatttca ttttgtaaaa cacaatatgt tgaacctaat aggatctttc ttggaaactg   304620
aacattgtcc tgggttttgg aggcatccca ttgaaattta gccatgattc catattcagc   304680
aaattgctgt ggacccagat acatcttcgc tgaccagaag tctttccaga gtggaagatt   304740
ttagtaaatg tacaagtcaa tcttgtagaa ttagataaaa tgcattctgt tttccatcac   304800
ttgccgatat ccccccactg ctaattaaag gaaaacacaat ccacaattga tttacttatg   304860
taaatgtaga ttacaaacca acaacatgat tttaagagtc ttaagaagtt gagggctatt   304920
ttgaatgttt actcttggag acatgtatat ttaggtgtcc tggtcaacaa gatcaattgt   304980
aggaatggtt ggtgcaatca cattggtcat taaatacaga catcacacat aatcaagcag   305040
atttagctca gggtatgggt aactcaacat atgaacacca ttcaaagtat ttccccaaaa   305100
```

```
ggctggcatg gtggctgaca tggtttggtt gtgtccccac ccaaatctcg tcttgaattc  305160
ttgtgagagg gacccagcgg gaggcaagtg aatcatgggg gcaggccctt cctgtgctgt  305220
tctcatgata gtgaataagt ctcatgagat ctgatggttt taaaaagggg agtttccctg  305280
cataagctct cttctgttgt ctgctgccat gtgagacatg cctttttacct tccaccatga  305340 ttgtgaggcc tccccaggca cgtggaactg ttaagtccat taaacctgtt tcttttgtaa  305400
attgcccagt ctcaggcatg tctctatgag cagtgtgaaa atggactgat atagtggctt  305460
acgcctgtaa tcctagcact ttgggagggc aaggcaggca gatcgcttga gctttgcagt  305520
ttgagaccag cctgggcaac atggtgaaac cctgtctcta taaaaatac aaaaattagc  305580 tgggtgcagt ggcacaagtg tgtattccca gctacttggg gacactgggt caggaggatt  305640
gcttgagcac aggattgctt gagctagaga tgcccaatgc atctcaaggg tgcagtgagc  305700
cgagatggcg ccacttcagc ctgggtgaca aagtgagatc ctgtctcaaa aataaaaaa  305760 atatttcccc aatggggaca tatggcttaa tagttagggt tattgtttgt agtgatgaat  305820
aggtttggaa ataggtagtg gtgataatta taccacattg tgaatgtaat gaatcccact  305880
gaattgtaca ttttaaaatg atcaaaatgg caaacttatc ccacacacaa ataaatagat  305940
atagatatac atagatatct tcatatggtt tttcttgttt tttaattttt tatttttta  306000 ttttatttat ttatttattt gagatggtgc ctccctctgt cgcccaggct ggtgtgcagt  306060
ggcatgatct cggctcactg caacctcctc ctcccaggtt caagcgattc tcctgcctca  306120
gcctctcaag tagctggtat tacaggcctg tgccaccatg ctctgctaat ttttgtattt  306180
ttagtagaga cgaggtttca ccatgttggc caggatgatc tcgaactcct gacctcaggt  306240
gatccgcctg cctcagcctc ccaaagtgct gggattacag gtgtgagcca ctgcgccctg  306300
ccttcatata ggttttaata ttagttttgc ttaatttaaa gacagtttga ggcagtacag  306360
cataaagtac tccccacatt tcatttattt agttttaatt gacaagtaat aattgtacat  306420
atttacgggg tgcatactga tgttccaata catgtaatat acagtgatca gatctaagta  306480
attagcatat ccattatcta aaacatttat catttctttg tgttgggaac attcaatttc  306540
ctccttctag ctatttgaaa ctacatatta tattatttt aactcagtc accctgcagt  306600 gctatggaac acgagaacct atttctcctg tttccccccc tccccacgaa gaaataaaag  306660
aggtgaaatc tgcacacaa agcaaaagga acaaagacat tcaggtactg gagttgagca  306720 taaatttttac ctcacaattt ctggcagata aagcaaaaag agagagaaaa acaattggtt  306780
ctgggattag tatttccggc aagagaaacc ttctcccttt tccctctgat tcttggtgaa  306840
gagcagttat gatgttggag ataaaggag aagatggcag tgatggttcc ttgttctttc  306900
cttctgcagt ggctgtcagc ttcgcctgtg atattaacag taagacagga aagcctgaga  306960
ccgcctcact aaagacagac ccttcccatt atgtgtcacg gcagccttca cccttgaatc  307020
tagaaaatac tacctgggcc gtgctaagtt tattcttaaa agcctaacac cgtgtagcta  307080
ccgctgccca atgcatctgc ccaaaacagc actccccaaa tcctgaatat gcatagaaat  307140
aacttttcag ttttcatgcc tactgctgaa ttgtaccaac agagattctg atttggaagt  307200
cagcggagga gtctatgcag tttaaatttt tacagacaac tcaaggtttt gtggatatat  307260
cctgagacag ctcagccctc ccaggctgtt ggtaccatag gggctgggag agattgccct  307320
cacttacccc gcaaacacct tgcaggatgc agaacagctc ttaataaata tgtgttatgg  307380
aaataaagga atgcccctgt gcttggaagt attaggctgc ctctctctct ctctgtctct  307440
```

```
gtctctcctc tctctctctc tctctctctc tctctctctc tggttcattt   307500
tcaatgccgc tgagtcatac agtgagaagc agcttagggt cattaagaga ttgaaacatc   307560
ggagaaaaaa agtgaatatg ttttcatttg aatctctatt tttaactctt tctgaccttg   307620
tctgtcaaat ttggctacct tgagactgtt gcagtgataa tgaaataagc ctatgctgtt   307680
ctttggaatc attttagaca tatacatgtc taatatatat atatatatat atatgtatat   307740
atatatataa aaaatactta ccatatgtga tcttgtttga catgccttt ttctatacaa   307800 aagcacatga atcaccatgc ttcagcaatg aagatgttgt gttttggact aaaggcagtg   307860
taaacacaac atgctattag cgttttctt aatcatcact accacccagc cgttgtcttc   307920
ttgcacaaga taataatagc atctcacatt tccatggagc tttataatgc atgaaggtct   307980
ttcacattca tcgttttgtt caatgtcata gggagaggga gcttcagtaa cctcaaagcc   308040
cagtgtgcag aaagagaaac tgggattgat tcaatcattt ggccacagtc ctaggactct   308100
tgaatgtgtg tgtaactcag gcagggtgaa atcccagaa gatacgtccc catcccaagg   308160
gcacctaccc aggttcaata acttggttac aactgacact ctttggatga tgctgcactc   308220
ttcacaaaca cgtatccaaa cctatcatga acccaaacca gagcaaacat caaatcccca   308280
ctcctaccac atattcacat cttgtattaa caccaaagcc tgaagcaccc tgacaacatg   308340
tgtccagaag atgttgaatg tcttccaccc tgactgccac taacctggtt aaagccagga   308400
ccaactttca cctggacaac tgcagtggac ttcttccaaa tgcacgctcc tgcagtcctg   308460
tccaccagtg gctcctgtga gctttacgaa accataaatc ctatcacatc cctgccatgt   308520
tccaactctt atgccttgtc attgctttac aataaattcc aacattttac tctctctttc   308580
aagtgtgaac tcactttgcc tactactgga ataacgttct ttcacatttc cttgctaatt   308640
atgagtcagc tacaccggga ctccttctgt tctcctcacc ctttaaacat atttcccatt   308700
tgaaacttcg caactcgtaa ttcttttcag gaatgtttcc cttcatcat cttgtagctg   308760 cttcgttgtc atcatttcct ttcatttcca cctcttcaga gaggctttgt ttagaagaaa   308820
acataggagc aaatatttgc cagctagggt tatgcaaaag tttcttacat agaacacaaa   308880
atgtaagaac cgcaagagaa tgtattgacg gggccttcca gacaccatga agaactcaga   308940
gagcaagctt cagattgaga gaaaacattt acaactaata tagcagagaa ttgacttgta   309000
actagaatat ataaaaatat ctcccaactc aatgataagt caggcaacct gcagagcagc   309060
agtcctcaac acttttggca ccagggactg atttcacgga agataatttt ttccaagtag   309120
gggaacggtt tcagtatgaa acttccacct cagatcatca ggcattagat tctcataagg   309180
agcaggcaac ctagatccct cacatgtgca gttcacagta gggttcacac tcctatgaga   309240
atctaatgcc accgctgaac tgacgagagg tggagctcag gtggtaatgt gagtggtagg   309300
gagtggctgt aaatacagat gaagcttccc tcgcttgccc accactcacc tcctgctggc   309360
ccagtcccta accaaaactg gtccatggcc tggggcttgg ggacccctgc tgtagaggac   309420
agaataacag ccccctacat atgttcacat cctaccttat gcagtaacac ggacttgact   309480
gacgtgataa agattttgag atggggagag tatcttcaag tatctaagtg agctcagtgt   309540
aataaaaata tccttataag acagaaactg gaagcttgga acaatagaag agctgaaggt   309600
gaaacagacg tcagacagag attaagatgc tatgctacat atatatatat attgcccagg   309660
aggattgctt tgttggagcc tataaaggtt tgtgagataa aagttctgaa gtggagaatt   309720
gttactatga tggttgctta aaatctagtt tttagaacag atgagtttt gactgtagct   309780 actctggtat gtgatccatt taatcatttt tttgtttaat taattctcag agagaaatct   309840
```

```
tagccccagc tatttaaatc tctccgtaaa taaagacttc caagcaccac tgggacagtt 309900
accaaaaatg acaaatcatt ggcaattcta acaataaact tcagtatagt aagagatata 309960
atggaactct gtaactgctc tcaaatcaaa catccctcct gcttagtgaa aacagaattg 310020
cactaatttc tctgatgcag tctcaaaatc gagccaccat ttcaggtttt gtaagaaaag 310080
ttgcggactt caggcttaga aaagacatcc cagttatgca ttgtggctga ggataacagg 310140
aagatgagaa ttaggatgta gctatcttca aaagaaaag tggcaaaaag aaagaaaaa 310200
ccttaatgtt agaacatata aaatagtat aaataattaa gaacttaaag aggcagagag 310260
tttggttaaa gcggcaagcc agcaggacaa ttttagtgtg tagcttaagg tacaatacat 310320
gcataatttg cccttcctca attctagaaa atattgtctg tcttcttcaa taacctttct 310380
attcctgaaa ctaagcattc cactgggatt ttagctattt tatgtgctgt catatttact 310440
ttgctagcgt gcatgtgatt acacctaagt tctaattcgt ctaatatatg tgcattactt 310500
tttcattcat ctaatatgaa ttctagttca tctaatatag tgttgtataa gttgtctttt 310560
tacttatgtg cattttacag tgccctgaat agcactgaag tacaaaatg tatcttaata 310620
tgtgttttat ctccatactt tgatggtgaa aaatattact ttccattcaa atgagtttta 310680
aaatagtctc attaaaaaca aatgaaaacg taaataaaaa aaaaaaaacc ttttctgtaa 310740
ttttcaaga tatctatgga aatgcactga actaccgcat cattttcccc cagattttgc 310800
ttgggtcatc atggctactt catacattgt tgaatgagca tttgccgtaa atctcatagc 310860
ataagtaaaa gctatgatgt gttttttgcc ttgtctttct cttttcactt taaacacata 310920
ataaacactt agtaagcaga ttgaataaat acatacccc tttatgcaaa attattcaca 310980
aataaatggt atctaattca ttcttttaaaa taccatcaga gaacacacaa tctcgcttta 311040
ccatctgtat aattttagag tcagagtcta atttgaccag cagtcaattt tttcccttttg 311100
gactcctttc atatattttga aggacatttc tttgttccta gtatgtgtag atgaagcaaa 311160
actaaactgc atggcttctg atattcatga aagcaggcta gtaggtaacc attttttgaac 311220
acattccaca ccaagcgcaa tgctgttttct tgtgcattgt ccagttgagt tcctcagctt 311280
gctatgggag ggctactatt ctcctcccca tttcacatat aaagaaagtg ggactttgaa 311340
atcttaagtc atgtgcttaa ggcttttgcaa tagattccac cacaaggatg tccaactgaa 311400
tccactgcaa gcaataactc caaaagcagt caccaagcaa atgcccttgg tgtaaagtga 311460
tacgttctgt aacagaaatt cattgaaagc catttactgt gccgagagaa taaagataat 311520
cacacaggac acttttggaa aggggcccac attggtagaa agagatggcc aggttctacc 311580
tgagtatgca ggtgacccct gcggaagatg cagagactga ccttcaggtc acactgacct 311640
ttcaaatggt gctgggtcca tgagctagcc gtgcagcttt tgtgtgcggcc atagcccaca 311700
ggaaggtgtg ctcaggcaag gtgttcaggg caatttatgg tcgcccagca gccctgcaga 311760
gggcgcccta gatcttgggg atttttatata aaaaggcaag catatcaaaa tgcaaggcat 311820
attctggaaa tagctagcaa gtgttgtggt ggatttgcag gctccagaac ataagtaggg 311880
catcccttga gaaggtcaca tgggcccaca cagaatgacc cttggattcc cagtaatgaa 311940
tttgtttctc caacacattc actttattgt gtgggtgtga ttgttgttgc taaaaaggga 312000
gatttaaatt atgaactaaa tataaacaga tattagcaat aaaacgtgaa tattccctat 312060
agtcacatgc ttcgaaataa tcaccctcca ctgtttgaat tccttccaga ttttattttt 312120
taataaaaca aatgggctgg acgcagtggt tcatgcctta atcccaggac tttgggaggc 312180
```

```
cgaggcgggt ggatcacttg aagtcaggag ttcaagacta gcctggacaa cattgcaaaa  312240
ccccatctct acaaaatata caaaaattag cagcaaatgg tggcacattc ctgtaatccc  312300
agctatttgg tgggctgagg caggagagtc gcttgaatcc aggaggcaga ggttgtagtg  312360
agctgagatt gcaccactgc actccagtct gggaagcaga gcgaaactct gtctcaaaaa  312420
aaatacataa aaatataaaa taaaataaat gatatgtagt attcagtagc ccactatttt  312480
ttcttgagat accttagatg tgtttctgtg tccatgagtg taaatactcc ttagcacttt  312540
atgcagacaa acagcatctc ataatatgga tccaaccaag acaatccatt caaatctctg  312600
acttgtgaac attcagcttg ctgctattgt ttgttttttaa aattacaatc cgtgtgaatt  312660
gtggagcctt gggtggctat ttttatgcat cagaataaag attttcatag aaagcattca  312720
aagaattagg actcctgggt cagaagtttc caattttcat tttcctgggt tttacccatt  312780
ctcttacact ggagaccatc atgatgatgt tgatggtgtg gaaattcaga ggaagctaaa  312840
aggacgtagc acccaaatga gcaggtcctg gggaactgta gttctcatct cagacactag  312900
gatgcagacc cagggaggga caagatgtac aagctctttg aaaactaaaa ccaaaggatg  312960
tgacagccaa ttgaatgaga gtcagcagca atctggagaa aatatctaag gagaaagtgt  313020
tcagttgaaa atactcaaag ttggctgggc atggtggttc acacctgtaa tcccagcact  313080
ttttggaggc tgaggcaggg agatcacttg agctcaggag ttcgagacca gcctggccaa  313140
catgatgaaa ccccgtctct actaaacata caaaaatcag ctgggtgtgg tggcgtgtgc  313200
ctgtaatccc agctactctt gaggctgagg caggagaatt gcttgaatcc aggaagtgga  313260
ggttgcagtg agccaagatc acactgctgc actccagctt aggcgacaga gcgagagtct  313320
gtctcaaaaa caaaaaaaga ctcaaagttg actcaaagag atttgtttcc aggctggcta  313380
ttcccaaatt ttcatttgca tgaaactcat gtatcaatta tcttcagatt ttgatgtttt  313440
attatttaat aaacaagctg tatttattat tttatatttt gttcctaaaa tatgatcaat  313500
ttcagttttt tttatttca tgtaatttaa actaaagcac ttaaaaaata cctatgcagc  313560
ttaattctag ataaatgtgt ggagatatta tcttttatga aaatactgca aggaatctca  313620
gtagtagttc ataggcccca gagtttggaa acctgtggta taaaaatcat ttgtctctta  313680
taattgtttt agattttctc tactgatatt ggaaatagac tttggttctg tgcaatactg  313740
ctgtgataac atgatacaaa tggagaatgg tctgctagta ctcattccat ttttaagtaa  313800
aaactaaaaa taaaaggcac tgaatttcaa gcagccctgc ctatcaggca acagaatttg  313860
aatgcagtgc atcagcttcc ctcccttcca gcccatcctg tgcaatgtgt gcttctgtgt  313920
taaatcctac atgttttcag tcagaaagtt aaaggttcac cttgtaataa atgcatttca  313980
tgaatgattt cctataaccg tcaaagatta gttttgcatc tgtttgactg attttttgttt  314040 tttatgcttc tgctttcatt ctaaccaaac agatttcttt ttgacctcat ttgcatgatc  314100
taacacaaat tctgtttatt ctcactgaag aattttttatt taaacatttt ctgtttggtg  314160
tcacttcttt agtttaaagg tgcacaaatg tatgtctgtg tacatataca tttatagtca  314220
cacatgcata tatatggtta tatatgcata tatatatata tatacataca tatattatat  314280
atatatacat acacacatat caggtgaatt acacacactg aaatggtgaa agatatttaa  314340
cttctgtatt cacttaatta tctcctggtt acttgtctcc aaaaaatgcc tactgtgttt  314400
atgcaaggaa tgatctccta aaagaaaatg gattgcagct ttaacgtcat gtaacaatgt  314460
cttttgttaa ttgaaagaaa aacaaatatct gaccccattg ggttccttac catttacttg  314520
cagtgcatgg agaaacaaaa gacctgcagt cattctccta agccctgtga tgtaattcaa  314580
```

```
aatgagagga aacatctaca ttattatcta taataaaaat tggaaacttt tctgttgtga  314640
caacaatatt aagcctgaat agaaatattc atgtttatat gatattcact tcagtcaaca  314700
tgcagcagga aaaactgtga ttcctatttt tagtcatctt ttccatgaaa cctgtttcta  314760
aataaccata ctaactaaat gtactagtct gttctcatgc tgctaataaa gacatacctg  314820
agactgggta atgtataaag aaaagaagtt taatggactc acagttccac atggctgggg  314880
aggcctcacg atcatggcag aagacaaagg agaagcaaag tcacatctta catggtggca  314940
ggcaagagaa tgtgtccagg ggaactgcca tttataaaac catcagattt catgacactt  315000
attcactatc atgagaacag catgacaaaa acccaccccc atgattcagt tacctcctac  315060
tgggtccctc ccatgacaca tggggattat gggagctaca gttcaagatg agatttgggt  315120
gaggagacag ccaaaccaga tcactgaacg tatctattga tatctcttgt gtgtgtatat  315180
ttgttattgt tgttccttcc aggaccctgg atgaaacttg gcatcaatgt agccattaac  315240
atggattcat tcacatggtc tcttttgcat ctttctttcg ttgttcaatt attggaggag  315300
aggttgctga ttacaagctt catattaggg agagtaaagc tcagaaacca aaatttcatc  315360
ggctaaaatg cttagagagt ttgtagccta aaggacctgt cagttaaagg agccatttgt  315420
tgtaaatctc tggttttaga caatcaagta gcttgttctc ttcattcacc ttgaacatat  315480
atttaaagtt aagtgatcta tccgaggaat gacttctcag gagcagcact catctttggt  315540
atcatgtgtg gctctttcca agttgatgag ctaccatcat tttgctttct acaatcagga  315600
ggcaaaaccc agtggtttag gtttgcagga ttcctaaaaa tattaattttt aatttgctac  315660 aataaatacc aggattcctg gtgtcaaaaa gcttgcaaaa aatcacacca ttagaatttt  315720
ttaagatcac tctttattta cacttaagaa gatagctttg ccaggaaaat gcctgccttc  315780 cttcttttcct tccctccttc cttccttcct ttcttccttc cttccttcct tccctccctc  315840
cctcccacct tccttacttc cttccctccc tccctcctac cttccttcct tccttcctcc  315900
tgctctccct ccctccctcc ttccctccct ccctccttcc ctccctccct ccttccctcc  315960
ctccctcctt ccctccctcc ctcctgcctt ccttccttcc ttccttcctc cctcctgctc  316020
tccctccctc cctccttccc tccttccctc tccctgctcc atcacatcac agagctgtag  316080
tgtgctgcct gttccttgcc tccagtctta ttcacaggaa aacctggcca ggtgctgatg  316140
aataaagaag aagacagatt gatagtgaga tctaattttc acagatcagg cgacttggga  316200
aaacaggtct ttttattttc aaatgctaac tttctgggct catagaattc tgtatcagta  316260
agcccacatg cttttttaagt ctgatttata gaaaacatga tttggccctc aaaacaatgt  316320
aacctcccaa cagattcatc tttaccacta cacagataga gctgattagt caagacagaa  316380
gaattgcaat agataaaggg tttaattcct gcagagctgg ctaaatggga gactggagtt  316440
ttattgttac tcaaatcagc cttcccaaaa atttggaggc ttgggttttt ccagaatact  316500
ttggcagaca ggggctaggg aatgagtgct gctgattggt tgaggatgca atgataggg  316560 tgtggaaaac agccctggtg cacccagtcg gcctctatgt ggggacacag aggagtcact  316620
ggtcctagta ggaccaatca gttgtcagaa atgcaaaagc ctgaaaagac atcttaaaag  316680
gccaatctgt actatgctta ttacctgggt aatgagataa cctgtacatc aaaccccctgt  316740 gacatgcagt tcacctacat aataaaccta caggtatacc cctgaaccta aataaaagt  316800 tttaaaaagg caaattttag cttctagtga ttggggaagt tgcaaatctt gtgacctctg  316860
gaataatggc tggtaatcat tcaactaagc ttacatctta gcagaattca ggcctctctc  316920
```

```
attctttaac ctggtggcct ttcattactt ttacaaaggt ggtttagttt taagagggc    316980 tattatcatt taaactacaa gttcaatttc tcccaaagtt agcttggccc gtgcccagga    317040
atgatcaaga acagtatgga ggttaaaggc aagatggagt tggttaggtc agatctcttt    317100
cactgtcata attgtctgac tattgtaagt tttgcaaagg tggtttcaag gtgaaaggac    317160
tatactctta aagagcataa aattattgca ttcattgtgt acctgaaaca ggcactcccc    317220
cttgttgata gtttaaaaag aaaaaaataa taatccctgg atgttgcaat aaatgaaaat    317280
gccatggcag aaactgtgga aacaccagcc tcaaaacacc acattgattt gttaaacttc    317340
agagatccat ggattgtcgt ttccctcagc cagcctgtag atatttggaa gaaatttcag    317400
aacctcaaag atcaaaccat ccaataggat gctgttagaa gaactaagat ttttgaaggc    317460
aggggatatt cattagcctg cttttggaaa ggttaaaaca ctctgatttt gctagggagg    317520
aagagtttat ggtggaagaa aggccaatga tttcctgcgt gttgaaaatc ttcatactcc    317580
tccacagaaa caaataagt caacaagtca ttctgcagaa ttgagaaaga gaacagtg    317640 agtgaagaaa agacgtgctg aagacagaat cgttctgtta aaaattgct cgtgccttag    317700 gaattaatca cctctttctt taatagggga agaaagcatt gccctgtggt attatagggc    317760
acctaaactg acatgattcg tcattgtcat ataaggatct tcgatctttt ctcccaagca    317820
aagcctgatg cctttatga acgatcgtgt caaagatata gtgatggaga caggtgttgc    317880
agaacatttt tggcatgaag cactaattag taattgctaa ttaaatgggg gaggaggctt    317940
gggtaatgtc tgatcgcacc cactaatcgt agctaatctc ccgtcacatc cctctgaact    318000
ttaaagaaga tcacattggt aggatgtgtc ttaagtatcc aacctcgcag ttgcgacgct    318060
gcctctcttt gaagctgcag gagatagtga ctcccgattc aggcttggag ttttattgt    318120 cattgttgaa cgaaaatcgt cctgtgactt tctttggagc caggccattt cctccttcc    318180 agctcagagc attttccac aggtgctcag gaaagctcat ggaagaaatg ctggttgact    318240
caattggtat gcagcctcat cctctactct ttttgtttta aagtagaag ccggcactca    318300 gtcactcctt ggaatgccgt caactttggt tagggacgtg ctttgaggga attggtttga    318360
tgttatttta gggcttaaag cagcctgtct tcatacaaac atgactgcag gtggccataa    318420
taatgtgctg agcatcccctt gaaatgagtg aatgacatgg ctcttggaaa aagaaattg    318480 tatagaaggg gcaaatatca tagttgggta gttggggaag gctcaaataa ggacgtgaaa    318540
atggttaaaa aaaaaaactt ttaaaaattc tttgtctttt tggaaggcat atccagtaca    318600
gatttggaca taaagttgga ttaaagttta tgcaatgaac taaacttgca ggaggcctta    318660
gaaaatattc ctagttttga atctgagtag gagagtgtat gtcttcccaa acttgacttc    318720
aaaacatcag aagaaagcag ttttccagg tcaagctatt tttcaataca gaaggaacaa    318780
aaaataaaat agattaactc ataactttgc tatcattaat accaaaattg ccattttca    318840 actactaagg agaaattaag aatcgtatgc cttgagtaaa atctagatcc tcaactcaca    318900
gaatccttct ttttaaaata aggaaggcca gttcctgata ttttgggaac agttggggag    318960
atgtgaatat tcattagctt ttgggtgagg ttcaataatt acatttttt gtatgtgact    319020 aatattttcg ctatgtagga aaatagaggt gtatactatt tacgagtcgg atctagtgga    319080
gtctgtaact tacgttgttt cttaagcatt gaaaggagtt aaaacaaaat gttaataact    319140
aattcagtga gaaagacagg cgcacactgc ctttgtatac atgcacatat tcttagacac    319200
agacacacat gtgcacttac gccccctccc cccccacac acgtactgtt ttccctgaaa    319260
aatttcttgt aggagtctgt tgcatttttc aaaaaagaaa atgaaaatgt gcacagaaat    319320
```

```
gataccttga acctagtaaa atttacgacg tcttctggga ttgcttcatg ttattaatat   319380
tttagattca tttttgccttc tctattagcc acatatatac acaaagatgc catggtatca   319440
taacatcaac ctaaaataac cattatttat ataattattt ctgccacaaa atttttctc    319500
ctgttcttcc tctaattggt gggggtgaga gttgaggaga gagagaatga agaagacaag   319560
ctatgagata tcttttcaaa tagcagagac acgtatgcac tttttctatt tggccaccaa   319620
aaatatcttg tgttcttttg tagggttttt aagtaccggt gaccaggcag caaaaggcaa   319680
ctatgggctc ctggatcaga ttcaagcact gcggtggatt gaggagaatg tgggagcctt   319740
tggcggggac cccaagagag tgaccatctt tggctcgggg gctggggcct cctgtgtcag   319800
cctgttgacc ctgtcccact actcagaagg taataatggc accccagggt gggcgggca    319860
aataccctga accaagaaat gaatggtcag agttcatatc tcagatgcat gtcctggtta   319920
ccagaagtca ctctggcaac agaaaatgcc caaaagatca aatgaatcca tcttcatgtc   319980
ttttaactca gcttttgttc catttgctct gtcacccagg ctggagtgca gtggtatgat   320040
catagctcat tgtagcttcc aactcctggg cttaaggctt ctcccatctc agtctcctga   320100
atacctggga ctactggctg ctttttaaaa ttttttatag agaagtggtc ttgctatgtt   320160
tgcctgggct ggtctcaaac tccaggactc aagcgatcct cctgccttgg cctctcaaag   320220
tgctgggatg acagatgtga gccaccatgc ttgatcagta atattttct cctaatttaa    320280
atgtgtgaca attaggtgtt ggttacaatg attggaacaa ataactact ttagaagtcc     320340
tgacactttt gttttttttt gccattctga ctgtatttga ctatttgaaa ttttattaac   320400
ttctagctac aacttagtaa aagtagtatg gaagagagac agtatgtcga taagggatgc   320460
gggtgtatag attttgtaac catcagggct tttagccaca tgttttttaa gaagtcgctc   320520
ctctctctaa ttcatattaa ttcttttaaat cttctggaaa tattgaaaca cgtctggtgc  320580
attcatttag aagtagattc tgggtagaag tagattctac ccagaggaat agtgtctctc   320640
tccctgatgg tctccctccc tcccttgctc ttcccctccc attcttctct ttccctctct   320700
cgtcctctct gtctctctcc ctctctatgt cctcctccct ctacctctct cctgctccct   320760
ctctctcttt tgctctgtct ctcaccctct ctctcccccct ccttccactg tctctcctcc   320820
ctccctctct ctctccccct cacactgtcc ccccactctc cctgtctttc tccctctctc   320880
tctcttcctc tctctccttt tctctgtctc cccactctct tactcactat ctcctttcct   320940
ctctctcttt ccccccttttc cctctgtccc tctctctctt tgtttctttc tctctctctc   321000
cctcccttttc ttcttctcct gcaaatatga ctttcaccaa aggacctcct tcctggtcag   321060
gtcagcatgc agcactaggg agtgtccaga gtttgctttc ccctctccct tcctctctct   321120
ctctcctgca aatatgactt tcacgaagga cctccttgct gggccagtca gcacgaggtc   321180
ctctgcttgt ccccgtggga gctccaaacc ctccctgggg ccctgctatt aacctggaaa   321240
aagctgatgt tggcaaagtg gagaaagagg aaaccacaaa aacacatgtg catcatgtta   321300
cctcaaccag atgtgcactt gaacgtgtag tcagcatagg cacccgtacc caaccagatg   321360
tgcacttgga cgcctaagca gtagatggtt atgctgccta agtaatggtc agcataggca   321420
gccacacccc tgagccctgc tggagtgcct gaggctttcc ccggaggctc actcagtgga   321480
ttcccagctg tccctttgtg aaggaggctc cctgcagtat ccgatgagag acttcaaaga   321540
ggagtccaca ggaatttgag gcaattggtt ctggaagcag gatcacaaat tcctggctgt   321600
ggcctaaaag gaagaggcag gaaaatctgc agtgcagatc cagccctggg ttgcctggcc   321660
```

```
acacgcaagt gaatattcct aatagccgtc tcagtcatca agacagcttt gtaatttgtt 321720
ctgtgttgtc agtggtcttc agaatggcac cacactgact gaacctgaag ttctcaaaac 321780
cttcatggaa ttttttttt ttttcaggga gtctcactct gtctcccagg caggagtgca 321840
gtggcacaat cttggcttac cgcaacatcc accttctgga ttcaaagcga ttctcctgcc 321900
tcagcctccc gagttgctgg gattacaggc gcccaccact gtgcccggct aattttttgta 321960
tttttagtag agatgggctt tcaccgtgtt ggccaggcta gtctcgaact tcctgacctc 322020
aagtggccca cccacctcga cctcccgaat gattattttt aaagttatca gctggatatg 322080
gtggctcatg gctgttatcc cagcactttg ggaggctgag cggggaggat ggcttgagcc 322140
caggagtttg agaccagcct ggtcaacata gcgagacccc gtttgtacaa aaatgaaaat 322200
aaaaaccagc tgggcctggt ggcgcatgct tgtggtccca gttacttggg gggctgaggt 322260
gggaggatcg cttgagccag ggatgtcgag gctgcagtga gctgtgaggt tccactccag 322320
cctgggtgac agagtgagac cctgtctcaa catacataca tacatacata aaattaaaaa 322380
gtatctttct ttagagtaac tgcaggactt tcttcacttc ggcaccgtct ggacaagttt 322440
ctggatcgct gtgctcctca gtgtcttcat tggcaagata ggacagatga gggtttcctg 322500
aaaatcctcca aactctgaat tccttgagtt tttagttcat aatgttttgc ccatgagacc 322560
aaatggcctt tgatttctta ctagtgctaa tgagggaaa ggctcatatt tgtattaact 322620
ttatttcaaa aacacgataa gtgaagaatc tgatgaacca tttggtagag agatttctat 322680
ggcattttg aaaatacctc gatttcact tttctcaatt gatataatca caattgtaga 322740
tttagaaagc agtcagaacc aacttcagga gtaatcaaac acatgtaagc cacattaatt 322800
ggagggaggt gttaattatt taagtcaata ggttggaaat tattatactt ttgcatcggt 322860
catttctgca aggcatgctt ctaaacagcc catcaatata atcacgaatt atgaaaaata 322920
caagccaggc actgaggctc ctgcctgtct atcatcccag caatttggga ggccaaggtg 322980
ggcagattgc ttgagtccag gagttcaaga caagcctgaa caacatggcg aaaccccgtc 323040
tctacaaaaa agagacgcat ctgttgtccc agctacttgg gaggctgagg tggaaggatc 323100
atttgagcct ggaaggcaga ggctccagcg agccaagatc ccgccactgc actccagcct 323160
gggtagcaga gtgataccct gtctaaaata aaaataaata tagccagact gtttgcctta 323220
ggaattcctt gcctggttat atggtctaat gaagacaaag tacacgtgga aagtgatagt 323280
tttatgaaga tgttcaccac agtattagta tcgtagcaaa gaatgaaatg aaaagctaca 323340
agatcaaaag gagaggaaaa ttataatgaa ccatatgtat ttactcaata ataatttaag 323400
aatttaccta agatatacat cagctggaaa aacagtttag acagctatat aaatattggg 323460
ctcagctatg caaacagac atttgaatgg agggaaagag ctaagaatta tgtgaactcc 323520
tagcatactc attacgctaa ggtgagttgt gtttaaagta tgaattctgg gtgatttttt 323580
tcattatcca actatttag tcttatcagg agttctgtta cttccctaac atacaaataa 323640
atgttttatg tatgttactt tatatacact actgcctaaa ttattgccag tacttatgag 323700
aagggcggga aaggaacttc tcacagcatt ttttccaatt ctgaatgttt taactaatga 323760
aagtatccaa tagaatacat attgactttc tcttttggtt ttttttttt tggacatttt 323820
aaaataatct tcagagccaa gcactcaagt caatacttgc acatttctga cagaaacgtt 323880
cccaggatgg ctttgatgac atactggtca aagccatatt ggtttcaagt tgcggtcctg 323940
tgtgtcatct ttgggcaatc ctccagtctt taaaatcacg tcttcctgat gacagttata 324000
ttttcctcat atttgattgc ttctgtgacc ttaaaaatcg acagggcatg aacttctgga 324060
```

```
ctcacaactg aatgccttat tctttagtgc ccgactcggg ctgggattca cggaaatggc   324120
aggaagcaag tgtaaatgga atgctgattt ttacagcgca cctctcttgt cctatcgtag   324180
ttaaaaatac agattttata cttctggaca tccgtgtagt agactgaact catggagaat   324240
tttaagctac acagaatttt actcctaaaa ttgcccatgc tttttcaagt ttctcagcaa   324300
gtggagcatt tttatatgtg gcaaaataaa atatacacat ctctgagttt ccaatggatg   324360
tagttttgaa agaagtgacc taaaaaatac tccttacttg ggcacccagt tgaggatttc   324420
tttaagcata gctagctgaa tgtatttatt ttaattggca aatcttaata tcttcattag   324480
actcaaggta gaagtagaaa tgcgctcctg aattagcact ctgaagttga ttcaagtgga   324540 tttcttttt tcccataatg aagagatacc tagttttgct tgtgagacaa gagggccttt   324600
gaactggtac tagcttaaag cattttttt cttggaaatg gggaatgcag ttgctcttgg   324660
agtttttata tatggcatct ggaggcaagg aagcaaaaac gacactaaat tgtggaagga   324720
aaaagaaatc acatgtattt taccagtgca ggagaagtgt caatgtggtt tcatttcctt   324780
aaactcgtgt gtgtgtgtgt gtgtgtagaa taacattccc taaaatgaat gttcaggagg   324840
aggggtgaag ggggaatgga aatgaaaatg ggtaaaaggg cccctgacag agctgaatgc   324900
tactacatcc agaaactcac atgcctgaga gacaatcaca gccttcattg ctcagtaaaa   324960
gctgcatttc tgtcctgtgg gtttcatt gcatgtccac aatttgcac ctgcaggtct   325020 cttccagaag gccatcattc agagcggcac cgccctgtcc agctgggcag tgaactacca   325080
gccggccaag tacactcgga tattggcaga caaggtcggc tgcaacatgc tggacaccac   325140
ggacatggta gaatgcctgc ggaacaagaa ctacaaggag ctcatccagc agaccatcac   325200
cccggccacc taccacatag ccttcgggcc ggtgatcgac ggcgacgtca tcccagacga   325260
cccccagatc ctgatggagc aaggcgagtt cctcaactac gacatcatgc tgggcgtcaa   325320
ccaaggggaa ggcctgaagt tcgtggacgg catcgtggat aacgaggacg tgtgacgcc   325380 caacgacttt gacttctccg tgtccaactt cgtggacaac ctttacggct accctgaagg   325440
gaaagacact ttgcgggaga ctatcaagtt catgtacaca gactgggccg ataaggaaaa   325500
cccggagacg cggcggaaaa ccctggtggc tctctttact gaccaccagt gggtggcccc   325560
cgccgtggcc accgccgacc tgcacgcgca gtacggctcc cccacctact tctatgcctt   325620
ctatcatcac tgccaaagcg aaatgaagcc cagctgggca gattcggccc atggtgatga   325680
ggtcccctat gtcttcggca tccccatgat cggtcccacc gagctcttca gttgtaactt   325740
ttccaagaac gacgtcatgc tcagcgccgt ggtcatgacc tactgacga acttcgccaa   325800 aactgggtac gttcatcttc gtgttgggggt atcactatcc ttgccacttg tttgtgtcct   325860
caatataggt gttgcttcta ctgccacgtg caggagcaca cacgcataca cacacataca   325920
catgcatgca cacacataca cacagacaca cgcttacaca cacagcagta acaggcagct   325980
tctcccccaa catctatggc aactcatttt tttctttact cctaaagtgt tataggagta   326040
aaacacttaa ctgtcaaacc agattttac tagagttcta attgcccatt gggaattcca   326100
gagttcctac ctgcaggtgc aggactcata catatatgat ggttctgtta acagctgatt   326160
aaacggtttt gttttttgtcc ttgttgtttt agagacacag tctcactctg ttgcccacac   326220
tggagtgcag tggtgcaaca gtagctcact acagcctcct tgaactccta ggctcaagcc   326280
atcctcctgc ctcagcctcc tgagtagctg ggactacagg tgcctgccac catgcctggc   326340 taattttaa ttttttttt ttggtagaaa gagggtctca ctctgttgcc taggctggag   326400
```

```
tatagtggcg caatcatagc tcactgaagc ctcgagctca tgggttcatg tgatcctccc 326460
atctcagcct cttgagtagc tgggactaca ggcgtgcacc accatgccct tacatggatt 326520
tttgtagaca cagggtttgc tatgttgccc aggcttctct caaactcctg gctcaaggg  326580 atcctcccac atcagccttc tgaatagctg gactacagg tgcacaccac cttactcagc  326640 taatttatt ttgttagaga cagggttttg ctgtgtcacc cgagctggtc tcaaactctt  326700
gggctcaagt gatcttccca cctcagcctc caaaagtgct gagattacag gtgtgagcca  326760
tcacaccagc cctcattaca gagttttaag tctaatttca accatatctc ttttgttaat  326820
ttgcaaggat atcacagcac atgtaccact tggggaactg tgttgattgc ctggccatag  326880
gaatgaaaac aaatatcata ataattataa agaaatataa atatatattc ctatatatat  326940
ttaatgtcta tataaaaata tagatattcc tatttgtata atatagtaca tttatatttg  327000
tatttgtata tatatacaca caaatatatt tgtatataca aatacaaata tatatacaaa  327060
tactatatat atacaatata tatacaaata caaatatata tatacacaaa tacgtttgta  327120
ttttctctgc tatataaata actagagaga gaaaatgaaa atatatgata tttgtatcat  327180
attgctatat gtcatgcata cataaacaca cacacacaaa cacacataca tgtgtatctc  327240
acaggaaagc tcatttattg gcctaaatat agtagaaaat ataaaatata caaaaagcat  327300
atatacaaca gagtctgcca atattctgct gagcggattc tctgcaaacc atggagaaa   327360 agaacccaaa acaacctaaa tagctccaaa cattgtggca tttttcatt ttctcttgtc    327420 taataatgta actgtggaaa tggatggggt gtcattctgt tctaccagtg tgtgcctcca    327480
tcatcaccct gagcctcttt acactgaatg agagagaaag atgtgcctgt cgcccaggga    327540
gggtaaatct tcccgtgcgg aatgaggctc tgagactgca gtggccctgc cacacatgag    327600
ttatgcacag taatccttag aagatctggg gatgctggtg gtttcaatgc ctacgtgttt    327660
agcagctggc atactgtaca aagattccaa agtggtttgg gtagggagtg gtttgagaat    327720
gttttgtgcc cttggcgaaa gtacagcatg ttttggagt ggaaaaggta tcacctggat    327780
accacctttc aataatcaga cttttgtagat ttggtctgag aaaggctacc cagaggagaa    327840
gagaggaggg acccacattt gatgcaaatg cttgtctatc actcaacggt tctttttgt     327900 gtgaagaaat gattgaaatc aaattaatac ttttttttaaa gtaaaccttg tttattagtt   327960
tgttgggact gctgttatca gagtatccaa aactgtatgg ctatgctggg cgcagtggct    328020
catgcctgta acccccagcac tttgggaggc cgaggcagga ggatcacctg aggaggccaa    328080
gagtttaaga ccagcctagg caacatagtg agagtccgtc tctacaaaac aaatgaaaaa    328140
atttagctgt gcatggtagc atatgccgag agtctcagct tctcaggagg ctgaggcaga    328200
gggatcactt gagctcagga ggtcaaggct gcagtgggcc atgtttgcac cactgcactc    328260
caacctgggt gacagaccga aacctttatc tttaaaaaaa aaaaaaaaa aaaaaaaaa      328320 aagcaccaaa aacggtgtgt cttataacaa cagaaatgta tcggttcacg ctttctaagg    328380
ccagaagttg caaatgaagg tgcttgcagg gccaagttcc ctccaaatct gtaggggag     328440 ggtatttcct tgctccttct tagttactgg tgtttgggtg cagtctttgg cattcctacc    328500
ttgcaggtgc accatcccac tctgtgtctt tgtcatctta cggcctccct gtgtgtctct    328560
gtctccacat ggccgtcttc atataagagc atctgccaag gtgcattaga agctcaccct    328620
actctagtat gacctcaact taacataaat agtcatatct gcagttaccc tatttccaaa    328680
taagctcaca tactgagata ctggggttat gacttcagcg tatcttaatt tatgggggaga  328740 cagtattcaa tctctaatac cctgtgaaat cagggccagg ccctcttttg tgacagcact   328800
```

```
gagataggcg gtgtctgccc ttgcagagaa tttcatcctc ttgaagccta aagacttcca 328860
tgagagtttc ccaacatggc tatactcatt caatcttcgc tacattggca tccaaacgta 328920
ttaccgactt ggtctgcaaa cactctcttt acttactctc attaaaaaca tatgcttttt 328980
cttttcctcc ttacatgatt tgaaaataaa ctttatgtga ttatcttaag tggaaagcta 329040
gaatcattcc tcatacattt tatggaacca ttaaaacaat agtgaaatct aaataatgct 329100
gttaaattct cattagctct tcctgacttc caaaggctat gagactgagg ctggctctct 329160
cattattaaa aaaaaataaa aaaaaaaaaa aaggaaaaaa gacagaaaaa gataaaggaa 329220
gttaattagt tccatgaggt gatcgttatc actgctgaca ccaaatggac gcttttacca 329280
agacatcacg aaggtctgag agagccgtga gaagagaata ccacaatgat ctctctgtta 329340
ttgagtgctt ttaatgccat gaatctgttt cttaaaatca cttggcttag agcctgtgat 329400
ttccaccctg catttaggga atacattcac gttgccattc atggtctgtg ttgagggtgc 329460
ttctagcttt catgaaggcc ctgacatggc tggaagagat gaggaaggaa taactgctag 329520
aacttggaga gacgctctga tgctactgaa atcaaaagct gcaggtagag agagttcatt 329580
gaggtaccca gagctcgaat gtcagtccgt ctgaagcctc tattttgtt tcttccgccc 329640 atgggaaaca tccctgaaat aacactgagt gtattaatgc agtgagctct tttaattcat 329700
tggaaaggta ttagaatgac tcaaatgatt cctcaaggaa gttactcaga acttacatct 329760
catgtgaaat gcaacgtgtg gattcaaata caaatagttt aagtgatcac acctccatgg 329820
cagccccata aaagaaggaa atggggaatt tcactgtcgg gcacagtctg gtgagctagg 329880
tattcgtcag tggatgacaa ggacttcagt tgcagttggt agttatttgt ttattgtaaa 329940
ttgggtggtg gcccgatcac tccagggcag agaaggattc cctggtcacc aggtgcagag 330000
aatgaaccaa actgatgccc gcaaggagaa agtatgggat gcaccttatc tgctgtcatg 330060
gtgtgagctg ccaagtttaa cgccattttg cagagcacac actcagatga tgactccacag 330120 aacaggaggg catatttctg cataccatca ctgttccctt ccagcactgg aggtgacagg 330180
aggaaacaag aatagctccc agcgtgtctg tcactacacg gtgccgtgga gaaggatcg 330240 cattgtgcca ggacatactt caccactctc agtgggcgtt aagtcaagcg ttctaaacct 330300
gcaggcacag ccagtctctc gatggcgcat gtgtttgcca agatgaagtg gatgggtct 330360 ggatgcttct atatagacat ctcaaagtag atggttctga cctttagtct aggtttgaag 330420
gcacatatac ctggtataca taaacctttg gttttgggat gagcacagaa aaatgatgtt 330480
gggatgtgca tggcggagaa aaggaaggaa ggagggaggg aatggaggaa agagagttca 330540
gacaaaggaa cgaagggagg gaaggaggga gggaggagg aaaagaaaag gagggcggga 330600
gggaatcaag aaaggagtaa aggaaggagg gaagggagga agaaagagg taagggggga 330660 ggagaggaag gaaagaagaa gggaaggaag gagggaggga aggtgaaagg aagaaaggga 330720
ggaaggaaga aaagatggaa ggaaggaaag gaaagagaga aaagagggaa gagaggaagg 330780
gagaagggag aaagaagaga ggaaggaagg aaagtagcga gggaaggaag gaaaaaatgg 330840
agggagagag aaagaaggaa gggagggagg aaggaagagg gaggaaaaag ggaatggagg 330900
aggagaggaa gaagggaggg agggaaagaa ggaaaacagg gaaaagagg gtaagagaga 330960 gaaaagaggg aaggggggaga ggaggaagga aagaaggagg gagggaggga caattggatc 331020
tttgcttata aattatgtca cctgtatatt ttcatggtag cattaggtga gagggctctc 331080
ccatcttaga aaggcggagt cagcgagtac gcatagtaga aatgaggagg aagtccctac 331140
```

```
ggaggctcta aattatgaaa accttgatca agaaaggatg ttgaaatcat tgaatgccag   331200
ggcctcaagt aatccttgct atttcttttt tattattatt ttgaatgggg aagcagttgc   331260
ccaggcctgt gcctgagggg gatcctcccc tgtagcaagg aggtgtttca atgttagtcc   331320
aggtcagagg actaaaatca tgctggaaga gaaccgtgtg agcccaaaca tgcagaggca   331380
ttgtagaaat aaggtagatt gagaccgttt ttggaaatca gctgcagtgt caaggagaag   331440
tgaaaactaa ctctaaagtt tcaaaagggt tctagagcat taaagtcctt ttcctggaaa   331500
attactttgg gaataggaga aaaagggttc gtccaagctg atcaatgaaa ttcaggtgct   331560
cagtgatcca ggattctttc attttgagct ctgtgtggaa agagatggac aaaaaggagt   331620
ggggaatctt ggtttattta taaggtatga caaagaacag tgctttaaag taaccaaaca   331680
atgcattata atatagaata gaagacctta tgtgctattg gaagtcagat atgagaagag   331740
agttttgtaa tggaaaatca gatcaacaca tatttttgatt tttttatgtt gttccatcga   331800
gtctgggggtt tgtacggcag attgatttct gtcctgtttg catcagctac catcactgct   331860
tttgaatgtg ctggtatcct atgattaatt tacgttcaac tattgttaaa tctttgggaa   331920
aaaaaagaag ttccaatgag gtatttagtg gggatggggtt acagagagtt gcagcgtaat   331980
tctggctgta aaggcgacct ttattaccaa aaaggaattt taagctgaat gaatgaacat   332040
ccccacctgg tgtggaagag gagtcactga atgcataata aactagtccg gtaataatcg   332100
ttaactgcga acaatgtttt gggtatgagg aaaacctgta ctacttaaag gaacagctga   332160
gaggattcac agatattttt agagagatca tagtactata tccatctcca gctaaagaaa   332220
tgaactagac cttagaaagg cacttgagtc tctgctgcca agatgacatc tcaaataaaa   332280
caggacaggt ggaaatggct gtgttaggtg ctgggggata aggaggaaga catgcattga   332340
gtcttttact agagagacca acttgtgttt ctgtcctcaa tcattatagt ctttaatttt   332400
actcacagga gtttaaacac ttcttaggct gaataaagtc taaaaaacaa aacactgata   332460
ccccacatct agacctcact gtctggaggg tttggtaagg gagaatgact tgggctatca   332520
taatctccac aagtttatct ggctttaaga attctggctg tgcatctccg agatctttaa   332580
tagacagacg gtatcaggtg gcagctcatt tatatggatt ttccaaatcc tctgctttat   332640
tcttcaagaa caaaatataa tgtgttttct ttacctttca aatatacccct gagttccttc   332700
gaaaatagcc ttgtacccaa catgaacaga atactccttt tcctagatgc tcactgctta   332760
atagatgagg tagccacaca tctaatagat ccaattcagt aaaattggat ccatggaaaa   332820
aaaggtagaa tcttcacttc catttgtttc tttagaatat taaaaatcaa taactaatat   332880
tagtggattt ttttcctaaa atattcattc acttattttt ctttcagtac acgttaaata   332940
actgaaaatt ttaaaattat ttcagaggac ttaaagagca aaagaaacat gagttgctgc   333000
attgaatcca acattttttc aaaaccatgt aagaatacat gcataataaa taaaaaaagc   333060
agaagacttt tcaaatatat tgtttatcag taaataagaa aactcatggt attagaacct   333120
atgagattat atatatttgt tctcacccta ttagtaaagt gaaaacacag cagttagtgt   333180
gcattcaact aaagggtaga ggtcaacttt cttttttctcc tgtattatgt tatacatcta   333240
atatctatat ctatagatag atatacacat acacatatat acacatgaca tacatatata   333300
tactgcatat agtatatagt tagtatgcag tataaactgt ggtatgcagt atacttgtat   333360
atagtatgta atatacaata tacttttatg cactctacaa tgtatacaat atagaaattc   333420
agtatgtact ctgatataca gtatatcact ccctacttct ccctccccttg caatattata   333480
ggtgttctat tttttatatt ggaagagagg gggtaatatt tcctgaattc ttaccatatg   333540
```

```
ccagacatct tgtcattatc tttcaacctt catcacttac ctccaaccct gatattttca 333600
tcagccatgt agaggagtaa gttaaggcca atactggctg gaaaacttgc ttaagatttc 333660
acagctctta actagccaga gctgcagaaa gttgaataca gggaaatgat ttattttatc 333720
accaccacag actcagactg aggggataaa atcttccttc agcaagtgtg gcgcctctgg 333780
ctcaagtata ttgtttgaat cctgcacagt gtctggtaat ggctacagat acatgatctt 333840
ccttggtcct gcagccttct gccatgcagg ccatgcaatg actggaggca gtttcacaga 333900
agtcccgcca aggagaagtt acctggaaga tagcccttag ctcacacctg gagccattga 333960
tcaggatgtt gcaactccct gcttgcctgg ttctgcacat cacatctcaa tgctcagtgc 334020
taactagtac ataacatttt gccatgcata atctcaaatc gtttttataa caaataaacc 334080
ttaagacgta attgttttt agcttacttt acaagccata aaaaaaatgg aagaaatgag 334140
catttggtaa tttattttt gaaggggaag tgttatccta aaagagtcag ttgcaaagat 334200
gtttattaaa ggccctatgt tttatgaatt atctccaaat ttttatgatt ctccttctac 334260
ctgtgaccac ttgtgcaaat aataagaaga taattctttg gctcatagtt tccaagcaca 334320
acttagcatc tgtaacagcc cttgacttgt ttctgggtgt cttttttatc ttaaacatgt 334380
taacctcatc ataactatat gtaccatttt agcaaacttc ttacagctaa catagcgtgc 334440
tttcatcttt ttaccttcaa atagagagca aacacatggt gcatatgtct atttacaaac 334500
actttgtaat tataaagcct attttattt ctactgttaa tatcaatttt cattgctaaa 334560
actgcaacat ttattcattt acttcaaaag caattcttga gcaagaaaga gaatacccat 334620
ttcttggaca atagcttctt aatcagaatt tctcaacctc agtactgtta acatttgggt 334680
ccagataact tctttgctgt gggggtctct cctgtgcacc agagggtatt tagtagcatc 334740
cctcacctcc acccttcata gaacaaccct tcgtctacgg aaaccaaaag tgtctccaga 334800
tactgccaaa tatcccttg gagcaaatca gtcctggatg agttttacag ttcgacaaga 334860
gtgaaacttg aaatactgaa atttttccta gagacactta gttttccttc tttccctta 334920 tttttgaaga tcatttgatg ccttaaaaaa tagtaaacat gttataaaaa ttgcataatg 334980
ctgctatcag gatttatatt taaaagaaaa ataagagcaa ttttttaaagg aaaagacaac 335040 atggtagaca ggtctaggat taaagcagaa tgtacctttg ctgcttgggt attttgtgct 335100
cattgataaa tatatatgaa gagcagattg taacttcctg atttattggt ttaagataat 335160
ttcacgtcac atgtggaaga gtatgacctt tcttttttc ttccttctat cctcagtgat 335220
ccaaatcaac cagttcctca ggataccaag ttcattcaca caaaacccaa ccgctttgaa 335280
gaagtggcct ggtccaagta taatcccaaa gaccagctct atctgcatat tggcttgaaa 335340
cccagagtga gagatcacta ccgggcaacg aaagtggctt tctggttgga actcgttcct 335400
catttgcaca acttgaacga gatattccag tatgtttcaa caaccacaaa ggttcctcca 335460
ccagacatga catcatttcc ctatggcacc cggcgatctc ccgccaagat atggccaacc 335520
accaaacgcc cagcaatcac tcctgccaac aatcccaaac actctaagga ccctcacaaa 335580
acagggcctg aggacacaac tgtcctcatt gaaaccaaac gagattattc caccgaatta 335640
agtgtcacca ttgccgtcgg ggcgtcgctc ctcttcctca acatcttagc ttttgcggcg 335700
ctgtactaca aaaaggacaa gaggcgccat gagactcaca ggcgcccag tccccagaga 335760 aacaccacaa atgatatcgc tcacatccag aacgaagaga tcatgtctct gcagatgaag 335820
cagctggaac acgatcacga gtgtgagtcg ctgcaggcac acgacacact gaggctcacc 335880
```

```
tgcccgccag actacaccct cacgctgcgc cggtcgccag atgacatccc acttatgacg    335940
ccaaacacca tcaccatgat tccaaacaca ctgacgggga tgcagccttt gcacactttt    336000
aacaccttca gtggaggaca aaacagtaca aatttacccc acggacattc caccactaga    336060
gtatagcttt gccctatttc ccttcctatc cctctgccct acccgctcag caacatagaa    336120
gagggaagga aagagagaag gaaagagaga gagaaagaaa gtctccagac caggaatgtt    336180
tttgtcccac tgacttaaga caaaaatgca aaaaggcagt catcccatcc cggcagaccc    336240
ttatcgttgg tgttttccag tattacaaga tcaacttctg accctgtgaa atgtgagaag    336300
tacacatttc tgttaaaata actgctttaa gatctctacc actccaatcg atgtttagtg    336360
tgataggaca tcaccatttc aaggccccgg gtgtttccaa cgtcatggaa gcagctgaca    336420
cttctgaaac tcagccaagg acacttgata tttttttaatt acaatggaag tttaaacatt    336480
tctttctgtg ccacacaatg gatggctctc cttaagtgaa gaaagagtca atgagatttt    336540
gcccagcaca tggagctgta atccagagag aaggaaacgt agaaatttat tattaaaaga    336600
atggactgtg cagcgaaatc tgtacggttc tgtgcaaaga ggtgttttgc cagcctgaac    336660
tatatttaag agactttgta aaaagaaaa atgtatatag ctgtgagttt aaacaaaaac    336720
cacaaacaga caaacaagaa aaaagctttt tattggtgtt ttcactttga aagagctttt    336780
agcaaggttg tgcttttcat tgtgctctgt acgtatataa atatatatat atatacacac    336840
acacacacac attagtcata tcacctctgt ttcctcccca acaaaagagg cttttcttct    336900
taattacttg tggtaaacaa agacatggga ttttcttaca tgagattctc atttgtagga    336960
ggatgtgatg tcccacagaa gacccagacg gtctgtgtgg cctatttccc ccgtcaggtt    337020
gcacaggtgc atgcaagagc attcttagga gaccactgtt ttgaaaaact tttgacttgt    337080
acgtgttagc cttcatgaaa ttgcagtaca gagatgggtc cccaaagtgg agtgtattta    337140
cagcttgtta aattagagac atgcacacac aaagaatcag tagggagaaa caaaaataca    337200
agtcccgttc tgtagctctg gccctttgaa tatgttaggg aagagttgct tcccatttca    337260
gggccctgcc aaaaaaagaa gaaagcttgc ctttggtggg gctatgcccc ttggagtaaa    337320
tacggctctg tgttccctag cagctgcggg agggtttggc cgatgaagta cctgctcagc    337380
ttagctaatc agattgaagg aagacatgtg tctttccttt ttgtttaagc actcggtccc    337440
ttatttatca gtaagcaggt ttttaaaaat cttttatatc attttatggga tcaaacatat    337500
gattgtctga aaacatcact ttttgtggat ttgtgtatcc ggtcaccaaa cggtgaatat    337560
tatagaagaa tgggggaaga aaggatagaa tattaaaact gctttgcatg ggttttctgg    337620
gaaattagga taacttcact gagaagacat tgaatggaaa ttattcaccc atttttaaatt    337680
ggtgacctag ggatcagaga tttgtctttc caacagcttg tcattttttc atttctcttc    337740
tcattttttca ggaaagtttt gagtgttata aggtggaagg aaacatagta gcaatggata    337800
cttttttgaa aaattattgc attaccaaga aacagtagcc aaagatattt gaagatcatg    337860
ttcctcggct ccattgtggg ttattctaga aatccagtct taaatctctc cgctaaagtg    337920
gacattcccc ataaaaattg tccagctgcc tggctctttt gcaataacaa cctttgatta    337980
ctgaatccct acactcaaac tatagtgata tatcagtgtt tgagagtgac ctctagaaaa    338040
aagaaaagtg ttttttagaaa tgcgtacaag tcacccccaa atcctattgc ttatcttggg    338100
ttaaatttga gagtgattct ctgtatataa atatgtgaaa tattattatc tcaacttagc    338160
acacgtgaag caacatttct ttcctacaga gaggtgtcat ggtaagattt cattccgaat    338220
tcattgtttc atagagctat gatcaggcca tttctgcaag caatgtatga ccccacctga    338280
```

```
gcaaccacaa ataggctctc tgtgaaacta caaaggaagt tatgtgtggc atccatgttg    338340
gtttcgtctg tctgtaatgt gaattccagt atttgtttag tatttccagt tgtctcctgc    338400
tagcaatatg tacagtaacg cgtcaggctt gtgacatttg aataaggaaa aacagagttc    338460
ctgttaagtg aataacttta gcttttacag gggattatga tcaaaagtga ttttagtaca    338520
tcttaaatga tatcttattt ctacatggaa agaagttata gaatcttcat agagttctat    338580
gagaaaaaat atacttgcta tctataaaaa agagaaaaaa gaaaaaaaat gagaaaaaag    338640
taagaaaaaa aaaaatcctg tcctaggctt ttactcttga tcttcaaagg cacgcagggt    338700
ttaatggttc cttgggttat tattttgcag ttttgttttt tattttgcct taagtaatga    338760
tagaagatat atatggccgg acacatatgt ataaactttt cagcagcatt tttaataata    338820
aaatatcaca gtattttcta atgctttgtg caaataa                             338857

<210> SEQ ID NO 2
<211> LENGTH: 5672
<212> TYPE: DNA
<213> ORGANISM: Homo sapiens

<400> SEQUENCE: 2
agaaggggaa ggctcctggg cttttcaatac atcctcctga atcataccte gtttcgggtt      60 ccctagaaaa atctggacgt gtaaaaagaa ctcttaacgg ccgatgcagc tcttccaaag     120
ctaaggctgc cttggagttt tcataagaaa ttgtccctgg aggtgttgga tgatcacagc     180
ttccttggag cattgcagtt gctggaatcc agtttcagga ttaagggagg gctgcctcct     240
tgcaatgggc tgccaagaaa acggctgtgc ttgttcttaa cctcaggctc tgtctgtgat     300
cagtctgaga gtctctccca ggtctactgc tccctggaaa gccctatctc tctgcaggct     360
cgcctctggg ctttgtctcc ttggagccac atcactggga cagctgtgga tgtggatgca     420
gatttgaacc atgtcacggc cccagggact gctatggctt cctttgttgt tcaccccggt     480
ctgcgtcatg ttaaactcca atgtcctcct gtggttaact gctcttgcca tcaagttcac     540
cctcattgac agccaagcac agtatccagt tgtcaacaca aattatgcaa aaatccgggg     600
cctaagaaca ccgttaccca atgagatctt gggtccagtg gagcagtact tagggggtccc    660 ctatgcctca cccccactg gagagaggcg gtttcagccc ccagaacccc cgtcctcctg      720
gactggcatc cgaaatacta ctcagttttgc tgctgtgtgc ccccagcacc tggatgagag    780
atccttactg catgacatgc tgcccatctg gtttaccgcc aatttggata ctttgatgac    840
ctatgttcaa gatcaaaatg aagactgcct ttacttaaac atctacgtgc ccacggaaga    900
tgatattcat gatcagaaca gtaagaagcc cgtcatggtc tatatccatg ggggatctta    960
catggagggc accggcaaca tgattgacgg cagcattttg gcaagctacg aaacgtcat    1020 cgtgatcacc attaactacc gtctgggaat actagggttt ttaagtaccg gtgaccaggc   1080
agcaaaaggc aactatgggc tcctggatca gattcaagca ctgcggtgga ttgaggagaa   1140
tgtgggagcc tttggcgggg accccaagag agtgaccatc tttggctcgg gggctggggc   1200
ctcctgtgtc agcctgttga ccctgtccca ctactcagaa ggtctcttcc agaaggccat   1260
cattcagagc ggcaccgccc tgtccagctg ggcagtgaac taccagccgg ccaagtacac   1320
tcggatattg gcagacaagg tcggctgcaa catgctggac accacggaca tggtagaatg   1380
cctgcggaac aagaactaca aggagctcat ccagcagacc atcaccccgg ccacctacca   1440
catagccttc gggccggtga tcgacggcga cgtcatccca gacgaccccc agatcctgat   1500
```

```
ggagcaaggc gagttcctca actacgacat catgctgggc gtcaaccaag gggaaggcct    1560
gaagttcgtg gacggcatcg tggataacga ggacggtgtg acgcccaacg actttgactt    1620
ctccgtgtcc aacttcgtgg acaaccttta cggctaccct gaagggaaag acactttgcg    1680
ggagactatc aagttcatgt acacagactg ggccgataag gaaaacccgg agacgcggcg    1740
gaaaaccctg gtggctctct ttactgacca ccagtgggtg gcccccgccg tggccaccgc    1800
cgacctgcac gcgcagtacg gctcccccac ctacttctat gccttctatc atcactgcca    1860
aagcgaaatg aagcccagct gggcagattc ggcccatggt gatgaggtcc cctatgtctt    1920
cggcatcccc atgatcggtc ccaccgagct cttcagttgt aacttttcca gaacgacgt     1980 catgctcagc gccgtggtca tgacctactg gacgaacttc gccaaaactg tgatccaaa     2040 tcaaccagtt cctcaggata ccaagttcat tcacacaaaa cccaaccgct ttgaagaagt    2100
ggcctggtcc aagtataatc ccaaagacca gctctatctg catattggct gaaacccag     2160 agtgagagat cactaccggg caacgaaagt ggctttctgg ttggaactcg ttcctcattt    2220
gcacaacttg aacgagatat ccagtatgt ttcaacaacc acaaaggttc ctccaccaga     2280
catgacatca tttccctatg gcacccggcg atctcccgcc aagtatggc aaccaccaa      2340 acgcccagca atcactcctg ccaacaatcc caaacactct aaggaccctc acaaaacagg    2400
gcctgaggac acaactgtcc tcattgaaac caaacgagat tattccaccg aattaagtgt    2460
caccattgcc gtcggggcgt cgctcctctt cctcaacatc ttagcttttg cggcgctgta    2520
ctacaaaaag acaagaggc gccatgagac tcacaggcgc cccagtcccc agagaaacac     2580
cacaaatgat atcgctcaca tccagaacga agagatcatg tctctgcaga tgaagcagct    2640
ggaacacgat cacgagtgtg agtcgctgca ggcacacgac acactgaggc tcacctgccc    2700
gccagactac accctcacgc tgcgccggtc gccagatgca atcccacttα tgacgccaaa    2760 caccatcacc atgattccaa acacactgac ggggatgcag cctttgcaca cttttaacac    2820
cttcagtgga ggacaaaaca gtacaaattt accccacgga cattccacca ctagagtata    2880
gctttgccct atttcccttc ctatccctct gccctacccg ctcagcaaca tagaagaggg    2940
aaggaaagag agaaggaaag agagagagaa agaaagtctc cagaccagga atgttttgt     3000 cccactgact taagacaaaa atgcaaaaag gcagtcatcc catcccggca gacccttatc    3060
gttggtgttt tccagtatta caagatcaac ttctgaccct gtgaaatgtg agaagtacac    3120
atttctgtta aaataactgc tttaagatct ctaccactcc aatcgatgtt tagtgtgata    3180
ggacatcacc atttcaaggc cccgggtgtt tccaacgtca tggaagcagc tgacacttct    3240
gaaactcagc caaggacact tgatatttt taattacaat ggaagtttaa acatttcttt    3300
ctgtgccaca caatggatgg ctctccttaa gtgaagaaag agtcaatgag attttgccca    3360
gcacatggag ctgtaatcca gagagaagga aacgtagaaa tttattatta aagaatgga    3420 ctgtgcagcg aaatctgtac ggttctgtgc aaagaggtgt tttgccagcc tgaactatat    3480
ttaagagact ttgtaaaaaa gaaaatgta tatagctgtg agtttaaaca aaaccacaa      3540 acagacaaac aagaaaaaaa gctttattg gtgttttcac tttgaaagag cttttagcaa     3600
ggttgtgctt ttcattgtgc tctgtacgta tataaatata tatatatata cacacacaca    3660
cacacattag tcatatcacc tctgtttcct ccccaacaaa agaggctttt cttcttaatt    3720
acttgtggta aacaaagaca tgggattttc ttacatgaga ttctcatttg taggaggatg    3780
tgatgtccca cagaagaccc agacggtctg tgtggcctat ttccccgtc aggttgcaca    3840 ggtgcatgca agagcattct taggagacca ctgttttgaa aaacttttga cttgtacgtg    3900
```

```
ttagccttca tgaaattgca gtacagagat gggtccccaa agtggagtgt atttacagct    3960
tgttaaatta gagacatgca cacacaaaga atcagtaggg agaaacaaaa atacaagtcc    4020
cgttctgtag ctctggccct ttgaatatgt ttaggaagag ttgcttccca tttcagggcc    4080
ctgccaaaaa aagaagaaag cttgcctttg gtggggctat gccccttgga gtaaatacgg    4140
ctctgtgttc cctagcagct gcgggagggt ttggccgatg aagtacctgc tcagcttagc    4200
taatcagatt gaaggaagac atgtgtcttt cctttttgtt taagcactcg gtcccttatt    4260
tatcagtaag caggttttta aaaatctttt atatcattta tgggatcaaa catatgattg    4320
tctgaaaaca tcacttttg tggatttgtg tatccggtca ccaaacggtg aatattatag    4380
aagaatgggg gaagaaagga tagaatatta aaactgcttt gcatgggttt tctgggaaat    4440
taggataact tcactgagaa gacattgaat ggaaattatt cacccatttt aaattggtga    4500
cctagggatc agagatttgt ctttccaaca gcttgtcatt ttttcatttc tcttctcatt    4560
tttcaggaaa gttttgagtg ttataaggtg aaggaaaca tagtagcaat ggatactttt    4620
ttgaaaaatt attgcattac caagaaacag tagccaaaga tatttgaaga tcatgttcct    4680
cggctccatt gtgggttatt ctagaaatcc agtcttaaat ctctccgcta aagtggacat    4740
tccccataaa aattgtccag ctgcctggct cttttgcaat aacaacctt gattactgaa     4800 tccctacact caaactatag tgatatatca gtgtttgaga gtgacctcta gaaaaagaa     4860 aagtgttttt agaaatgcgt acaagtcacc cccaaatcct attgcttatc ttgggttaaa    4920
tttgagagtg attctctgta tataaatatg tgaaatatta ttatctcaac ttagcacacg    4980
tgaagcaaca tttctttcct acagagaggt gtcatggtaa gatttcattc cgaattcatt    5040
gtttcataga gctatgatca ggccatttct gcaagcaatg tatgacccca cctgagcaac    5100
cacaaatagg ctctctgtga aactacaaag gaagttatgt gtggcatcca tgttggtttc    5160
gtctgtctgt aatgtgaatt ccagtatttg tttagtattt ccagttgtct cctgctagca    5220
atatgtacag taacgcgtca ggcttgtgac atttgaataa ggaaaaacag agttcctgtt    5280
aagtgaataa ctttagcttt tacaggggat tatgatcaaa agtgattta gtacatctta    5340 aatgatatct tatttctaca tggaaagaag ttatagaatc ttcatagagt tctatgagaa    5400
aaaatatact tgctatctat aaaaaagaga aaaagaaaa aaaatgagaa aaaagtaaga    5460
aaaaaaaaaa tcctgtccta ggcttttact cttgatcttc aaaggcacgc agggtttaat    5520
ggttccttgg gttattattt tgcagttttg tttttttattt tgccttaagt aatgatagaa    5580
gatatatatg gccggacaca tatgtataaa cttttcagca gcattttaa taataaaata    5640 tcacagtatt ttctaaaaa aaaaaaaaaa aa                                   5672
```

<210> SEQ ID NO 3
<211> LENGTH: 21
<212> TYPE: DNA
<213> ORGANISM: Artificial sequence
<220> FEATURE:
<223> OTHER INFORMATION: polynucleotide

<400> SEQUENCE: 3

```
cggctgcaac ttctcgcgca a                                                21
```

<210> SEQ ID NO 4
<211> LENGTH: 816
<212> TYPE: PRT
<213> ORGANISM: Homo sapiens

```
<400> SEQUENCE: 4

Met Ser Arg Pro Gln Gly Leu Leu Trp Leu Pro Leu Leu Phe Thr Pro
1               5                   10                  15

Val Cys Val Met Leu Asn Ser Asn Val Leu Leu Trp Leu Thr Ala Leu
                20                  25                  30

Ala Ile Lys Phe Thr Leu Ile Asp Ser Gln Ala Gln Tyr Pro Val Val
            35                  40                  45

Asn Thr Asn Tyr Gly Lys Ile Arg Gly Leu Arg Thr Pro Leu Pro Asn
        50                  55                  60

Glu Ile Leu Gly Pro Val Glu Gln Tyr Leu Gly Val Pro Tyr Ala Ser
65                  70                  75                  80

Pro Pro Thr Gly Glu Arg Arg Phe Gln Pro Pro Glu Pro Pro Ser Ser
                85                  90                  95

Trp Thr Gly Ile Arg Asn Thr Thr Gln Phe Ala Ala Val Cys Pro Gln
            100                 105                 110

His Leu Asp Glu Arg Ser Leu Leu His Asp Met Leu Pro Ile Trp Phe
        115                 120                 125

Thr Ala Asn Leu Asp Thr Leu Met Thr Tyr Val Gln Asp Gln Asn Glu
130                 135                 140

Asp Cys Leu Tyr Leu Asn Ile Tyr Val Pro Thr Glu Asp Asp Ile His
145                 150                 155                 160

Asp Gln Asn Ser Lys Lys Pro Val Met Val Tyr Ile His Gly Gly Ser
                165                 170                 175

Tyr Met Glu Gly Thr Gly Asn Met Ile Asp Gly Ser Ile Leu Ala Ser
            180                 185                 190

Tyr Gly Asn Val Ile Val Ile Thr Ile Asn Tyr Arg Leu Gly Ile Leu
        195                 200                 205

Gly Phe Leu Ser Thr Gly Asp Gln Ala Ala Lys Gly Asn Tyr Gly Leu
210                 215                 220

Leu Asp Gln Ile Gln Ala Leu Arg Trp Ile Glu Glu Asn Val Gly Ala
225                 230                 235                 240

Phe Gly Gly Asp Pro Lys Arg Val Thr Ile Phe Gly Ser Gly Ala Gly
                245                 250                 255

Ala Ser Cys Val Ser Leu Leu Thr Leu Ser His Tyr Ser Glu Gly Leu
            260                 265                 270

Phe Gln Lys Ala Ile Ile Gln Ser Gly Thr Ala Leu Ser Ser Trp Ala
        275                 280                 285

Val Asn Tyr Gln Pro Ala Lys Tyr Thr Arg Ile Leu Ala Asp Lys Val
290                 295                 300

Gly Cys Asn Met Leu Asp Thr Thr Asp Met Val Glu Cys Leu Arg Asn
305                 310                 315                 320

Lys Asn Tyr Lys Glu Leu Ile Gln Gln Thr Ile Thr Pro Ala Thr Tyr
                325                 330                 335

His Ile Ala Phe Gly Pro Val Ile Asp Gly Asp Val Ile Pro Asp Asp
            340                 345                 350

Pro Gln Ile Leu Met Glu Gln Gly Glu Phe Leu Asn Tyr Asp Ile Met
        355                 360                 365

Leu Gly Val Asn Gln Gly Glu Gly Leu Lys Phe Val Asp Gly Ile Val
370                 375                 380

Asp Asn Glu Asp Gly Val Thr Pro Asn Asp Phe Asp Phe Ser Val Ser
385                 390                 395                 400

Asn Phe Val Asp Asn Leu Tyr Gly Tyr Pro Glu Gly Lys Asp Thr Leu
                405                 410                 415
```

```
Arg Glu Thr Ile Lys Phe Met Tyr Thr Asp Trp Ala Asp Lys Glu Asn
                420             425             430

Pro Glu Thr Arg Arg Lys Thr Leu Val Ala Leu Phe Thr Asp His Gln
                435             440             445

Trp Val Ala Pro Ala Val Ala Thr Ala Asp Leu His Ala Gln Tyr Gly
450                 455             460

Ser Pro Thr Tyr Phe Tyr Ala Phe Tyr His His Cys Gln Ser Glu Met
465                 470             475                 480

Lys Pro Ser Trp Ala Asp Ser Ala His Gly Asp Glu Val Pro Tyr Val
                485             490             495

Phe Gly Ile Pro Met Ile Gly Pro Thr Glu Leu Phe Ser Cys Asn Phe
                500             505             510

Ser Lys Asn Asp Val Met Leu Ser Ala Val Val Met Thr Tyr Trp Thr
                515             520             525

Asn Phe Ala Lys Thr Gly Asp Pro Asn Gln Pro Val Pro Gln Asp Thr
                530             535             540

Lys Phe Ile His Thr Lys Pro Asn Arg Phe Glu Glu Val Ala Trp Ser
545                 550             555                 560

Lys Tyr Asn Pro Lys Asp Gln Leu Tyr Leu His Ile Gly Leu Lys Pro
                565             570             575

Arg Val Arg Asp His Tyr Arg Ala Thr Lys Val Ala Phe Trp Leu Glu
                580             585             590

Leu Val Pro His Leu His Asn Leu Asn Glu Ile Phe Gln Tyr Val Ser
                595             600             605

Thr Thr Thr Lys Val Pro Pro Asp Met Thr Ser Phe Pro Tyr Gly
                610             615             620

Thr Arg Arg Ser Pro Ala Lys Ile Trp Pro Thr Thr Lys Arg Pro Ala
625                 630             635                 640

Ile Thr Pro Ala Asn Asn Pro Lys His Ser Lys Asp Pro His Lys Thr
                645             650             655

Gly Pro Glu Asp Thr Thr Val Leu Ile Glu Thr Lys Arg Asp Tyr Ser
                660             665             670

Thr Glu Leu Ser Val Thr Ile Ala Val Gly Ala Ser Leu Leu Phe Leu
                675             680             685

Asn Ile Leu Ala Phe Ala Ala Leu Tyr Tyr Lys Lys Asp Lys Arg Arg
                690             695             700

His Glu Thr His Arg Arg Pro Ser Pro Gln Arg Asn Thr Thr Asn Asp
705                 710             715                 720

Ile Ala His Ile Gln Asn Glu Glu Ile Met Ser Leu Gln Met Lys Gln
                725             730             735

Leu Glu His Asp His Glu Cys Glu Ser Leu Gln Ala His Asp Thr Leu
                740             745             750

Arg Leu Thr Cys Pro Pro Asp Tyr Thr Leu Thr Leu Arg Arg Ser Pro
                755             760             765

Asp Asp Ile Pro Leu Met Thr Pro Asn Thr Ile Thr Met Ile Pro Asn
                770             775             780

Thr Leu Thr Gly Met Gln Pro Leu His Thr Phe Asn Thr Phe Ser Gly
785                 790             795                 800

Gly Gln Asn Ser Thr Asn Leu Pro His Gly His Ser Thr Thr Arg Val
                805             810             815

<210> SEQ ID NO 5
<211> LENGTH: 21
```

```
<212> TYPE: DNA
<213> ORGANISM: Artificial sequence
<220> FEATURE:
<223> OTHER INFORMATION: Primer

<400> SEQUENCE: 5
aaagccctat ctctctgcag g                                              21

<210> SEQ ID NO 6
<211> LENGTH: 22
<212> TYPE: DNA
<213> ORGANISM: Artificial sequence
<220> FEATURE:
<223> OTHER INFORMATION: Primer

<400> SEQUENCE: 6
tgagtagtat ttcggatgcc ag                                             22

<210> SEQ ID NO 7
<211> LENGTH: 22
<212> TYPE: DNA
<213> ORGANISM: Artificial sequence
<220> FEATURE:
<223> OTHER INFORMATION: Primer

<400> SEQUENCE: 7
aagaacaccg ttacccaatg ag                                             22

<210> SEQ ID NO 8
<211> LENGTH: 23
<212> TYPE: DNA
<213> ORGANISM: Artificial sequence
<220> FEATURE:
<223> OTHER INFORMATION: Primer

<400> SEQUENCE: 8
gagacattat aaaaccctcc tag                                            23

<210> SEQ ID NO 9
<211> LENGTH: 22
<212> TYPE: DNA
<213> ORGANISM: Artificial sequence
<220> FEATURE:
<223> OTHER INFORMATION: Primer

<400> SEQUENCE: 9
ttagcattgg tgagtcagtg tg                                             22

<210> SEQ ID NO 10
<211> LENGTH: 22
<212> TYPE: DNA
<213> ORGANISM: Artificial sequence
<220> FEATURE:
<223> OTHER INFORMATION: Primer

<400> SEQUENCE: 10
ccgtcaaaac gagaagtgga ct                                             22

<210> SEQ ID NO 11
<211> LENGTH: 20
<212> TYPE: DNA
<213> ORGANISM: Artificial sequence
<220> FEATURE:
<223> OTHER INFORMATION: Primer

<400> SEQUENCE: 11
```

```
cttttctat ttggccacca                                                    20

<210> SEQ ID NO 12
<211> LENGTH: 21
<212> TYPE: DNA
<213> ORGANISM: Artificial sequence
<220> FEATURE:
<223> OTHER INFORMATION: Primer

<400> SEQUENCE: 12
ttcttggttc agggtatttg c                                                 21

<210> SEQ ID NO 13
<211> LENGTH: 20
<212> TYPE: DNA
<213> ORGANISM: Artificial sequence
<220> FEATURE:
<223> OTHER INFORMATION: Primer

<400> SEQUENCE: 13
agctgcattt ctgtcctgtg                                                   20

<210> SEQ ID NO 14
<211> LENGTH: 20
<212> TYPE: DNA
<213> ORGANISM: Artificial sequence
<220> FEATURE:
<223> OTHER INFORMATION: Primer

<400> SEQUENCE: 14
tctcccgcaa agtgtctttc                                                   20

<210> SEQ ID NO 15
<211> LENGTH: 20
<212> TYPE: DNA
<213> ORGANISM: Artificial sequence
<220> FEATURE:
<223> OTHER INFORMATION: Primer

<400> SEQUENCE: 15
ccaacttcgt ggacaacctt                                                   20

<210> SEQ ID NO 16
<211> LENGTH: 20
<212> TYPE: DNA
<213> ORGANISM: Artificial sequence
<220> FEATURE:
<223> OTHER INFORMATION: Primer

<400> SEQUENCE: 16
accccaacac gaagatgaac                                                   20

<210> SEQ ID NO 17
<211> LENGTH: 20
<212> TYPE: DNA
<213> ORGANISM: Artificial sequence
<220> FEATURE:
<223> OTHER INFORMATION: Primer

<400> SEQUENCE: 17
cacgtcacat gtggaagagt                                                   20

<210> SEQ ID NO 18
<211> LENGTH: 20
<212> TYPE: DNA
<213> ORGANISM: Artificial sequence
```

```
<220> FEATURE:
<223> OTHER INFORMATION: Primer

<400> SEQUENCE: 18
gacggcaatg gtgacactta                                              20

<210> SEQ ID NO 19
<211> LENGTH: 20
<212> TYPE: DNA
<213> ORGANISM: Artificial sequence
<220> FEATURE:
<223> OTHER INFORMATION: Primer

<400> SEQUENCE: 19
tcctcattga aaccaaacga                                              20

<210> SEQ ID NO 20
<211> LENGTH: 20
<212> TYPE: DNA
<213> ORGANISM: Artificial sequence
<220> FEATURE:
<223> OTHER INFORMATION: Primer

<400> SEQUENCE: 20
aacattcctg gtctggagac                                              20
```